US008071299B2

(12) United States Patent
Weber et al.

(10) Patent No.: US 8,071,299 B2
(45) Date of Patent: Dec. 6, 2011

(54) METHODS FOR PREDICTING THE RESPONSE OF MULTIPLE SCLEROSIS PATIENTS TO INTERFERON THERAPY AND DIAGNOSING MULTIPLE SCLEROSIS

(75) Inventors: Frank Weber, Ottobrunn (DE); Bertram Muller-Myhsok, München (DE); Manfred Uhr, Stockdorf (DE); Susanne Lucae, München (DE); Daria Salyakina, München (DE); Florian Holsboer, München (DE)

(73) Assignee: Max-Planck-Gesellschaft zur Förderung der Wissenschaften e.V. (DE)

( * ) Notice: Subject to any disclaimer, the term of this patent is extended or adjusted under 35 U.S.C. 154(b) by 355 days.

(21) Appl. No.: 12/280,665

(22) PCT Filed: Feb. 27, 2007

(86) PCT No.: PCT/EP2007/001689
§ 371 (c)(1),
(2), (4) Date: Dec. 8, 2008

(87) PCT Pub. No.: WO2007/096197
PCT Pub. Date: Aug. 30, 2007

(65) Prior Publication Data
US 2009/0186773 A1    Jul. 23, 2009

(30) Foreign Application Priority Data
Feb. 27, 2006   (EP) .................................. 06003978

(51) Int. Cl.
*C07H 21/04* (2006.01)
(52) U.S. Cl. ...... 435/6.1; 435/6.11; 435/91.1; 435/91.2; 536/23.1; 536/24.3

(58) Field of Classification Search ........................ None
See application file for complete search history.

(56) References Cited

FOREIGN PATENT DOCUMENTS
WO    2005/054810 A2    6/2005

OTHER PUBLICATIONS

Leyva, Laura, et al., IFNARI and IFNAR2 Polymorphisms Confer Susceptibility to Multiple Sclerosis but not to Interferon-beta Treatment Response, Journal of Neuroimmunology 163:165-171 (2005).
Martinez Doncel, Alfonso, et al., Interleukin-10 Polymorphisms in Spanish Multiple Sclerosis Patients, Journal of Neuroimmunology, 131:168-172 (2002).
Mihailova, Snejina, et al., Pro- and Anti-Inflammatory cytokine Gene Polymorphism Profiles in Bulgarian Multiple Sclerosis Patients, Journal of Neuroimmunology, 168:138-143 (2005).
Sriram, U., et al., Pharmacogenomic Analysis of Interferon Receptor Polymorphisms in Multiple Sclerosis, Genes and Immunity 4:147-152 (2003).
Swanberg, Maria, et al., MHC2TA is Associated with Differential MHC Molecule Expression and Susceptibility to Rheumatoid Arthritis, Multiple Sclerosis and Myocardial Infarction, Nature Genetics, 37(5):486-494 (2005).
Wergeland, S., et al., IL-10 Promoter Haplotype Influence on Interferon Treatment Response in Multiple Sclerosis, European Journal of Neurology, 12:171-175 (2005).

*Primary Examiner* — Jeanine A Goldberg
(74) *Attorney, Agent, or Firm* — Pillsbury Winthrop Shaw Pittman LLP

(57) ABSTRACT

The present invention relates to a method of diagnosing a predisposition of a multiple sclerosis (MS) patient for responsiveness to a treatment of MS by administration of interferon-α (IFN-α) and/or interferon-β (IFN-β) and means to perform the method. Furthermore, the invention relates to a method of diagnosing a predisposition of a patient for developing multiple sclerosis (MS) and corresponding means.

6 Claims, 14 Drawing Sheets

Figure 1:
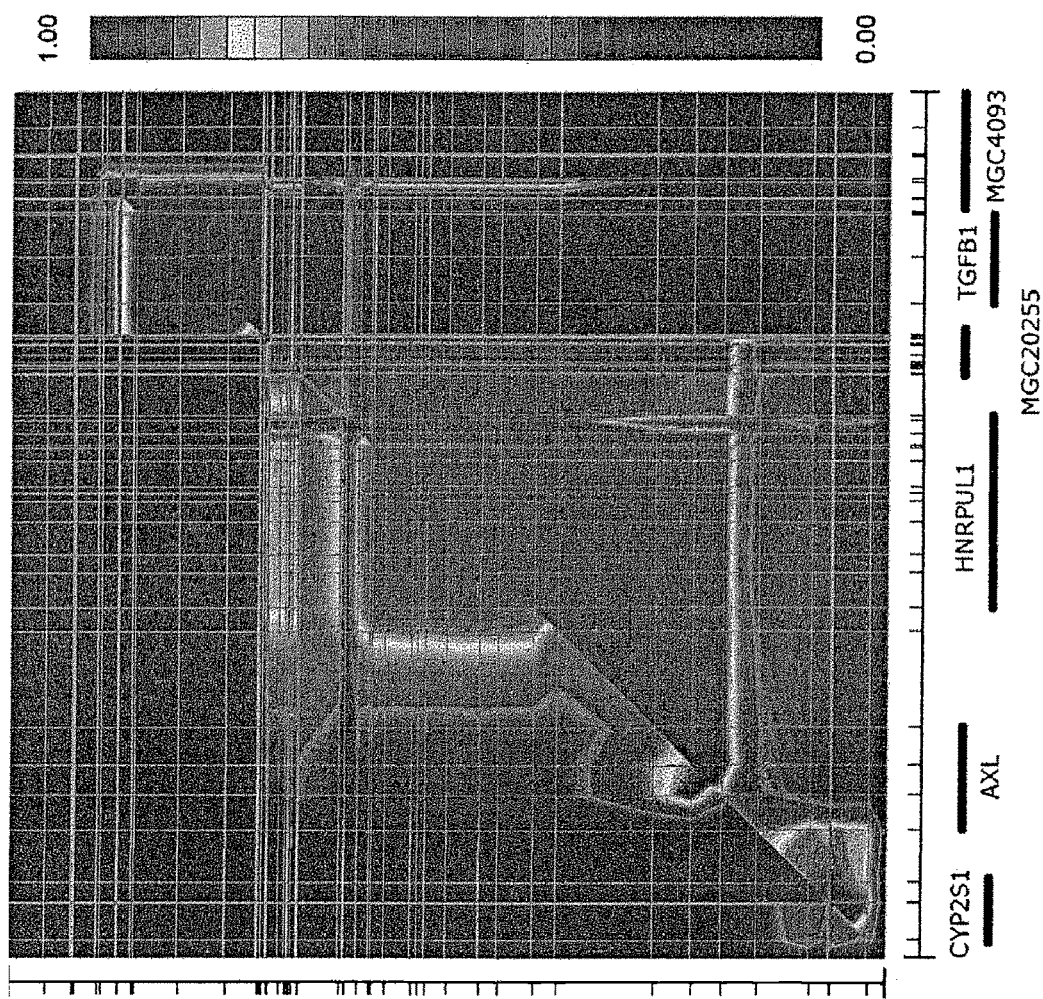

SEQUENCE LISTING

```
<160> NUMBER OF SEQ ID NOS: 211

<210> SEQ ID NO 1
<211> LENGTH: 162203
<212> TYPE: DNA
<213> ORGANISM: Homo sapiens
<220> FEATURE:
<221> NAME/KEY: gene
<222> LOCATION: (1)..(14330)
<223> OTHER INFORMATION: CYP2S1 gene
<220> FEATURE:
<221> NAME/KEY: variation
<222> LOCATION: (1230)..(1230)
<223> OTHER INFORMATION: rs338600  T/C
<220> FEATURE:
<221> NAME/KEY: variation
<222> LOCATION: (13000)..(13000)
<223> OTHER INFORMATION: rs338584  C/G
<220> FEATURE:
<221> NAME/KEY: gene
<222> LOCATION: (25709)..(68557)
<223> OTHER INFORMATION: AXL gene
<220> FEATURE:
<221> NAME/KEY: variation
<222> LOCATION: (35377)..(35377)
<223> OTHER INFORMATION: rs4802112  G/C
<220> FEATURE:
<221> NAME/KEY: variation
<222> LOCATION: (35447)..(35447)
<223> OTHER INFORMATION: rs4803448  C/T
<220> FEATURE:
```

```
<221> NAME/KEY: variation
<222> LOCATION: (35553)..(35553)
<223> OTHER INFORMATION: rs4803449  T/C
<220> FEATURE:
<221> NAME/KEY: variation
<222> LOCATION: (41782)..(41782)
<223> OTHER INFORMATION: rs4802113  C/T
<220> FEATURE:
<221> NAME/KEY: variation
<222> LOCATION: (49640)..(49640)
<223> OTHER INFORMATION: rs2304234  C/T
<220> FEATURE:
<221> NAME/KEY: variation
<222> LOCATION: (63412)..(63412)
<223> OTHER INFORMATION: rs2304232  G/A
<220> FEATURE:
<221> NAME/KEY: variation
<222> LOCATION: (68874)..(68874)
<223> OTHER INFORMATION: rs1946612  G/A
<220> FEATURE:
<221> NAME/KEY: gene
<222> LOCATION: (69310)..(114485)
<223> OTHER INFORMATION: HNRPUL1 gene
<220> FEATURE:
<221> NAME/KEY: variation
<222> LOCATION: (69912)..(69912)
<223> OTHER INFORMATION: rs3760660  A/T
<220> FEATURE:
<221> NAME/KEY: variation
<222> LOCATION: (74951)..(74951)
<223> OTHER INFORMATION: rs2304230  C/T
<220> FEATURE:
<221> NAME/KEY: variation
<222> LOCATION: (82380)..(82380)
<223> OTHER INFORMATION: rs8103839  G/C
<220> FEATURE:
<221> NAME/KEY: variation
<222> LOCATION: (86169)..(86169)
<223> OTHER INFORMATION: rs3745295  G/T
<220> FEATURE:
<221> NAME/KEY: variation
<222> LOCATION: (92979)..(92979)
<223> OTHER INFORMATION: rs8105901  A/T
<220> FEATURE:
<221> NAME/KEY: variation
<222> LOCATION: (97359)..(97359)
<223> OTHER INFORMATION: rs12327659  C/T
<220> FEATURE:
<221> NAME/KEY: variation
<222> LOCATION: (98998)..(98998)
<223> OTHER INFORMATION: rs3752705  G/A
<220> FEATURE:
<221> NAME/KEY: variation
<222> LOCATION: (100362)..(100362)
<223> OTHER INFORMATION: rs2053086  C/T
<220> FEATURE:
<221> NAME/KEY: variation
<222> LOCATION: (105863)..(105863)
<223> OTHER INFORMATION: rs11879562  C/G
<220> FEATURE:
<221> NAME/KEY: variation
<222> LOCATION: (108567)..(108567)
<223> OTHER INFORMATION: rs7248164  T/C
<220> FEATURE:
<221> NAME/KEY: variation
<222> LOCATION: (109136)..(109136)
<223> OTHER INFORMATION: rs11881953  A/G
<220> FEATURE:
<221> NAME/KEY: variation
<222> LOCATION: (111531)..(111531)
<223> OTHER INFORMATION: rs7245398  G/A
<220> FEATURE:
<221> NAME/KEY: variation
<222> LOCATION: (115299)..(115299)
<223> OTHER INFORMATION: rs1865053  C/T
<220> FEATURE:
<221> NAME/KEY: gene
<222> LOCATION: (116980)..(131674)
<223> OTHER INFORMATION: MGC20255 gene
<220> FEATURE:
```

```
<221> NAME/KEY: variation
<222> LOCATION: (123873)..(123873)
<223> OTHER INFORMATION: rs8109627  C/T
<220> FEATURE:
<221> NAME/KEY: variation
<222> LOCATION: (124054)..(124054)
<223> OTHER INFORMATION: rs8109167  T/G
<220> FEATURE:
<221> NAME/KEY: variation
<222> LOCATION: (125354)..(125354)
<223> OTHER INFORMATION: rs1865052  A/G
<220> FEATURE:
<221> NAME/KEY: variation
<222> LOCATION: (125772)..(125772)
<223> OTHER INFORMATION: rs1865051  C/T
<220> FEATURE:
<221> NAME/KEY: variation
<222> LOCATION: (125868)..(125868)
<223> OTHER INFORMATION: rs16958994  C/T
<220> FEATURE:
<221> NAME/KEY: variation
<222> LOCATION: (126025)..(126025)
<223> OTHER INFORMATION: rs16958996  T/C
<220> FEATURE:
<221> NAME/KEY: variation
<222> LOCATION: (126073)..(126073)
<223> OTHER INFORMATION: rs16958999  G/A
<220> FEATURE:
<221> NAME/KEY: variation
<222> LOCATION: (126663)..(126663)
<223> OTHER INFORMATION: rs3826714  G/A
<220> FEATURE:
<221> NAME/KEY: variation
<222> LOCATION: (128007)..(128007)
<223> OTHER INFORMATION: rs7257310  T/C
<220> FEATURE:
<221> NAME/KEY: variation
<222> LOCATION: (130196)..(130196)
<223> OTHER INFORMATION: rs2241720  C/G
<220> FEATURE:
<221> NAME/KEY: variation
<222> LOCATION: (130468)..(130468)
<223> OTHER INFORMATION: rs2241719  T/A
<220> FEATURE:
<221> NAME/KEY: variation
<222> LOCATION: (130493)..(130493)
<223> OTHER INFORMATION: rs2241718  A/G
<220> FEATURE:
<221> NAME/KEY: variation
<222> LOCATION: (131493)..(131493)
<223> OTHER INFORMATION: rs6957  C/T
<220> FEATURE:
<221> NAME/KEY: variation
<222> LOCATION: (132083)..(132083)
<223> OTHER INFORMATION: rs11880564  A/C
<220> FEATURE:
<221> NAME/KEY: variation
<222> LOCATION: (132394)..(132394)
<223> OTHER INFORMATION: rs12985162  A/G
<220> FEATURE:
<221> NAME/KEY: gene
<222> LOCATION: (137537)..(160703)
<223> OTHER INFORMATION: TGFB1 gene
<220> FEATURE:
<221> NAME/KEY: variation
<222> LOCATION: (144348)..(144348)
<223> OTHER INFORMATION: rs11466345  C/T
<220> FEATURE:
<221> NAME/KEY: variation
<222> LOCATION: (148747)..(148747)
<223> OTHER INFORMATION: rs1800472  G/A
<220> FEATURE:
<221> NAME/KEY: variation
<222> LOCATION: (161183)..(161183)
<223> OTHER INFORMATION: rs1800469  A/G

<400> SEQUENCE: 1
taactagccc agccgcgcgg agcgcctggg agaggagaag gagccgacct gccgagatgg    60
```

```
aggcgaccgg cacctgggcg ctgctgctgg cgctggcgct gctcctgctg ctgacgctgg    120
cgctgtccgg gaccagggcc cgaggccacc tgccccccgg gcccacgccg ctaccactgc    180
tgggaaacct cctgcagcta cggcccgggg cgctgtattc agggctcatg cgggtaaggg    240
gctctgggga cgtcctggct aggggtggga ggattcctgg gagagaaacc cgagtgccag    300
ggtgaggggc ttttcgggta tcctaggag gaggcagggg cagggtccc aaggcaaagg      360 ggctgctgct gtcctgggt tggggcagg agcaggttgt ccaggctga aaggggaga        420 ggtgcccggg agagaggatc gtgggtggg ggaccagggc taggaggggc agagacctct     480
gcctacagaa tcctgggaag gtgatgggca gggaccgagg ctgaaagaga caggagtcct    540
ccagccgagg agaagctgat gcagctgggc ttgtcccaga gggagaggta gctggagcca    600
tacaggtggg gcatgctgaa gagggcacaa agaagaaaag ggggaggcgt ccctgcgggg    660
agttggaggc agagaagagg ctggagggtt gcaggctcag agaggggtc ccgctgaagg     720 aatctgccag cagagaatgc aggatgggag gatgggtgga gctcagttgg gagttcctgg    780
gactggggag gaaggagagc aagaaagaag gcagaggcag ccccagcctt aggggatagc    840
aggtgggagt gggcagaggc ctgaagtttc ccattcaaaa ggattctggg tgacttcaag    900
gacgtagaaa aagggtggg gtcttgggg agagatgggg cggatactca gcagtgtctg      960
ctccagaatt tcagggtttt gtggtgactg aaaggggtgg ctggatattt ggggggcagg    1020
gagggcccta aggaattaag ggagacccaa actgcttctg gattgcccag cgtcagaggt    1080
tagggttcag caggaagcaa gggaacgaca ggaagttggg ggatgccact gaaggatgta    1140
ctgggggagg aggcccggga gcctagtgca aaaagagaac tgagcctcag ctatttctgc    1200
tgggatgggg gcaggttcct ggtagagggt gtagaagcta gacccggtgg ctcctcaagt    1260 gacagggcc atgatggaga caccttggat cgaagaggtc acagcaccct cctctttctt     1320
cctccctacc cccagctgag taagaagtac ggaccggtgt tcaccatcta cctgggaccg    1380
tggcggcctg tggtggtcct ggttgggcag gaggctgtgc gggaggccct gggaggtcag    1440
gctgaggagt tcagcggccg gggaaccgta gcgatgctgg aagggacttt tgatggccat    1500
ggtaagtcaa gggctgctag gccctccgct cacagcctgc caccacttac tggtgtgtga    1560
cctttgcaca tggcttagtc cctctgttgc ctcatctgtc aaatggagtg ataacagtgc    1620
ccatcagccg ggtgcagtgg ctagtgcctg aaatcccaac actttgggag gcggaggtgg    1680
gtggatcact tgaggtcagg agttcgagac cagcctggcc aacatggtga accctgtctc    1740 tactaaaaa tataaaaatt agctgggcat ggtggtgcgt acctgtaatc ccagatactt     1800
gggaggttga ggcaggagaa tcgcttgaac ccgggaggca gatgttgcag tgaaccaaga    1860
ctgtgccact gcactccagt ctgggcaaca gagtgagcct ccatctcaaa caaacaaaca    1920
aaaagcagtg cccatcatgt aggattgagt gattgagtga ggactgagcc ttgtgcaaag    1980
tgagcactca ctaatcacca ggttgtagta tcagtgataa ccatcaatga tccaggtaaa    2040
gccctgaggg ttcagaaaga tgccggagcg cttcaaggt gctgggatt ggtgggcaag      2100 ccctcgaata atagaaacag ttctctgtat tacaacagaa agcaggaggc ccatgctggg    2160
tgctgccagg aactcagtag taactaagac agcaccggtg ctgcttcccc agcgcaccta    2220
ggccagtggg gaaacagact caccacacag tcccagccca gagtggtcag ggccaagatg    2280
gggaagcacg gggagaaagg tcagggtggg atggggaggg gtcagggcaa gaggggtcag    2340
ggccaggctg agggaagccc tgggactgta ggaatttaga ggaggtacct gacccggcat    2400
gtttggtgag ggagcttcag gaagtcttcc tggaagagag gctgtcggag ctgagactca    2460
```

```
taagatgagt gggagggtg ttccaggcag aaagaccagc acctacaaaa gcatgacttt    2520
gagagaagca ttcatccatt caactgatga attttcagac tgggcacgct ggctcatgcc    2580
tgtaatccca gcactttgga aggctgaatg ggaggatga cttgagccta ggcatttgtg     2640
acaagcctgg gcaacatggt gagaccctgc ctccacaaaa caaacaaaca aacaaaaaat    2700
cattatacct ggtaccatgg gtaccaggta catagaaatg actcaggcag atatggtgtc    2760
ctctcctact gtgggagagg cgggcttata ctgcagtaag acaatagagg gagggaatat    2820
aatcctaaaa tgagaggtac agatttgaga gcaaacacag gcacaggca tatgtacgag     2880 ggtaaagagg gaatcaggga aggcttctca gagaaggtga catttaagcc gggacatgaa    2940
ggatgaacga gttagttcac caaggatggg atggaaaggg gtgagagtga tggaggcaga    3000
gggaactgca ggatcatagg cctagacagg ggatcctgac gcccttgagg aagtgagaga    3060
agaccagcgc agtcgtagtg ggttaagtaa caaagctgag aagccaggga aatccctggt    3120
catgcagggc ctgtgagtca cgtcagagtg tttgggcttt tgttttttcct gggagcagtc    3180 gattttaagc agggaacagc tgtattcaga gttgggaaga tcctgtggtt gctgcctgaa    3240
ggggatgaaa ctgaggcta ggagcccagg gtgataggga ggatccaggg tgatggggag     3300
gctgggaggt ccgcggtgat ggaccagggc tggggccagg ggatggggag aaggagtaa    3360 ttgggagagg cctggggctc tggccgagga atggatggtg ggctgaaaca gggagaggag    3420
agatgcttag gccactttgg aacacagtag ggcaaggaca ggagacaccc aagggggaagt    3480 gcccaagaga ccacgacagg ctggcattgg acagggaagg tctgtctgga gcaggtgtct    3540
tggataaggg aggaaaatgg tgcagttcca tcctcctccc tctctgttca acctctaaac    3600
tacatggggc acaggaccca gtgggactcc ataaatgatg ggatggtgg atggaaggaa    3660 ggaaggagga aacaactctt cattcatcct ggttatttac agaacaggcc aggtgcggtg    3720
ctcacgcttg ccattctagc actttgggag gctgaggtgg gtggattacc tcaggtcagg    3780
agttcaagac cagcctagac aacgtagaga aaccccatct ctactgaaga tataaaatta    3840
gctgggcgta gtggcatatg cctgtaatcc cagctagtcg ggaagctgag gcaggagaat    3900
cgcttgaacc cgagaggcag aggttgcggt gagctgagat cgtgccattg cactccagcc    3960
tgggtgacaa agcaagacct cgtctcaata ataataataa ttacaaaaca gaaggagcct    4020
gggtcatccc agctacctac ttttcaggag aatgtactcc cttacccaag gcaaaggat     4080 gggagaacca gtttgattat gcatttattg agcacctact gagtcctcat ccctgggcta    4140
ggctggaatg gactcagatg gagcctgaag agtccccctc agggaacctc actagaaaga    4200
aggaggaatc ggccgggcgc ggtggctcac gcctgtaatc ccaacacttt gggaggctga    4260
ggtgggtgga tcacaaggtc aggagatcga gaccatcctg gctaacacag tgaaaccca    4320 tctctactaa aaatacaaaa aatgagccag gcatggtggc gggcgcctgt agtcccagct    4380
actcaggagg ctgaggcagg agaattgctt gaacccggga ggcagaggtt gcagtgagac    4440
gagatcacgc cactgcactc cagcctgggc aacagagcga gattccgtct caaaaaaaaa    4500
aagaaagaaa ggaagaaggg ggaatggggg agaggggccg gtcccttttt gagtctagcc    4560
ttctgcgcag gggttttctt ctccaacggg gagcggtgga ggcagctgag gaagtttacc    4620
atgcttgctc tgcgggacct gggcatgggg aagcgagaag gcgaggagct gatccaggcg    4680
gaggcccggt gtctggtgga gacattccag gggacagaag gtcagcatgg cggggtcacc    4740
ccagggtctc cagccgagtg aaagggaaaa ctctccctact gtggctgggg gtggccccaa    4800
cccaggtcct ggaatgggca ggaggggaag ccttgaactc tagggctggc ctgggggttc    4860
```

```
tgttcactgc caccttctgt ctctgtccca ctgtctctcc gaggctgtca tgacatctct    4920
ctgtgtgtct ctggtgctat catcccattc ttcctgggtc tccatctctc tctctgtctc    4980
ttttctttct ctctccttc ctctattttt tgggccctca gtctatctct gtttctgtct    5040
ccctgtctgt gtgatggtca ctctgtttct ttctccctgt ctgtttctct gtccctatct    5100
gtctgtatcc ttctttgcct gtttagctct ctccctgcgc tgtccatcca tctttccctg    5160
cctccctgtc tctctctggt tgggttcagc tccaacctgc tcccctctgc ctggctccat    5220
cacagcctac ctccctgccc ccattccccc caggacgccc attcgatccc tccctgctgc    5280
tggcccaggc cacctccaac gtagtctgct ccctcctctt tggcctccgc ttctcctatg    5340
aggataagga gttccaggcc gtggtccggg cagctggtgg taccctgctg ggagtcagct    5400
cccaggggg tcaggtgagt gggtgggacc cctctccaac taccttccct gaaggttcct    5460
gccaaggtcc catgagaact agctgccctt ctccccacag acctacgaga tgttctcctg    5520
gttcctgcgg cccctgccag gcccccacaa gcagctcctc caccacgtca gcaccttggc    5580
tgccttcaca gtccggcagg tgcagcagca caggggaac ctggatgctt cgggccccgc    5640
acgtgacctt gtcgatgcct tcctgctgaa gatggcacag gtgtgggaag ggtgcaggga    5700
ccccctctct gaatgggcat ggtgacctgg caggtcccca gccaggtgtc cctggggacc    5760
tcaattgggt tcctctctct ttctctctct gcatgtctct gtgagtatga gtgtctctgt    5820
gcatgtgtgt gcatcccttc tctgcacatc tgtctgtccc tttcagggcg ttgctctcac    5880
tgcctctccc gcccccgacc tgggcatttg tgccgggctg tctgtctctc cagcatctct    5940
cctctttctc cctcccacct cggcccttgt gttcaggccc catgcccagg gtcctacacc    6000
agcaatcccc aggatcactt catcccatcc cctgcagcct ccccagactt ttatgtaaat    6060
tcacaatttt atgtgaatta tggtcattta ttaggaagcc ttgcaatatc aagttatgtt    6120
aataaagtcc actttattaa ttatataaga acaatatttc ttttccttt tttttcttt     6180
tcttttaaa gagacaggat ctctttctgt tgcccaggct agagtacagt tgcaaaatca    6240
tagctcactg caaccttgaa ctcctgggct caagcaatcc tcctgcctcg gctcctgag    6300
tagctgggac aacaggtgtg caccaccaca cctggctaaa tttttttttt ttctttgtag    6360
agatagactc tcactatgtt acccaggctg tcttgaatt cctgggctca tgtaatcctc    6420
ctgctgcctt gaactcccaa agtgctggga ctataggcat aagacatcat gcccggtcgg    6480
gcacagtggc tcatgcctgt aatctcagga ctttgggagg ccgagacggg cggatcacct    6540
gaggtcggga gttcgagacc agcctgacca acatggagaa accccatctc tactaaaaaa    6600
aaaaatacaa aattagccgg acgtggtggc acatgcctgt aatcccagct actagggagg    6660
ctgaggcagg agaatcgctt gaacccggga ggcttaggtt gcggtgagct gagattgcac    6720
cattgcactc cagcctgggc aacaagagcg aaattccatc tcaaaaaaaa aaaaaagaa    6780
aaaagaaaa aagacaccat gccctataag taaactagaa ttaaggtgac tcctaaggaa    6840
ataaatagtt tttaactgta cgaacttttg gaagaatggg gccaattctt taattaaatg    6900
cagcctccct gtttgtggag aaagaaaaat ttttcttaac cctattgccc catttctttt    6960
ctctttatt gaatattttt tagttttaac tatagtaaaa tacacataac gtttaccatc    7020
ttaaccattt ttaggtatac agtacagtag tgttcagtac attcatactg ttatgcaatc    7080
agtctccaga actcttcatg ttgcaaagct gaaactctat acccattaaa caactgcctg    7140
ttcctccctc ctccaacccc tggcaatcac cttttttttt ttgagatgaa gtctcactct    7200
gtcacccagg ctagagtgcg gtggctcgat ctcggctcac tgcaagctcc gcctcccggg    7260
```

```
ttcatgccat tctcctgcct cagtctccca agcagctggg actacaggtg cccgtcacca    7320
cgcctggcta attttttgta ttttttagtag agatggagtt tcatcgtgtt agccaggctg    7380
atctcaaact cctggcctca agtgatccac ccgcctcggc ctcccaaagt gctgggacta    7440
caggcgtgag ccactgtgcc tggccaggaa gtagactctt gatattagtt ctctctggtt    7500
gaaatgtttt taaaaatgaa agagaatgac taataacaaa aacacagaaa gttataagga    7560
ttgatgaaga tgtggagact ttgaaaccca tgtataccat tggtgggaat gtgaaacgac    7620
gcagccctgt ggaaaatggt acagcagtta cctgaggtca ggagtttgaa accaacctgg    7680
ccaacatgca gaaaccccgt ctccattaaa tgtacaaaaa ttagccaggc atggtggtgc    7740
gcacctgtaa tcccagctac tcgggaggct gaggcaggag aattgcttga acccaggagg    7800
cggaggttgc agtgagccga gatcgtgcca ctgcactcag cctgggcaac aaagcaagac    7860
tctgtctcaa aaaaaaaaag tctacttccc aaccttccca aaaatttatc taaaccccgt    7920
gacaaaactt taacttgtgt ttccgacccc aggcttggct gttctggaca tttacttccc    7980
aaaggctgtg ttctctcagc ccctctgcct ggtttctttc aggaggaaca aaacccaggc    8040
acagaattca ccaacaagaa catgctgatg acagtcattt atttgctgtt tgctgggacg    8100
atgacggtca gcaccacggt cggctatacc ctcctgctcc tgatgaaata ccctcatgtc    8160
caaagtaaga gccttttcca cttgccaggc cttgggaaca gaagtcaggg ttctaggctg    8220
agcaaggtgg ctcacgccta taatcccagc actttgggag gctgaggcgg gctgatcact    8280
tgagaatagg agtttaagac cagcctggcc aacacagtga aacccatctc tactgaaaaa    8340
tacaaaaatt agcgggtgtg gtggcatgca cttgtaatcc cagcactcag gtggctgagg    8400
agtgagaatt gtttgagccc aggaggtaga agttgcagtg agctgacatc acaccactgc    8460
actccagcct gggcgacaga gcgagacact gtttcaaaaa aaaaaaagtg agaattctag    8520
agggaagagt gggtgggcca agcagacagg ctgagttaga tctttgaggc atcgatgggc    8580
atggcgtttg agatgtcgag gagccagaag aggttcagga gttgctgatt gcagtatgag    8640
gcacagtgaa aaacaaggca ggtgtctgtg ggcctcatcg ccttagtgat acattaggtg    8700
ccttatcctg agccatgggg agcaatgcaa tgactttgag caggggaggg caaggtcaaa    8760
ttggtttttt attttatttt tttttacttt ttgtggggga tagactctca ctctgttgcc    8820
caggctggag tgcagtagtg cgatctcggc ccactgcaac ctccggcctc ctgggttcaa    8880
gcaattctcc tgcctcagcc tcccaagtag ctaggattac aagcatgcac caccacgccc    8940
agctaacttt tgtatgttta gtagagacag gttttcccca tgttggccag gctggtcccg    9000
aactcctgac ctcaagtgat ctgcccacct cagccttgca aagtgctggg attacaggca    9060
tgagccaagg cacccagccc aactctagca ttttcgggtc aggcagctgc tgtgggccat    9120
ggggacgggc tgacctggaa tatgggagtg gaggtcctgg tagtgttgca ggagtggaat    9180
tagctgtgac ttccagcagt gacttgggtt ctctgagtct gtttcctcac ctaggaaatg    9240
gggatggata caatatgta cctcacaagg gtgctatggg aattaagaaa gtatggatga    9300
gccaggcatg gtggcttata cctgtaatcc cagcactttg ggaggctgag gtgggaggat    9360
cacttgaggc taggagttca agatcagcct gggcagcata atgaggccct gtctctaccg    9420
aaaatagaaa aattagctgg gtgtggtggt gcgtgcctgt ggtcatagct actcaggaga    9480
ctgaggtgga aggatcacct gagcccagga ggtgagatga aggctattac agtgagccgt    9540
cattgtacta ctgcaccagc ctgggcaaca gagtaagacc ctgtctcaaa aaaaaagag    9600
agagagagaa ggccaggtac ggtggctcac atctgtaatc ccagcacttt gggaggccaa    9660
```

-continued

```
ggcaggtgga tcacctgagg tcaggagttc gagaccagcc tcgctaacat ggtgaaaccc   9720
tgtctctatt gaaaatacaa aaatgagctg ggcatgatgg caggcgtctg tagtcccagc   9780
tactcgggag gctgaggtgg gagaatctcc tgaacccggg aggcggagtt gcagcaagcc   9840
aggatcgcgc cactgcactc cagcctgggt ggcagagcgt gtaatcccag ctactcagga   9900
ggctgaggcg ggagaatcgc ttgaatccgg gaggcagagg ttgtggtgag ccaagatcgc   9960
accattgcac tccagcctgg gcaacaagag caaaactccg ttgcaaaaaa aaataataat  10020
aataaaatga aataaaataa aataaaataa gagagagaga agatagatgg aacacccaac  10080
acacaagatg tgtggtcttt gggctcagtg agggctgggg gaccactcct ccccacctgt  10140
cagcctcacc ccaaactaca gctatgcaag cagatgggct tctgagagga ggatccctgg  10200
gccctacccc cgtctgactc ctgccctcct cttgcttgca gagtgggtac gtgaggagct  10260
gaatcgggag ctgggggctg ccaggcacc aagcctaggg gaccgtaccc gcctccctta  10320
caccgacgcg gttctgcatg aggcgcagcg gctgctggcg ctggtgccca tgggaatacc  10380
ccgcaccctc atgcggacca cccgcttccg agggtacacc ctgccccagg tgggtatgcg  10440
tatggctgcc acccatggtt ctctgcctcg gggcctgagc ccgggtggtt tgctgtcagt  10500
gtctccctga cttttcttg atcttagtgt ctctctctct ctctctctgt ctttatctcc  10560
ctctctttct ctgtctctgt cttcctcctc cactcctacc ccctgcatc tttcttctcc  10620
ttctttctct gacaccccct cccttctgc atatattttt tttctttttt tgagacagag  10680
tctcgcactg tcgcccgggc tggagtgcaa tggcgtgatc tcagctcact gcaacctccg  10740
cctcccaggt tcaagtgatt ctcctgcctc agcctcctga gtagctggga ttacaggtgc  10800
ccaccaccac gcccagctaa ttttttgtat tttagtaga cacggggttt cattatgttg  10860
gtcaggctgg tcttgaactc ctgacctcgt gatctgcccg cttcggcctc ccaaagtgct  10920
gggattacag gcgtgagcca ccgcacccag ccatgctttc tgcatctttt aactcttct  10980
gtttcttttt ggtttgtgtt ttcttcccct ttgactctat ctctgggccc catctgcccc  11040
acagatctcc caattctacc tccttccaag gtggttggga caatcgaatg aggtaacata  11100
cagagaagca gtttgaaaac tgaggagcaa gtccaggact aagggaagcc ctcttgaccc  11160
ttagcccctg ctgcagacac attctctcct ctgtctctct ctctcaatct cagtgccctt  11220
cactggagag cagctccgat gcagaaccaa aaggggggcga tgtttcccca gaaacccag  11280
cagtttatgc aagcagctcc ctcctccacc ttcactgcag aatcaaacct atggcagtta  11340
ggatccagtg ctgctatgct gctatttct ttttcttctt cttctttttt ttttttttt   11400
ttttccgag atggagtctc gctctgttgc ccaggctgga gtgcactggc gtgatctcgg  11460
ctcactgcaa cctccgcctc ccaggttcaa gcaattctct tgcctcagcc tcctgggtag  11520
ctgggattac aggtgtatgc caccacaccc ggctaatttt tgtcttttta gtagagatgg  11580
gttttcacca tgttggtcag gctggtctca aactcctgac ctcatgaact gcctgcctcg  11640
gcctcctaaa gtgctgggat tacaggcgtg agccactgca cctggcctac cccctcctgt  11700
tttgtagatg gggccttggg caaatcactt ccccccctga acctcaatat atccctcctc  11760
tacattagaa acaataatag tatcaacttg aagctgtaag ataatgcttg taaaacaaac  11820
accaactcaa ctcttgggaa ccggtcctgt gtaccaggca gcaacaattt aatgatgata  11880
atgacaggta tccaggcttg aggacctgct ctgcaccagg ggttattctg agtgctttgc  11940
atatctatta tctcatttaa tctttaaagc aaccctatac cattatcatg cccatcttac  12000
agataaggaa actgagagct tgaaaagttt ttagaggatt tgccaaggtc ccccagcctg  12060
```

-continued

```
caaatagtag attcaagatt tgaactcaga gactatgcct taactactat tctttgcctt    12120
tctttctttc ttttttctt tctttctttc tttcttctt tctttctttc tttctctctc     12180
tctctttctt tctctctttc tttctttctt tctctctctc tctctttctt tcttttcttt    12240
ttctttctct ctctctctct ttcttcctt cttcctcct cccttcctcc cttcctccct     12300
tcctgtcttc ctctctttct ctcttcttt cttgacaggg tctctctttg tctcccaggc    12360
tggggtgcag tggtacaagc atagctcaca gcagccttga actcctaggc tcaagtgatc    12420
ctcccacgtc agcctcctga gcagctggga caacgggctc ataccaccat gcctggctaa    12480
ttttttaatt tttcctagag acaaggtctt gttatattgc ccaggctggt ctcaaactcc    12540
tgggctcaaa tgcttctctc acctcagcct cccacgtggc tgggattaca ggcatgagcc    12600
actgcacgcc actcaacact ccacaaatgt tgatgccatt aggttttgtg aactagtgtc    12660
cctgcacccc gagacttgta ctccacactc gaggaccaaa tggactgggg tgggaagggg    12720
tttatagttt cattattatt tccctcagg gcacggaggt cttccccctc cttggctcca    12780
tcctgcatga ccccaacatc ttcaagcacc cagaagagtt caacccagac cgtttcctgg    12840
atgcagatgg acggttcagg aagcatgagg cgttcctgcc cttctcctta ggtatctgct    12900
gcagccctgg gtatcacaag caggtgctgg cgaactccag gcatctgtgc cagctggggg    12960
cacccttctg caccctgggc ttactgttgg ctcctccacc tgctgttccc cccgtgggcc    13020
tgggtgtgag gaatactgac tcagccctct ctctctctct ctcctcacca gggaagcgtg    13080
tctgccttgg agagggcctg gcaaaagcgg agctcttcct cttcttcacc accatcctac    13140
aagccttctc cctggagagc ccgtgcccgc cggacaccct gagcctcaag cccaccgtca    13200
gtggccttt caacattccc ccagccttcc agctgcaagt ccgtcccact gaccttcact    13260
ccaccacgca gaccagatga aggaaggcaa cttggaagtg gtgggtgccc aggacggtgc    13320
ctccagcctc aacagtgggc atggacaggg ttaatgtctc cagagtgtac actgcaggca    13380
gccacattta cacgcctgca gttgttttcc ggagtctgtc ccacgcccca cacgctcact    13440
tgactcatgc tgctaagatg cacaaccgca cacccataca caactacaag ggccacaaag    13500
caactgctgg gttagctttc cacagacata aatatagtcc atctgcaatc acaagcacat    13560
agccaggtaa cccaccaact cccctggatc tgcagcccac acgtgggagt ctggctgtca    13620
ccttcacaag ccacagaaac ggccacacat gttcacagct cacacgccct ctccattcat    13680
cgaacttctc agtgtccctg tccctggtgc ctggcacagg gaacagcatg cccctccgg    13740
ggtcatgcca cccagagact gtcgctgtct atggccccaa ctcatgctcc ctctcttggc    13800
tacaccactc tcccagcctg tgaccaccga tgtccacaca ccccaaccaa cttgtccaca    13860
cagctaccca cgtacgacat cgtcctggct ccccagagta tcttcccact gagacacgcc    13920
gcccccacag aggcacagtc cccagccacc tctgcaactg cagccctcag tcaccccttt    13980
ttaagcaccc tgattctacc aaatgcaaac acatctgggt ctgcgattat gcacagagac    14040
tttggacata cgaggaccct cagaccggag gaacacctgc ccaaccccaa cacgtgctta    14100
tgtaaccacg tggaaagcgg cccctgctgc ccctccacac acacatacac actcactgat    14160
ctacagcccc tgttcggcgt cagagtcccc actagaccca gtggaagggg ttagagacca    14220
agtaggggcc agtttccaat tcaccctgtc agggagtgag ccggatctga cgttccttgt    14280
gacttaaggg tccggcttgg gaattaaagt ttgtttctgg cctttagcct actgcgtgtg    14340
tgacccgtgt cagtcactgt gagtaagggg tgggacagg ggagtccacc cctcccctga    14400
ggctgggcgg gagctgaaaa acatggccac cgcccaccct ggctgttgac atcaggacca    14460
```

```
gatgtggagc tgggaggagg ggcagggctg gtgacgccct gggcctcatt tccaaaaagg    14520
gccaaggtgt ccggcggtgg gaagtgggca aggaggggg aacccaagct ggactgtgga    14580
ccttgggggc ttcctcagcc agggagagcc tgaagccaac tagatccaga ccctagagac    14640
tcttcaaact tgagtacagg aactagcttg caacacagac tctaagccca ctcccatttc    14700
ttccaccctt tttctcttgc ctccccttca caaggaaacc agaggcattt gtaaatttcc    14760
tttctttttt tttttttttt tttttttgag acggagtctc actctgtcac ccaggctgga    14820
gtgcagtggt gtgatcttgg ctcactgcag cctccgcctc cgggttcaag ccattctcct    14880
gcctcagcct cccaagtagc tgggattaca ggtgtgtgcc accacgccca gctaattttt    14940 gtattttag tagagatggg gtttcaccat gttggccagg ctggtctcga actcctgacc     15000
tcagatgatc tgccagtctc ggcctcccaa aatgctggga ttacaggcgt gagtcgctac    15060
tagataaatt tcttatctag caaagaagtt tgcaaacata cgcaaaagta gaaagataca    15120
atgagccccc aggtgcccat cacccagcct catttcaata gtcatcaact ttctgcagct    15180
tttacttcat ctatatcctt ttctgcctct tttttttttt ttttattttg agatagggtt    15240
ttgctttgtt gcccaagctg gggtgcagta gcatgatctc atagttcact gtggcttcag    15300
actcctaggc tcaagtgatc ctcccgcctc ggcctccaag cagctgggac tacagatgcg    15360
tgccaccaca cccagctaaa tttcttattt ttattttcta tagagaaagt ctcactatac    15420
agcctgtgct ggtctcaaat tccaggcctc aagagtttcc atcccagcct cccaaagtgc    15480
tgggattata ggcgtgagtc actgcaccct gccctgatat ttttatttta tctattgctt    15540
tttatttact tatttatctt ttattttga cacagagtct cactctgttg cccatgctgg    15600
agtgcagtgg catcatctcg gctcactgta acctccgcct cttaggttca agcagttctc    15660
ctgccttgac ctcccgagta gctggaatta caggtgcctg ccaccaagcc tggctaattt    15720
ttttatttgt agtagagatg gggttttgcc atgttgacca ggctggtctc gaactcctga    15780
cctcaggtga tctgcccacc ttggcctccc aaagtgctga gattactggt atgagccacc    15840
gtgcctggcc acctattgct ttttaaagat tattttttta ttattattat tttttattt    15900 gagatggagt ttcgctattg ttgcccaggc tggagtgcaa tggcgtgatc tcagctcacc    15960
gcaacctccg cctcccaggt tcaagcgatt ctcctgcctc agcatcccta gtagctggga    16020
ttacaggcat gcaccaccat gtccagctaa ttttgtattt ttagtagaga cgaggtttct    16080
ccaggttggt caggctggtc tcaaactccc aacctcaggt gatccgccca tctcggcctc    16140
ccaaagtgct gggattacag gtgtgagcca ccgcgcctgg ccttaaagat tattttaagg    16200
caaattacag aaagcaattt aatgcacatt tctgagagtt aaagatattt tgcccttga    16260 cattttatga ggacagtttt caaacatgca gcaaagttga gggaattgta caaggaacac    16320
cttgtgcact tcctgggttc tcccactagc actttgctac actgctttct gacgtttcta    16380
cacacctgac caccagctca ggattttatt atttatctat ttattttgag acagagtttt    16440
gctcttgttg cccagactgg agtgcaatgg tgtgatctcg gctcacggca acctccacct    16500
cctgggttca gtgattcttc tgcctcagcc tcccaaaata gccgggatta caggcatgcg    16560
ccaccacgcg tggctaattt ttgtgttttt agtagagacg gatttctcc atattggtca    16620 agctggcctc aaactcccga cctcatgtga tctgcctgcc tctgcctccc aaagtgctgg    16680
gactacaggt gtgagccact gcgcctggcc aatttttttt tttttagac gaagtctcac    16740 tctgtcaccc aacctggagt gcagtggcat gatcttggct cactgcagcc tccacctccc    16800
aggttcaagc gattctcctg cctcagcctc ctgagtaact gggattacca gcgagcgcct    16860
```

```
ggttaatttt tgttttttta gtacagatgg ggtttcatcg tgttggccag gtgtgagcca   16920
ccatgcccag accagttcag gacttttag gcatttccga gtaaacgcac gtatcagttc    16980
atcaaaaaac ttaagcaatg catatatcat tagcgaaagc ttctttttta aaaaaaaaaa   17040
tccaagatgt taacacttta ttggcttaag ttctatagag atagcacaaa acagagaata   17100
atagagaact gaaagatgag attggaatca gatcctaact ttgccacctc ctagctggtc   17160
acaccttgac tgaggcttta ccatcttaaa gccttaataa attgataaga tgtaagaaat   17220
gtgggccagg cacagtggct cacacctgta acccttgttg agggaccgag gtgggaggat   17280
tgcttgagcc caagggttca agaccagcct ggccaaaagg gcaagactct gattcaaggg   17340
aaaaaaaaaa aatccagaaa gaaatgtgaa aactttcaga acttcgtagg aaataaatat   17400
ctgctaagtt cttcttggat ttaatattat tactattttt tatatgtcgg tgcactttga   17460
aaaggaatga agtttaaggt tttcttcttt taaaagtaag gcaatggggc caggtgcggt   17520
ggctcacgcc tttaatccca gcactttggg gaggctgagg caggcagatc acttgaggtc   17580
aggagttcga gagcagcctg gacaacatgg tgaaacgcgg tctttaccaa agatacaaaa   17640
actagccagg catgatggca ggcacctgta atcccagcta ctcaggaggc tgagacagga   17700
gaattgcttg aacccagcag gcagaggttg cagtgagcca ggactgtgcc acagcactcc   17760
agcctgggtg acagagtaag actccatctc aaaaaaataa aaaattaaat taaggcaatg   17820
atttgcattc ctttgcagtc aaaattcaca ttcagggaaa tctggaatca ggtagaaata   17880
caagcagacc tatttattta aagaggtggg ctatagccgg gcatggtggc gggcaccctgt   17940
agtcccagct acttaggagg ctgaggcagg agaatggtgt gaacccggga ggcagagctt   18000
gcagtgagcc gagatcacac cactgcactc cagcctaagc gacagagtga gactctgcct   18060
caaaaaaaaa attttttttt ttaaataata aaaaaaataa taaagaggcg ggctgggcac   18120
ggtggctcac gcctgtaatc ccagcacttt gggaggctga ggtgggcgga tcacgaggtc   18180
aggagatcga gaccatcctg gttaacatgg tgaaaccccg tctctactaa aaatacaaaa   18240
aagtagccag gcgtggtggt gggcgcctgt agtcccagct actgaggcag gagagtggtg   18300
tgaacccggg aggcagagct tgcagtgagc tgagatagtg ccactgcact ccagcctggg   18360
cgacaaggca agactctgtc tcaaaaataa ataaataaat aaatacataa atacataaat   18420
aaataaataa agaggcatgt cggcctgggc atggtggctt atacctataa tcttagcact   18480
ttggtaggct gaggtaggag aatcgcttga gcctaggagc ttgagaccag cctggacaat   18540
atagtgagac cccatctgta caaaaagaa aacaaacaaa caaacaaagg cacagactt    18600
gcactgtatc aatataaaag ttgacatcag gatgatttca gtagcaagta aaaaaataca   18660
gaaactcaaa atggcttaaa caataaagaa gaattattgg tccccaaagt aaaaatgaa    18720
tcggtgtggt cttcaaatag ttttctgcgt gtgttaaaat atacacataa taatattatt   18780
ttaaccattt agaagtatac aatttagtag cattaaatat attcgcaatg gccaggcgt    18840
ggtggctcac gcctgtaatc ccatcacttt gggaggccga gacaggcgga tcacctgagg   18900
tagggagttc gagaccagcc tgaccaacat agagaaaccc cctctctact aaaaatacaa   18960
aattagtcga gcgtgggggt acatgcctgt aatcccagct actcaggagg ctcaggcagg   19020
agaattgctt gaacccggca ggtggaggtt gcagtgagca acctgcactc cagcctgggc   19080
aacaagagtg aaactctgtc tcaaaaaaaa aacaaaaaaa atattcacaa tgttgtataa   19140
ccatcacaac tatttgtgcc caaaatgttt ccattgtttc caacaaaaac tacccattaa   19200
ataataactc tggctgggcg tggtggctca cacctgtaat ctcagcactt tgtgagtcca   19260
```

```
aggcaggcgg atctcttaag cccaagagtt caagaccagc ctgggcaaca tagggaaacg   19320
ctatctctac aaaaagtgag actggtgtgg tggtgcacac ttgtagtccc agttactcag   19380
gaggctgagg tgggaggatc acctgagcct gggaggacaa ggctgcagtg ggctttgatc   19440
acaccactgc accccagcct gggtgacaga gtgagcccat ctcaaacaac aacaacaaaa   19500
aacacaataa ctccccatta aagtttattt tttaaaagtc aaaactacaa tactcatttt   19560
cacacctatc acaacgaaca attctgttat tcattcattg tattcatagt gattcatagt   19620
gttcacattt tcacatttct ctgatagtct cataaatgtc cttttttttt tttttgaga    19680
tggagtctcg ctctgttgcc caggctggag tgtagtggca tgatctcggc tcactgcaac   19740
ctccgcctcc ggggttcaag tgattctcct gccttagcct cccgagctcc caagtagctg   19800
agactaccag tgtgcgccac cacacctggc taatttttgt attttagta gagatggagt    19860
ttcaccacgt tggtcaggct ggcctggaac tcctgatctg ctaatttgcc tgccttggcc   19920
tcccaacatg ctgggattac aggtgtgagc cactgcacct ggcctgtcct ttaaaaaaaa   19980
aaaaaaaaa agataggctg gagtgcagtg gcacaatctc tgctcactgc aacctctgct   20040
tcccaggctc aagtgatcct ctcgtctcag cctcctgagt agctgcgatt ataggcacac   20100
accaccacac ctggctaatt taaaaaaaaa ttttttttt tttgtagaga tgggatttca   20160
ttatgtttca caggctggcc tcaaactctt gggctcaagc aatcctctct ccttggcctc   20220
ccaaagtgct ggaatattaa tgtctttaa aattggtttg ttcaaatcag aatctgaatt    20280
ttgtttgaaa tgtctattaa gttttaaaa tctgtaactg ttaccatcc tttacatgc     20340
cattaatttc ttgaatcaac tgggtctttg gccctgtgca attttcaca ttctggatta    20400
ggctggcagc atcttgtgg tgctgttcaa gatgtccttc tgttcccagg atctcctgta    20460
aactgggaat tagatcagat tcaggctcat tctggcaaga gatcctccct ggaggtgctg   20520
ggccacatct tgttgcatca cattgcaaaa ttgatggtcc catgtgtagt gacgcttaaa   20580
attaacgtgt ccaggtcctg atccctctgt tagaaactct gccaaccagc caggtgcaca   20640
gtgactcacg cctgtaatcc cagcactttg gaaggccgag acgggaggat ctcttgagcc   20700
taggagtgca aaaccagccc agataacaaa gtgagacact gtctctacga aaacttaaa    20760
aaattagcca gttattgtgg cacacacctg tggtcccagc tacttgggag gctgaagtgg   20820
gaggatcact tgagcctagg aggtcgaggc tgcagtgagc tgtgttcatg ccactgcact   20880
ccagcctggg caacagagga agaacgtatc aacctttcac ttgccttagc agagggatcc   20940
tttaaaacta gatcagatgg tatcactcct gttcatatca tagttaaaac aaagaccaaa   21000
gtttttgcca ggccaaggct tgccctcacc ccaagcccac cttccctcta ctcctgcccc   21060
caactgttcc agccacaaac aggcctcctc acagttcttc acatgcctgc cacacgcctg   21120
cctctgggcc tttgcactgg ctattccctc cacctggaat gctgttcccc acagggctca   21180
cttgctaatt tacttcagat ctcaatcata gcctgagaga agccttcccc catcatcctc   21240
tctaaaacag caccccacacc tctcactatc ccctgctttc ttttccttt tcttttttg    21300
ttttttgttt tttgttttgtt tgtttgtttt ttgagatgga gttttgctct gtcgcccagg   21360
ttggagtgca atgaagcgat cttggctcaa agcaacctcc tccattgggg ttcaagtgat   21420
tctcctgcct cagcctccca gtagctggga ttacaggtg tgtaccacca cacccagata    21480
attttgggtt tttaaaattt ttttttaag acggaatcct gctctgtcac ccaggctgta   21540
gtgcagtggc gtgatctcgg ctcacttcct gcaacctctg cctactgcat tcaagcaatt   21600
ctcctgcctc agcctcccga gtagctggga ctacaggtgc gcaccaccac accaagataa   21660
```

```
tttttgtatt tttagtagag acagggtttc accatgttgg ccaggctggt ctcaaactcg   21720
tgaccttgtg atccgcctgt ctcagcctcc caaagtgctg ggattacagg cgtgaaccac   21780
agtgcctgac taattttgt attttagta gagatgggtt tcaccatgtt ggccaggctg    21840
gtctcaagct cctgacctca ggtgatccgc ccacctcggc ctcccaaagt gctgggatta   21900
taggcatgag ccactgtgcc tggcccttgc tttattttc ttcactgcac atcttgcaac    21960
atgataagta tttatgtgag tgttatttct cttcccttt gaatgaaac tccagtagga     22020 tgtggacttg tcttgctcat gtagaaacc ccaccccagc accacctgtc catcttttct    22080
tttctttttt tttagagat agggtctcac tctgtcatcc agactggaat gcattggcac    22140
catcatagct tgttgcagcc tcaaactcct gggctcaagc gatcctcctg cctcagtctc   22200
cccaagtagc caagactatg tgtgcaagaa cacctggcta attaaaaaaa ttttttggaa   22260
gacacagggt ctggctatgt tgccaggctg gtcttaaacc cctagcctca gcaaccctc    22320 caacctgggc ctcctaaagt gtgggattat aggtgcgacc cactgcaccc agccccgaat   22380 cttttctct ttttgggg gggagggggg atggtctctg ctgtcaccca ggctggagtg      22440
cagtggcata atcctggctc actgcaacct ccacctccca ggttcaagag attatcctgc   22500
ctcagcctcc caagtaactg ggactacagg tgcacaccac catgcctggc taattttttt   22560
tgtattttta gtagagatgg ggttttaaaa tgttggcaag gctagtctcg cgctcctgac   22620
ctcaaatgat ccacccaccc gggcctccca aagtgctggg attacagatg tgagccacca   22680
agcccggccc ccgtctcatt tttaaaatg catttcaaag taaattgcag gcacatagca    22740
ggtgctcagc aaatagttca tatagttcat gagtgaatga attcacaggt tcaagtaggc   22800
catcaaccag ctgggtccac tgagccctag ggtgggcagg ggcccccaa catatctaaa    22860 caagtgaaca gatctttgca catatttgca cccctcaaaa atgccacaat aggccgagcg   22920
tggtggctca cacctgtaat cccagaactt gggaggccg aggcaggcac atcacctgag    22980
gtcaggagtt tgagaccagc ctggccaaca tggtgaaacc ccatttctac tatgaataca   23040
aaaattagcc aggcattacg gtagttcctg cagtcccagc tactcaggag gctgaggcag   23100
gagaatctct tgtacctggg agttggagtt tgcagtgagc ccggattgcg ccactgcact   23160
ccagcctggg tgacagcgag agaccatctc cccaaccaaa aagaaaaaaa gagatcgggc   23220
tgggtgcagt ggatcacaca gtgggtcacg cagtgggtca cgcctataat cccatacttt   23280
aggaggccca ggtggaatga ttggccaggc ttacctcgtg atccactcgc ctcggcctcc   23340
caaagtgctg ggattacagg cttgagcagc cacgtctggc ccctaaaaca gtttttaaa    23400 attagccagg tgtgcttgca cacatagtct ggctactcg gggaggctga ggcaggaggg    23460
tcacataagc ccaggagttt gaggcttcag caagctatga tggcgccact gcattccagt   23520
ctggatgaca gagcaagaag acagaatgct tgaactggga agtggagttt gcagtctgct   23580
aagatacagc caccgcactc cagcctgggc gacagagtga gactctgtct caagaaaaaa   23640
aaaatgccac aataaggaat tgtccccttt atggcaggcc ttttacaggg cggtgaagat   23700
gcagcagttc ccaaaatata cccagtccct tcccccgcag agcccacagg ccagtgggag   23760
gagacagatg tgagacacat aatcatgcca ataaatatat aatgacaacc caggcaaagt   23820
gttgccaagg aaagggacag catgttggga gtgaacaata tgaggaccta gattgggctg   23880
ggggggccag gcagtgatgc gatggagaag ggatgataga gttggggaca aagtgctgca   23940
ggaggttgct ccaagtcctc tgaggggggct ctttgggtga gaaagcgaga gaagcctggg   24000
gaggcgaggg gagggtcaca gaaacataag gagtttaggg ttctgctgaa aggtttgggg   24060
```

```
cagaggtggg aaagggtttg gtttgagatt gggaagaagc cttctgactg ttgagtggga   24120
gacaggttgg aaggagcaac agaagccagc agcccatggc cgggcacagt gacccacgcc   24180
tgtaatccca gccctttggg aggccgaggc gggcagatca cgagttcagg agttccagac   24240
cagcctggcc aacatggtga aacccgtct  ctaccaaaaa tacaaaaatt aacctggcat   24300
ggtggtgcac acctgtaatc ccagcaactc aggaagctga ggtgggagga tcacttgaac   24360
ccaggagatg gaggttgcag tgagccgaga tcgagccatt gcactccagc ctgggcaaca   24420
aagcaagact gggtctcaaa aaaaaaaaaa aaaaaaaaga cacagcccag ggagacaacg   24480
gtgaagggcc ctaagtggcc agtgacaagg agctgggagc ttgccctgag ggcagcagga   24540
ggccatgggc aagcagagaa gggacagggt aggatttgac tttcagaaac agtcctctgg   24600
ttgctaaatg ggagaaagga gtgacagtag aggcaggaga aggcaggatc agacgggggt   24660
gctgggaagg ggcaggtaga agagacatca ggaggccaaa cagataggac tttatgatgc   24720
accgtaggta taccagtacc caaacacagg tggccaagag cagagggata gacgcccagc   24780
ctcctcctca cagacatcca ggcatgcaga gccctccacg tgccaaacac acagggccga   24840
ggaatggaag tgcagcagag ccgatacgca ggcagcagat ctgcaataac caggacacac   24900
agtcccacca aaggagaga  gcagtggaat gatcagggct cactgcagcc tcgatctctt   24960
ggactcaagc gttcctctca ctccagcctc cctagtagct gggaccacag gcacacgcca   25020
tgatacctgg ttaagtttta atttttaaac ttcttgtaga gatgggggtc tcagtgcatt   25080
gaccagtctg gtctcgaact cctgggctca agcgatcctc ccaccttggc ctcccaaagt   25140
gctgggatta caggagtgag ttactgtgcc cggccaacaa ctattcttat tcccatttta   25200
cagatggaca aactgaggct caggaggcca gtcacttgcc tgtagcccac agttagtggt   25260
agcactggga ttccaacttg ggtccccttc atgtcgcctg tatttggtgt cccatttagg   25320
cgtccatgca ggttttggcg tgtctgaaga tctgtgtctc cccaagtaag tgtcccccat   25380
ggatgcccac ccagccgtgt cctcctgtct ctgaggtttc tccaggaatc gagctcctgg   25440
cctggcttgt ctgagtgtgt ctgtgggcca gtagcatgcc cctgcccgtc tgggtccctc   25500
tgcgtgtctc tgcttgtcct agcctgtgtg tgtcagtgac gtctaagagt gtgtgtgcgt   25560
gcgtgcgtgc gtgcgtgtgt gtgtgtgtgt gtgtgtcctt gtccgaggag ccgagagagt   25620
gagggggaat gaagggccaa ggaggcctgg ctggggctgg gctgggggtg gaggcgggga   25680 gagggcgtc  acggcctgag ctgagagggg agtggagttc tggaggaatg tttaccagac   25740
acagagccca gagggacagc gcccagagcc cggatagaga gacacggcct cactggctca   25800
ggacaggggg cacagccacc agggtcccct tcccctcct  cagctccctc cctggcccct   25860
ttaagaaaga gctgatcctc tcctctcttg agttaacccc tgattgtcca ggtgcccct   25920 gggctctggc cctggtgggc ggaggcaaag ggggagccag gggcggagaa agggttgccc   25980
aagtctggga gtgagggaag gaggcagggg tgctgagaag cggctgctg  ggcagagccg   26040 gtggcaaggg cctcccctgc cgctgtgcca ggcaggcagt gccaaatccg gggagcctgg   26100
agctgggggg agggccgggg acagcccggc cctgcccct  ccccgctgg  gagcccaaca   26160 acttctgagg aaagtttggc acccatggcg tggcggtgcc ccaggatggg cagggtcccg   26220
ctggcctggt gcttggcgct gtgcggctgg gcgtgcatgg ccccaggggg tgagtgatgg   26280
gggctccttg gggcagggat cccctcggag gggctggggc aggggtagga ggtgggggat   26340
gatggcaggt gtggggggcc tgggctggct taggagtttt ccttgggacc acagaaaagg   26400
gacttcaagg gagggagaca cagactcaga gacaccaagt gcggcagagg gagagaaaga   26460
```

```
ctgagagagg aactgaaggg caggggggac agaagagagg acccggagag acagacagac   26520
aaggagaagc tgagggcagg ggtggggct ggacctgaga agggggccat ggggagaggg    26580
gctgagctga gggtcgccag gaaggaagaa atctttccga aggggcaccg agtcaggcag   26640
tgggatgagg agggctctgg agccctgggg gaaaacgctt ctccctgcca acaccacccc   26700
cctgacccgc cacttgtccc taccccacca gtccactcca tctctgggga ggaggctctc   26760
actttgtctc tctgtctctg cctccagctc tgctatctct gtgggtctct gtttctctct   26820
ctttcacagt ctctgccttt atctctccct gctctctgag tctctctctc tcttctcagc   26880
ctccctctgt gactgtatcc cccctccgcc cccacctttt cttctctctt gagggctgtt   26940 tcttcattt ttctgtcttg ccttgtatct gtgctcctct ctgtctcatc tccctgcct    27000 ttctctggct tctccctccg ccaccaccct tatctccccc caccaccacc cttatctctc   27060
tcccccaacc cctgattctt cccctccatc caccagcacc agcgcgacct gttaagtctc   27120
tagagaccta agagaggacg gaggggcag gggctggccc tgccaggcag tgcagggcgt    27180
gggaggctgc cagatcccga gcctccttcc cgacgggatg gacgctagat cccagtccct   27240
tgggagggct cccgtcctcc tctcagagcc tccgccctcc accccactct gaggtcactc   27300
tgcaactatg tcggcctaag ggcctggcgg ggtcctggcc gccggtgggc aggcaaggac   27360
agggtggaac tgagggccgg aaggagctgg ggggttccta agctaactct tcccatctcc   27420
cctccaggca cgcaggctga agaaagtccc ttcgtgggca acccagggaa tatcacaggt   27480
gcccggggac tcacgggcac ccttcggtgt cagctccagg ttcagggaga gccccccgag   27540
gtacattggc ttcgggatgg acagatcctg gagctcgcgg acagcaccca gacccaggtg   27600
cccctgggtg aggatgaaca ggatgactgg atagtggtca gccagctcag gtgtgtggcc   27660
acatccccga atcccactcc cacctccgtc acacagaggg cagaaagccc acctgggtgg   27720 gaacccagt ttgaccactt gtcagccgtg cggctttgag catgtgatgg aacctctagg    27780
tttcgttttc ctcttctgca aaatgagtta ataataggac atacttcgtg gttgtcatga   27840
gcttccagac tggacaccct cttttccgttc tgacagaccc cctcccagtg tccagctctg   27900
accctgaacc tctctgtctc tcctcttgcc ctgtcagaat cacctccctg cagctttccg   27960
acacgggaca gtaccagtgt ttggtgtttc tgggacatca gaccttcgtg tcccagcctg   28020
gctatgttgg gctggagggt gagctctggg gtcaggggtc ctgaggggtc agaggacatg   28080 tgcgctcat aggttgtggg aagtcaggaa tcctgagggg tcaaggtcaa agggtgctgg    28140
aggattcagg atgaacctag cgtcatacag cctaagaatg tcagagtttt gggtggtcaa   28200
gaagctggga gtccatataa gttatggtgc caaggctggg ggattatatg ttctgggtga   28260
aaagacttct tggggtagt tggatgtcct aggcatcaga caccatcagg tcacaggagg    28320
ccattctggt cttcagataa ggcgtcagag gcacgcaacg taccctgtc cccacgaccc    28380 cagcggtctc tttttctca tccatagaat gagatgagga tgagctgtca gacattctgg    28440
aagagagaca tgaggagctc agctatcgtg gggggtctga catgggagga atcagatatt   28500
ggggtcacgt gtgtgttggg tatggctcag gtgccctcgg ggatcagata aggcaagtca   28560
atgaccctgc agggtgggtt tgctgcccaa agcctacagc atcctagtgg tgagtcaggc   28620 atcttgggc ctcagaggga ccccagcctc taccactgcc caccccgcta ggcttgcctt    28680
acttcctgga ggagcccgaa gacaggactg tggccgccaa caccccttc aacctgagct    28740 gccaagctca gggaccccca gagcccgtgg acctactctg gctccaggat gctgtccccc   28800
tggccacggc tccaggtcac ggccccccagc gcagcctgca tgttccaggt gagtccgggg   28860
```

```
atgtgggtca gctccgaata gggggccggg cagggctgaa gtcaggagca agggaacatt  28920
gctacctctg cgtgagtgtc tgactgtcct tctgtccctc actgtctgtc tctctcgttt  28980
ctccctctga gtctgtctct gcctctctgt ctctacctat cttatttctc tccgtatgcc  29040
tttttctgtc tctttctgtc tcttggtgtg tgtgtctttc tgtctctctt tgtatgtgtc  29100
tctctctctg tctctctgct tctctctccc tccattcacc ccggcctctc tctgaataga  29160
attctttgtc ctgggtttcc tctgagctgt tccatggctc gagtgcgtgt gggcctggtg  29220
cccctttgtc agcccttgac ccaagcaggg caccggaatc aaccgtgccc tcctctcctc  29280
cgcctccctc cacaaccggc ccacctcctg ccctaacaag cctgctggcc tcagtcaaag  29340
ggaggatgtc cagcccggtc cccactgggg agatggaacc caaagaagag agagcaggaa  29400
gaaagtagga gacagaggct gggcgtggtg gctcacgcct gtaatcccag cactttggga  29460
ggctgaggcg gcggatcac gaggtcagga gatcaagacc atcctggcta acacggtgaa  29520
accccatctc tactaaaaat acaaaaaatt agccgggcgt ggtggcgggc gcctgtagtc  29580
ccagctactc gggaggctga ggcaggagaa tggcaggaac ccgagaggcg gagcttgcag  29640
tgagccgaga ttgcgccact gcactccagc ctgggcgaca gggcgagact ccatctcaaa  29700
agaaaaaaaa aaaaaagaa agtgggagac agagagagat agaatgacat acactggaag  29760
ggacaggcca cagtgaccca agatgaacat agacaggaca gagaggccgg gcatggtggc  29820
tcacgcctgt aatcccagca cttgggagg ctgaggcagg tggatcactt gaggctggga  29880
gttcgagacc agcctggcca acatgacaaa actccatctt taccaaaaat acaaaaatta  29940
gccaggcgtg gtgacgggca tctgtagtcc cagctacttg ggaggctgag gcaggagaat  30000
cgcttgaacc cggagatgg aggttgcagt gagccgagat cacaccactg cactccagcc  30060
tgggtgacag agcaagactc tgtctcaaaa cgaaaaacaa aacaaaatga agacaggac  30120
agggaagttg gagtgacaga aaccctctcc ttcttgggga ccattccctt ctgcaccatg  30180
cagacgagga aggaccgagc tcagggttat gcagtggtca ggggcatcac tgggggaccc  30240
tggattcagg gggttctccc tactgaagga ggaaagacag aggagcagat ggcagaggct  30300
ctgtaaagga aggaggctgc agcctggagg gcatcagctt cccgcactcc caacctgctg  30360
cctctctctg ctggaatgag gaggggcctt ctgactgggg gtctccaggg tggagggagg  30420
agctcacatt ctcagcattc ctgggaccct gagttgcaag gaagacctgg tgagcatgct  30480
gaccccagag gagtgactca ggcccatggc tcgagtggct gagtagggac cagggttggg  30540
gatcgggcat gagtcagcct ggcaggtccc atgagaaggg gaggggaggg agagaaatgg  30600
gggctgcaca ggtgtgagga tctgtgcatg tctgtgtggt ggtggtgggg tgtctggata  30660
tctgtgtgtt ctggatctga gtgttagtgt atccgtcagc acaacctctg tgtgagggtg  30720
tgccttggcg agggtggact tctgtggatg tcccatgtgt ggtgtgtgtg tgtgtgtgtg  30780
tgactaaata tatttccttc agcttggatt ctgtcccaat atgtgtttgg atctttatag  30840
catgtctctc tctctacgtt tcttagggt tgcccgtgtg tgggtgtctg tgtgtgtgcg  30900
catgatggag tgtaccagtg tcagcctgtg tctgtccctc ttttttgtgt ttgtgtgttc  30960
acagctggga ctcactgtat gaaagtaaag tgtgcctgga gggtagtggg tttgggcta  31020
tggtgcacac ctctctgtat ggaggtggta gtgtcagccc acaggtgtgc agctatgggt  31080
gtgagagtgt cctagtgaga gcttgtgttc ccttgcagaa tcagaacgtg tccatggata  31140
acttgtgttt cttaccacct ttttttcccc ttatttttttt tcaagataag ctcccgctgt  31200
gtaacccagg ctggagtgca gtactgtgat catggctcac tgtagcctcc acctcctggg  31260
```

```
ctcaagcaat cctcctacct cagcaccctc ccacccctca agcagctggg actataggca   31320
tgtgccacca tacccagata gttttttgaat tttttggtag agacagagtc tcgccatgtt   31380
gcccaggctg ctcttgaact cctggcctca agtgatcctc ccgcctcggc ctcccaaagt   31440
gttgggattt acaggcgtga gccactgctc tcaaccctca gcctcttacc agctttctgt   31500
gtgtgtccat agatgtctct gtggcgtgtg tgtatatgtc acagggtaag catgttggtg   31560
tatgactgta gtcacagacc tgtgtgtgtg tgtgtgtgtg taacagcacc ctctgcttct   31620
ctctggtctc cctgtgtgtg cactggcccc tgctgcctct gagtacatga cctaaggatg   31680
cttaccagtc agcgtataga tgtgtctctg tgtcaatcta tgtgtccatg gcagtgtctc   31740
catccttgtg tgtctgcatc aggcctgcgc atctacgaaa ctgtgttttt ttgttttttg   31800
gggtttttgt tttgagacgg agtctcactc tgtcacccaa gctggagtgc agtggcacga   31860
tcttggctta ctgtaacttc cgcctccggg gttcaaggga ttctcctgcc tcagcctcct   31920
gaggagctgc gattacaggc acgcctggct tattttttgta ttttttagtaa agacagggtt   31980 tcatgacagg tttgtcatgt tggccaggct ggtctcaaac tcctgacctc aagtgatcca   32040
ccggcctcgg cctcccaaag tactgggatt acaggcgtga gccaccgcac ccagcgcaaa   32100
tgtgtttttg tatcagtctg tgtctgggtg aacatgaaac ctgggcgcat ccagctccat   32160
cttatggcgt agatggaggc ttggctgtga ggtgtacgcg tcggtgtgtc tgtgtctgag   32220
caggtcaaaa tgacccttca ttgtgtcctg gtgtgtatct atctgtccac ctcaactcca   32280
tgtacgctgt tacgtggtgt gtgtctctga atatacaggg acatttaagt ttctgtgtgt   32340
gttggcatca gcctagatgt acattgcgtc gctaggtgtt tgtaatcaat gtgtacatgt   32400
gtgactgtgt gtttatgtgt ttgtcccacg ttggcttgta tgcatacatg tctctttatg   32460
aatgtacatc agtgtcagcc cgcgtgtata tgtgtgagtc acggtgtttt tgtgtcactg   32520
tgtttgtgac atcagccctt gcatatctgt gtgccgttaa cttaccaagc gctgcgtctt   32580
ctgtgctaat aacagcccct gtgtgtttaa gtgtgattca ttgtgagtgt gtgtgtgggg   32640
gggtttgctg tgtgaaggaa tttcgtccgt ttgtgtgcgt ctgtccctct atctgactca   32700
gggcgtgccc ctcctccttc catccctctc attctctgga aaagctgggg cggagagcag   32760
gggttgtggg gggatggtca ggacatctgg aaagcacatc tggaatcggc ctgctcctgt   32820
cgtcttgcgg taaagcaaga accttctgga ggggaagggg tcccagttcc tcctgtcccc   32880
ttcactcaag gtgcggccgt tggggcctgg aagggggat cccggctctg ctccgcgcc   32940 cccgaagccg gccggaagcg ctgggtggg gaggtgcccc cggtgactca cgcggggca   33000 ggaatgctgc ggtcggaacg ggacccggct ccagaaccca cctccagccc cagggcttct   33060
ccggccggcg cgccagctc ccgcgcgctg accctggcgg ggccccacgt gccaggtggc   33120
tggacccgac ccaggctccc cgccccact cgggccgccc gcccgggact gtactgtttc   33180
tcctccgggc ggcgcggggg ctgcgggcgc gggccttca gggcgcggag gctgcggag   33240 cgggcacctg accttgtctg ggaacggcca cctaggaagc cgcgactgag gagctcccct   33300 accctccct ttccggcctc tgcagacttt gcaccattcc actccctccg ctgacgagag   33360
aaaggaaact ttgtgtctgc ggatggagag cctcccttgc caacgcggtg ggaacagagg   33420
cgtacacgca cggagcaaac acgagagaca cgtacacaga tactcaacac atgcacgtac   33480
acaccatcca cagatacacg caggtcaca aacataccag ctcagaaaca caaacacaga   33540
tgcacaagca cacgcgtaaa caacacgcag aactgcagtc gcacttacaa gacttggtcc   33600
cagggccggg caccgagtgg ctctgcctgc gatccagcac tttgggaggc cgaggcggga   33660
```

```
ggatcgcttg gggccagaag tttgagagca gcctgggcaa cgtggtgaga ctctcctctt   33720
ctctacaaaa aaaaattgaa aagttagcca agtgtggtgg ccgcctgtag tcccagctgc   33780
ttgggaggat gagacaggag gatcgcttga gccctggagg tcaaggcagc agtgagccgt   33840
gattgtgcca ctgtactgca gcctgggaga tagagcaaga acctgtctca aaaacaaaa    33900 cgaaaaactt ggtccttctt acatcctagc gcagacattg tgtgtgtgtg ctgggggagg   33960
ggggtgtcta tgtttctacg tgtatctgtg ttggggggatt cccccttattc accaggatac  34020 gttctctaag agcccccaca aaagcctgaa acaatgaata atactaaacc ctgtatatac   34080
tacacataac tttctttttc cttcacaatt tcgcagatag attgttttct tactatagat   34140
cttagcaacc tcagtacata tatatatgat tatcttttc taagtggaga atttttcacct  34200 tttcacttaa aaggaagcac tttaaggctt ctctttggcc tatccgaatt gcagccatca   34260
ctattttgca ccctggggcc ttttttttt tttttttagac agagtctctc tctgtcgccc    34320
aggctggagt gcagtgtggc gaccttggct cactgcaacc tccgcagccc gggttctagc   34380
agttatcgtg cctcagcctc ccgagtagct gggattacag gcacgcgcca ccatgcccgg   34440
ctgatttttt tgtattttta gtagagacgg ggtttcact gtgttgccca ggcttgtctt     34500
aaactcctaa tctcaagtga tccacccgcc tcggcctccc aaagtgctgg gattacagat   34560
gtgagccata gcacccggcc aggcgattat ttagataaat aagagtttct tgaactctgc   34620
acttgagcac tgcagtacca ggacagttga tctgatagct aagtgactta cagacaggta   34680
tcagatacag cactgagatg ctggacaaag gggggattca cgttctaggc caaccagagt   34740
gggatggcat gaggtttcat cacagtactc agaacggcat gcaatttaaa acttaggagt   34800
tatatctgga attttccatt gaaatatttt tagaccaagt gtaactgaaa cctcaaaaag   34860
tgaaacctcg gataaagggg gactgatgta cgttgtatag cggtttgtgt tgggtatctc   34920
tgtgtgcttg caggtctgtg tctctcgtgt ttgtctctgt aattgtacgt gcttctgtgt    34980
gtgcacgctg gtcataccaa caccaacacc accacgttag ggagggaagg caatccacct   35040
tcactcgaaa acagttactc aaggccgggc acggtggctc acacctgtga tcccagcact   35100
ttgggaggct gagatgggca gatcacttga ggtcaggagt tcgagaccag cctggccaac   35160
atggtgaaac cctatctcta ctaaaaatta caaaaattag ccgggcatgg tggcgcgctc   35220
ctgtaatccc agctactcag aaggctgagg caggagaatg gcttgaaccc aggaggcaga   35280
ggttgcagtg agccaagatc atgccactgc actttagcct gggcaacaga gcaagactct   35340 caaaaacaa aagaaaaaaa cagtcaagac acaatacgtg aactccccta tggaattaca   35400
catgctcata tttctacacc tatgcccagg aatgctcata agtacacagc tgaacacaat   35460
ttcactcact cattcaacaa gcatttatgg cacacctatt gtgtgccagg ccatcctgac   35520
acagcagggg acgaaacaga cacaaccccct gccctcctag agctgacatt ctagtgggag   35580
aaactgacaa tggcaaggt acttgggtaa caggtaaagt atgttgggtg atgagaagaa   35640
ccaaagagga aaagtaaagc gggaagggga tagatttgga gaggaagctc caattagctc   35700 caatttatt gtatttttc tttcttctt tgtcttttct tttctttctt tttttttga       35760 gacagagttt cactcttgtt gcccaggctg gagtgcaatg gcgtgatctc agctcactgc   35820
agcctctgcc tcccgggttc aagctattct cctgcctcag cctcctgagt agctgggatt   35880
aaaggggcct gccactatgc ccagctaatt ttttgtattt ttagtagaga cgaggtttca   35940
ctatgttggc caggctggtc tcgaacttcg gacctcaggt gatccaccca cctcggcctc   36000
ctaaggctgg gattacgggc atgaaccacc gtgcccagcc tttatttttc attttattat   36060
```

-continued

```
ttttagtttt tttgagacag ggtctcactc tgtcacccag gttggagtgc agtggtgtga    36120
tcacagctca ctgcagcctc cacctccccg ggcacaggta gtcctcccac ctcagcctcc    36180
caagtagctg ggactacagg tgtgcaccac cacacccagc taattttcct ctttttttgta   36240 gagatggggt ctcaccacgt tgcccaggct ggtctctaac tcctggcctc aagcgatcct    36300
cctgactcag cctcccaaag tgctgggatt acagtcatga gtcactatgc ctggccaagc    36360
tccaatatta acagggtggc caggcctagc ggactgagag tgttgttga ggaacaaaaa     36420 tgaaagaaga gggtgcgagt catgtagaca tttgtggaag actgttttga gcacagggaa    36480
cagtgcacag ttcttggagt ggaaacatgc ttcatgtatg tgttccagag acactggagg    36540
ccagtgtggc cggagaagag cgtgtgacag ggagagtggg agaggggttg gtaggaggcg    36600
agcttagaga tgaacagaca tgtctccatt gatgtacagc catgggccag tttccctaag    36660
tgtgtctagc aggtgtgtgt gctcatactt tgtgtccttgt gagttagtga gggtgcctgt   36720
gtttgtgcat gtgagtgtgt gcatgttttgt gtgtctcctt tgtgtgtgtgt gtctgtgtat  36780 gcttttgtgt gtctatgtgt gagtatgtat atatgtgtct atgtccatat atatgagcac   36840
gtgtatttct gtgtgtgtct atatatgtgt atatgagtat gtgagtatct aggtgtacga    36900
atctgtgtgt gtgagacaca gtgtgtgtgt gtggctgtgt ctgtttctgt gtctgtgtct    36960
gtgtctgtgt gtgagcatat gtgtttatat gtgtgtgtat gagtatgtgt ctctggggtg    37020
taagaatgtg tgtgtgtgcc tgtgtgtgac tgtgtgtgag tctgtgtgag catgtgtgtg    37080
tatgagtatg tatctctctc tggggtgtaa gaatgtgtgt gtgtgtgtgt atgcgcctgt    37140
gcctgtgtgt gtgtctgagc atatgtgtct atgtgtgtgt atgagtgtgt gtctctatct    37200
ggggtgtaag agtgagtgtg cctgtgactg tgtgtggttg tgtgtcttca tgtgtgtttg    37260
tgtatgtgtg tttttgtgtg tgtatgcctg tgcctgtgtg tggctgtgtg tctttgtgtg    37320
tgtctgtgtc tgtgtgtctg tgtgtatgag tgtgtgtgcc tgtgcctgtg tgtggctgtg    37380
tgtgtctttg tgtgtttctg tgtgagtatg tgtgtctatg tgtgtgtatg agtgtgtctg    37440
tctctggggt gtaagaatgt gtgtgtgaga cagtgtgtgt gcctgtgcct gtgcctgtgt    37500
gtgtctgtgt gtgtctgtac tatgtgtgtc tgtgtggcgg gaggttaggg ctgaaaccaa    37560
gccatccttg tgtttgggga tggaggctgt gttcctaact cattgccctc aactctgcta    37620
accctccctt caggcaagtg cctgtgtggg ctgcactgcc cctggtcagg caggccatgg    37680
taggagtggc ccggcatggc cccggagccc ttcctgcccc tctctgatat tggacccttc    37740
cctcatatga ctcccctaggg ctgaacaaga catcctcttt ctcctgcgaa gcccataacg    37800 ccaaggggt caccacatcc cgcacagcca ccatcacagg tgacagagtt gggaggtggg     37860
gagctgggcg tcagagggtg gggtttgggt ccggggtcag agtgggggca gagagcaggg    37920
tagggagctt tgagcaaagg ctccccaggg tcaatctctc ccgtttgtcc acagtgctcc    37980
cccagcagcc ccgtaacctc cacctggtct cccgccaacc cacggagctg gaggtggctt    38040
ggactccagg cctgagcggc atctacccccc tgacccactg caccctgcag gtgagactcc    38100
caaacttggt tcatttcagt ctcaggcctc cttccaccca catccacaac ccccatcctc     38160
tccctgggaa cccaccactt ctcggccact gttgagaagc agtagagcct gggggggttaa    38220 gccagatgtc ctgggttcga atcctagctc caccaccttc tggctgtgtg accttgggta    38280
ggtggcttaa tctgtccggg gctcagctct cttgtctaca aaatggacat aatggtagtg    38340
cctacctggt atgcttagtg tgaaaattca atgagtgaat gcaaattacc aacttaaaat    38400
ggtatataga acataggaaa caaatttaac aaaattggcc aggcgcggtg gctcacacct    38460
```

```
gtaatcccag cactttggga ggccgaggtg ggcggatcac ttgaggtcag gagttcgaga   38520
ccagcctggc caacatagtg aaaccacatt tctactaaaa atacaaaaat taactgggcc   38580
tggtgggacg cacttgtagt cccagctact ggggaggctg aggcaggaga attgcttgaa   38640
cctgggaggc ggaggttgca gtgagccaag atcgtgccac tgctctccag cctgggtgac   38700
agagcgagac tctgtctcaa aaaaaaaaa gaaacaacaa caaaaaaat ttaacaaaat     38760 gaaaatgatc agctgtttta attattttca gtattagtga tgttaactct agccagagtg   38820
ggagccctga dacagcagag tctggagcca tttctgtcac cactggatac ccagaaccct   38880
ccacttctcc catcccagcc ctggccactc tgtgtggtca ctgtctgggg atgggtctgt   38940
cccctactgg aatgtgagct ctgacagggc agggctggag ctgtcccagt caccactggc   39000
tcctcattct tgcccagcac aggaccagac atagagtagg gaatattcgc tagaaggata   39060
tattacaacc cagatgagct agcccagcc tctgccctca agttgctcct agaataagaa    39120
aaccaaaacc aggccaggtg tggtggctta cacctgtaac cccagcactt tgggaggcca   39180
aggctggtgg atcacctgag gtcaggagtt cgagaccagc ctggctaaca tggtgaaacc   39240
ccatttctac taaaaataca aaaattagc cgggtgtggt ggcacacacc tgtaatccca    39300
gctactcagg aggctgaggc aggagaatcc cttgaaccct ggaggcagag gttgcagtga   39360
gccgagatcg tgccattgca ctccagcttg ggtaacacga gcgaacttcc gtctcaagaa   39420
aaaaaaaaaa agaaagaaag aaagaagaaa accaaaacca aaacaaaact cacagatctg   39480
taaatataag gcctaattct ggtctgaagt tctctgagat tagaaagttg gagatggggg   39540
gtggacagtg cctatgatgg tagatgacag taatgaagaa tgaccaattt ctactgagtg   39600
tccgctgtgc accgggtctt gcattaacgc acacctgctc gtgtgtttgt gaaggagggt   39660
ctatggatac acccattttc cagatgaaga aactaaggct cagagtggtt aaccagattg   39720
tccaaggtca catcaaaccc atgtcatgct cctaacctcc ttagaaactg tttttttgttt  39780 tttcttttct tttttttttg agacagagtc tcgctctgtt acccagactg gagtgctgtg   39840
gcgtgatcac ggcttattgc aacctccgcc tcctaggttc aagcaattct cttgcctcag   39900
cctcctgagt agctggtatt acaggcgccc accaccacgc ccagctaatt tttgtatttt   39960
tagtagagac agggtttcac catgttggtc aggctggtct cgaactcttg acctcaagtg   40020
acccgcccac ctcggcctcc caaagtgctg ggattacagg cgtgaggcac cgcgctgggc   40080
cctgagaaaa tgtttagagt cagtgcttga ttaaacagga attgtcttat acttacatgc   40140
tctgagcaca accccatctg cttgtcgttt taaacctaga aaatagtggc tattggctgg   40200
gcatgatagc tcacgcctgt aatcccagca cttcgggggg ctgaggcagg tctgtacaaa   40260
aaattcaaaa aaattagctc agtgtggtgg cacacacctg tagtcccaga tactcggag    40320 gctgaagtgg gacaatcacc tgagcctggc agtcaaggct acagtgaggc aggattgaac   40380
ctctgctctc cagcttgggt gacagagtaa gactctgtct gagaaaaaaa aaaacaaaaa   40440
acagtggcta ttaatcttcc cgttttcaag gtgaggaact gaggcccaga gaggggcccc   40500
ctctctgggc ctcagttcct cccatcctcc tccctcccc ggggctagaa agccgaagct    40560
gagattcaat cccagaggcc agctggattt gggagacctc aaatgccagg tcaggcataa   40620
gttgcactct acccacatca ccaagtgtcc ccaggaaagc agaagtgtgt cctcttccct   40680
ttccaggtct cacttcctgc tgcacatggg ctagggctga agagttccag tgggagggtc   40740
acagccgtcc cagggaaaag agaagtggga gcaggcatgg ggagaccaac tgtctgtacc   40800
catctcctct ctgtcctggt agaggttcct cttcctgtct gtcactgcag gtcagagagc   40860
```

```
aggcatggtg acagcctcac cccctcctcg tacccaccat ctgccccac tcctccccag    40920 gtctcatggt ggtgtcatct ccctccatgg gggctgtgtg actttgggca agttgctgaa    40980
cctctctggg ccttggcttc cctgtctgta aatggggat gagaaaagaa attgacccca     41040
tagggtggta gtgcgaagtc aatgagttca tccagtaatg tgcttgacag agagcttggt    41100
acatatttgg cactcaagaa atatttgcta ggccgggtgc catggctcac acctgtaata    41160
ctagaccttt ggaggccga ggcaggtgga tcgcttgagc ccaggagttt gagacctgcc    41220
tggccaacat ggtgaaacgc catctctcca ataattaaa aaattaggtg gggctgtcat    41280
tacaccactg cactccagct tgtgtgacag agtgagaccc tgcctaaaaa aaagaaaaaa    41340 gaaaagaaa gaaagaaaga aaacaaacgt tagctgttga taattataat gtgcaaagca    41400
gtttatatgc atcatgtcat taaaccttat accctgacaa gtaagaactg tgatgcccat    41460
tttccagaga cagaaactga gactcagaga agttaagaca ctcactctag gtcacacagc    41520
aaacaacatc caacacagga cttagatcca aggaatctgg cttagagcc cacaccctgt     41580 ggcagtaaac tccttcctga catactgtgt ggctgtatgg ctggagtctc cagggtgaag    41640
gggaagccct tggctgcacc attcctgagg cgtggctgtg aattgtgtgg ttatgggggt    41700
tttgtggttc catgtggcag ggctatacag atgtgtacac cagtggtggc ccctccact    41760 ctgagtgtgc cattcctcgg gcggaatagg tatgggaacc tgtgccgcta tgcagagctt    41820
gacacttgtt gccaggaaac acataaaa taataagtga caggccgggc acggtggctc      41880
gtgcctgtga tcccagcact ttgggaggct gagcgggcag atcacctgag gtagggagtt    41940
tgagaccagc ctgaccaaca tggagtaacc ctgtctctac taaaaataca gaattagccg    42000
ggtgtggtgg tgcatgcctg taatcctagc tactcaggag gttgaggcaa gagaatcact    42060
tgaacctggg aggcggaggt tgcagtgagc cgagatcatg ccattgtact ccagcctggg    42120
caacaagagc gaaactccat ctcaaataaa taaataaata aatagataga tagatagata    42180
gatagataga tagatagata gataataaat gacagtatgc acaagcagtc ttctaaatgc    42240
ttacatgccc caattcagtc aaccctgtga agtggggagc cactgtcatc ccattttaca    42300
ggtgagaaga ctgaggcaca cagctaggga atgatagagc ctggatttga gccccagatc    42360
cagcatccgt gctcctcagc actaggctaa actgcctctg tgcacagaca agaggtattg    42420
ttaccattac tgatattctt accgccagta gagcaaagac tctggggaca ggatggggtt    42480
taggtcccag cttcatcagt gacaaactga tgaccttgaa caagtgattc cgtctctctg    42540
ggcctcagtg ttgtcatctg tacagtggga ataagcataa tgcttaccac aggacaacag    42600
gattgatgtg agggccaaat gaattcagat ttgtcaaggg ctaagaaagg cactcagtac    42660
atgttggacg tgttttatct ttttttatta agataatata taacatagtc aggtgaggtg    42720
gctcacgcct gtaatcccag cactttggga ggccgaggca ggtggattac ctgaggtcag    42780
gagtttgaga ccagcctggg caacatggtg aaacccttc tctacacaga ataaaaaaaa     42840
agccgggtgt ggtagctcac acctgtaatc ccagcacttt gggaggccga gggggcgga    42900 tcacttgaga tcaggagttc aagaccagcc tgaccaacat gatgaaacct cgtctctact    42960
aaaaatacaa aaagttagc caggcatggt ggcacatgac tgtagcccca gctactcgag    43020
aggctgaagc agaagaatta cttgagccca ggaggcggag gttgcagtga gccgagattg    43080
taccactgca ctccaacctg agtgacagag caagactctg tctaaaaaa aaaaaaaaa     43140 aaaattagtc aagcatggtt gctcacgcct gtaatcccat ctacttggga ggccgaggca    43200
tgagaattgc ctgaacctgg gaggcggaga ttgcagtgag ccgaaatcac gccactgcac    43260
```

```
tccagctcag gtgatgaaat gagactcata ggccgggcac ggtggctcac acctgtaatc   43320
ccagcacttt gagaggctga ggcgggcgga ttgcctgagg tcaagagttt gagaccagcc   43380
tgactaacat ggtgaaacgc tgtctctact gaaaatacgg caattagtcg ggcgtggtgg   43440
tacgcgtagt cccagctact tgggaggctg aggcagaaga attgcttgaa cctaggagac   43500
ggaggttgca gtgagccaag atctcaccac tgcactatag cctgggcgac agagcaagac   43560
tccctctcca aaaaaggaa aaaaaaaaaa aagaaaaag aaatgagatg tataacatgc   43620
ataatcttca gtgtacctct agatcaagct cgtctaacac atgtggccca ggatggcttt   43680
gaatgcggcc aacataagt tcgtaaactt tcttaaaaca ttatgagatt tgtttgtgat   43740
tttttttttt aacgcatcag ctatcgttag tgttagcgta ttttatgtgt ggcccaagac   43800
aattcttctt ccactgtggt ccaagaaagt caaaagattg dacacctttg agattgttta   43860
acacacatat tcaccatgta accaccatcc aaatcaagac acagacccct ccagtcccca   43920
agaagtctcc ctcaggcccc agagatggcc acccttctgc ttctagaaca ttgcttttgc   43980
ctgtagtata atgtcatata aatggggcct cacagtatcg tgctattatt atgatgatca   44040
ttactattat ttgagacaga gtcttgctct gttacccagg ctggagtgca gtggtgtgat   44100
cttagctcac tgtaacctct gcctcccagg ttcaagtggt tctcctatcg cagcctcccg   44160
agtagctggg attacaggcg agcgccacca catccagcta atttttttaca ttttttggaag   44220 agatggggtt tcaccacgtt ggccaggctg gtcttgaact cctaacctca agtgatcgcc   44280
caccttggcc tcccaaagtg ctgggattac aggcgggagc caccgtgccc agtctatttg   44340
cgttattatt gtcatcacac tattattatc ggtgctgacc acccgccatg cactgtggca   44400
tcctttgggc ataactacac ttaatctta aacaatcctg taaggcactt gatcctctaa   44460
ggccccgtgt gcccaaggaa aaaactgagg ctcagagagg aagagtctt gccagaggtg   44520 gcttttggaa gtggtgacag aaccacattg tatacagcca aatgatctcc ttgctttgca   44580
aatccaggtg cccgtgttat cctagcatgg cactgcaaca cacacgcacc cttgaaaagt   44640
tgtgtagtca caccagacca ccaccactgg gagctgtgtg accatctcgt gtgattgctt   44700
ggctgtcccg tcctcacacc cttgcctctc ctcaggctgt gctgtcaaac gatgggatgg   44760
gcatccaggc gggagaacca gaccccccag aggagcccct cacctcgcaa gcatccgtgc   44820 cccccatca gcttcggcta ggcagcctcc atcctcacac ccctatcac atccgcgtgg   44880 catgcaccag cagccagggc ccctcatcct ggacccactg gcttcctgtg gagacgccgg   44940
agggaggtaa gaagggttgg ggagggacac gtcaccactg ccccaccgga ccttgcttat   45000
atcagtgcca ccccccattgt ccccctttcac tcctttaccc ctcatggcct caatctcctt   45060
cccatccaat ctctgacccc tcagcagcac tgcccgctgg cctctctccc agcccttctc   45120 tccctgtgc ttcctctcat gggaggcctg cacgagttgc ccacgtgtgt gcccttggca   45180
ccctgcaccc acttcctggg aacagggag ggggtcagga agaggtgggg gtgccagctt   45240
cccctcttcc ctgtcctcca gtgcccctgg gccccctga aacattagt gctacgcgga   45300 atgggagcca ggccttcgtg cattggcaag agccccgggc gccctgcag ggtaccctgt   45360 tagggtaccg gctggcgtat caaggccagg acaccccaga ggtgggtgct gctggtggga   45420
ttggagtgga gtggcttggg gaggaggag gagaacatat cagggcagac atagatggtt   45480
gtgaaggttg ggtagtacac aattgctcta tgcctagggg gcacattcag ggaaggttca   45540
cattcacatt ctggggagaa taaggggtc taagggaggg catggggaat ggctgttttt   45600
gaaccactgc aaaagcattt cagcagactc atatttacta tataacgatt ttacagcaga   45660
```

```
tagttatata gcaccttggg gaaggggtac cttttcctga ttttcacaaa ggcactccta    45720
tcagggctag caatacccctg acatagggag ggaggatgaa aagggaagct agaaggggat    45780
ggagggatac aggttaaagg atgaggatga gagatgaagg ggaggacgag aaggatgag    45840 gagttggagg atggggagag cgttttgaga aagagatggg gcattgagcc cgagagtgaa    45900
ggcttaacag ctgggggta aggttctacc ctgatgccac ttctggacct cctaggtgct    45960
aatggacata gggctaaggc aagaggtgac cctggagctg caggggacg ggtctgtgtc    46020 caatctgaca gtgtgtgtgg cagcctacac tgctgctggg gatggaccct ggagcctccc    46080 agtaccctg gaggcctggc gcccaggtaa gtccaaagcc atgcccaacc tgcttcaacc    46140
ctgtctctcc ctgacagccc tgacttactc cttgtacctt tcagtgttac cgcaacttag    46200
gccctgttcc taccctgagc cttactgaga gctgccctca ctcccttacc catgccaacc    46260
cctcactccc ttacctgtgc cacggcctca ctcctttacc cgtgccacac cctcactccc    46320
ttacccgtgc cacaccctca ctcccttacc cgtgccaaac cttcactccc ttactcgtgc    46380
cacaccctca ctcccttacc cgtgccacac ccttactccc ttacccgtgc cacgccagtc    46440
ttgtcctctc tgagcacatc tcctctctgt cctttcttct cacagggcaa gcacagccag    46500
tccaccagct gggtaagggc ttccacaccc catctcctcc ttccctaccc tcaacaccta    46560 gtggggcac tgtcaccatg catactcatt gcacatccct ttcatgtttc tctaactcat    46620
cactctaacc tacttcttga gtttgtgtgg tccttgatgg aggtgcctat aatggcctag    46680
catagcacat tgtaggtatt caggcaatga cagatgagtg ggtggatgga tgaacaaata    46740
gatggatgga tggatggata gatatatgga gggtggatgg gtgggtgggt caatggatga    46800
atagaggatg gataggcggg tgaacagata aatgactgga tgtcgagtgg ataaatggat    46860
gggtagatgg atgggtggat ggatggatgg gtggatatat ggagaatgga tgggtgtgtg    46920
ggccaatgga tgaatagagg gtggataggt gggtgaacag ataaatgact ggatggtgag    46980
tggataaatg gatgggtaga tggatgggtg gatggatggg tgggtggata tatggagggt    47040
ggatggatgg atggttggat atatggaggg tggatgggtg ggtggtcaa tggattaata    47100 gatgggtgga taggtggatg aacaaaagat gactgggtgg tgagtggata tatggatggg    47160
tagatgggtg gatggatgga tggatggatg gatgaatgga tggttggata aatggatgga    47220
tggacagatg gatggatttg tgagtggatg aatggatggg tagaaaggtg gatggatgga    47280
tgaatgaggt atcctcctca catccatccc tctcaaatat ttctctaaca attctcaaac    47340
attcctccta cacccattgt cccctctggg cactattatg gttcactctt gtaactcaac    47400
ccactagcct tcaatactcc tcacatccct tcctacattt cttcacatac gctttccacg    47460
cttattccac cctcctttca catatatccc attataatcc gttcctccca catgacccca    47520
aaggcccatt gcacaacaca cttctcattc acaaactctg cacaccttgt atgcacttac    47580 catacccttcc acattgcaaa cactgaaaaa cattgtccac aactttccca cacctgattc    47640
tccttgcatg cttactgcac actccataga catcattccc tcacccttca ctaatcccaa    47700
cccatctcac tctgcacact cacccctgaac cccttgcata tcagcacat aatgatcttt    47760 atttcttaca cactccattc caccccctgcc cttttacac cccctttctg tgcacccat    47820 acttctcatc tgccccttcta acatcttttg catgctcact gcacacttct ctcacactgc    47880
aattacatcc ttaaaattcc ttgctcactc cttgtatcta agacttcacg aatactcttc    47940
ccacttcaca caccccaac ttttccagca gccatccaac cctgtatatg cttaccatgc    48000 cccttttggat atttatttca ccctcattcc tggctttatg gaaaccattg tggccgggtg    48060
```

```
caatggctca cgcctgtaat cccagtactt tgggaggcct gagacaggtg gatcacctga   48120
ggtcaggagt tcaagaccag cctggccaac attggcgaaa acccatctct actaaaaata   48180
caaaaattag ctgggcctgg tggtgcgagc ctgtaatccc agctgctcgg gaggctgagg   48240
cacaagaatt gcttgaacct gggaggcgga ggttacagtg agccaagatc atgccactat   48300
actccagcct gggcaacaca gcaagactct gtctcaaaaa aaaaaaaaaa agaaagaaag   48360
aaagaaaaaa agaaagaaaa gaaaagaaa agaaaaaaaa attagccagg tggcacagac    48420
ctgcagtccc agctactcag gagacatggt gaaaccctgt ctctaccaaa aaaagaatac   48480
aaaaattagc tgggcatggt ggtgcacacc tgtaatccca gctacttaga agctgaggca   48540
ggagatttgc ttgaaactgg gaggcagagg ttgcaatgag ctgagaccgg gccactgcac   48600
tccagcctgg gtgaaagagt gagaccctgt ctcaaaaaac aaacaaacaa aaaagagac    48660 aaagaaaacc cttttgtagt cattgcattc tcttcaaaag atgttcctta gtccgccctc   48720
cttgcacacg cttcatgcac catcctacac tgcaaggatc ttcttcccca ctcacctgct   48780
tatctacact ctagtccacc cttcttgcac aatcatcaca tttctcacac taacctatgc   48840
tgcttgagat ttctccacac ccatctcatg ttcatctagc cctcttggca cactcataac   48900
gcgttccaca catctctccc tcccattcca cactcactgc acactcctca aatatccatt   48960
ccactcttct gttttttggg atcttggtgg cataatattt ggtagcttaa agtaaggaaa   49020
actgcaaacg cccaaacaga gacttgaacc ctgaaccctc aggttaaaag tctgatgctc   49080
taccacctga actatcctgg cactctcttt tttttttttt tttttttttt tttgagatgg   49140
agtcttgctc tgtcacccag gatggagtgc agtggcccag tctcggctca ctgaaacctc   49200
cacctcccag gttcaagcaa ttctcctgcc tcagctcccg agtagctggg attgcaggtg   49260
tgcaccacca ccccagctaa ttttttgtata tattttgttt aagtagagac agggtttcat   49320
catgtcggcc gggctggtct tgaactcctt gcctcaagta acccaccgc cttggcctcc    49380 caaagtgctg ggataacagg catgagccac cacacctggc ctccatccca ctcttaactc   49440
acccatccta caactttcac acacttctgc tttaacctgc acttgtatca catccattgc   49500
atgccctgtc cagcccagcc cattcagata tgtgaatgca tccatcacac acctcatcaa   49560
gtatgtgcac atctttgccg aggccttctg cctccctccc acatcacccc tttgggtccc   49620
agagagctgg atccaaggcc tcatccatga cctgttcctc ataccccctg atagtgaagg   49680
aaccttcaac tcctgccttc tcgtggccct ggtggtatgt actgctagga gcagtcgtgg   49740
ccgctgcctg tgtcctcatc ttggctctct tccttgtcca ccggcgaaag aaggagaccc   49800
gttatgggtg agttggaacc acatggggag gctgtgtggc ctgggatgga gaggctggag   49860
gcagggaggc cagtgaggag gctggtgcag gaggagtgat gactaagaat cagaatgagg   49920
gcaagggaag ccaggcgtgg tggctcacgc ctgtaatccc agcactttgg gaggctgaag   49980
caggtggatc acttgaggtc aggagtttga ccagcctg gccaacatgg cgaaaccctg     50040
tctctactga aaaatgcaaa aattagcggg aagtgtaggc acacgcctgt ggtcccagct   50100
acttgggagg ctgaggcacg ataatcactt gaacccggga gatggaggct acagtgagct   50160
gagatcgcat cactgcactc cagcctgggt gacagagtga gatcctgttt tcaaaaaaaa   50220
gaatgagggc aaggggtgt gtggaatgaa tggaaggcag aaggtagctg cccaaggcat    50280
gctcagcaaa tgttagcaca gagggcaggc agggcttgag gctgagatgg tgcttgctca   50340
actgctggtt gagtaggggg ttccacatgg ttttccctg ccctcaccta ctcccctcc    50400 cccccagaga agtgtttgaa ccaacagtgg aaagaggtga actggtagtc aggtaccgcg   50460
```

```
tgcgcaagtc ctacagtcgt cggaccactg aagctacctg taagtgaacc ctatgcccca    50520 ctgcccctggc ctggatctaa aggctgtaga gaatctggcc tgctgggctt ctgtacatgt   50580
gtgagccaaa agtttctaaa ggccttggga tactagaatg tcagaaccac agaccctaga    50640
aataacagat ttgtggaacc acaaagaact ttcaaggaat agaatcttag acacagtaaa    50700
tcttagaaac accaaggctg ggtgtggtgg ctcatgcctg taatcctagc gcttcggggg    50760
gccgaggtgg gaggatcact tgagcccagg agttcgagaa cagcctgggc agcatggtga    50820
aaccctgtct ctacaaaaaa aaaaaattag ccaggtatgg tggtgtgccc ctgtactccc    50880
tgctactcgg gaggctgagg taggaggatc acctgagccc agggaggtca aggctgcagt    50940
aagccgtgat cacaccactg cactccagcc tgggtgacag agcaagaccc tgtctcaaaa    51000
aagaaaaaaa aataaaagaa agaaaagaaa caccaaacct cagagccatt ggatcttaga    51060
agatgtaatg atgatgataa tgatgaagat aatgacaaga agaaaatgat gatgatgatg    51120
aaataatgtt gagattagat ggtgatgatg tgataaaaat cacaggcaac cctagcacta    51180
cctatgtggc aggctctgtt ctaagcattc tacatgtatc tcctcgttta accctcagag    51240
caacccaagg acacgggttt cttttttctt ttttttttctt ttttttttttg agacagagtc    51300 tcgctctgtt gcccaggctg gagcacagtg gcacaatctc agctcactgc aaccttcacc    51360
tcccaggttc aagtgattct tatgcctcgg cctcccgaat agctgggatt acaagtgcat    51420
ggcaccacat ctggctaatt tttgcatttt tagtaaagat ggggttttac taaccctgtc    51480
tttgttagcc aggctggtct tggaactcct ggcctcaagt gatcaacctg ccttggcctc    51540
ccaaagtgct gggataacag gcgtgagcca ccacgcccag ccagaggtgg gtttcttatc    51600
accttcactt cacagatgag gaagctgtgg catagagtgg ttaagtcact tgcccaaggc    51660
cacacagctt gtaaattgga tagctgggat ttgaacccag gtactttgc tctgaagtct     51720 atactattt ttttttttt ttgatagaat cttgctctgt cacccaggat ggagtgcagt      51780
ggcttgatct tggctcactg caacctccgc ctcctggatt caagcgactc tcctgcttca    51840
gcctctcaag tagctgggac tacaggcaca tgccacaacg cctggctaat ttttgtagtt    51900
ttaatagaga caaggtttca ccatattggc caggctggtc tcgacctcct gaacccgtgc    51960
ctcccaaagt gctgggatta caggtgtgag ccaccacgcc tggcctgaag tctatactct    52020
gaactgccac actctactac ctcttggaat tataaattgg tagagagata gaatcgatct    52080
tggcctgaaa aattatatgc atgtactcta cacccttata cttttgaaat cataaaatct    52140
tagaactata gactctccat tagaaggctg gaaagccatg caaggtctca gccgaggagg    52200
ggatctcaga ggcccagtca aatctgttct ttcggctggg tgcagtggct cacgcctgta    52260
atctcaacac tttgggaggc ccaggcgggc agacacttga ggtcaggagt tcgagaccag    52320
cctggccaac atggcgagac cctgtctcta ctaaaaatac aaaaattagc cagatgtaat    52380
ctgtaatccc agctacttgg gaggctgagg caggagaatc tcttgaacct gggaggcgga    52440
ggttgcagtg agccgagatc gtgccactgc acttcagcct gggtgataga gcaagacacc    52500
gtctcaaaaa aaaaaaaaa aaaaaggaat ctcatctttc cagttaggga aactgaaatc    52560
cagaaagaaa atggaagagc taggtctctt cctagcatac agcgagaaag ccgccagggc    52620
cccaggggga tgtttggaaa gggctgggaa agacatttat ttaagaagag aaggaagaag    52680
caacgatgtc ccagtgattt aactgagtaa catacagcat ccattctcag ggtgtgagcc    52740
tggtcccctg tggtccctga gacctttgca gggggcccat aaggtcaaat ctatttcat    52800 actattacca agacattatt tgcccttttg ctttctcatt ctctcattag cattcagcgc    52860
```

```
agttttccag aggctccctg acgtgggatg atgtcatcca acactctgac agctgatgga    52920
ccttgtgctt gtatattctt gttttaaaaa tttatcaggc tgggcatagt ggcacatgcc    52980
tgtaatccca ccactttggg aggccaaggt gggcaaattg cttgaggtca ggagtttgag    53040
accagcctga ccaacatggt gaaaccccat ttctactaaa atacaaaaat tagctgggtg    53100
tggtggtgca tgcctgtaat cctagctact gggaggctg aggaaagaga atcgcttgaa    53160
cccgggaggc ggatgttgca gcaagctgag gttgtaccac tggacttcag cctgggcaac    53220
agagtgagac tgtctcaaaa aaaaaaaaaa ttaaataaac ctgataggtt ttcttttgag    53280
gccaggagtt tgaaaccagt gtgggcaaca tggcaaaacc ccatctctat ttaaaaaaaa    53340
aaaaagaaac acaaaaattt gccaggtgtg gtggtgtaca cctataattc cagctgctca    53400
ggagggtgag gcaggggaat cacttgaacc tgggaggcgg aagttgcagt gagctgagat    53460
tatgctactg cactctagcc taggcaacag agcgagactc ggtttcaaaa aaaattttttt    53520 tatttttta gagatggggt ctggctatgt tgcccaggct gatctccaac tccaggcctc    53580
aactggtcct ccttccttgg cctcccaagt tgctgggtga accactgtga accactgtgc    53640
ccagctagtt ttatttttga atacagaaat attgatatat atgtaacata acaaaagct    53700 ctttctagtc ctcaataatt ctaacaatgt aaaggtgtcc tgatgtcaat ttgtttgaga    53760
atgattatat aacaaagaaa atggataaat tacaattaca ctcaacaact aaattaaaac    53820
tatttcatag acatcatgtt gagtgaaaga agccagacac aaaagagaat atactatgtg    53880
attccatttt tataatattt caaaactaat cgattgtaac agaaatcaag aaagtggcta    53940
ccccaggagg gcaggtcatg ttctgttctt ggcctgagtg ctagttacac atttgtgttt    54000
gatttgtgaa aatccactga gttggccagg cgtggtggct cacgcttgta atcccaacac    54060
tttgggaggc caaggtgggc agatcacctg aggtcggag ttccagacca gcctgaccaa    54120 catgagaaa ccccgtctct actaaaaata caaaattagc tgggcgtagt ggcacatgcc    54180
tgtacttggg aggctgaggc aggagaatcg cttgaacctg agaggcggag gttgcggtga    54240
gccgagattg cgccatcgca ctccagcctg ggcaacagga acgaaactcc atctcaaaaa    54300
aaaaaagaaa agaaaatcca ctgagttgct tacttatgat ttgtgcagat tatacttcaa    54360
taaaagaaaa tattttgtg tgtgtgtttt gtttgagatg gggtcttgct ctgtcaccca    54420
ggctggggtg cagtggcatg agctcagctt actgcagcct ccaccctgg gctcaagtga    54480 tcctccaacc tcagcctcct gagtagctgg gactataggc gcgtaccacc acacatggct    54540
agcttttgta tttttttgta gagacgggga ttcgccatgt tgcccaggct ggttttgaat    54600
tcctggactc aagtgatcca ccggcctctg cctcccaaag tgctgcgatt acaggcatga    54660
gccactgcat ccagcaaaaa gaaatatttt tatttatt tatttattt tattttattt    54720 tatttattt ttgagacgga gtcttgccct gtcacccagg ctggagtgaa gtggtgcgat    54780
ctcagctcat tgcaacctct gtctcttggg ttcaagtgat tttcctgcct cagcctcccc    54840
agtagctggg actacaggca tgtgccacca cacacggcta attttgtat tttttgtag    54900 agacagagat tcgccatgtt gcccaggctg gtcttgaact cctggactca agtgatccac    54960
ctgcctctgc ctcccagagt gctgggatta caggcgtaag ccactgtgcc cagcaaaaga    55020 aatatttta acaactggta cagcaggca ctgacccatc agggtgccca ctggagcaag    55080
agcgtggcca ggctttaccc cttgagttcc ctttgaggga aggttcaggg ggtccagagg    55140
aggagctggg gtggaagtag aggggtgctc agggcagttg ctaattttaa atcagtgcag    55200
aagtatgtca gtgtttcaac aatggatcta tccctactgg tgggtgaatg tcacctgaat    55260
```

```
gtcagccctg ctccatgact ctgtccaccc caaccttgca tgcagtgaac agcctgggca    55320
tcagtgaaga gctgaaggag aagctgcggg atgtgatggt ggaccggcac aaggtggccc    55380
tggggaagac tctgggagag ggtgagtccc ccggcagcat acacacatcc ttctgaactt    55440
ctgagatcct gcacttccac actcccaccc aactatagga aatacagtcc ccacgggccc    55500
tctgaggtca gtgtctccct ctggcccccc acaggagagt ttggagctgt gatggaaggc    55560
cagctcaacc aggacgactc catcctcaag gtggctgtga gacgatgaa gagtgagtta    55620 cgtgcacatg tgtaggaccc ccagctcctt ccctatgccc ctgagacaga agagagcaag    55680
caagttagcc atagcttaga acttctggtg tttccagata ggcaatggag cccctgccag    55740
gtacctcaat agaaggaatt gaatatgggg agattagtac aaaggtggga gacgggttga    55800
aggaacaact gggggcaggg agggaaacca gagatgagca gcagcaggaa gtcacttccc    55860
ccgctaggcc tgaagggtag agggagcaag tggtgttacc agaatccaca gctagggaca    55920
ccaggcagga gctggtatca cagagttaga ggctgctctg tgggagctaa aaacccagaa    55980
tagcactttg ggaggccgag gcagcagatc gcttgagtcc aggagtttga gaccagccta    56040
ggcaatatgg tgaaaccaca tgtctatgaa aaaaaaaata ataatagtaa caaaaaatta    56100
gctgggcatg gtggcacacg cctgtagtcc cagctacttg ggacactgag gtgggagaat    56160
cacttgagtc tgtgcggcag aggttgcagt cagctatgat catgccactg cactccaatc    56220
tgggtgacag agtgagactt tgtcttaaaa aaataaaaca cacatggctg ggcgtggtgg    56280
ctcacgtctg taatcccagc actttgggag gccaaggcgg gtggatcaca tgaggtcagg    56340
agttcgagac tggcctgatc tgcatagcga aaccccacct ctactaaaaa tacaaaaatt    56400
agccaggcgt ggtggcaggc acctgtaatc ccagctactc gggaggctga ggcaggagaa    56460
tcgcttgaac ctcacaggcg gagattgcag tgagccgaga tcgtgccact gccctccagc    56520
ctgggcgaca gagcaagact ccgtctgaaa aaaaaaaaaa attaaaacac acacacgcac    56580
acatgggcga cacaaccacc accaagggaa taccagaagc agagagaggg tgaaataccc    56640
tggcttctcc ctttctcccc gctacctgcc agtctcccat aagggcctac ctcccattgg    56700
caaatcccaa gaggaaacca ctaggaaagg gagcctggga aatgtagttt tcaggggccg    56760
gcccactgtg atacatagtg gagcaggaga agctctagaa tgaggcatac ctggctgaat    56820
catttaccag ctatgcgatc tcaggcaaat gactttccct ctctgagcct cccacctgtc    56880
atctggaaaa aaggacccta atgtccccac cttccaaagc tgttttgagg caaagcactt    56940
catgctgagg gtggcaagta ggacatgctt gttaatgtgg agtaggacta tattatttcc    57000
attatcagag agggcaggag ccatttcagg gttacacagc acaggaagtc cagggctaag    57060
ttcttcacac acagggaagg agaagcatag ggcattcaga ttggggctgg tggtgaatag    57120
agaatgatcc tttctgaatt acagggctta aaagcttggg ctatgaagtc attcccact    57180 cattcgttca ttatggagca cctcctgtgt accaggttat tttgtttgtt ttgctctgtt    57240
ttgttttgtt ttgaggagga gtctcactct gctgtccagg ctggagtgca gtggcatgac    57300
ctcagctaac tactacctct gcctcccagg ttcaagcgat tcttctgcct cagcctcctg    57360
agtaactggg actacaggtg tgcgccacca cgcccagcta ttttttgtgt ttttagtaga    57420
gacgggtttt caccatgttg gccaggatgg tctctatctc ttgacctcat gatccacctg    57480
cctcggcatc ccaaagtgct gggattacag gtgtgagcca ccacacccag cctacgtttt    57540 ttgtttttg agacagagtc ttgctcgttg cccatgctgg agagcagtgg caggatcaca    57600
gctcactgta gtctcaacct ctgaggctca agcgatcctc cccactcagc ctcccactgg    57660
```

```
ttatagtctt ggcctgggtc tgaatctcag ccgtgcaacc tgggcaagt cattttgcct   57720 ctgtgagcca cagtgtcctg aactgttaaa tgggatgata cttgtttggg tccccagggc   57780
aggtagggaa gtgctgggaa gcagcctggg cagttgtgag caggtggacc ctggagccag   57840
actgcccggg tttgagatct gcctcttcca cctccaagct gtgtgttccc ttaggcagac   57900
tcctaacctt tttgtgcctt gctttcttca tctttaaaat agagataggc cagggacagt   57960
ggctcatgcc tgtaatccca gtgctttggg aggccgaggt ggaggatca cttgaggctg   58020 ggagtttgag accagcctgg acaacatagc aagactccct ctcaaaaaat tggctgggca   58080
tggtggctca cacttgaaat cctagcactt gggaggcca aggcaggcag atcacttgag   58140
gtggggagtt tgagaccagc ctggccaaca tggtgaaacc ccgtttctac taaaaataca   58200
aaaattagct gggcatggtg gtgcatgcct gtaatcccag ctactcggga ggctgaggta   58260
cgagaatctc ttgaactggg gaggcagagg ttgcagtgag ccaagattgc gccattgcac   58320
tcaagcctgg gggacaaggg cgaaactcca tctcaaaaaa aaaaaaaaaa ttatcccggga   58380 tggtggtgcg tgcctgtggt cccagctact caggaaggca agcctaggag ttcgagccta   58440
acctccagtg agctatgttt gctgtgattg catccatcct gggtgacagc gcaagaccct   58500
gtctcaaaaa ataaaaataa aaacaaaaa caaaacaaa acaaacaaa acaaaaaacc   58560 aataaaatgg gaatgataat agtagcacct gagaagatta aatgagttaa tatatataaa   58620
gttggccaag cgcagtggct gacgcctgta atcctagcac tttgggaggc cgaggcgggc   58680
agatcgtgag gtcaggagat cgaaaccatc ctggctaaca aggtgaaacc ccgtctctac   58740
taaaaataca aaaaattagc cgggtgtggt ggcacacgcc tgtagtccca gctactcagg   58800
aggctgaggc aggagaattg cttgaacccg agaggcggag gttgcagtga cccgagatca   58860
aaccactgca ctccagcctg gacaacagag tgagactcca tctaaaaaaa aaaaaaaaaa   58920
gaaaatatat atttttatata tatatatata ttatatacac acacacagac acacacacat   58980
acacatatca catataaagt gctgagtatg gtgcctggta cttactaatc atgtttgatg   59040
aagatgagtg atgatgatga tgatgatgat gatggagtgg aggtggaggg agagtcctcc   59100
ctctcctccc ctcctcctca cgacctttct ctctccctca agttgccatc tgcacgaggt   59160
cagagctgga ggatttcctg agtgaagcgg tctgcatgaa ggaatttgac catcccaacg   59220
tcatgaggct catcggtgag agaggggcag attcaagggg tctacaagcc ccatggggggc   59280 catagcagag ggaagagccc tgcttctggc cctgggaaga tcaaacttcc aggcttcctg   59340
ctccccgctc cttcagggtc agcaggcttc cccctcctag tctccctcag cttggaatgt   59400
gacctctgat cattcccaga aatagctgag gtccccagga gggctccgga acgtccctg   59460 ggaactctgc tggaaacagc ttctctgcag cttggtcctt gccactgcca ctaccccaa   59520 acaatatggt ggccagattg gatgggtagt gagaaggaga ggctggaggc tggctggtgg   59580
ggggcttggc ttcccccttct gcccagcagg agtgacaggg ctacctgggg ggctcaggtt   59640 tctgttttcca gggttctgaa cgagagagct tcccagcacc tgtggtcatc ttacctttca   59700
tgaaacatgg agacctacac agcttcctcc tctattcccg gctcggggac cagccagtgg   59760 taagggggcgt ttaatcattc agtctacaaa tattaactga gcatctatca ggtacccagt   59820
gctgctcaga ccctgggaag accacggtga ccaggagctt gctctcctgg agcatttctt   59880
ccagcagggg aggggcggat gataaacaag ctaataaata cctaagcgag atgatttaaa   59940
tgtttaagtg ctaggaagga aatacagtag gatggaagat aaggaggcca ggcagtgaat   60000
ttgggtggac gtggaagatc ttgccgagga ggtgaccgtg aaggagttgg ggctggggag   60060
```

```
atgtctggag atctgggcag gaagcgaccc aacagagcg cacagcatag gcaaaggctc   60120
ggaggtggga atgatcatcg tttgtctgaa gaccagacag gagtctggtg ggagtgtcag   60180
tcaagggcaa gaacataggc aatcaagtcc aagaggaagg ctggagcaag tttataggac   60240
cttgcaggcc atggagaggg gttggggttga attgtcaggg ccatgggaaa ccactgcggg   60300
cagagctagg cttgcacaga gggatggagg gaggagggat cgcatcaagg actctgttga   60360
cctctcctcc cacctgcctt ggctccccag tacctgccca ctcagatgct agtgaagttc   60420
atggcagaca tcgccagtgg catggagtat ctgagtacca agagattcat acaccgggac   60480
ctggcggcca ggaactgcat gtgagtgcct ttcaggggacc cccccccccc aactgctcct   60540
gcactccctg agggagttcc ctccctcctt cttaggatgg aagcagggct agacacccgc   60600
tgagggcagg tcagaactca ggaccaggaa agtcagtaag ggggtctggg aaggcttcct   60660
ggaggaggtg agtcctgaac tgagatctgg aaggagcatt tggatgcgga gagggaagag   60720
accagaaggt gggctcagtg cacagcatga ggtgagcaaa ggggctgagg tgaccgatgg   60780
gggtggggac acgtgagctg catctctgtc ccactccatg ctgggtgtct tgcctggggc   60840 tgcccttttgg aagcggccac actggataag aaaatcaaac tccccaccaa tggacaagca   60900
gaaaatatgc cagatggggt gcagtggctc acgcctgtaa tcccagcact ttgggagtcc   60960
gaggcgggtg gatcacttga ggccaggagt tcgagaccag ccttggtgaa accccctgtc   61020
tactaaaagt acaaaattca gccggtgcg gtggtgtgcg cctgtaatcc caacacgaga   61080
attgcttgaa cccaggaggc ggaggttgca atgagccgag atcgcatcac tgcactccag   61140
cctgggcgac agagcaagac tctgtctcaa aaaaaaaaa aaaagaaag aaagaaagaa   61200 agaaagaaaa aagaaaatag taacctgtag tcccagccat tcccaaggct taggtgagag   61260
gattgcttga gcctcgagac cagcctgggt aacaacaacg agacaccatc tcaaaaaaaa   61320
agaaaaaaag aaaagaaaga acaaaaaatc ccccaaaagc cagaatagag ggtaagggga   61380
gggtagaagg tggagggaat ggaaccacag agttagaata ttagtcttgg ccaggcgcag   61440
tggctcacat ctataatccc agccctttgg gaggctgagg caggaggatc acttgtaccc   61500
aggagttcaa gaccagcctg gcaacatag tgaatcctgt ctttacaaaa aataaattag   61560
ctgggcatgg tggtgtatac ctgtggttcc agctacttgg gaggctgagg tggaaggatt   61620
gctagagccc aggaggttga ggctgaagtc agccatgatg gtatcacttc actactgcct   61680
gggcaacagg gcaagatccc atctaaaaaa aaattgatgt atattttaca tacactaaaa   61740
tatacacatg cagctcagct cgatgaattt ttatgggtat agaccatgt aaccactaga   61800 tgaaggtaaa gaatatttct tagccccagc aggctccttc atgcctcttc gtcttcccaa   61860
tcactaccgc caagtggtac ccactatcct gacttctcag tgctagttta gcctgttctg   61920
aaaagtcata caaatgggat catgcagttt gtactgcttt gtgtctggct tctatggctc   61980
agcatgatgt ttttgagatg gatctgtgta ggggtagttt gctctttttc tttgctgtgt   62040
ggtatggtat tccatcatat gaatgtcctg tggattttct tttcttttt tctctttctt   62100 tcttttctt tcttttcttt cttttctct ctgtcctttc ttctttcttt tctttctctt   62160
tctctctctt tatctccttc cttccttcct tccctccctc cctctctctt tcccttttctt   62220 tcccttttt tcttttctttt cttttttgtt ttgacagagt cttactctgt cctttagggt   62280
ggggtgcagt ggcatgatca tagctcactg tagcctccaa ctcctggctc aagctatcct   62340
tctgcctcag cctcctaagt agctggaact acagacatgt gccaccatgt ccagctaatt   62400 tttaaattt tttgtagaga cagggtcttg ctttgttttc caggctggtc ttgaactcct   62460
```

```
agcctcaagt gatcctccca ccttggcctc ccaaggtgct gaaattacag gcttgagcca   62520
ctgtgcctgt tttttttttt gtttgttttt gagacggagt ctcactcact ctgttgccca   62580
ggctggagtg cagtggcgtg atctcagctc actgcaacct ccgcctactg ggttcaactg   62640
attctcttgc ttcagcctcc caggtagctg ggatttcaga tgtgcaccaa cacacctggc   62700 taattttgt acttttagta gagacagagt ttcaccacat tggccaggct ggtctcaaac   62760
tcctgacctc aagtgatcca cctgccttgg cctcccagag tgctgggatt acaggcgcca   62820
gccaccatgc ccagccatgt tctgtttctt aatctgggtg ctggttacat gggtgtgtgt   62880
gtgtgtgtgt gtgaaaattc agtgagctgc ttacttatga cttgtgcaca tttccatatg   62940
tacagtatac ttcaagaaaa aaaaatttca tcaaggaatc aaacccaagg aaggacctta   63000
gaatctagca aagagccaaa attgggaagt cctgaggaag ccctttgtcc catcctcact   63060
tgacagagtg aacaagaagt aaagcagttc ccttctggac tgggatgaag gtttaggaga   63120
cagatcccca cccgcagcca ggacagtgag ggaggaggt gcagatgtgt ctgagagcca   63180
gggcaggctt cctggtggag gtgactgatg ccctgaccct gttcctttcc ccaatccaaa   63240
caggctgaat gagaacatgt ccgtgtgtgt ggcggacttc gggctctcca agaagatcta   63300
caatggggac tactaccgcc agggacgtat cgccaagatg ccagtcaagt ggattgccat   63360
tgagagtcta gctgaccgtg tctacaccag caagagcgat gtggtaggtg cactcccgcc   63420
aagagtgggg aaccatggga gggcatggcc tgaccatcac acactatgcc tgggtggctg   63480
tggatgcaag ggtcacaggg acatgtgggc ttcccttttgc aggggcttgt ccacatgggc   63540
tgggcatgtc ttggggtatg gtgggcatct ctgaatagtg gtgtgtacat gcccaggata   63600
aatacaggcc cacgtgtgca tggtagcaat gtagacagtt taggttagaa gaagctgcag   63660
tgattatgcg tgcatgtgcg cacactcata gaatgtggac agccagggtg tgcagagtgg   63720
cacatgagct catgtgtcca tgaagtgtgt atatgtgtgt gatggtgagc atgtgtatgc   63780
atccacaaaa gttacttatt catgtgtata cccgtgtcaa gtattttta tatatatata   63840 ttttctttt tttgagatgg agtctcgcac tgtcacccag gctgcagtgc aatggcatga   63900
tctcagctca ctgcagactc tgcctcccgg gttcaagcaa ttctcctgcc tcagtctccc   63960
gagtagctgg gattacaggc gcccaccacc atgcctagct aattttgta ttttagtag   64020 agacgggtt tcactatatt ggccaggctg gtctcaaact cctgacctca ggcagtccgc   64080
ccacctcagc ctcccaaagt gctgggatta caggcatcag ccaccgcacc cggctaaagt   64140
attatgtttc tatgaatact tgtgatgctc ccagaggatg gttgtgaaca tgtgtacata   64200
agtgtgggtg tacccatgaa cctgggtatt ggtgcgggtg attctgtgca ggagagactg   64260
tctaattccc tctgccctc acagtggtcc ttcggggtga caatgtggga gattgccaca   64320
agaggccaaa ccccatatcc gggcgtggag aacagcgaga tttatgacta tctgcgccag   64380
ggaaatcgcc tgaagcagcc tcggactgt ctggatggac tgtgaggacc cttaggtctc   64440
ccccaaccca gaattcattc caaacccctg actaccccca gatggccctc acaggtccag   64500
gactctctat aacccagaca gaatccctga gaatgctgag tgaccacttt gcccctcacc   64560
aatgctctga gtagggccat cactaaccag tggggtgcaa atcagctaaa ggcacccttt   64620
cctcctttgt ctgtgtgggc tgaatcagcc cctggctcc ccaccccaa gccaggtatc   64680 cttgggtagt gaataacagc acagtcttac ctggcggccc tgcctttggg acatgcactc   64740
ccagagactt ctcattccag actcctgagc acaccatgct tccccgacat gctcctcaac   64800
acctgagact ctctgcaaaa cccttcagtt tgttttattg gccttctcca gactcaggtc   64860
```

```
tcctctgaga tatttgcagg atccttcagg gaatgcttac caaactttgc aatattggag   64920
tatgcggaga aggccgtgac atttagctag cactttgagg gtaaagagag gatgactttg   64980
ggtcaggagg agacagcctg gggcgtcaga ctcctcagtc caccttgggt actccaagag   65040
ctgagacgag taaaaataac agctaacatt ttcatataac tgactagaag gcactgtttt   65100
aggtgcctgg catgtgtcaa atcatttggt ccttaccaca gccatgtgat gtagataggt   65160
atcattatga ttcccattct gcagataaga aaacccagtc ctacagggag ggtaatttat   65220
ttttatttat tgacttgagt ctcgctctgt cgcccaggct ggagcacaat ggctccatct   65280
cggctcactg caacctccca ggttctagcg attctcttgc ctcagcctcc caagtagctg   65340
ggactacagg cgtgtgccac catgcccagc taatttttt tgtattttta gtagagatgg   65400
ggtttcacca ccttagccag gatggtcttg atatcgtgac ctcatgatcc acccgtccca   65460
gcctcccaaa gtgctgggat tataggcatg agcctccacg cccagtctgg gagggtgatt   65520
tatttgccaa agattgcaca gctggtgtgt ttgttatcta tatccccaaa tcaagtagtt   65580
taaaacaaca aacgtttatt atctcacaca atttctgaaa gttggatact gggaacagct   65640
tagcagggtg attttggttc aggatctcta atgaagttac aaagatatca ctggggggctg   65700 cagtcatctg aaggttggga ctggaggatt gctttcaagg tggcttactc acatggctgt   65760
agcaggaggc ttcagttcgt tgccatgtgg acccctttgt ggcactgctt gagcttactc   65820
acaacatggc aacccaggag aaagtgcgag gaagccacat gccttttatg acctagtctc   65880
agaagtcaca cacaccatca cttctgccaa atcagaagca agtcactaag tcctgcccat   65940
gctcaagagg agaggattta ttctccgtct tttgcaggga ggagggtcaa agaatttatg   66000
gacctatttt aaaccagcac agcttgtaag tggcatagcc aggctttgat gcaagtctgt   66060
tctggggagc tggaaggtct gttctagcaa accctcatca gaatactact ccatatacag   66120
acaggtttcc cgagacccctt cccagctcct gagtctccca ggaccccaact cagaaattct   66180 tgggaattcc caaatcccca tagatggcct caaactgctg aggctcccta taaccctcta   66240
aaatgccccc agtccctgaa gtgtcctaaa atgtccccag gcttccagaa tgcaccccctt   66300 ctgagtccct gctcaatctc ccacccctca ttttgctgcc ctaggtatgc cttgatgtcg   66360
cggtgctggg agctaaatcc ccaggaccgg ccaagttttta cagagctgcg ggaagatttg   66420
gagaacacac tgaaggcctt gcctcctgcc caggagcctg acgaaatcct ctatgtcaac   66480
atggatgagg gtggaggtta tcctgaaccc cctggagctg caggaggagc tgacccccca   66540
acccagccag accctaagga ttcctgtagc tgcctcactg cggctgaggt ccatcctgct   66600
ggacgctatg tcctctgccc ttccacaacc cctagccccg ctcagcctgc tgataggggc   66660
tccccagcag ccccagggca ggaggatggt gcctgagaca accctccacc tggtactccc   66720
tctcaggatc caagctaagc actgccactg gggaaaactc caccttccca ctttcccacc   66780
ccacgcctta tccccacttg cagccctgtc ttcctaccta tcccacctcc atcccagaca   66840
ggtccctccc cttctctgtg cagtagcatc accttgaaag cagtagcatc accatctgta   66900
aaaggaaggg gttggattgc aatatctgaa gccctcccag gtgttaacat tccaagactc   66960
tagagtccaa ggtttaaaga gtctagattc aaaggttcta ggtttcaaag atgctgtgag   67020
tctttggttc taaggacctg aaattccaaa gtctctaatt ctattaaagt gctaaggttc   67080
taaggcctac tttttttttt tttttttttt tttttttttt tgcgatagag tctcactgtg   67140
tcacccaggc tggagtgcag tggtgcaatc tcgcctcact gcaaccttca cctaccgagt   67200
tcaagtgatt ttcctgcctt ggcctcccaa gtagctggga ttacaggtgt gtgccaccac   67260
```

```
acccggctaa ttttatatt tttagtagag acagggtttc accatgttgg ccaggctggt    67320
ctaaaactcc tgacctcaag tgatctgccc acctcagcct cccaaagtgc tgagattaca    67380
ggcatgagcc actgcactca accttaagac ctactgttct aaagctctga cattatgtgg    67440
ttttagattt tctggttcta acattttga taaagcctca aggttttagg ttctaaagtt     67500
ctaagattct gattttagga gctaaggctc tatgagtcta gatgtttatt cttctagagt    67560
tcagagtcct taaaatgtaa gattatagat tctaaagatt ctatagttct agacatggag    67620
gttctaaggc ctaggattct aaaatgtgat gttctaaggc tctgagagtc tagattctct    67680
ggctgtaagg ctctagatca taaggcttca aaatgttatc ttctcaagtt ctaagattct    67740
aatgatgatc aattatagtt tctgaggctt tatgataata gattctcttg tataagatcc    67800
tagatcctaa gggtcgaaag ctctagaatc tgcaattcaa aagttccaag agtctaaaga    67860
tggagtttct aaggtccggt gttctaagat gtgatattct aagacttact ctaagatctt    67920
agattctctg tgtctaagat tctagatcag atgctccaag attctagatg attaaataag    67980
attctaacgg tctgttctgt ttcaaggcac tctagattcc attggtccaa gattccggat    68040
cctaagcatc taagttataa gactctcaca ctcagttgtg actaactaga caccaaagtt    68100
ctaataattt ctaatgttgg acacctttag gttctttgct gcattctgcc tctctaggac    68160
catggttaag agtccaagaa tccacatttc taaaatctta tagttctagg cactgtagtt    68220
ctaagactca aatgttctaa gttctaaga ttctaaaggt ccacaggtct agactattag     68280
gtgcaatttc aaggttctaa ccctatactg tagtattctt tggggtgccc ctctccttct    68340
tagctatcat tgcttcctcc tccccaactg tgggggtgtg cccccttcaa gcctgtgcaa    68400
tgcattaggg atgcctcctt tcccgcaggg gatggacgat ctcccacctt tcgggccatg    68460 ttgccccgt gagccaatcc ctcaccttct gagtacagag tgtggactct ggtgcctcca     68520 gagggctca ggtcacataa aactttgtat atcaacgagc ttctgtctcc tcttgtctcc     68580
ttttagctgt gatgtggccc cattccctgg caattcagtt cccccatcag aaaaaagaag    68640
ggcttggtag ggtcttggaa ttctgtcctc actagagagg gtagaaatga acacacagat    68700
agacaaaaag acatacaagc aaagagatgc aggttctcag aaaccccag tgaggaactg     68760 gcatacagat ccaggatcac agacacacac acacacacac acacctgttc cgccgcaaac    68820
taacagacac atgaattaat ggacacaccc aggaggacct ggtcacaaat acagagactg    68880
aaactcagac gcatagagta acacagacac acagaattac acagacacaa gcatatttac    68940
aaacatgctc aggcagatac ccgccacgaa taggaagaga cacagaccta gagtcaagtg    69000
acacaaatac tcaagagaca tgtagagtac aacaggtact cacaaccccg aacgttcaga    69060
ctgacataga aacacaggca cagaacacct ccgatcatca cggacccaca aagggcctcc    69120
agcgaagacc agcccaccgt gtctggcacg cactcgcgag cgggcgttcg cgggtgtggc    69180
cggcagcaaa tggagaaacc cttggcagcg cccggacgcc ctccagtggc ggctcctgag    69240
aaccggggac agttcaatcc gggccacaaa cttttttaga acaaatcatt gtgggaagct    69300
gggaggagag agagagagag gaagtcggac gtgggcgagg ggcggggtgt ctggactgga    69360
acctctgggc ccacgtgagt gtctgtcccg ctgctgagtg ggtgctgtgt gtttgggttg    69420
ctgtagtgtt cgcttgtagt gcaactatcc tgtgttatct ttattattcg atgccgcctg    69480
cctctgcgga ccgtagtggg cacatctaca ctgcagcggg gtgccttacc caaagcagat    69540
cggaattggg gccgggcgcg gtggctcacg cctgtaatcc cagcactttg ggaggccgag    69600
gcgggcggat cacttgaggt caggagttcg agaccagcct ggccaacatg gtgaaacccc    69660
```

```
gtctctacta aaaatacaaa aattagtcgg gcatggtggc ggggacctgt aatcccagct   69720
actcggaagg ctgaggcagg agaatcgctt gaacacggga ggcggaggtt gcggtgagct   69780
gagatagagg ccctgcactc cagccagggt aacaagagcg agactccgtc tcaaaaaaaa   69840 aaaaaaaaa aaaagaacaa caaaaaaaag aactggatgc gtctgatctg acgcacgcct   69900
gtttgtttac gactgcgggg tgtgcctttg tctgagtaga gatagtgtgt ggcttttgcg   69960
ggcttaacgt gtggctcagg aggcagtggg agtctgcatc atgtatcccg attgcgtctt   70020
actcgagttt tgttttgagt tagaggcgac aggtggtgca gcgttagaca ctgggaagct   70080
ctgtggcttt tgtattcctg agcgcgaagg ttaatgacgg atccgtgggg ttgagcttgt   70140
cggtacagac gccagacagc ccgatttacg ggaacagccg attagaggat cgggagagc    70200 ggtcggtgaa cttctggatg tctttcggga ggggaaggct ctatggtcgc gtgcagagcg   70260
cccgttccac gtcaggtacc cgaccataga gcaaggcggc cgcggactac ccaagggaag   70320
gggaggccgt gtcctttaca acttgcctcc cgttgttagt ctagtttcta tagccaaacc   70380
ttcgggactc tctcaactca aaattttgct tttcctaaag gcaactgggt tccttccaga   70440
ttacgaactg tgtatccact taatctctat ttcgtatacc tcctcctaca gcgaaatttg   70500
tgaggcagtc ctctgaagca cggccaatct ggtgaacttt tcctaaaatg agccatcgct   70560
accagcttta gtgagctaag acaataactg cgattggtgg gcagattgtt ttgaaaccgc   70620
cctaacggca aggggcgggc tcctggtgaa ttcatctctt tccggtttct taaaggcaac   70680
aggaaggagg ggtttctgcc gaccctccat ttgattggtt ctagtggttt tacccgctcg   70740
gactcctcaa ggggcgggag atgtacacca atcggaatgt gtgttacaga gacacttagt   70800
ttgatgaaag gactgcgcag gaaaggccgt gggacactca ttctgagatc ttaccgttga   70860
ttggaccaaa ttgttactcc cttatttca ttggaccta cggcagccgg cgcgcgagag    70920
ttacccaatc agcaagcgct ccgcctcctg ccttttcccg ccctccgctc cggcctcggc   70980
ttcgacgtag gccaacgctt cctccccagt agctcctagg ccttctcgtg gccgttgttt   71040
tgaaaacggc gctctgattg gctaggtttc cgggcccgcg cccgttgccc cacgcactga   71100
ccaattggca ctcatgtaac atcggacgag gcacgagtga gggggaggc ggtggcggcg    71160 gccattttga gccgctgccg ccattggagt gggccccccc cctttccccc ttcgcctcct   71220
gacaggaaag gtttaagggg gacagagccc tgggaggccg ggccgggctc ggggccacc    71280 ccggggccc gggccatgga tgtgcgccgt ctgaaggtga acgaacttcg cgaggagctg     71340
cagcgccgcg gcctggacac tcgaggcctc aaggccgagc ttgctgagcg gctgcaggcg   71400
gcgttggagg ccgaggagcc tgacgacgag cgggagctcg acgccgacga cgaaccgggg   71460
cgacccgggc acatcaacga ggaggtcgag accgaggggg gctccgagct ggaggggacc   71520
gcgcagccac cgccgccggg gctgcagccg cacgcggagc ccggcggcta ctcggggccg   71580 gacgacacatt gtgagagtgc gcggggcggg ggccggggag cccggagcct gggccgagga   71640
aagggctgtg ggacgcggga gtccagcgcc tgaggtcggg gagacgacct gaggatcggg   71700
ggatcccgct acccgccgcc gaaaaggatc tgggaccag ggcccagca cgaccggagg     71760 gtggatcctg acactcagtg caggggggac actgggggag gggcctctgg gtttcggagg   71820
tgagggacgg gggtggcggg gaggattccg taccgtaggg atcggagacc ggaaactgct   71880
ttctggagcc gaagagagtc ggaagaacaa gaggttttcc gtttggttg ggagggtct     71940 cgaaaatggg gatcctaggg tacggagctc cgtgggcttg gcggtcgtgc tagcccagtg   72000
tgtgggctgg ggggtgggga gccgtgtttc cagggtgggg aaggaatgtc caggtgtgcg   72060
```

| | |
|---|---|
| gggctgcgag agttctgagg aaggaggatc ctggaatatg ccgctggatg cgatcctggg | 72120 |
| cgttctccta tttgggtacg ggggtgggtg ggagaggtgg aggcgctggt gtctgtggct | 72180 |
| ggggagggtc ctaatggact cagtgctttg gagtttggct agtgagcatt taggggctgc | 72240 |
| gggagattga actaggggc accccatct ctcttccggg gctggaaggc cacccttgaa | 72300 |
| gcaggcacag cctggacatt aggtgctggg agatctgggg actttctggt tggcttctag | 72360 |
| aagaggtata gggagccctg tgtccagag gctggcgggg gagaggatgc tttcctggac | 72420 |
| aaaggatctg ggggtctaga gctaagaaaa ctgagggcaa ataactcttg aggctgctgc | 72480 |
| tgactggtct ggagctaact gtggggtttt tggagaacag agggtagctg ggggtgggat | 72540 |
| gggggcagat gagttggtaa cattccaagt ggatgaaata tgtggcggga gacagaggat | 72600 |
| cctgtgtcca gcacaggagt acgtatctgg cttagcgaat atggggaggg gggaggccgt | 72660 |
| agggagcaaa gagaaagaaa cctgttgact tcactggagg cctcagagtg gagtgtgggg | 72720 |
| aatgtttctg gacctgagcg tctccaggag aaatctcgac ggttcccaga agcagttatt | 72780 |
| tgtgtaccca gggagtgggg gccctcgggg agcagcacgg aactcttcat cagccaggag | 72840 |
| ctgtgactct gggaatgggt tcgggtagac ctgcggttgt ctgaggagag gaaaacctga | 72900 |
| tatgggacgg cgtgaatctt cagttagaaa aaaagcagct ttcgggccga gtgcagtggc | 72960 |
| tcacgcctgt tattccagca ctttgggagg ccgaggcggg cggatcacga ggtcaggagt | 73020 |
| tcaagaccag tctggccagc atagtgaaac cctgtctcta ctaaaaatac aaatattaac | 73080 |
| cggatctggt ggtgtgcgcc tgtagtccca gctactcggg aggctgaggc aggagaatcg | 73140 |
| cttgaacttg ggaggggggag gttgcagtca gccgagatta cgccattgca ctccagcctg | 73200 |
| ggcaacaaaa gtgaaactcc gtctcaaaaa agaaaaaagc agctttcttt ctctttttt | 73260 |
| taaatacaga tgggggtct cgctatgttg cccaggtgg tcttgaactc ctgggttcag | 73320 |
| gtgatctcac ctcggcctcc tgaagtgctg ggattacagg cgtgaatcac tgcaccaggc | 73380 |
| ctcagggcag cttctagta ggactgggaa atggggggac tggaaaggtt aaggagtaag | 73440 |
| tagaagggat tctggcgtaa gagtttgtgg agttttctg aaaagagggc accctgggac | 73500 |
| ttggggctaa ggggataagg agagaaatga ggtaacagaa gagacaggat ttgggggttgg | 73560 |
| aattggatac ttgttcataa gagaatttcc cggaggggagg agtgtggatt tggggtaggc | 73620 |
| agtggcctag agattatcga ggacccaggt gctggaaaga ggacttccca ttgcagagac | 73680 |
| ttgtgaagaa aggagtgggc ctgtgtgtgt gtctagagca ggagggatcg tggcaggaat | 73740 |
| gcctagcaag aaagggtagt gggttagtag tgacctggtg gtctgggcag agagtcatct | 73800 |
| ctgagaggaa agcgaattag gtgctttgga gcgtagactc tagactaaga cagacttcgt | 73860 |
| ttcaaatctg gcttaaagat attggcaagt cacttcacct ctgtgggcct ggtttcctta | 73920 |
| atgtgtaaaa tggggttaat caacaaatag tgtgttcaca gcccctccaa cccctgaggg | 73980 |
| gtgttatgaa tgagatcaca tgtgaaggc ttatcactgg gcctgccttt tatgagaaga | 74040 |
| gggatgtttt agagaatgga gaaggaccct agaattatag cttctccagg aggggctgcc | 74100 |
| tctgtgaaca caggagagag atgctgggga aagaggctt tgtgggaaga ggagcattgt | 74160 |
| gcttggagcc tggaagcagc agaatagttt gaaagggccc catattccaa ttaaggagat | 74220 |
| aatgctattt cttcctctct cccttacttg ctacaacaaa gtcctttgag ccccttcat | 74280 |
| gcctccctta agccctcctt caaccttggt aaacagaccg gtagcaaacc acatgacctg | 74340 |
| tgactttcct cccttttgggc tgcacctggt ttgtgcccag atgtatttat cctctgagaa | 74400 |
| ggaatccgat cagttagcaa gtggcagaat agtctctcct tcccttggt tctggctcac | 74460 |

```
ggctcctggc atagccactg gtagggccct tggggcccta actgagagct agcccctggg   74520
gaggagagcc tgtatgctgc ccatcctagc tttctaaagt tctctctggg tttggctgca   74580
aggttcttga gggaatttct ggttttagtt ccacctctga gctttcacac gtgttatccc   74640
aaccccagta acattctcca ttctcatcac tgagtcatta cctgtgtatc ctttgaatca   74700
aggcttatct gttattttcc aggtcccttt cttcattcct ggtactactt tgtagccttc   74760
aacacaatca tattaaattt ttgtgtgtct ttaagatttg tctgtctcac taaactgaag   74820
gcttcagtgg ggcaagcttg tcttcagctg tatcccaggc tctggagtat agtatgcatg   74880
ccatgaatag ttaatattat tattcttacc actcttagtt gagctcctgg acctgcagat   74940
gccttctgga cgctttggtc cagggttctt catgaaccgc ccctctaatt ggccattttt   75000
aattttgttt taagatgcca tggacaatat taccaggcag aaccaattct acgataccca   75060
agtcatcaaa caagaaaacg agtcaggcta cgagaggaga ccactggaaa tggagcagca   75120
gcaggcctat cgtccaggta ggaaaataca catggttcat ctctttggat ggaaacaatc   75180
tacatggagc ctttaccccc tgcttagagc gggtcttccc agagaaactg tgcatctttt   75240
ttcttgggca gttcatctaa acattgtcac tctggcaaga attgtttaaa ggaaagatct   75300
cagtcctatt tccaagtgtt gggagagggg aggttccatg gtatctgtaa aaaagtgatg   75360
ttagtatcag ccgggtgtgg tggctccctc ctgtaatccc agcactttgg gaggccgagg   75420
caggtggatc acctgaggtc tggagttcga gaccagcctg gccaatatgg tgaaacccgt   75480
ctctactaaa aatacaaaaa ttagccaggc atggtggcag gcacctgtaa tcccagctac   75540
ttgggaggct gaggcaggag aatcacttga acccaggagg cggaggttgc agtgagccga   75600
gatcgcgtca ttgcacttca ctcagtctgg gcaacaagag tgaaactgca tctcaaaaaa   75660
aaaaagatgt tagtataagc accctggaga gttgagaccc ctagactaat acttgaatct   75720
tatttagaat cttagaatgg gggagccaga aagagccttc taagtctaat ctggtatttc   75780
tcatgttctg aagattattg tttcagggga tattattagg ggattctcag aaaagggttc   75840
cttagccaaa tgtgtctgga aactgtagca tgtgctatat cgtctcttgg aaattcactg   75900
tgcttgttag aacattaaag gctctgagaa gtccagaatt taaaaaaaaa aaagaaagt   75960 gtgtgtcagg cctcaggcca ggtgcgctgg ctcataccta taattccaac actttgggag   76020
gccaaggtag taggatcatt tgagaccagg agttccagac cagactgggc aacatagtga   76080
gaccccttct ctacaaaaaa tttaaaaatt agccaggcat ggctatgact gactacatgc   76140
acacacctat agttaaagct actcaggaga caaaggtagg aggatcactt gagcccagga   76200
gtttgaggct gctgtgagct atgattacac tactacactc cagcctgggt gacagtgcaa   76260
gaccctgtca cgaaaaaaaa aaaaaaaaaa aaaacctaa aattaaaagt aggttagaac   76320
acagtggctc atgcttgtaa tcctagcgct ttaggaggcc aagtcaggag gatcacttga   76380
gcctaggaat ccaagactag cctggcaaca tagtgagacc cctgttgtct ttagaaaaaa   76440
ttaaaaattg cctgagcatg gtgacatgct tgtagtccca gctactcaga agactgagtc   76500
aggaggatca cttgagccca ggagttcaag gctgcagtaa gctatgatcg tgcacggcac   76560
tgcagcctgg gcgacaggaa gaccttgcct taaaaataaa aacaggccga gtgcgatggc   76620
tgttacatgc ctgtaatccc aacactttgg gaggctgagg tgggaggatt gcttgagtcc   76680
aggagttcaa gaccagcctg ggcaacataa ccctgtctct ataaaaaata aaatattac   76740 ctgagcatgt tgcacaatc ctatagcccc agctactctt ttttttttt tgagacgaag   76800 tctcgctctt gttcccagg ctggagggcg atggcgcgat ctcagctcac tgcaacctcc   76860
```

```
gcctctcggg ttcaagcgat tctcctgcct cagcctccca agtagctgag atttcaggcg   76920
cctgccacca cacctggcta attttttgtat tttcagtagt gacggggttt taccatgttg   76980
gccaggctgg tctcaaactc ttgacctcag gtgatccgcc cgcctcagcc tcccaaagtt   77040
ctggggttac aggcgtgagc cactgaaccc ggccaagtcc cacctactct ggaccctgag   77100
gtgggaggat cacttgagct aggaagttga ggctccatga gccatgatgg cagcactgca   77160
ttccagcctg gcaacagta agcctctgtc tccaaaaaaa tttttttttt aattaaattt   77220
aaaaaccttg tgtcttcttg ggctggtgtt gctgaaaata ttttttttaa taaaaaata   77280 gacaaaaaac cttgtgttgt atcgtttaaa cttaggattt cccaatcatg ttaagtatat   77340
gtctttacag aacaaagttc cccatgatgc caactctccc ttccctttt tttttttttt   77400 tttttgagat ggagtctcgc tctgttgccc aggctggagt acaatggtgt gatcttggct   77460
cactgcaacc tctgcctccc aggttcaagt gattctcctg cctcagcctc ctaagtagtt   77520
gggactacgg gcgtgccacc acacccagct aattttttgt gtgttttag tagatgtggg   77580 gtttcaccat gttggccagg atggtctcaa tctcctgacc tcatgatctg cctgcctcgg   77640
cctcccagag tgctgggatt acaggtgtaa gccactgcgc ctggcctctc ctccccattt   77700
tatagattga ggagttggct tgtccgatgg cagagctggg gctacaacct agcatacttg   77760
ctcccaggct agtcctcttg gttaataagc agcattcctt atcatttgtg ccttactatt   77820
tggaaagcag ggtcccacta ttgagaactg atggagcccg gactgacccc cagttttgtg   77880
ctgcttttac tgtgttgtgg cctcccagtg ccttttctta gtgtatctgg ttgattttgt   77940
ctaacgccat tctggttcat ccacaaagtt aaatccccag acatttcttg tgggtggctc   78000
agaactttac tgaatgtagg ttaaaccgca gatttgtgtc aggctctgtg agacttgtag   78060
gatcattcag ccacaggaga atattttctg tgccgttatc cacagacatt catcaggagc   78120
cctgtgtgag cccaacctat tgctgggaac cagggaagct ctcttcagga tggctgagca   78180
ccatcccagc cctagagaac caggagactt ttctgagaga tgtggtccac atgccgaagc   78240
tggggagtga tccaaaatgg tctggggttg aatgcagaaa tgagtagatg tgaatgagct   78300
tcagcatcag ggattaatgc tgtgggagaa atgaaggtag cctacatctg tggtttgctc   78360
ttggttaggc actgattcct ggagtctgcc tgagactagg acttacccgt ggtccacagc   78420
acggtatccc atcctgactt tctgttaatg gtatgactta agaggttat tgcacctatg   78480 ggatggctta accggagtga ttctggcctc ttttggtagg gtaactaaag cccgtagagt   78540
tagctgcagc accacagtac cctgttgaat tcatcctctc cccctccctt gccagactga   78600
agaagctttg taagaactaa ggcagagagg ttctttggga agagaaattg gagaatttag   78660
ggtcatggta tctcagatcc taaccctgtt ctccagtatg gccttcttgg ctggctcagc   78720
aggcttctgt tgaactcagc aagctgcctg tgcccagccc ttcatcactg tagtgaggat   78780
cctgctcaca tctctcaagg gaaaagggac cagaaaagtg atagctgggg agcttgcgag   78840
tgtcttgacc atctgaattt gtcttgacaa tagaaatgaa gacagagatg aagcaaggag   78900
cacccaccag cttcctcccg cctgaagctt ctcaactcaa gccagacagg cagcaattcc   78960
agagtcgaaa gaggccttat gaagaaaacc ggggacgggg gtactttgag caccgagagg   79020
ataggaggtg ggtgtatgag gcagcagtca cccttgctct ggtaggtttc tatatccata   79080
gcctcgtgct tgctggggac atttgcacta acctagaggg gctgagtaaa gattccctct   79140
gctttcacac tcttcctgtc ccttcccgta cttgctacca gattcagctt tcctaaactt   79200
ttggtccttc ccccagttcc tcccttctta cctgcagggt aacttctaaa tatcttagac   79260
```

```
tttcacgcgt gagatgccag cctgcctgtt ctgtcctttg ccttactgcc cctgcagtca   79320
gctgcttgat acccgtaatg aaagaaatat ctgtttccta acactactcc caaatacaca   79380
tcctcttccc attcatccac tcattcagtc agttctcaca gtgctgtcac gaagtgccca   79440
ctcttgggct ggacactagc aacatacaga tggacagtgg gttttgcctt ctgttgttcc   79500
agtgtgggga ctcagacaca tacactagta agccacaacc tctgaggtga gtagtcagga   79560
tgcaggtgag tttcaggagt tcagaagagg gagcagcctc tgctttggtc atttcccttc   79620
cctaacaagc ccttccctcc tttccctcca gaccaagtcc ttcccttccc tccttccttc   79680
cttcagttcc tgtctgaagc cttttgcaat tatgaaaact aggaatggcc actgtactca   79740
tctggactag tcatctgaca ttctatttcc tatctggcgg agtccacctt ctaactagct   79800
tgttactgtc tgagacaggg cctggatctc acaggctatg atttaagtta ggacatggat   79860
cccacctcat atggggttct tccactgcct cccacagagc agaagcctgg aagctactta   79920
ctgatggaga gcaaaggaag aacactcgct ctgatcctgg gctggcaggg aaagtttcct   79980
agaatggact taacatgtga tgagcacagc tcatccatgt tagccctggc ctggcgaggc   80040
cagaggggcc ctccaccaga gggaagcctg ctgctgggag agtcagcagc caaatgggca   80100
tgggctcccc atctgtgcat gcagtgcact gcgaccaccc agactgtcca ggcaggaccc   80160
tgagtgttag attctacctt tctacccttc ttcctcgttc ctgtacagca gaaaccaaca   80220
gtgttaagtc cctttttag cgttttggta ggaaaatgaa tatcgtttat aatttaggac   80280
actgaaaaaa atgggtcatc tcaaattctt acagatgtag gattttaaga agcctggtac   80340
atggatagat agtaattatt gggatttata taggctcttg cacattcccc ttcctggcca   80400
gcacccttt gggataccac agcctccaaa cagtaacaga gatcagtgtg gaagtggttg   80460
tcaacatgca gagggtatgg atcagaatct ttgggtgtaa aaaagagtg aaaaaattcc   80520
ctaaatgatt ctgatgcccc ccttcagcag agcatgcctt cttcaatccc tgtctccacc   80580
gtaggagttg acggtcattg ctctccttgc aaggatgtag ggtttcagag ttcttttgcc   80640
cacctctgtg gaaggaaatg gagattcagg aagcagtctg gaggccactc atagattaca   80700
gcagaacatt cattttcttt cctttgtgct catccattgt tcttgtatga cttaaccct   80760
gtttctaata caggggccgc tctcctcagc ctcctgctga agaggatgaa gatgactttg   80820
atgatacccct tgttgctatt gacacctgta agtcttggga gtgtgcatct aattctgcct   80880
tacagtcagt atggggaaat tgtggtcttg accttcacca gaatccctgc tgggcaccgt   80940
ccaaagacat tgttagtcca catgtgagac acggcttagc tctggagcaa gagtactggt   81000
ttggaggcaa aagacctact cccaactcta gcagtgggac cctgggcaag tcattctact   81060
tctctgagct tcccttcagg aaggagtaaa tctgctgtac taacctcaga ggattttcag   81120
ggagactcct cagtggatat aggagcaatc tggaaaaccc tgaaccgccc tgtacacaca   81180
ggggttgtca tctaatcagg aagggaatct gagtgcagct ggggaaactt aactctttga   81240
caaccagttc ccgtttccat cagctgctca agttcctggt gaaaccaatg ccactgtgtc   81300
ctgtgaggca ctaacctggc ccgccctgct gtctgtcctc cagttcagtt ttcttttccac   81360
tggataagtg gctttcacct tcactgtgca tctgagcatt tggaggaatt attataaagg   81420
tccttcgct cagacctcct agtcaagagt ctaagtggtc gagcctatga atctaaattt   81480
ttacatgcac ccagaagccc aatcaggtct gagaacactg cacttctcaa cagagcagaa   81540
gataagcagc aatttattca tctatttcta cagaagcttc tgtttataaa gcactggcta   81600
catgctttag taagagataa aaatatacac aatctctaat atcacaagct ctcgaaaaca   81660
```

```
acatctaccc agagtagagg taaacattgt ttaaaaagtg ttgggtggca gtggttcatg    81720
aggcagcgtc tagatgaaat gcaaatgtac agatcatgac ggtcagcctt tagagaaagg    81780
agagcgcctc atgggaggga tggtcaggaa aggctttctt ggaggcgtga ctggctcctt    81840
gaatattgag aatattgaga agggtaagag caacagtagg agagtcctag gcccatgaaa    81900
ggaattagga gcctatgggg cacctgggca ttggttcctg ggtggcaggt gtggatcagg    81960
gtcagatccc tgtatagcta ttggaaacag aagtccggtt cccaaattga tagaattacc    82020
acagagggcg gtaggaatat atggtggtgg tgattaacct ttttgtattc taaaaactag    82080
tttgagcctg ggtaacatgg cgaaaccctg tctacgaaaa atataaaaat caccctggca    82140
tggtggcata tccctgtagt cccagctgtt caggaggctg cggtgggagg atggcttaag    82200
cgcaggagaa cagaagttgc agtgagccga gatcatgcct ccgtactcca gcctgggtga    82260
caaagcgaga ccttgtctca aaaaaaaaaa ttaatttgaa actgctgagg atatggaccc    82320
tatccctagc aaatacacat ccccaccaaa gacatgtgtt gacaatttct gaggataccg    82380
ctgaagcccc atccttggat cccaccagat aaagaacccc agttcctctc tgaggtcata    82440
caggccaatt tgcaatactg cacatcctcc ctactcaaag ggagagaggt tgagggtgt     82500 gctggttcct tttgaaactg cccccatgat gtgttcactg tgtactcctg gtcagcactt    82560
ggggaagttc cctctgcctg cttctttctt aggacttcta aaacatcagc caggccgggc    82620
gtggtggctc acgcctgtaa tcccagcagt ttgggaggcc gaggcaggtg gatcacctga    82680
ggtcgggagt cgagaccag cctggccaac atggagaaac cctatctcta ctaaaaaata    82740
caaaattagt caggtgtggt ggtgcatgcc tgtaatccca gctactcagg aagctgaggc    82800
aagagaatca cttgaacccg ggaggcgag gttgcggtga gccaagatcg caccattgca    82860
ctccagcctg ggcaaaaaga gtgaaactcc gtctcaagaa aacaaaacaa aataaaaaca    82920
tcagccaact gtgggcattt tccttcacag ataactgcga cctccacttc aaggtggccc    82980
gagatcggag tagtggctat ccgctcacaa ttgagggctt tgcatacctg tggtcaggag    83040
cccgtgccag ctatggggtc agaaggggcc gtgtatgctt cgagatgaag gtgagtagga    83100
gcaagagaag gggaagggac agagaagtcc atccattgta atatcctgat accagccacc    83160
ttggtcagag ctgcaactgc aaaagagatt ggattgtgca ataccatgtc caagcagaca    83220
aaactgtgat gaactcaaga caactacatc attgctaaat atcatatcag aaaagcaggc    83280
caaccatgca ttgcttcatc aagcagatat ttccttggtg agatttgacc caggtattat    83340
gtagtcaacc agtgtagtga tgacatgttt gtagaactga gaaagaagt tgtttggaag     83400 aaaagtgatc tagaaagaat agactcagat gtcacttatt aaagggaggc cagagggaga    83460
acagggcaaa gaactgccag cttaggccag cctctgctgt catctctcca cagttccatg    83520
tcaagttatg tttatgaaaa taatagatgc tcatgtttaa caaaagttca gacagcacag    83580
aaaagtacag gataaaacag gttattctcg ccaggtgtgg tggcttttgc ctgtaatccc    83640
agcacttttg ggaggccaag gcaggtggat cacaaggtca ggagttcaat accaaactgg    83700
ccaagatggt gaaaccctgt ctactaaaaa tacaaaaaaa ttagccgggc atggtggcgg    83760
gtgcctgcaa tcctagctat tcaggaggct gaggcagaga attgcttgaa cccaagaggc    83820
agaggttgca gtgagccgag atcacgccac tgcactccag cctgggtgac agagtgagac    83880
tctgtctcaa aaaaaaaaa caaaaaaaca aaacaaaaa aaacaaaaca ggttattctc      83940
atgtcctctc agttcccatc ctaccatcct actccctgga gggaacttct gtgttaacaa    84000
tttcttacct gtggtttgtg tatccaaact tactgatgat agctaataag tatagagctc    84060
```

```
tttgcatgca caagatacag caccaagctc tttacatgga ttatctccat taatcctcac   84120
agtaccatct ggaaacaggt actgttagcc ccagttttta gaggtagaag ctgaaacaca   84180
gagggttata ttttattgac cacgacacca ttgatgtaag ttgtgcatta ttttatgtac   84240
ctctcataga gaaacactgc aacaaaataa actacgcagt gttttctttt tttgtttgtt   84300 tgttttttg tttttgagat ggagtttcac tcttgttgtc caggctggag tgcagtggcg    84360
cgatctcggc tcactgcaac ctctgcctcc cgggttcaag caattatcct gcctcagcct   84420
ccccagtagc tgggattaca ggcatgtgcc accctgcccg gctaattttt gtattttag    84480 tagagatggg gtttctccat gttgatcagg ctgggcttga actcctgagc tcaggtgatc   84540
tgcctgcctt ggcctcccaa agtgctggga ttacaggcgt gagctgccgc acccagcata   84600
cgcagtgctt tctcatcaca tttattgtaa aatggatcct gatttcagag attttaaaat   84660
gtgtgtctga aaagccagtg aggccacagg tagatacgga tattcggcag tctagtcttt   84720
taatacgaaa ttaagtcaga aggcttttt tttttttta acttaatact gtatcttgga     84780
cattttccca tagcagtaca ttagcccaat gtactgcttt gctccttgtt ttttgtttgt   84840
ttgattgttt gttttgtttg ttttgttttg ttgacggagt ttcacttgtt acccaagcta   84900
gaatacagtg gcgcaatctc tgcttactgc aacgtctccc tcctgggttc aagcgattct   84960
cctgcctcag cctcccaagt agctgggatt acaggtgcat gacgccacgc atgcctaatt   85020
ttttgtattt ttagtagaga cggggtttca tgatgttggc caggctggtc tcgaactcct   85080
gacctcaggt gatccaccca ccttggcctc ccaaagtgct gggattacag gcttgagcca   85140
ccgtgcccgg cctactttgc tcttttttaac tgttgcatca tattttgtgg catggatata   85200
ccataatcag tgctttattg atattttttc tgatgttaaa atatatatat atatatat     85260 gtgcacatat atacatccaa tgctgcacag aatgttgcat atacaaatac agtcacacat   85320
acgtagacat acttgtccac atattagtgt atctatagga tgctgagtta tagagcatgt   85380
gcatttatgg ggttttgttg ttttttctt ttaatgtttt tgtaaagatg gggtcttgct    85440
atgttggcca ggctggttcc taactcctgg cctcaagcca tcctcctgcc ttggcctccc   85500
aaagtgttgg gattacaggt gtgagtcacc atccccagcc atttacagtt ttgatagaga   85560
cttctagatt gccctctaaa gacactgtaa cagtttatct ttctactaga tgttacaaga   85620
gtctcttaaa ctaaaacata accgtatttt gaaatgcctg tctctgtggc cctgtactct   85680
actgatccct ttggaggccc tggcttcgat tcggttcaac aggcttttca gagctgctta   85740
aacgcttctt ctccagcaag aaaagccatt gctattttt aatgcctgat atgcttccct    85800
cctatattgg ctcataacct acggcctcca gagaagcaac cctgagccct tttgtcctct   85860
ttcctcagat caatgaggaa atctccgtga agcaccttcc gtctacagag cctgaccccc   85920
acgtggtccg tatcggctgg tccctggact cctgcagcac ccagctaggt aaggaggggt   85980
cagctatgca gtccagagaa tagagtgact gtccctaccc ttggattttc aaggctccta   86040
agcttccttt tccagcgtca gacttagaat agaactaggc tgaagtggaa caggtacaag   86100
gattaggtat atgccactgt ctctgtcatg ctgtattcaa ctgagaggac tatggtcatg   86160
aaacaactgt tctgtgaaga atcaattctt atccttcatc ttttaggaga gggtccaaaa   86220
ttctctttag gaatctattc cctttctgta aaaggatca gtgtctcctg cccttaaacc    86280
aagctgctga taagttccca agctccatta agttctgtct gtattttctg tccggagcct   86340
aacctagagg aaaaagggga gcagagacca gtgaggccag ggctagttgg gagaggggca   86400
ggggctgcct attgaaaggt tttgaatttt gcgggtcccc aggcttcaat gaccttctgg   86460
```

```
tcccaagtga ctgattattc tgaccaatgc tgacacctcc tgccttccgt ttatgatcat    86520
acaaacgttc caattatgaa aataatatgt gttgcgtata agaattcagg ccatacagaa    86580
agggaaaaat gaaaatcctt cctaaacctg tgagagaaac taaccaatgt taacattcca    86640
tttgtagtct tctggacatt tattttttg tacatcttta aactggatca cactaggact    86700
actttgtata gccttgtttt aatgtatgat gggcatattt ttgtaaataa ctgcagcttt    86760
ttgactactg cataattttc cattttatag ttgcattatt taacaagtcc ccttctgtag    86820
ctcatttaaa cttattgcaa attttgctg ttttaacact tgagccatta tcctggtcca    86880
taattgcctg accacttaag actaatcttt aaaaatagat gatattctca ctcacaagtg    86940 tttgttaaa aaatatgttc acatggactt agagagtgga ataatagata atggagactc    87000
agaagtgtta gggggtaaca aggtggagga ggatgagaaa ttggttaatg ggtacgatgt    87060 acattttta ggtgatgaac accctaaaag cttgaccact atgcaatctg tgcatgtaac    87120
agaattgcac atgtaccca taattggta cctcctcaaa aaggtagata tgttagcacc    87180 aaaaaaaaa agtatacagt tttcatttcc atatgtgtta gcactttta tttaagactc    87240 ataagtcatc tcatcttatc tctgtctccg ttttgagatg taggtggtgg cagttgatag    87300
ggatggggaa acagcccagg aggtcaagca ccatatccag ggtcacatag ctggtttgta    87360
gcagaacgag ccctggcatt catgcttgtc ggcccctgct tttctaacag catactcttt    87420
gggttctgcc cggaatctct aactcaggtg tcagccagag cccttgggat ctctcagtca    87480
tatcacttca gcacccagtt ctgtagcctg aggaaatcta gtacctttcc caggggtcag    87540
tcctcatggt ctccaggagc aaaatccagc cccttcactg atttctacca caagtagact    87600
ggactgaata ttgggtgtca caaggaaggg ttgcatctca gcatacagcc attctcctcc    87660
atcccaactc ctgtcttcct tcctcccttt cttttcaaat tctcccctct gtgcagagtt    87720
attcagttga gctcctactc ccagactgga caatgaaacc catcaagccc tccaagttct    87780
acatcattaa gggcttcctt tcacccttcc ccaccccat tttaaaaagg catctgatta    87840
ataaaactag taaagaaaat gatttttttc ttcaaaaata aaagtatgtg gcagccattg    87900
aggctgttat gaccatcgca ggtttaacct gcctttgcct atttcttccg tcaggcgaag    87960
agcctttctc ctatggctat ggaggcactg ggaagaagtc caccaatagc cggtttgaaa    88020
actacgagga caagtttgca gagaacgatg tgattggctg ctttgcggtg agtgctagca    88080
gcctgtggga gttggcagaa ccagatgttg ggctacagac ttcttttca ggatacctct    88140 atccattgtc tgccccatat ccagccactc tcgccatact tctttgtctc tgcttgacag    88200
actggaatgt ttactgtcat tttgtgggaa attctgtcat tccatctcct ctggtcttgt    88260
gtgcaaagtt ttcagatgac accctgaaga ggtttgggga cttcaggtgt gcatagcctt    88320
cctccgttcc taggtaccag agtaacattt tctaaacaaa cctaggaatt tcttatcttt    88380
cattgctagg aaatagcctg tctgctcctg aaggcagtgg tattggctct tgccccatgt    88440
tggcatcatc ttatcccaaa acttctccct ttcttcatct cacattggtt gagccaggct    88500
tcctacaatg cactgccttc tggaagagta gagatgatgc aaaacagaac agctgttgct    88560
gccatacttc agtctttgag aacagtgacc agcagtcacc ttgctgtgca gtatggctgt    88620
cagctctggg ctggactccc tggacccagt tatgttcttc cattcaagcc ctgggcaatt    88680
tacccttctt gttttcagt tccctctaaa tgagaatctt tgcacctacc tcagaatttt    88740
gtgtggagtc attaagttaa tccattaaaa gcacttataa taatgcctga cacacagtaa    88800
gtgctcagta aataccactt aatactgtta acattaggag ttataagaga tgtttgtaaa    88860
```

```
atgtgccgta aggcccccaga ggaagtgacc acctggatgg attcatcctc tgaagcttat    88920
tcttttgcct tccttcatat ttgtacacat gtactcttcc ttcttctttt ttatttattt    88980
atttattttt gagatgagtt ttttgctctt gttgcccagg ctggagagca atggtgcgat    89040
ctcggctcac cacaatctcc gcctcctggg ttcaagcgat tctcctgcct cagcccctg     89100
agtagctggg attgcaggca tgcaccacta cacccaacta attttgtatt tttagtagag    89160
acggggtttc tccatgttgg tcaggctggt ctcgaactcc cgacctcaga tgatctgctc    89220
gcctcggcct tgcaaagtac tgggattaca ggtgtgaacc accacgcctg gccccttctt    89280
cttttttaa  ctttgagata aattcaaact cggaaaagct tgagaataaa gaattctcac    89340
agggccttat ccagattcta acatttgcca catttgcttt accattttca tgtttatggt    89400
gtacatacac atagagagtt aactcttcaa caatgtgttt gaattgcact ggttcactta    89460
tgtgcatatt ttttctttt  tttctttttt ttttttttg  agacggagtc tcgctctgtc    89520
gcccaggctg gagtgcagtg gcgggatctc ggctcactgc aagctccgcc tcccgggttc    89580
acgccattct cctgcctcag cctcccaagt agctgggact acaggcgccc gccactacgc    89640
ccggctaatt ttttgtattt tttttttagt agagacgggg tttcaccgtt ttagccggga    89700
tggtctcgat ctcctgacct cgtgatccgc ccgcctcggc ctcccaaagt gctgggatta    89760
caggcgtgag ccaccgcgcc cggccatttt tttcaataaa tatattggaa acttctttgg    89820
agatttgcaa caatttgaaa caacagacat agcctagaaa tatcggtaag attaagaaaa    89880
agttaagcat gtcatgaatg cataaaatat aagtaggtac tagtctgttt catcattttac   89940
tagcataaaa tatccacaaa tctattacaa aaagttaaaa cttatcaaaa cttgtgcaca    90000
cagactctac atggtaccat tcacagttga gagaaatgta aacaaacagt acagtattaa    90060
atcataactg ttttttatttt attttttga  agacagatta ttttctctgt cacccaggct    90120
ggagtctcgt ggcgcgatct caactcactg caacctccgc ctcggggtt  caagtgattc    90180
ttgtgcctca gccacccgaa tagctgggat tacaggtgtg caccaccacg cctggctaat    90240
tattgttttt tgtttgtttt gttttgagac ggagtcttac tttgttgcct aggctggagc    90300
acggtggcgc aatctcggct cactgcaacc tccgcttcct gggttcaagt gattctcctg    90360
cctcagcctc ctgagtagct gggattacag gtgcacgcca ccatgcctgg ctaattttg    90420
tattttagt  agagttgggg tttcgccgtg ttggctaggc tggtcttgaa ctcctgacct    90480
taggtgatcc acctgcctcg gcctcccaaa gtgctgggat taccaagtgt gagccactgc    90540
acctggccta atttttgtat ttttagtaga tgggggttt  caccgtgttg gccaagctgg    90600
tcttgaactc ctaacttcaa gtgatctgcc cacctcggcc tgcgaaagtc tgggattac    90660
aggtgtgagc caccaagccc agccaactgc ataaaattaa ccagcgcata ctgtaataat    90720
tttgaagcca cctcctattg ctattatggt gagctcaatt gttgcaagtt tctacttaaa    90780
acactgtgtg tcatacatct tcacgtgagc agttctttc  ggtaaattgt gtatcacagt    90840
aaaaagtgat ctcgcaattc ttgtgtattt tttaatcatg ttactgcaat atcataagcc    90900
ttgagtagca ccatgggatc catacgaagt tccactagtg atgctggaag tgttgctcag    90960
aagcagaaaa aagttatggt attacaagaa aaatttgaat tggttgatat gcactataga    91020
ttgaggtctg cagctgtagt tgcctgccat ttcaagatta atccagcata aggaccactg    91080
taaacgaaaa aaagaaaaaa ttcccgaagc catcactact gctgtgctag caggtgctaa    91140
atccctgcac ttttttatcat atattgacaa tgcaaggccg gacactgtga ctcacacttg    91200
tagtctcagc actttgggag gccaaggtgg gcagatcgct tgagcccagg agttcaagac    91260
```

```
cagcttgggc atcatggtga aaacaaactt ttaatatttt ataaacataa aaattaactg    91320
ggttggtgat gcacgcctgt agtcccagat aggaggctga ggatcgcttg agcccaggag    91380
gctgcagtgg gttatgattg cccactgca ctccagcctg gatgacagaa tgagactctg    91440
tctcaaaata aataaataaa actgcagctt ttgtgtaggt acagagttgc tataagaaag    91500
gcatacctgc cgggcacggt ggctcacgcc tgtaatccca gcactttggg cggccaagga    91560
gggcagatca cgaggtcagg agatcaagac catcctggct aacacagtga aaccccgtct    91620
ctactaaaaa tacaaaaatt agccgggcgt ggtggccagc gcctgtagtc ccagctactc    91680
gggaggctga ggcaggagaa tggcgtgacc ctggggaggcg gagcttgcag tgagccacga    91740
ttgcgccact gtactcccgc ctgggtaaca gagcaagact ctgtctcaaa aaaaaaaaa    91800 aaaaagggca tacctatagg ctataattca agaaaaagtg aagtcattat atatgacaac    91860
ataaagcaaa agaaagggga aagatctaaa gctgctgaat ttaatgccag caaaggatgg    91920
tttaataact ttagaaagag gtttggctta aaaattcttt acaggaaagg cagcttctgc    91980
caacgaagag gcaacaaaca agttcccagg catcattaag gtataattga agagaaggga    92040
tatctgcctg aacagatttt taatgccaag tgcagtggta tgatctcagc tcactgcagc    92100
ccccgcctcc ccggttcaag ctattctacc tcagcgaccc aagtacctgg gattacatac    92160
ttgcgccacc acacctagct aataatttgt attttttgta gagatggggt ttcgccaaac    92220
tcctgagctc aagcaatccg ccctccttga cctcccaaag ttctgggatt ataggccgga    92280
gacaccatgc ccagcaaatt ctgtcagatt gatgatcagg actgttactt ataaagctgg    92340
taactctcaa accctaaatc ctcaacacca gttgccagtc atttggttgt acaacaagaa    92400
ggtgtggatg atgaaaatcc ttttttctaga ttggttccat tgatgctttg tttctgaagt    92460
taggaaatac ctttccaata tgtggttccc ttttaaaatt attttgatat tggagaatgc    92520
caccaagaac cccatgagtt tagtacagaa ggggtcaaag tggtttattt gtccctaaac    92580
aatgggctga cccttgaact ttgcagggat taggggcacc aaccccatg cggtcaaaaa    92640 tccacgtata gttttttgact cccaaaaact taactactgg ctgagcgcag tggctcacgc    92700
ctgtaatccc agcacttcgg gaggccaagc tgggtggatc acttgagccc agaagttcaa    92760
gaccagcctg ggcaacataa ggaaaccctg tctttaccaa aaatagaaat aaaaattagc    92820
tgggcctggt ggcacacgcc tgtggtccca gctactcagg agactgaggt gagaaaaaaa    92880
aaaaattaat agcctactga taacataaac agtcaattaa cacataggct agtgtctaca    92940 attttatgc actcatatga catacctaac ttttccttat ttttttttc agtatttcta    93000 gtcatagga tctgagagtt ttttcaaatt gttgcaagtg tccacaaata ttttcagtat    93060
attgaatgaa aaagtacac atgtaagtgg acctgcccag cttgaagcca gtgttgctaa    93120
aggtcagctg tgttttcatc tgacccattt gagaggaggt tgcatacatc atgtcttcat    93180
tactttggtc tgtattcctt ctttctttt ttttaataa atgagacagg gtcttgctgc    93240 atttcacag gcggtgatcc ctcttctgat cagcatgaga gttttgactt gctttgtttc    93300
ctaccttggc tagttcaccc ctccttaggc aacctgatgg tccctaactc ccaggaggtc    93360
accatatcaa tgccgaactt agtgtggaca gccgattggc atagtgcact acagcccaga    93420
actgggctca agccatccac cccaacctag tagctgagac tgcaggtgca cggcactgtg    93480
ccaggctcgg tgtgtactct tttttttttt ttttttttt tttttgaga gaagtctcac    93540 tcttgtcccc caggtttgag tgcaatggct ttatctcggc tcactgcaac ctccgcctcc    93600
ccgggttcaa acgattttcc tgcctctgcc tcccaagtag ctgggattaa ggcgcctgcc    93660
```

```
accatgcctg gctcattttt gtattttta gtagagacgg ggtttcacca tgttggccag   93720
gctggtctcg aactcctgac ctcagatgat ccgcccgcct cagcctccca aagtgctggg   93780
attatagatg tgagccaccg cgcccagtcg gtgtgtaccc ttttgagac ggagtcttgt   93840 tctgtcgccc aggctggagt gcagtggcgt gatctcggct cactgcaagt tctgcctccc   93900
aggttcaagt gatttttttg cctcagcctc tcaagtagct gggatcacag gtgcacacca   93960
cgacatctag ctaattttg tatttttagt agagacaggg tttcaccatg ttggtcaggc    94020
tagcctcaaa ctcctgactt cgtgatccgc ccacctcggc ctcccagagt gctaggatta   94080
caggtgtgag ccaccacaac tggctgattc ttaagagtaa agatattaat gacagtaaag   94140
ttattaaatt taaaacttga tataatgcta ttatctactg cgcattcaaa ttttgtcact   94200
tgtcccaaca atattctttc gtccagttga gtttctagtt caggatctga tctggcctgg   94260
gatcatattg cattctcttg ccatgtgtct ttagtttcct ttagcctgaa acagtttctc   94320
agcctttttt tgcatttcag gatctcagta tcttttgtt ttttgttttg agacagagtt   94380
tcgctctgtc acccaatctg gagtgcagtg gcgcaatctc agctcaccac aacctccacc   94440
tcccaggttc aaacgattct ccagcctcag ccgcccgagt agctgggact acaggtacgc   94500
gccaccacac ctggctaatt tttgtatttt tagtagagtc ggggttcac catgttggcc   94560 aggctagtct cgaactcctg acctcaggtg atccacctgc ctcagcctcc caaagtgctg   94620
ggattacagg tgtcagccac tgcgcccggc cctcaatatg ttttcaataa acatttta    94680 aaatgaaaac tgtgttcata ctctacaaat tgttcggttt taaaccttgc atttttttcc   94740
cattgaagag taaatcttgg ccatctttcc ctgtccacac agacaatata tagatctagc   94800
tcagttaaag ttgtttctta atagttaatc attgtgaatt gattttttca agaatagggt   94860
ttccaaaaaa aaatcgagga atgtaaaagg ggatacagtg taaagtcttc tttagacacc   94920 cccctcccg ccccacccat ttttcacata taccctcccc agcatgtgaa cccactggta    94980
ctcggggttt catctttttt tttttttttt taacttgtat gtcttggggg tcttttatt    95040 tatttaattt ttttgagaca gagttttgct cttgttgccc aggctggagt gcaatggcat   95100
gatcttggct caccacaacc tccgcctccc agattcaagt gattcttctg cctcagcctc   95160
ccaagtgctg ggattacagg catgcgccag catgcccggc taattttgta gttttagtag   95220
agacagggtt tcaccatgtt ggtcaggctg gtctcgaact cccgacctca ggtgatctgc   95280
cctccttggc ctcccaaagt gctgagatta aagcgtgag ccaccatgcc cggccttggt    95340
ggggatcttt ttatggtact accaagagag cttctttgta ctttatatt gtctgtagtc    95400 attgtatgac tgtaccataa ttgatttaac ctagcgcctc cctttggtgg acatgtcgtt   95460
acttttgcag ctttgtattt agtgactgta atggctgtct agtattctga tgcagggg tt  95520 tgggtaccct gctttaattt agcccgtctt cctgttagtg gctgtgaaag ttgtttcctg   95580
gaacagataa atgcggcttg tctttttcc atttactgga gtaacttgga gatctttg     95640 tagccccaca tatggatctc ctgtgcaatt tagccactcc tacttcccca ttggagcaca   95700
ttttccgtgc tggcatgagc atttgcaca tagaattttg cattcttgtg ggaatgtagt    95760
tgtattcctt cttgaaagtt agattctaag tcaaaggtat atttaaat tttcatagct     95820 accaccaaga ctacactcca aacaggttgc agtaattaa cttgtcactg tgtgacagtg    95880
tttgccaaag tctgttcttt cagagtatga ggttcttg gtatgtggca gtatggaact     95940
ctaggccttg actcttgctt caaccagaac atctctgcat ccagtcttaa gattccttat   96000
atagttttct ttgttcagaa gataccacaa ctttaaaaag gctcagggtg aggagttggt   96060
```

```
gggggtgtaa aaatcattgg tctcctggaa caagagggga ggacattggt gtcaaatatc    96120
aagtcctcaa tttgcaaaac aaaaaggtaa aacagccttc caagtggaga acagaataac    96180
ccatttcagc aaaccataaa gagtatgata cttagagcct agggacaaca gaaagaggtg    96240
tgagacacca ggctataaaa atggcaggct ctgaattatg ccaggcttca ggagtttggg    96300 tcttttaggcc tgggactgac acaggagtgt tcagcagga acaacaacac aactccactt    96360
gccttttgga cagatggctc tgttggtggt agatgggttg gttgagggcg ccggtttctg    96420
tgcattatgg gaagttccta tagtgaagct ggtggccata aggaaggcta actaacacca    96480
acagtcatac ctgctctcca tggtcttttt tttttttttt ttttgagaa ggagtcttgc     96540 tgttgcccgg ctggagtgct gtgacatgat ctcggctcac tgcaacctcc aactccctag    96600
ttcaagtgat tctcctgcct cagcctcctg agtagctggg attacaggca ctcgccacca    96660
tgaccagcta atttttgtat gtttagtaga cggagtttt caccatgttg gccaagatgg     96720
tcttgatctc ttgacctcat gatctgccca cctcggcctc ccaaaatgct gggattacag    96780
gcgtgaacca ccacatccag ccgctctcca tggtcttgac gtgggtgcat gcttagagat    96840
gaacaggcat gagggcctct gacacagagc tgtgccctgt gagcactgag gaggttaatg    96900
aggaagctcc tcaagggagg gtgcttctgt cgcttcttga agggcaattc ccaaggtggt    96960
cacctgaata gagaaagaaa ttatactttc atatcagaaa gcgaaccgtg tattttgctt    97020
cagtctgcta tctaatctca agtttgagc cttttcttct ctgagatggg catttagaaa     97080
aatatttaac aaacgtttta aaatataaa ttttaaaaag gcaaaaaaac actaagaaaa     97140
aaaagagcct ctcgtatcct gcagccaaag caatgtttcc aaaacacagt tttgagcagg    97200
ctgctcctct attcaaaata agtcagacac tctgctctgc caccagcatc aagttcaaat    97260
tcctgcggta aattagagtc cctcacatgc cgaggtaggc cgtgtcccct cccaccactt    97320
cagtcccagc cccttatttc tagcacagtg cctgacatct tgcagtgata gctcacattc    97380
cttgtgtgct cactgtgtat taaatgtact agcccattta acagttagaa taaacatagg    97440
ctgtataaaa tattattacc ccgccccct tttttgata aagaaacaag atgaaataac       97500
ttaaccaagg ccacaagtta gtaaatggta gaactgaagc catccacctt ctaaaatggg    97560
atcataggct aggcgtagtg gctcacacct gtaatcccag cactttggga ggctgaggcg    97620
ggtggatcac ctgaggtcag gagttcgaga ccagcctgac caacatggag aaaccccgtc    97680
tactaaaaat acaaaattag ccgggcgtgg tggcacatgc ctgtaatccc agctaattga    97740
ggcaggagaa tcgcttgaac ccaggaggcg gaggttgtgg tgggccgaga ttgcgccatt    97800
gcactccagc ctgggcaaca agagtgaaat tccgtctcaa caaaaagagg ggggatctta    97860
attactaact ttagcaattc ataagtagt tgttacagaa taaatgaatg tggtccctgc     97920
atggctcttc agctgttcct gaattacttc ccctcatct tttatgcctc agccaatctg     97980
accttgtgtt ctgtcactgc taggcttata tacaagcaac tgagaaacct cagaaacttg    98040
cttctaggta ggtcatctta ctgaattatg atagagtgtc cttgtctcat tccccactgg    98100
tcgctaagct ctgtcggtcc cagattatgc agacatgtgt atcagaaaga gtacgaactc    98160
agggaacatg ttgaacaagc tgaactcagt tcgaaaggc cctgcggtgg ctttccttca     98220
tctgttatat tcatagactg ccctttctgg gtttcttttg tttgttttg tagagatggg     98280 gtctctttct gttacccagg ctgtacttga actcctggcc tcaagcatcc tcctgccttg    98340
gctgctcaaa gtgatgggat tataggcgtg agccactgca cctgtctcct catcagtttt    98400
caggacagga ctggaccacc ttttccttcg tcttcatctc agtctaggca caagactcaa    98460
```

```
atacttggag cttcttaaaa ttacctgctt taggacaggt gcagtggctc aagcctataa   98520
ttccaacagt ttggcaggcc aaggtgggaa gatcacttga gtccaggatt tcaagaccag   98580
cctgggcaac ataacaagac cctgtctcta caaaaaaatt taaaaattag ccaggtgtgg   98640
aacatgcctg tagtcccagc tactcaggag gctgaggtgg gaggattgct tgaacctgga   98700
agtttgaggt tgcggtgagc cctagctgtg ccactgcact cagcctgggg gacagggtga   98760
gaccctgtct caaaaaaaaa aaaacaaaa aaaaaaact cttgcttact tgcttcatat   98820
ccaccaactt tggggtctta ggcaaggagg actttgggct ggacattctc tgagatgttc   98880
actgatgctg cccagcttac ctgtatgttg gggaaggatg cacttcaatc tggaaagctg   98940
tccacattct actccctgca tctactgtcc tcacatttga ctcccagtgc ctatggcgag   99000
agttggcaat catattcctt tggcttttc tcctaggatt ttgaatgtgg aaatgacgtg    99060
gaactgtctt ttaccaagaa tggaaagtgg atgggcattg ctttccgaat ccagaaggaa   99120
gccttggggg gtcaggccct ctatcctcat gtcctggtga agaattgcgc agtggagttc   99180
aacttcggac agagagcaga gccctactgt tctgtcctcc cggggtttac cttcatccag   99240
caccttcccc ttagtgagcg tatccgggc accgttggac caaagagcaa ggcagaatgt    99300
gaggtgagtg gggccagaat gtattggtgg ccaccttgct gccaagacag aggagacaca   99360
cacacacaca cacacacaga cttgctgcga gagtagcctt ggggcaagtg gccactttgt   99420
cccagctcct cagggttgga ctcagagctg aaaagctgct ctgagtgtga ggtgaggggt   99480
gttggtgtga cctaagttga agtcggagag gctacctaaa tctcagaaag attgcatctt   99540
cttcttaagt gaggccagaa taggggaaaa ggaggctttt cttacagcag aaaaggacac   99600
taggcgcttc ttggggagtg cactgtgcca ccaagtgttc ttttttttc tttagagaca    99660
gggtctcgct ctgtcaccca ggctggagtg cagtggtgcg atcacggctt actgcagcct   99720
tgaccttcca ggctcaagtg atcctcccac ctcagcttct cgagtagctg gaccacagg    99780
tacatgccac catgccaggc taacttttt agccactgag cctggccac cgagtgttct     99840
tgaaggaggt tgagtaagtt ccacctctca cccagagcta tcaaaagata aatggccttt   99900
gggaagattt gattccaaga gctatactag tgtcttttt cttaaaacaa tattttctt     99960
gtatgtgtaa gttatttatg cttgttctag aaaattaaga agtaaaaaat ttaaattttc   100020
ataatgccat catctacaaa taagtttact tgcagagttt tggagttcat ctgttctttt   100080
taatgtctaa gtgcctgttt tatgctcaca acatttatc attgagattc tatggtataa    100140
gcattatgat accctgctct tttcacttca cattattttg tgagctttat cccatcacat   100200
aaaaacctct ctttgaacat cattttttct tttttaaaaa tccttcaagg gaatgaacgt   100260
cattcttaat ggccttacaa actcgccact cccccctagt cgggcattta agatgcatct   100320
gtgtttacca aattctaaat gtactgatta gatacaattc acgtccttgt gtgtgcagct   100380
ctgttcctat ttcatactta agaaagttg taccacttct acccactcca tggggccagt    100440
cccagtacac agccttccct gggctattgc agggggcggg gaatgggtca cataatcctg   100500
taaatgggct gggtttggtg gcaaatgcct ataattccag cactttggga ggccaagaag   100560
ggaggaggat cccttgagta taggagtttg agaccagtct gggcaacata aggagactct   100620
catttctacc aaaaaagag agaaaaagat tagctgggtg tgatggtttg tatctgtagt    100680
tctagctact ctggaggctg atgtagaagg attgcttgag cctgggagtt caaggctgca   100740
gtgagctgta attgggccat tacacgccag cctgggcaat agagtgagac cctgtctcaa   100800
aaaaacaaaa tactataaat gctaatgatg acagcacttg gttttttgtt tttgttttcc   100860
```

```
cccgaaagtc ctgggattat aggcgtgagc taccgtgcct ggccagcact tgacttaatg  100920
ctcaccctgt cccaggcact gtgctcagag tctgacaagc ctgatctttt tgaatcccga  100980
taccagtact gtgaggtaga tggtattact gcttccgctt tgtagaggca gccacagctc  101040
agaggtccag agtcacactc acagtcacca ccgagccaag tggtgccata ccaccatgcc  101100
gcaacacctt ccctgtcttg ttcttgtaga ttctgatgat ggtgggcctg cctgctgctg  101160
gcaagaccac atgggccatc aaacatgcag cctccaaccc ttccaagaag tacaacatcc  101220
tgggtaccaa tgccatcatg gataagatgc gggtaaggcc agccactgga ctctccttac  101280
tcacctccaa cctactgagt gctgccctgc aactaaaatc actcacccct caccaattcc  101340
tgcccgcagg tgatgggcct acgccggcag cggaactatg ctggccgctg ggatgtcctg  101400
atccagcagg ccacccagtg cctcaaccgc ctcatccaga ttgctgcccg caagaaacgc  101460
aactatatcc tagatcaggt acttaatgat gaccattgtg tcctcaggag aagggagggg  101520
accccttgca tgcctgagaa tctccctctg gtcccttcct tttttccccc gtaatgatga  101580
tggactgctg tgctagtcgg gggggtcaga ccttgtcata catgatgaca tggtactaca  101640
cacagctgag cctggactgg gatcatgatc taggcctact tactcagact catcagcagc  101700
cccaaagaac atcaggtaag aactgtttag caaaatggaa ggagtatgga tttccaagcc  101760
tgagagactg gagcttgaat gccagctcgg ctactcccta gctctgtgcc tttgggcagc  101820
tgactttatt ctctgaatct ccatctcttg gtttgtaaaa cagggatctc aataccatct  101880 gcaccccccta cgcaggacct ggcacttagt agctggtgat tattgttaaa tactctacag  101940
aataggtaga gtagctttca tgccaacagc agtgctgtaa ggtaaatgct attattgctt  102000
ccgtcatttt ctcttcacaa atacgtgatga ctggcaggta catacctaag tcatattttc  102060
tacctacact tcagttaatg gtggagttct taacatcagg gaccttggaa cctttgtatt  102120
tgaacataaa tattgtatgc agctgcaggt gtatcctttt tatgaaaaag aagggaaaaa  102180
aaaacagttt tttgtcccta tctttcagca ttctcaaaag gatgagtgac ccaaaaatca  102240
ttacagattc ctgtctcaga gtaatgagtt ccacatggtt attgcctatg caacgtcatt  102300
gcctattgac atttgtcctg aaggcttttca caagtaacaa agggtgtctc cttatttttct  102360 atgtttgggg atctgtgaat gagcctctgt tcccttcagc cttgcatttg tgctttctta  102420
agaacctgtg agtgagcaaa tatgtaaact aagtaacacc ctgcccttgt agccttcctg  102480
aagtgccttc catacgtgta ggcctggata cttggtgacc atgagttcaa agggctcctg  102540
ataagagtgg aggtggggac agcgtttggc tttgtcagaa tggtagtttg cttgttagaa  102600
aggaatcgcc agagaccgag ttgccttcac ataggaatga ggatcctaca caaaacagtt  102660
gagcacagga tagtctaaaa gccatccgtg gttatccccc cagctcatat tgtgtacaat  102720
cagtgttctc tccgctttga agatttgtct tttaaaccct tggcctcact ttacctgatc  102780
ctccttgtcg gggcattcaa gaatttttt agtctgtatt gaccccagtt ggactcattg  102840
tcgtgaaagg gagagcagta ataccatttt aacactctga ggatacatac ctcttttgga  102900 tacccctagcc agtattcctc cctgtctttt tcttggtttg ctggttaaat cagctgtgaa  102960
actcatttca aatatgtggc ctaggggaga atgattatag tctagagtgg atcgtctaac  103020
atctctgtcc aggatgctga agtgggtttt ctctggaagc caggcccatg acagctttgc  103080
actctgaaga cctactgtca gccttcttgg ctgctgctgg cttgttcagg gacagggtct  103140
agggctgtac caggtatgcc tgtggtcttc agggctacca gcctcctgct taagggacat  103200
gtgggtcagg ccaagagatc ttggccaaca atgagacaga gaacctaaac tctgaaggct  103260
```

```
ggggaggagg gttctctggt taaccacaga ttggaggatt gcctcggggc ctgaagccat 103320
aggctactca ggctgaggga gggattgtaa agccagtggt ttcacctgtt ttggcctaaa 103380
ccccaaaagt gggttccaga aaactctggg tatgagaaag agggagggg  aagttgtgtg 103440 tttgtgtata gagggttcag agcaggcccc tggccaatcc tggcacttcc attccaccag 103500
ctttggcggt gacaggtaag ttgatgatgc atagctgtct cctgggctag gtggaatttc 103560
caaaggggaa acccatacta caggcaaaat ccctgcagtt cctggatctc agcccagaac 103620
catcttttgc ctttactggt ttttcctgag tggtcagatc tccccagatt tggctcttcc 103680
agcctcctgt tatgtaggtt ggccttagaa atgctcatcc ttgagaggga aggagaggtt 103740
gtctgcagaa gccaggtggg cctttgtaag ccaggattct gtgtttgtct ggccaggact 103800
ctaactccta ccctgggatg tatgtgattg ggcacaaact ctcaggtata tcggggcttt 103860
gacctacatt ctgtgataac ctgagtagcc ttttgagatg atgtgggcat cacagctgtg 103920
gaacatcaga agaggaaaaa gaggtagacc agagaggaag ctgaagcctc tgcagaggac 103980
tataggactg ctaagtcacg cactcagtgt actgatagat cacagctctg ctgacttccc 104040
aaacagccat agtctagaat ggttgggcc  atggtgggaa tttggggaag ctttctggag 104100
gtggaatgtc tgagtcgggg cacagaggat gattaaaaga gttggggctt tgtcctgagg 104160
agagtgggga gtcatggtta ggttttcatc cggaggaatg tggataaatt tgcctggcta 104220
gtaaaaggct gcagaggaga gagaaaggtg gagtagaagg ccacattgct tcaggtgtct 104280 cttggggtc  ctctgttgga ggtgggaagc ctctggaatg agatgctttc tggccttgtc 104340
ccagagggcc tcaaaatgga gtacagaaca ggaactgact ggcctgctgt gaggcaaaca 104400
agttgccttt ctggaggctt ctggggagcc tccgcagggc catgttgccc aagcccaccc 104460
cagagtaggg cactgttgcc tgggagttcc gttagagggc tctaacagct agagccaggc 104520
caggcatcag ttagaatcag ggctggatgg gttgacgtca cagtcagaac atgtcgttct 104580
agtcctcatt tgcatcctgg tcagcaggtg ccacactttc gcctgaaaca gaaacccagg 104640
gctagaatag tctcccaccg taacctgtgt cttatttgca ggcctggag  gaaggatgtt 104700 tctttccttc atccccagcc agccatccct agagcctgaa gcccattcca ttcttgacac 104760
accagccagt tctcttccta taaatgtggt tcttttgact ggaattcacc tcactctgag 104820
cccaaagtaa atctttcctc atcagccttc actttgctcc tcagatctag ctaggttcct 104880
cctgctgcca gtatgaccct ggtgagctgt gacaagtgag agtagacagg gacagtgggg 104940
cttgagagat cctgggctgt cacatcatca ttcgtacctg ctgtgttccc tcctccctcc 105000
ctcagactgt tatacaccaa aactccccat atagcttctc tgagaaaccc aactcttgtc 105060
ccttagtcca tgtcacaggg ttcagggaac acagacagcc acattttctc ttggaatcaa 105120
catcttcaag cagggtggga ctgggagaag cagaagctag gcagagggaa ccaaagcagc 105180
tggaaaagct gacctagctg ttgtgctggt ctcatagcaa cagctgccag cagccccag  105240 cgaccacaga agtgctgggc tggcccaggg gctgtgacct cactgtgttt gctgtggcaa 105300
cagccaccag cagctaattc cctttcctcc aggaaagcca agtatttgca tttctgctgg 105360
tgtggtttag atactcttct tcccttcccc aaacgaagga gtaagtggag ggaggtgcag 105420
tcttaaaaac cactgctgag ttgattctca gcacctcaat tccaaagtgc ctgagaagcc 105480
atctctgagt ctacccactt ccaaggacaa aggccagcta tttataagtc caatctgctc 105540
cacctccatt cctctcatcc catgaagctg caggggctag ccgtcttggc agcattgctt 105600
ctcttctctg tcccctcatc aggacattga cagggcagtt gtaccacatg gaagacctcc 105660
```

```
aggactgtca ctccatgccc tcgcagttca gaggaatcaa agtaggatca cttaggggca  105720
aaaaaaaaaa aatgcagaat ggtctggggc catattcacc ctggcaccta cctactctga  105780
gcttttgtgt cagaagaaaa ttatatttag ctgaggaagc caaactcttt cttcctatga  105840
ccagatgcca cgttctgctt tgcttttagg aatggagtca agaagagta gtggggagag   105900 gggacttaac ttttcctctg taacatgatg ttccttttca aaccatttgt ggcccaagtg  105960
ctctttgtgg gccggtgtcc aagacgcccaa gaacagtatg tgtgtgcctg tcacccacat 106020
gactgcccac atcctccttc gtgagggtag ggacactttc cctgggggac agggaagaac  106080
attttttcct ggcgcgtgtt tcagggccag aggatctggt tagtttaagc aactgcaccc  106140
acggccccag aacttccagc agatttgtgc tggagtcctt ggcccctggc taatccacat  106200
ccagcaccct gttcctatgt cttagaagac gatctcttga aaccttgttt tttcctcaag  106260 cttcaattt ccttggtatt ttccattggg aagcctctcc tggatagtca gtcctgtagg   106320
tcttattttc agatccactc tgggtgttga cttttcactg cccactcctt tggcactagc   106380
cagagatttt tacatctgca aatgctctcc agagccagga cgagggtgat gatccttgtc  106440
tttcagacga ggaaatttga gactcaggct acttggggac ttgtctgagt ctcacaaata  106500
gtaaagggca cagcggggat ttcaagccca agtttcttcc ccaaagcctg tgttcattcc  106560
accctgtctc actgttcctg cttttctgct tgggaggtca ctataagctt aaccttttct   106620
ttggtctgag ttgcttcaag tcaacatgac agtataaata tctacccagt gatgaccaca  106680
tcaatggcag ctcacagttg ttgagtgttg gctatgagcc agggcctggg cttagacgag  106740
ggcttttact cacgtggact cattcagtcc tcacagcaac cctaagacat ccatgccgtt   106800
ttcccttttc agggcttgat tttacagagg agcaggctga ggctgggcca tcccagtgca  106860
ctgcccgctt cctgtcaagg tgtcttctgc cctggaggcc acctgtgtcc ccctacttga  106920
gtagtttctt gcactttgtc aattgcttta tggacattct cttactcagt ccttgccagc  106980
ccagggaggg aggcttttca accccgtatt acagatgagg caactataag gactggccaa  107040
ggtatgttag tagccacacc aggacttgac cctagactct ttgcacccaa gcaggccaca  107100
tcttcagaat acatttttt ttttttggtc catttgtata tacccccttta cagactgttt   107160 tccccatctg tggcttcttt cttgggtccc tattagagcc actaaaaaat tgtttaaatg  107220
cagttaaaaa ctccttactc cgtttctgct gagttcctga gtttccatag ggagggtacc  107280
tgtataggtg cctgggtctt acttctagag gttcaggctc aggaagtctc aaatgaagtt  107340
tgagctgctc acttttttaag tagtgtcctc gtgattcaag tatacaggct gagtctatgg 107400
aaccctgaat ccaacagagg taggccccat tcccaagggg cccgacatga aggaggtgtt  107460
cggtaaatgg aagccgatgt tgttactgct ctcaaccaca tatgtgctag agcaccgctc   107520
tgccagcacc agcccaggac acacctgcca tcacttagag gaagggaagg aaacattagg  107580
agcaaaactg cacttgcgaa aagcagagtc tcctgatgtg tagagcttgc tggttagaag  107640
cttgtgggtg aggctgatgt ttcagagaag gactgaggga ataaaagaac caatgttaat  107700
aagaacaaac tacaaaactg tccaaggag ctggttaatt agtagcatag ctaatctata   107760
ggtattacac agccattaaa aaagaatact gcacagaaaa acttcagaga aagtttcacg  107820
ttacatgaaa aagcctcagg aggatgtgca taatacaatt cttttttgtgt aaaaaaatca 107880 catagatatt tctaaaagtg cacggaagaa attcattctt cattctctct gggaagtagg  107940
gctggcacta agggaacaca gggggttttttc ctctaaactt tatgccttat actgtgaatt 108000 ttttttaccaa gagtatgtat tagcttttag aatagggaaa agaaattgta aggtccagta  108060
```

```
ccaagaacaa ataggattaa aaagcaaagt cccaaccatt aggaatcctt tgccctgtgc   108120
ctgtctgcag ccacttacct aagtcaattc atttgctgag ggtgactcaa gaatcttcta   108180
agtaaagaag agctgtttcc tgagtttctc tgcttacaag gagcactgat atccttttct   108240
cagtccctgg cctacataat acccctcaga ggaaaaaacc aactcttaat gtaccatctc   108300
ttgcctcttc tgttaccttt cccttagaca aatgtttatg ggtcagccca gagacgaaaa   108360
atgagaccat ttgaaggctt ccagcgcaaa gctattgtaa tttgtcccac tgacgaggac   108420
ctaaaagacc gaacaataaa gcgaaccgac gaggaaggga aggatgtccc agatcatgcg   108480
gtcttagaaa tgaaaggtag gaaatgagtg cttcccagag gaacgtcaat gcagggtcct   108540
ggagagaaga agctctttac tcagtttgtc cttccctggc tccccagtga tttctttttt   108600
gatcttactc tttctttgct tctgctttgt cccttcctty tctaccacag ctgtgaatgg   108660
aaaagctacc catctgtctt atgttggggt tttcaggctg gatggggctg gggcagcaca   108720
agggaaagga tgtatgggag ctaaagctga aagtcctgtg tgctcaccct gcctctggtc   108780
ccagatgggc tgactgtggg caggcctcag tttgtttctc tgtaaatata gggatggtga   108840
tgccatctgt ctgacccatt ccctggggtg aggcctgagg gagctgtgca ctgtgtctag   108900
gtgggtctta gccacctctt cagaaaacgg aggagtcttt gttagcccct gacacttagc   108960
aggctgaggg gttggggctt tgtctacctc tttctctctc tctctgtttt ttttttttt    109020 ttttttggaa gagggagtct tgccctgtca cccaggctgg agtatagtgg tgcgatcttg   109080
gctcaccgca acctccgcct cctgagttca cccagttctc ctgcctcagc ctcccaagta   109140
gctgggacta caggtgtcca ccaccatgcc tggctaattt ttgtattttt agtagagatg   109200
gggttttgcc atgttggcca ggctggtctt gaactcctga cctcaggtga tccacccgcc   109260
tcggcctccc aaagtgctgg gattacaggc gtgagccacc gcgcccgccc ttctgtctat   109320 gtcttttctta ttcactattc cagttttctt caccttctcc cttctggaag gccactcttc   109380
tgggtggagg ggaccagact tcagaaggta ctgacctctt cttcttgttc tctttggggc   109440
acttccttcc tcctagccaa cttcacgttg ccagatgttg gggacttcct ggatgaggtt   109500
ctgttcattg agctgcagcg ggaggaagcg gacaagctag tgaggcagta caacgaggaa   109560
ggccgcaagg ctgggccacc ccctgaaaag cgctttgaca accgaggtgg tggtggcttc   109620
cggggccgcg ggggtggtgg tggcttccag cgctatgaaa accgaggacc ccctggaggc   109680
aaccgtggcg gcttccagaa ccgaggggga ggcagcggtg gaggaggcaa ctaccgagga   109740
ggtgagacat ctcacacaca gcactctcca ctttctgttc ccaggttggg gctgggcttt   109800
gactgcttat tcaatcagca actgaagttt tctgagctcc agctgtgagt tatactctgg   109860
tagaaaactt gaaacaagtc agacacggag acctcagaaa cgctcccact ttcccactcc   109920
ctggacgctg gttatgaagc cctttgccca tttgcatatc acagtgcaca ttctgtcaca   109980
ttgctgtcat ttttgtgaac cttcccccat ctgaccatga gctccttgga aataggatct   110040
agatcaaaat ctattggaaa tgggggctac atctttggcc aggtctgaag aggactagat   110100
gtgactcgtt catggctgtc accagtgctt agcttcctct catttttttt tttttttttt   110160
ttgagacgga gttttgctct tgttgcccag gctagagtgc aatggtgtaa tctcggctca   110220
ctgcaacctc tgcctcccgg cattcaagcg attctctcgc ctcagtctcc tgagtagctg   110280
ggattgtagg caagcaccac cacgcccggc taattttgta ttttagtag atgggggtt    110340 tctccatgtt ggtcaggctg gtcttgaact cctgacctca cgtggccac ccgccttagc    110400 ctcccagagt gctaggatta cagatgtgag ccaccgcacc ctgccagctt cctctccttg   110460
```

```
agcatctcct tcctgcatat tcaacagcta ttgagatgct gggacacaga aacccaggac   110520
tgccttggtc tctgcctcac cattcttgca gtccagtgaa tgagacaaac ctgtcataag   110580
ggctgggaca ggggagtatg cccgggggtc tagagaatcc cagaggacat gctttgttgt   110640
tcaccttgag ttcttgctct cgcctggcc atgccggctc acagtagtca ccaagacaac    110700
ccagttccct ggggttgcca tttgggaatg atggcgcctt tcatctggat ttctccaaca   110760
caggtttcaa ccgcagcgga ggtggtggct atagccagaa ccgctgggt aacaacaacc    110820 gggataacaa caactccaac aacagaggca gctacaaccg ggctccccag caacagccgc   110880
caccacagca gcctccgcca ccacagccac caccccagca gccaccgcca ccacccagct    110940
acagccctgc tcggaacccc ccaggggcca gcacctacaa taagaacagc aacatccctg   111000
gctcaagcgc caataccagc acccccaccg tcagcagcta cagccctcca caggtgagag   111060
aatgagtgtg tgtttgtatg tagtgatcgc acgtgtgctt ttgaacctga gcaagttagg   111120
tggaggcgga tctggggaaa tcaacacatg ccccagctac tggtcttcac tctaacctct   111180
agcctgccct tctttctccc tggccgtgat cttgactcag atggacccta cacattccca   111240
gatcccctcc aaacccagga gtaaatgtag accttcccag aacctgctct tctcccacca   111300
ccctcaaggg gatgggctgt aagcactgat ccctccagca agtacattat tcttggctag   111360
tgtcactaac ctcactaaat ccccaagaaa gcacttgact ggagtcaccc cttgcccagg   111420
ctggctgacc tctttgtctt ttggacataa taaccagggc actaaggttg ctgaggactt   111480
gccctctgca cagagagctt caatcctgag cagctccagg ctcagttccc gttcttggaa   111540
agccagtgcc ctggctctgg tatgcacagg ctcctgtaaa ccagagaggt tttcagttat   111600
cgcacagcca tttcccaagc actttcctca tgccgggcct ggaatcagct gccaggagac   111660
caatggatgg ttcccaggcc cagctaacta gaatatttct tagaacaaga gttgggcagg   111720
cacagatcca aaccccagc cccacaacat cctgtttctg tgagcttgga caaatagctt     111780
cccgtctctg ggcctcattt tcctcataaa ggtgttagta gaagtcccctt ccaaggtttg   111840 ttgtgaggaa tgggtggcac tatagctctg ggactaggca gacctggggt caagtccttt   111900
ttccttggcc cagaaatttc atcttgagcc tcagtttctt tctctttaaa atggggctag   111960
tgggacctac ccctaggttc tatatggaga ttatatgatg taatgatcca acctgtactt   112020
gggaagcact tagtcaattg ccactactgt ttctcagcag atcttccagt aacaactacc   112080
accacctgtt gagtacccag tggtttatac acacaagctt attggatacc cagggcaagc   112140
taaaggagtt gttcttgttc tattgtgatt ctcattttat aaaaaagaaa actgagattt   112200
caagaagtgc cgtgtacctt gctccctggg ggtctcagag ctggggttag agtccacatc   112260
acagccctgg ggcttgccct tcatcctgcc ctaccatggc atggagctgg ctctcctcct   112320
tctcagccca caaacaatgt ccactaggca agggaagggc ccctgtgggc caaccactta   112380 aaaaggcccct ttttccatcc cagcatttca catctgcaga tttcctctat ttcacagagc  112440
tttggctttt ttccctccac tttccagccg agttacagcc agccacccta caaccaggga   112500
ggttacagcc agggctacac agccccaccg cctccacctc caccaccacc tgcctacaac   112560
tatgggagct acggcggtta caacccggcc ccctataccc caccgccacc ccccactgca   112620
cagacctacc ctcagcccag ctataaccag tatcagcagg taggtgccag actggggggc   112680
aactggatgg agagacttcc atgggcccct cctgggtgtg tattcccaga cttaagtccc   112740
tgcttatccc taaaaagaca gcctgctggc ctcggcctgg cgttcatctg gtgcagccat   112800
tccatttggt caacacttct gcactggttg ctaggtaatt ggtatcctag cccccctccac   112860
```

```
agtctagcaa gtgaagggga agggctggcc taagtaccag gggcctcaga gtcctctttc    112920
agcaccatag acagggggct ccaaatcctg ctgcaggttg gtgcccaggc ccccatacct    112980
gttactaaat cttttgacta tgatatctag ctatacccaa aaggcactgg gttgacaagc    113040
tgagacctgg gcttcagtcc ctaactgcct acctgtgtgg tgtcaggtct ttccaaggtg    113100
ccttgatttc tctgtcaggg gacctgtgtt caactgttgt cactgcagct gtctctgccc    113160
taggtgaggg tggggctggt ggggaggcta aatgtgtggt ggatgcagga caacttggtg    113220
ttcttggttt cttttcccag tatgcccagc agtggaacca gtactatcag aaccagggcc    113280
agtggccgcc atactacggg aactacgact acggagcta ctccgggaac acacaggtg    113340
gcacaagtac acagtagcca gtgtgaccca gaggctcccg gaggcccctg ccggcttcct    113400
ccaccagcgc ctgcctcggc ccctcctctg ccccgccag atcccgtggt gctgggatg    113460
gggtcatccc agggctgcct ccctccagcc cactgcctcc cctctgaggg gcttccttcc    113520
cctccatagg gccaggcatt ttttctgga ttcaaacagg caacaatgac cttttatttt    113580
ctgtttgtcc ccacctcccc agccttccac ctcctgttct tcctaccttc ttcctttttg    113640
actaaataat ccccacctcc cttgatcata cagtgaggct acagtgactg aggggagaat    113700
cccctcctgt tcactctccc aaccctgctc cagcccctca gcttcccaga ccctcatgca    113760
gttggttgta aattctccca ggagctgttt tactgtctac ttttcaggat taaaaaaaaa    113820
atcaaaactt aaaaaaaaaa aagtttaaaa agcaaaatgg ggaggggag gaagcagtga    113880
cttttttttg gtaattatgc gcttttttt aattttaga atttgtcttt ttactgtggg    113940
tgggctgttg atatttcatc aagataagca tttctttcct gagttcaggt gactgaggaa    114000
gagccacaaa acaaaacaca acaaaaccaa accacagaat catctttaac ccaacttttt    114060
atacgatgcc ccagttcccc ataactttgc acacaagctt ctgtgttcag ttgaattgta    114120
actgcttttt gtatttggag agagtgacta ttgaacttga aaccttttat tccgggcgtc    114180
ttggtagttt ctggtgggat tcagtgggtg agagggaaga aggggaggtt gggggctcc    114240
ttcccttcag aacttgaagt ttctcccact gcctcctctc cagtggtctc ccaggtgcca    114300
gacccaaaag cttttcctac agtgatacccc tttattttta cttcccccttg actcatatgt    114360
tttaacatga ttttaacaaa ctgcacttat taagaaatgt gtttgccctg ttttgtttgg    114420
tttcgttttg ttttctttga ataaatgaca tggcacctcc tagcaggaag gaagcagggt    114480
tgaaaccctg aagtgttact gcagttggcc gttaattggg gtgggggcct ctttaagg    114540
aaattattta ctcattcatt aaacaactta actgagggat tcatgtgcct ggccccgatt    114600
ttggtgctaa aaatgcacgc ttaaacaagg gtccctggtt taaaatccac tagttcattt    114660
ttaaagtgct tctcttgttc tctacctctc acagtctaaa atccctccag gagttttga    114720
gtaaaggaca tggaacaggc ctctaggtgg agggatgggt gggactgatg gggcagagac    114780
cagggctggt ttgtttggca tcatcactgg gcatccacag accacctgcc tcaggcctgg    114840
cctgtgtgca gcacggagga cagttcctgc ctgttctgtg tttgggctc atgggattc    114900
caggagcttc atgtttcagc cagtgtgtgt gagccacctg ctgtgttctt cagctgtcct    114960
ggacagtgct ggggacatag tatggccacg gcagtcctgg acccgttct cacagagctc    115020
ccactccaga gagaacaaag acctgccagc accaagtggt cagctgtgag agcctggggt    115080
ggtgtgcagg gagggcttcc tggaggagtg agccagggta aaagactcca gattgcatcc    115140
ccatggccca tcttccccctt ccttagcaac cttatgtctt cgttccctca tacatgtgt    115200
gttcctggct ccttgtgaga gacaatgctg ggccacagga gaagccaatt cagccccaat    115260
```

```
cttccctggt gggagctcag agccttgtga aggggagacg ggcaacaaaa acaagggagg   115320
gaaactgact agtctcagaa tctcgggtag ggcatcagaa cgtgagaagg aaccaaggtt   115380
ggtggctaaa agggacccta gaatgcgcca gagaggaggt ggcagggcct ttagtctgga   115440
aagtcccctt cccttcatgt ccatatgctg ggctacagcg ccctctgctg gcctctcctg   115500
gtaatgccta ggaatctggg ttggtaaata gggacctcct tggctttctt ccacaactcc   115560
agacctcaag ggaatgcaaa tggggaagct cttcctctgt tctcagccag tttttctcac   115620
acgtctcatc tccagtccct tgatgcccac tcccttcaga ataaaggagg tcaagccact   115680
tactatggct tatgaggccc tgcatggcct agcacctggt aacatcgctg gcgccctctc   115740
tttctgctcc cccttt gaat atcaaatcag tgtttatttt gttctgagga gccataagtc   115800 cttttt ggaa cccacaaatg atgccatgaa ccactgcatt ggagaataca gaggtacatg   115860
gaattttgca taaaaattca tgaggttctc aaaacctcca cagcccaatc atggctttca   115920
agttagagct cctttcctat gccctgaccg tagtgaagtg cttgcagcaa ccagaaccgt   115980
ccgtacgtgc catcctcctc aagactcttc cctaccttcc tcttaaccca gctcctactc   116040
gttcttcagg tcttagcttg agggtaccct cccagaaaga aggcttcctt gaccctccag   116100
cctggggtgg acagctccct cagccctctg gatccatcaa agccctggcc actgagtgac   116160
atgtctgtct actctgctgg taacacctaa atagagcccc acccatccca tagggaaata   116220
aggaccagag ttgtcttgtt tcacacctgt agatttcctc caggtcctgg gaacacaaaa   116280
tgggaagttc tatctcacta tccatctcat gccagccaga gacagggtat gatgacgaaa   116340
gtaagccagg ctggtggctc acgcgcgtaa tcccagcatt ttgagaggct gaagcgggag   116400
gattgcttga ggccaggagt tggggactag cctgggcaac aaagtgggac ccctggctct   116460
acaaaaaaat tttaaaaatt agccgggcgc ggttgtgcgc gcctgtagtc ccaagtactc   116520
caaaggctga ggcaggagga tcacttgagc acaggaatgt gaggttactt gaactgtgat   116580
cgcgccactg cattcgtcta ggcgacaaag cgagaccctg tctcaaaaaa aaaaaaaaaa   116640
aaaagagtca aggcttagta atattcctga attcctgaag gagttaagaa aggaaaagga   116700
caagcggggg tctaaacgag agcacgaacc ctcagcgtat gacggctcca ggctccgggg   116760
gaaagtcctt tagccatcca tcccaaaatt aagcacgctg ggagctggag tcacagcagt   116820
gataaaacga acaatgattc tggttcctac tgactgacag gagaggttta agggtctctc   116880
actctccggg gagcccctt ccttcctggc tgcggagggc ggagcccgag agaggcacgc   116940
atgcgcaatg caacgtctgc cttaggcccg gaacttcggt gcctgggcgc agcggtgcac   117000
ccggacccgg aacattctca ggcgaaagtg tctcttgcgt gcgtgggccg gaggttagtg   117060 tgcgggccc gccgggcggt tgaaaagtcc gagagaatca ggatggaggc cgtgcgacg    117120 gcgacggcgg cgaaggaacc cgataagggt gagatcttgg tcacgcgcag gcggcgggtg   117180
ggtgcggttg cggtgtctct aggaaatgat tcccccagga acgcgaagta ggactcgttt   117240 taggggaca cccacccccc tcagctttac cggtcctctt cactactttg cccagattat   117300
tccctccctt gtcgcgggct gaccttcttt tcctccattc cttcccccg aaattaacct   117360 cttcccagtt ccagaccaat cctttccatg tccctaattc atttccttac caggctaact   117420
ctcaaattaa cagaaacctc tctaccccgg cctaattcct gcattgcctc agaccagccc   117480
ttctcaaatt acctccttcc ctgtaccaag ctgagccttc ccttgctctc tagacgaatc   117540
ctcctacctt tccaggctaa acttctacct gcctcatgca aacttatccc aatctaacga   117600
ttccttcatt tcattgtaac tccgtttcc cccaaagtcc gaaatccagc caggctcctt    117660
```

```
tcaaagtcct tactcaattt ctgtgctttc ccacaacctt caaagtaatc cgacgtcggg   117720
tgaggtgtga ttggaagcgt ggctccaaca ccactggcca agaattggta attgtggaag   117780
ccagatggag atgattggta tatggaggta gggggagaat tgtcgttgta ctttctactt   117840
ttgtgtatgt ttgaaatttt ctaaaaataa aaaatttaac ctaaaaaaag tcttaaggcc   117900
gggtgcagtg gctcccgctt gtaatcccaa cactttggga ggccaaggca ggagagttgc   117960
ttgagcccaa gagtttgaga ccagcctggg caagagagag aaacctgatc tctataaaca   118020
tttaaaaatt agccaggcct ggtggctagg gagtagctag gacaagctac tcaggagact   118080
aaggtgggag tgtcactcga atcctttgag attgcagtga cctaagatta ttacaccact   118140
gcactccagc ctctgcagca gagtgagact tgagcccagg agtttgagac cagcactggc   118200
aacatagcca gaccccatct ctacaaaaaa tttaaaaatt aaggccgggc ccggtggctt   118260
acacctgtaa tcgcagcact ttggaaggcg gaggcaggaa gatcacctca ggtcaggagt   118320
tggagaccag cctagccaac atagcgaaac cccatctcta ctaaaaatac aaatattagc   118380
caggcgtcgt ggtatgtgcc tgtaatccca gctactcggg aggctgaggc accaactgga   118440
atcacttgaa cccgggaggc ggaggttgca gtgagcagag atcgcaccac tgtactccag   118500
tctgggtaac agagcaaaac tctgtctcaa aaaaaaaaa attagccagg tttgatggtg   118560
cattcctgtg gtcccggcta ctcaggagtc tgaggcggga ggatcacttg agcccaggag   118620
gtcaaagctg cagtgagctg tgtttgcact attgcattgc agtctgagca acagagcaag   118680
accctgtttc aaaaaaaaga aaaaaatttt gtctcttggc cccatctgtc tccttcagag   118740
agtcatgtat acttggtctt catttcctcg tctcctgctc acgactgtct gacttttctc   118800
ctaagaaact gctctgatta gggtctgcac tgacttcccc catgttgttc aattcagtcc   118860
ccccattcag gttttttgttt gtttgtttgt tttttgagag agtctcactc tgttgcccag   118920
gctggagtgc agtggcatga tctcagctca ctgcaacctc cacctcccag gttcaagtga   118980
ttcccgtgcc tcagcctccc aagtagctgg gatcacaggt gcccgccact atgcctgtct   119040
aattttgtat attttttagta gagatggggt ttcaccatgt tggccaggct ggcctcgaac   119100
ttctgacctc aagagatcct cctgcctcag cctcccatag tgctgggatt acaggtgtga   119160
gccaccacac ttggcccatt caggtttttt ttcttactag actggactag aattaaatgc   119220
tgttgatcct tccatccttt ttgcatgttt tcctttggct tcagcgacac cacagtgcct   119280
gatttcctgc ctgtctctca ggctgctcct tctcagcctg actttgtttc ccaggggtgc   119340
tgtaacaaag tactacaaac tgcatggctt caaacaacag aactttattc tctcatagtt   119400
ctcaaggcca gaaggctgaa gtcagtgttg ctgaactgaa atccaggtgt ctgcagggtc   119460
gtgcttcccc acaggctctg ggagaaaacc catttcttgc ctcttccagc cagtggtggt   119520
ttctggaatt ccttggcatg tggctacatc actccaatct ctgcttcccc ttttgacgtt   119580
gccttctttt tttttaagac ggagtctcgc tctgttgacc aggctggagt acgtgatctc   119640
ggttcactgc aacctctgcc tccggagttc aaacaattct cctacctcag cctcctgagt   119700
acctgggact acaggagtgc gccaccacac ctggctaatt ttttgtattt ttggtagagc   119760
gccatgttgg ccaagctggt cttgagctcc tgacctgaag tgattctctc accttggcct   119820
cccaaagtgc tgggattaca ggggtgagcc attgcaaccg gcctcttttt ttttaagata   119880
acagtaatgg gctccaggga ttacgatgta gctatctttt gcacagccag tttttagctt   119940
cagaggcatg tcctccccgc atctgtgcag tgcttttcc tggaccctct tgtcatccct   120000
ctcccactcc cctgtgccct ccccagtccc tacctctcat ttctcttggc tttggttctt   120060
```

```
gtcttgattc tgatgacacc cacagctctg tctccagccc aacatttctc tcctgaggag   120120
tctggaggcc cgtgtagcag cagtcggacc attcccctgg atgcctccct tacttccagc   120180
acgtcagccc tgtggctcct ccactcagcc tcctgacatc tttctgattc gctcactcat   120240
gatcctgttc cttcctccac agccctgcc cttgtccagc tcagtcttca gctgcatcag   120300
tgatttaaat cctccctgat acacacaaca catgtatgtc acctgtgact tctttcctcc   120360
ccaacccagc cacgctgctt aaagttgtct ctatattctg ttttcacgta tttcctgctt   120420
gccgcaggct tgctccctcc actcttggga aacaagtctc accaaggttt gcccagcgct   120480
ccgctttcct gttttctttc cattttttg agacagagtc ttcactctgt cacccaggct   120540
ggagtgcaat ggctgatctc ggctcactgc aacctctgcc tcatgggttc aagcgattct   120600
tgtgcctctg cttcctgagt agcagggatt acaggtgccc accaccatgc ccagctgatt   120660
tttgtatttt taatagagag agggtttcac catgttggcc aggctggtct tgaatttgtg   120720
gcctcaagtg atctgcccac ctcggcctcc caaagtgctg gattacaggc atgagccatg   120780
gtgcccagcc agctttcctg ttttctttgc ccatattatt gttgatcctg actgtctccc   120840
acatcagact gggtgctccc tgagggcagg agctggactg gattcatcct atggatcctc   120900
agcattgcct gacttagggc ctctcagaga tttagtgttt ttttttcttt tttttttttt   120960
agagttttgc tcttgttgcc cagactggag tgcaatggca cgatcttggc tcaccgcaac   121020
ctctgcctcc caggttcaag ctattctcct gcctcagcct cccgagtagc tgggattaca   121080
ggcatgtgcc acaatggctg attttgtatt tttagtagag acggggtttc tcccagttgg   121140
tcaggctggt cttgaaatcc cgacctcagg tgatccacct gccacagcct cccaaagtgc   121200
tgggattaca ggcgcaagcc accgcgcccg gcctaagatt tagagttatt aaagagtggt   121260
tgggtgaacg catgaatgca tgagagagtg aatgaatgag taaacaaatt agcaaatgta   121320
ttaacgattt aaagaattga gtggatcaat aagtcaggcc tcagggcctt tgcagtagtt   121380
gttgcctctg cctggaattc tcttttccaa gagacctcat ggcttaatcc ctcaccacct   121440
gaggtctcta atcaaatgtc actttttggg caaagccttc tctgagcctt ccattttaaaa   121500
ttgcagcctt ggccaggcat ggtggttac actgtaatct cagcactttg gaagcctgag   121560
gcaggaggat cacttgaggc caggagttca agaccagcct gggcaacaca gcaagaccct   121620
gtctctacca aaaaaaatta aaattaggcc gggtccagtg gtgcacgcct gtaattccag   121680
cactttggaa gatcgaggtg ggaggattgc ctgagctcaa gagattgaga ccaccctggg   121740
caacctagtg agaccttgtc tttactgaaa cttttttttt tttttttaa tttaaagatt   121800
ggcagggtgc aggccaggcg cagtggctca cgcctgtaat cccagcactt gggaggccg   121860
aggcgggtgg atcacgaggt caggagttcg agaccagcac agccaagatg gtgaaaccct   121920
gtctgtacta aaaatacaaa aattagccgg gcatggtggc aggtacctgt aatcccagct   121980
gctcgggagg ctgaggcaga gaattgcttg aacctgaggc ggaggttgca gtgaatcaag   122040
attgctccac tgcactccag cctgggcgaa agagcgagac tccgtctcaa aaaaaaaaa   122100
aaaaaaaaa agattggcag ggtgcagtgg cacacacctg taatcccagc actttgggag   122160
gccgaagggg agtggatcac ctgaggtcag gagttggaga ccagcctagc aacatagcg   122220
aaaccctgtc tctactaaaa atacaaaaat taaccaggca tttggcttgt acctgtaatc   122280
ccagctagtt gggaggctga ggcaccaacc acaataactt gaacccagga ggcggcagtt   122340
gcagtgggca gatctcacgc cattgcactc cagcctgggc aacaagagca aaactccatc   122400
tcaaaaaaaa aaagaaaaa aaatttaaa gattaactga gtatggttgt gcatgcctgt   122460
```

```
agtcctggct gctcaggagg ctgaggtggg aggattgctt gagcccagga gttcagggtt    122520
acagtgaacc atggttgtgc cattgcactc cagcctggca atggagcaag gccttatctc    122580
ttaaaaaata aaaataaaaa taggccagtc acagtggctt acacctttaa tgcccagcac    122640
tttgggaggc caaggcagga ggattgctgg agccctggag ttcgagacca gcctgagtaa    122700
catgtcaata ccctgtctct acaaaaaatt taaaaattac acaggcatgg tggtatatgc    122760
ctgtggtcct agctacacgg gaggctgaga tgggaggatc gctcaagccc aggcggtcaa    122820
ggctgcagtg agctgtgatt gcgccctgca ctccagcctg ggtgaccgag caagaccctg    122880
tctcgaaaat aaaataaaat tgcagcctcc tccacctctt ccctcctcct tccctgttta    122940
tttttccgca taactccagg aaacacctaa cacattatgt tttcggtaat tatgttgcta    123000
attgtttgtg tcccctactg aaatgtcaac ttttgctcac tgtggtttct ctagtgccca    123060
gaacagtgcc cagaatatag tcagtgccca gtaaatgtga gctgagtgag tgactaagcc    123120
cccagtccct tcccacactc ccatctctga actaaccaat ctctcctttc ctcaggctgc    123180
atagagcctg gacctgggca ctggggtgag ctgagccgga caccagtccc atctaaaccc    123240
caggacaaag tggaagcagc tgaggcaaca ccagtggccc tggacagtga cacctccggg    123300
gctgaaaatg cagcagtgag tgctatgctg cacgctgtag ccgccagccg cctgcctgtt    123360
tgcagccagc agcagggtga acccgacttg acagagcatg agaaagtggc catcctggcc    123420
cagctgtacc acgagaagcc actggtgttc ctggagcgct tccgcacagg cctccgtgag    123480
gagcatctgg cctgctttgg ccacgtgcgt ggcgaccacc gtgcagactt ctactgtgct    123540
gaggtggccc ggcagggcac tgcccggccc cgcaccctgc gtacccgcct gcgtaaccgg    123600
cgctatgctg ccctgcgaga gctgatccaa ggtgtggggg ccagatgggc gacagtgggc    123660
acatatgggg agggagggga gactgaggca gagggaatta gagaaaagaa tacaagagca    123720
gagacagaga tcctgggaga gaagttctga gacagagaca gggacacagg aagagactga    123780
gacagaaatg taaagtaagg gggagagata gacagggtc cagggaagag aatgggacag    123840
acaatgagaa tagatcagaa tttagtagat gtcagaagtg gcatttcaga ttggtaggct    123900
gaggacacag tacacagtgc tgtgataatt ggtcatacct aaggaacaaa acatgagatc    123960
cctacctcat accatataca gaggcatcag gggaaaccaa aaggagtatg tacatgacct    124020
tggggacaca gaagccttct gaacaagaca cactgtgaaa accatgaagg aaaaaaaaga    124080 tagcttttg accatgacat aattaaaagc atccttgtga ccacaacacc agaaccaaag    124140
ttaaaagatg agagtgaatg aagcagagtg agttaagttg ccgttaggga gaaggcacaa    124200
gttatagaga ggttcacaga gaaagagaga gaggctgggc atgatggctt atgcctgtaa    124260
tcccagcact ttgggaggtc aaggtgggta gattacttga gctcatgagt tcaagaccag    124320
cctgggcaac atggcgaaat gctgtctcta caaaaaatac aaaaattagc tgggtgtggt    124380
ggcgccctag ctactcagaa ggctgaggtg ggagaattgc ttgagcctgg gaggtggaag    124440
ttgtgtgagc tgagatccca ccactaagct ctagcctggg cgataaagcc agatcttgtc    124500
tcaaaaaaaa aaaaaaaaaa cacagatgtg gaaatgagga tgaaacagaa ggaagatgag    124560
gccgggcaca gtcactcaag ccggtgatcc cagcactttg ggaggcgag gtgggggtgg    124620 acctgaggtc aggagttcca gagcagcctg gccaacatgg tgaaacccca tctctactaa    124680
aaatacaaaa aaattagcca catgtggtgg caggcaactg taatctcagt tacttgggag    124740
gctgagggag gagaattaca tgaatctggg aggtggaggt tgccaaaaaa aaaaaaaaaa    124800
gaagaaagat gaatgaggtg ggggtaggtg acagaaactg aaaaaagcag gaaagataga    124860
```

```
aagatggaga taaaggaaga gatggagaga gatccagagc cggggtgggt gataatccaa   124920
gttggggaga aggagggata gaaactgaat ctgctagagg ctgggcacag tggctcagac   124980
ctgtaatccc agcactttgg gaggccgagg caggcaaatc acttgagata aggagttcaa   125040
gaccagcctg gccaacatgg tgaaacccg gctctactaa aaatacaaaa aaaattagcc    125100
aggcactgtg gcaggtgcct ataatcccag ctactcagga ggctgaggca ggagaatcac   125160
ttgaacccgg gaggcggagg ttgcagttag agttaatcga gatcacacca ctacactcca   125220
gcctgggcaa cagagcgaga ctccatctca aaaaactgag tctgctagag gatgccacaa   125280
acagctgggg gtaagattgc tggcaggagt ggggaagctg agcaggacag ggacagtcac   125340
agcctatggt gctacagagg ccaggagtcc gagcagtttc tttgccctgg actctgaaga   125400
cacggctagg accagtggag gggagggacc agggcaggtt taactgttat ttgagggaca   125460
gagtcactcg tgcagaaaca ggcagccagg ggtgatgcag ggaactcaag ttttggggta   125520
gtggggaagc caggcccacc tgaggggttg ctgcatagag gagcactcga gagaggatgg   125580
atctagggcc ttccaccacc aggaggcttt cccagggata cacgggcaga tgccccacct   125640
gacctgatcc cttgcacaca catgccaaat ccacgtggat gtacacacat acacgcccca   125700
cagtgaaggc gtgtccactg ccagccagac tagggcccca caaacaggca cacaacctag   125760
agacacacaa cctctgctgc attgtcctgc atgctgacac ccagacagac aggtgtctgt   125820
gggcatatgc tgggcctcac aggacatgtg tgtgtacata ggccatgcac acgtccatgg   125880
gcaggagctt gtgcatcgtg cctggacaca gttgtacacg agctccagac cgtcagagcc   125940
tcagaggcca ggatgtagcc aggtctgccc atgcacacac atgcttggat gcatgaatac   126000
atgaatacac aggaagatag aggctgggcc acatacacac actcaggtgc ctgcacgagt   126060
aatcacatgc acgtgacctc aggtgcctgc atgagtgctt gcgcacacag cttcaggcac   126120
ctgcatgagt attcacgtgc atgcctcagg cgcctgcatt attcacacgc acgcctcagg   126180
cgcctgcatg agtactcacg cgcacctcag gtgcctgcat gttttcctgt gttttttgaat  126240 gtgtgcatac acacacttgg actgtgtatg cacatcatcc cacaagcatg atcacacaca   126300
tacccacatg gacactatct gctcagtcgc tcaccccatg cccaccctgt ctctcctctg    126360 tgcaggggc gagtacttca gtgatgagca gatgcggttc cgggccccc tgctatatga     126420 gcagtacatc gggcagtatc tcacccagga ggagctcagt gcccgcaccc caacccacca    126480
gccccccaag cccgggtccc ccgggagacc tgcttgcccg ctctccaact gctgctcca     126540 gtcctacgag gagcgggagc tacagcagcg tctgctccaa cagcaggagg aggaggaggc    126600
ctgcttggag gaagaggaag aggaggagga cagtgacgag gaaggtgagg gccagtagca   126660
gggagacccc agattccaga caccccagcc ctaggcctgt ctgtctccac ttcatggcag    126720
caggctgggc ccccaacctg caaaagccga cattgcgtcc ctcccctgcc cagcctgact   126780
ctctgtgtat gcccttccaa ccgctgcagc atccccatcc cccactctga ggcaccaaat   126840
gaaccctcgc ctccaggtct ggacaggctg ttccctccgc caggaatgcc tctcctccca    126900
cccttcaggt ctcagatcct gacccgagga tacagtctcc agagcactat atggtcatgt   126960
gttttatgcg tgtccctgga gggcagggac cagggccatc tctgtcacta gtgtgttccc   127020
agagccaccc agcgcaaggc tgggcacagg agcagcagct ctctgtggac tctgtgctca   127080
gtgcctgccc gagtgcaccc gcattcacac cccctctcct ctccctctgc agaccagagg   127140
tcaggcaagg actcggaggc ctgggttccc gactcggagg agaggctgat cctgcgagag    127200
gagttcacca gccgcatgca ccagcgcttc ctagatggca aggacgggga ctttgactac   127260
```

```
aggtgctcct gtgcctccac ctccccatcc cccagcccag catcccacgg cctttggtca    127320
catgcagagc ccttaacaag ctgtgggggt ctcccttttgt ggagctacaa ggccccaaaa   127380
cagttccagg atgtggggtt gaacagccaa aggaagaggc tgggtgacct cggactagcc    127440
ttgtccatct cagaccctca gtctcctcac ctctaaggca ggggatggac agggatgaca    127500
tatagctcag tatcaatgaa accctgaaac acttccctcc tggcaatggc agaggctact    127560
accccaagcc ccccaagtct ccctaggaag cccaacctct tccgcttcac cttggacctc    127620
ctcatgctgc aggaagtaac ccctggcaaa gttcatgccc ggcatggagg ggcctgcact    127680
ggctgccccc acagttacag ttgttcattt ctccagtagc accccagggc tgagacacgt    127740
gggccacctg ctttggaaaa ggacccagga gagtgatgtg tcagtcaaag attggttttg    127800
tcatttaagg tagcttttgcc ttgtggtccc aaacactggg cccagcagca gaggaccctc    127860
cttggtttca catccagccc cgatgacatg tgaaatgtgt gaccacacat aagcggaccc    127920
tacgtccgtc ctgaggtggg ctcatcagga aagtgggaat tgtgattgcc cctgccgtgg    127980
ggcccagcca tggtcaccag agcctcttcc cattctggga tccctggctc ttgaatggaa    128040
tctggctgct ccacttccag ccaggcaggc ctgctcagag ccccagttcc tgcacgcaaa    128100
gtggtgagca gagggcctgg accatgggga ccctcattca gcaggcatca ctgctgttcc    128160
caagccaggg cccaggagga aattgggggt ggcaggggacc acagtgtgtt gcctcggag    128220 ggcagcagtg gccccgacgt gtcccccatc cgtgcattca gttggcatgt gctgagcatc    128280
tgtgatgtcc acaggctctg gggataaggc ggggaccaaa accaacgaaa ggcttccctg    128340
cctgaaaagg ggtcccactc tagtgaggaa gatctagaat tttctagcac ttcatggtga    128400
tggggccatg aggaaaagtg aagcagtggg aggggagtga cagggtggct agggaaggcc    128460
tctctgaggg gctgacagca aaggcctgca ggaagtggga ggagcattcc tggcagaggc    128520
catagtaggt gccagagccc ccagcagcac caaggggcag aaggggctgg agcagtcgca    128580
aggggtcgca aggggtagg agatctctga gtggccaaat caagctaggc ttggcaaccc     128640
aagtgcgtgc tgctgggttt acttgctgcc ttagggcatg ggcagctgtc ctgcctgtgg    128700
tcagctctgg ctaatcccgg cctctatcca ctggagggca gtagcaagcc cccagtgatg    128760
acgtcaaaat gtcaaaatgc cgtggggggca aaattacccc caagtggttc tttgttgaga    128820
gccactgcct gcttgagaat gtaagcccat gtgtcgccac attttacagc ttttttaagaa   128880 aaactagagc tttggggttt tttttagaca gggtctcctt tgtcacccag gctggaatgt    128940
ggtggtttga tcatagctca ccgcagcctt gacctcctgg cctgaagtga gcctcccgcc    129000
tcagccaact gagtaagctg ggactacagg tgctcaccac cacgcctggc tactttttca    129060 attttttttgt agagacaggg tctcccttttg ttgcccaggg ctccaactgc tgggctcaag    129120
ccatcttcct gccttggcct cccatagtgc tgggattgca ggcatgagcc accatgccca    129180
gcccagagtt tttgtgcaaa ctctgatttg gaaaatgttc ccttgagttt taaaccctga    129240
gagttttaaa cactatctcc cttgggaggg tcagctctga cggctgccag cacatggcct    129300
ttgacatcag ggtgccccag gcctttgacc tgggcatccg agggtcccag ggagaccag    129360 tccttgacag cctcctcctc ctgcagcaca gtagacgaca accccgactt cgacaacctc    129420
gacatcgtgg cacgggatga ggaggagagg tactttgatg aggaagaacc tgaggatgcg    129480
cccagcccag agctggatgg ggactgatgg ccgccaccct tcccaccgcc tgccccatcc    129540
ccatccccaa caaggcagct gattccaggc ctgctcagtg acccttttctc taggggggaca   129600 tcagggcagt gccccacaac ccacacacac caccatctca ctgggtctag tctcatctca    129660
```

-continued

```
gacaaccccc accccactg tttctggggt tccctttctc atctctccca ccctgtctcc    129720
tgcctctgtc tttcttggtg tctgtctggg cttctttctg tctctttctg tctttctgtc   129780
tctctcccta cccccgctcc ctctttccag tgctctggct ggctgtctct cccttttctcc  129840
ccctctctct ctgccttagg ctctgtctcc accgcagggc ccaaggtgaa agtcctcccc   129900
ttgccggagg ccagctggca gggccttttcg tggctggaag tggccagttt ggttccggtg  129960
ctgaccccta ggcccagcg cagctgcctc ccgtgctgtc tgtctccccc tctctgttta    130020
tgtctgcgct gtgtctcaca ctcagagcct ccttgcttct gttaggttcc catctctcct   130080
tctgcctcac tctgggcctc ttcttttctac ttgtacattt ccacctctct aggcctctgc  130140
tctcactgtc cctctctgtc tgtctctcag cctttatctc tgggttttga tcccccactc   130200
caggctctgg gccccttctt cccccttccc tcaaacctgg ctgctatagg cagcagaacc   130260
ctgaccactg agtaatacag ccccaggggga gggaggagac cccaggcagg gaggatgggg  130320
gcagctctct tctctcccca ggacccaggc tgtggatcac ggggcctgcc agcttgagtg   130380
tagagggagg ggggactcta cccttctcag ccccaccagc cccctctgc ccaaccacaa    130440
ttttcccttc ctccgccttc ctctccctct cctgtttaca ctccccaaat gcacacaggc   130500
tgttatcatg ggtcctgagt catcccacac acagcctgcc ccagcgtccc tgccccagc    130560
tggccgcagg gcccgcccca tggagccccc tgccgccctg ggctaatggg agccagatgg   130620
ccgcctggtg actcagccac cgggcctgtg ggaacccagg cgtcccgcct tccatgccc    130680
ccacacccgg ctcctgctcc cccagcagac acacacagga gggcctggcc actgttgagg   130740
gggcacacag ggcaagggtc accaagtcgg ggcctaggga ctcctcatgc ctctgagatg   130800
gaatggtggt atcctgccgt ggccaagcct gaaggaccct caaaactgcc tcctggagtc   130860
cacggttcct gacctccgag cctcagctat gccctctggg tcaaccagaa ttagagccag   130920
acagggaaag tgagagctgg atggaggcag acaagatgct cagagcgact attaaagaac   130980
gaaagcctct gctacggagc gcttctgtcc tctgtcaggc ccgagcgaag tgcctgacac   131040
cgggttggat cctcagatgg ccccatgaac tagtgaagtg ggtcaaagga ggcctggaaa   131100
gatgttgctt cctcaaggcc actcggccat cagaggcaga aatgaaacag gaacccaggc   131160
ctagaatcac aaaggtccta gaaaccactt ggctgtctgg cctctcaggt gtcagggcca   131220
tccagagtga gacagcattg gagggacaag tgtgcatgca gatgtcctca gacgggaagg   131280
tttgagaagg gtcagatggt aggcgggcct aacaagggct ccgtgctagc cactgtcccg   131340
cacacagaca ggatcaggtc atcttgatat ggagatcagt ccccaaatca ctgaattgtc   131400
ccagcagtgc tatgccctag gtactaccaa tatcactcct ctatttccca gaggaggaag   131460
cagcagctag actccaggac cttggggtca tacctctcag aaagccaaga gtgcaggatg   131520
agagctgtct gtctcttacc tgcctgtatt tgtgcccat ttttaaagag cagagggcct    131580
gggccacagg aaaggtatca gcccttggtg ataggcacat ttttaccag tctatcattt    131640
ggtcattaaa tttgtttaca atatactttg ctatacgtaa atttgttgtg taggtttta    131700
aaaagcgatg agagacacag aaattgagtc agaattaggg ttagtcagat ggtcaagacg   131760
tgagcatcta gctgacagac agaggtggag ccagtcccag ggacagggat tagatgggga   131820
gacaggaaga gaggtggaga cagagtgggg tagggatgac gggagacaca ccccctggtc   131880
actgcctctg agacctgggg gtggtgggcc ccagggcggg tgcctcccat cccctccca    131940
gttctcccgg ggtcggggta ggtggaaagg ctgagtcagg gagggcgggc ccgctggga   132000
gacaaccct aggtgggcat ccggcccca ccccgtgtc tcctgtccgt cctggccctg     132060
```

-continued

```
gcctggctcg ctggcctggc cgacaccccg cccccacgt ctgacacctc catgcgtcct   132120
gccaaagcaa gctgcctccc tgcactcttc ccctccagc tccagtcact ctgtccctct   132180
gtcccccgtc ccttctccct gcttctgtgc gtttctttcc agccctctgc cttcctccct   132240
caccgccact gctctgtctt ctcgttctgt ctccacacct ctggctgtcg gtgtctcccc   132300
gtgactttcc gtctcccctc tctctcctcc cttgttttc ccatgcctct ccctccctcc   132360
ctccctccct ctcctcccca ccttttccac tccatgtccc cagccattct ccatctctgt   132420
tctcagctcc tgtcacctcg tttccccatc cctttctctg ctggagtctc cctctggggg   132480
gctctgtcct ctcctcactt tgccctttcc ctctcgctgc tgtgtgtctt ggcccgcccc   132540
ccgtgccccc catctcctct gtctcccaca ctctgggaag cccggctggg atatccaggt   132600
tggagcctca ctggcggcca ctggaaaccc agaatgaggg gtcatcgcct ctcgcccacc   132660
cagaaagggc gcaggagggg gcagcaaggt tgcggggcct gtctggccag aaggaaatgt   132720
ctgtgctgtg gcctggtcac ccccgccccc aggacctgct gggctgctgc cgcccccggc   132780
cggggctgag gccgagtaaa cacagcaaac acagccgccg gcagcctggg atatttatac   132840
cgaggctggg cgtgggtcca gtgcccacca cagcccctgc cctgccctgc cttgcctgct   132900
gccacagcca gctccgagcc agcgtggcac cagccggcaa ggggacgcgc cgcagacaca   132960
gcctgcgctg ggtatggagg ccaacaggca ctggccgctc atgatgcagg cggctccatg   133020
gacgcaccct gtccccctcc cctgaaaaca ccagcacaca atgtggaccc acactcgcag   133080
ctgctcacaa acacacatcc acccctgctg agaacgcgaa atcccctcaa cgatgatgca   133140
aaacagaccc acacaactcc acacactgca gtcaccagcc tacatgtggg aacacagcat   133200
gcagacacca ccttagcacc tgctcacagc acccacaggc tgggaacacc agtccctgag   133260
atggacacac agccccgaag tacagccctc cctcacacag acaaacactg agaaccacag   133320
gaagcatgct ggatgcacac cacgtagaca aacatgctca gaataccagc gacacatgca   133380
ctgatcacag tgcaacccag aaacaactca actcatctgc ctcatatgta agaaacacac   133440
acggccgggc gcgtggctc atgcctgtgt ctcagcactt tgggagacca aggtgggtgg   133500
attacaaggt caggagttcg agaccagcct ggccaacatg gtgaaatccc atctctacta   133560
aaaatacaaa aattagacgg gtgtggtggt gggtgcctgt aatcccatct actcgggagg   133620
ctgaggcagg agaatcgctt gagcctggga ggcggagctt gcagtgagac aagatcgcgc   133680
cattgcactc cagcccaggc gacagagcaa gaccccgtct tacacatata cacacacact   133740
cactcccctc tcctggagaa acaccattcc cacagatgat taacatatgc agaaaacacc   133800
acatttcaag tcaaacttac acttaaaaat gcacaaattt acactcagaa gaacagtgaa   133860
gatgttgaga aaaatatcag acacacaata tgccccagat acatggccga cttgcagaat   133920
caaacagtgc cagagcataa aacccacaga aaatacaaca gcttgcccag cagaaataca   133980
aaatgcagac gcacacccca gaaatgcagc gcagccacaa acacacgag ctaacacgtg   134040 ctggggacac acatagacaa gaccatccat accaaacagc acacaggccc ccagaacacc   134100
catgccagac gcagctcacg ccacaaagct tggaatcacg cacacaataa gttcctgaac   134160
acacaaatcc gaatccacac tggaacctca aatactctgc atgtccagag actaagggg   134220 aaggggcttt ctctcaccca ccaatctccc cactcccct tgctgacccg gtcccagcc   134280 ccgtcttggg ggcggggag ggggcaggaa ggcctgagct ggcctccccc agcagcttcc   134340
tgccccacgg gggctggaca ggaagctggg gctccagccg gaacccaggc tcccccacg   134400 acttccctct gtggccccgg gccgcctgca gaggcagggg cggggcaggg ggaggaagcg   134460
```

```
gggagcccca aaccccctgc cctgcccctg cggtcggcca caggcggggg cagacttgtc    134520
ccgacggggc tgagccaccc atcgggcctg ggtgccaggg tggcagggca ggggcagtgc    134580
gcacgcggcc agaggaaggt gctgagccca cagtttcccc tccccgccct gtggggctgt    134640
gccagctcag ccggcagccc tgggcaggtg ggcggggtgt gtcatgaggg cgtgttgggc    134700
aggccgacca caccgcgaat gtgcagccag cacttgtcct caggccgagg cacgagctgg    134760
ggctgggcat gtgagggccg cgtctgccac cctgggggtg tgtctgctcc gtctgggacc    134820
ctgggtgtga cagtgtgtct gggcgtgacg tgacggggtc gctgcaatct gtgggccct     134880
gtgggactcc ccaggctgga attgtgcgtg tgtggcggag ggtgtgggat gtcagactga    134940
gtgggtaaga ccgacctgct gtctgtgagg ttgtgacgtg tcagacctct gtgtggggtg    135000
tgtctggtgg gactgtgaca ggtccgactg tggacatgca ccctggacct gtttgtgact    135060
gtgaacccat ggaggaggag gtggctgttg agggatccat ttcctgtccg ggctctgatg    135120
ccgtgatgcg tgtgcgtgca tgacactgtt tgaatcagtg tctggtgtgc ggtggttgcg    135180
accatgaccc tgtggaatat atttgtatat gactgtgttg tgccaggtcc ctattgaagt    135240
ctctgctcgt gttgtgtccc agtgaggctc cgaggctggg tggtgtttac gtgatgggct    135300
gacactttct ctatttgtat ctgtgtatat gtgggctgca gctgctgcca aatgacacag    135360
cccatgtgtt acgggccctg caggaatctc tgtgtgtcca cggcggctct gagaggtgaa    135420
tatttgtgta gtgtggggca ccgtccgtgt ttcccgccgt gtgagtgtgt ctgcatgtgt    135480
acacgcacca catcctcata gggctgcagc gattacagcc gagtcactgt gtcctagctt    135540
gtgactctgc ctcttggggc cagacctcag catctctata cctatccatt tgttggcatg    135600
tccttgcata gtgaactcct gcctcccac tcctccctca gccctgtgtg ctttgggacc     135660
tgaggccaga ggagtaacca catttctacc cctatgctga gctgggaggg ccccaggtcc    135720
ctggcaccca gacccagtgc tgccaacagc tctcatgccc acaggcaaag gaaccgcagc    135780
actcatactg tccttcctcc caggacaatc actgggtgtg gggaagtgaa acctaggaga    135840
aagagcagaa actgagaggc aggagaaaga ggaagcagga gagaattcac aagcaggacc    135900
atagcagatg ggaagaaatg gagacagcag agggagaccc acctgtggct gctgccattt    135960
cttgcctgga cagctggtct gtctgtgctc accctcaccc tgacacttct gtccactccc    136020
aaccatgagc aagacggcgg accctctgag cgcctaggtc aaaccctgcc atggctcctg    136080
tcttccttga gtgcaagttc tttttttttt tttttttgag atggagtctc actctgttgc    136140
ccaggctgga gtgcagtggt gcgactttag ctcactgcaa cctctgcctc ccctgttcat    136200
gcgattctcc tgcctcaggc ccctgagtag ctgggataca ggtgtgcacc acaatgccag    136260
actaattttt ttttgtattt tttattttta tttatttatt tgagatggag tctcactctg    136320
tctcccaggc tggagtgaag tggcgtgatc tcggctcact gcaacctcca cctcccaggt    136380
tcaagcgatt ctcctgcctc agcctcctga gtagctgaga ttacaggcgt gcgccaccat    136440
ggctaatttt tgtattttta gtagagactg ggtttcacca tgttggtcag gctggtctca    136500
aactcctgac ctcgtgatct gcccgccttg gcctcccaaa gtgctgggat tacaggcgtg    136560
agccactgcg cccagccttt ttttgtattt tagtagagac agggtttcac catgtggtcc    136620
aggctggtct caaactcctg acctcaagtg atccccctgc ctcagcctcc caaagtgctg    136680
ggattgcagg tgtgagccac cgtgcccagt ctttttttt tttttttttt aaagatgcag    136740
tcttggctgg gtgcgctggc tcatgcttgt aatctcagca ttttgggagg ccgaggcggg    136800
cggatcacct caggtcagaa gttcgagacc agcctgaaca acatggtgaa acttcgtctc    136860
```

```
tactaaaaaa aaatacaaaa ttagccgagc atggtggcgc atgcctgtaa tcccagctac  136920
ccagctactt gggaggctga ggcaggagaa tcgcttaaac ccgggaggca gaggttgtgg  136980
tgagccaaga tctcgacatt gcactccagc ctgggcaaca agagtgaaaa tccgtctcaa  137040
aaaaaaaaca taaaaaaaag atggagtctt gctttgtcac ccaggctggc atacagtggc  137100
acagtcaggg ctcactgcag ccttgacctc caggatcaa gtgatcctcc caccttagcc  137160
tccagagtag ctgggaccac aggtgtacat tttttaaaag tgttttgtag atatagggtc  137220
tcactatgtt acccaggctg gtctcaaatg cctggattca agtaatcctc ccatctctgc  137280
ctcccaaaag tgctaggatt acaggcgtga gccaccccgc ctggcctgaa ctactatctt  137340
ttattgtctt cttcactatc ccccactaaa gcaggttcct ggtgggcagg aactcctccc  137400
ttaacctctc tgggcttgtt tcctcacctt taaaatgggt gttatcagag tccctgcatc  137460
tcagagtgtt gctatggtga ctgaatgagt tcattaatgt aaggcacttc aacagtgccc  137520
aaggtgctca ataaatagat ctaactacag tagtgttccc cactggtccc ctgtgccttg  137580
atgccgggca aggaatagt gcagacaggc aggaggaggc agagagggag agagagggag  137640
tgggagtggg ggaacgtcag ggatggagac cccaggcagg cgcccaatga cacagagatc  137700
cgcagtcctc tctccatctt taatgggcc ccaggtgggc ttggggcacg ggtgtcctta  137760
aatacagccc ccatgggcaa ggcagcgggg gcggggcggg gtggggccgg gcctgccggg  137820
gcggggcggg gcggggcggg acctcagctg cacttgcagg agcgcacgat catgttggac  137880
agctgctcca ccttgggctt gcggcccacg tagtacacga tgggcagcgg ctccagcgcc  137940
tgcggcacgc agcacggcgc cgccgaggcg cccgggttat gctggttgta cagggccagg  138000
acctgcgggc ggcgggcggg gtcagggctc agggctcgtg gagggaggaa aacgcccctc  138060
cactgcccca tcccccaccc gctaccgcgc cagcctctct cacttcgtct ctccccgcat  138120
cccctcttcc catctccaat tcggtctctc ttatcttcta acatcctatc ttattctgtc  138180
tctccccacc tgtctgattt tcttttttgtt ttgagactgg gtctcgctct gccacccagg  138240
ctggagtata gtggcacgat catggctcgc tgcagcctca acctcctgag cgcaagccat  138300
cctcccgcct cagcctccgg agtagctcca accacaggga agcgccacca ctcctagctt  138360
ttttttttt ttttttttt ttttggtag agatgggatc tcagtctgct gcctgggcta  138420
ctctcgaact cctgggctca agcgatcctc ctgcttcagc gtcccaaagt gttggtatta  138480
ccatcgtgag ccgccgcgcc cgcctgattt tctttctcag tctctgtccc tcctcatctt  138540
cgcctcttgc cttgttgtgt atctgtcttt gtctctcctt ggcctaactc tgtgtctgta  138600
tctgtctctc tcattttgtc tctccatttc tgcgttttc cttccatctc cctgtctctc  138660
ttctcccctt cacccccatc cctctgttac ttcactctgt gggtcttcat agctcatctc  138720
cctctggccc ctgctcagag cccctctcta gcttcctgcc tctctcccca tctctttatt  138780
cattcccctc cccaccccat ccctctcttt ctccccatcc tgccaactca cctctctgac  138840
tttacttctc tttctctctc ctcttcctcc gtcctggctc cccccaagcg catctcgtag  138900
cccggtgggc cagacgtacc ttgctgtact gcgtgtccag gctccaaatg taggggcagg  138960
gcccgaggca gaagttggca tggtagccct tgggctcgtg gatccacttc cagccgaggt  139020
ccttgcggaa gtcaatgtac agctgccgca cgcagcagtt cttctccgtg gagctgcagg  139080
caggagagac gcgtcagggg cagggagggg ctaccaccat agaagccaca tgcccctcct  139140
ccccaggtgc gtgtgtcacc ctaggttgcc ccccagccc tatctccatc tgggtctccc  139200
ttgcacccac tgtgttaata acaacacaaa tagtcatgat aatcactaac acagattaag  139260
```

```
cacttcctcc agtgctaaga gcaatgtaat aattaatttc acgcaatgct taagacaagc 139320
ctgtaagaag ccagatgacc atccacgggg gggctaaata aatcatggca tgccacaccc 139380
tggaacatac aaaataacac agctccatgt aaactgatct gctctatttg tgcaacaaat 139440
gtttattgaa ctactactgt gtgctgggct gggatctact gtggactgag acaaatgaa  139500 acagatagaa ataggctagg catggtggct cacacctta atcccagcac tttgggagga  139560
tgaagtggga ggatcgctgg agtcgaggag ttcgaggttg cagtgaacta tgataacacc 139620
actgcatgcc agcctggaca acaaagtgca agaccctgtc tctacaaaat ttttttttcaa 139680 ttttttttaaa aaagagacag aaatctctgc cctccatggg catgctataa attgtcttgt 139740
cactcctctg ctctgaacct ggctccatct cacggcaaat gcccaagtcc tcaccgtgag 139800
ccacaaggtg ctatcaaatc tggctgatct caactccctc tctcacgcct actccactcc 139860
agccacactg gcgtcctgtc tgttcctcag acagtcttat ttcggggctc ctgcatctgc 139920
tgttccctct gcctgccttg ctagtcccac agatacccac tccagcttgt tccttcactt 139980
catttcttct ttttttttct attttttttt tttttttttt ttgagacaga gtctcactct 140040
gtctgccagg ctggagtgca gtggcatgat ctcggctcac tgcaacctcc gcctcccagg 140100
ttcaagcgat tctcctgcct cagccttccg agtagctggg attacaggcg tgtgccacca 140160
tgcccggcta attttttttgt cttttttagta gagacagggt ttcaccatgt tggccaggct 140220
ggtctcgaac tcctgacctt gtgatccgcc cacctcagcc tcccaaagtg ctggtattac 140280
agacctgagc cactgcatct ggcctattta ttcttttttaa tttgttattc tttttagaga 140340
cacggtctca ctatgttgct gaggctggtg tcgaacttgg gctcaaacga tccgcacgcc 140400
tcggcctccc aaagcattgg gattactggc atgagccacc acacctggcc ccttcacttc 140460
atttaaacct tagctcaaat gtccttcact cagggaccct taactcctaa agcagtgtct 140520
ggaatgcagt aggtactagt aaatatcagt tacatgactg aacatcacct cctcagagat 140580
acctttctga gccatccttt ccaaaatatc caagtgactg ttagttccat ttagtgcaat 140640
acggtattgc agttatgcaa gaaaatataa aaatgtctgc atttgaaatg gggcaaaatc 140700
ttaattaccg atgacgctgg atgagagttt acgggcattc attatcttca ttgcttttgt 140760
atacatttga aattttccat aataaggaa tttaaatcag aataggaaaa ataacagttc 140820
ccaatatcta ttactctctg cctgccttct tctggtttat tttacttctt agaactgtca 140880
aagaggccgg gtgcagtggc tcacgcctgt aatcccagca ctttgggagg ccaaggcggg 140940
tggatcacct gagatcagga gattgagacc agcctgacca acatggcgaa acccgtctc  141000 tactaaaaat acaaaaatta gctgggtgtg gcggtgcttg tctgtaatcc cagctactca 141060
ggaggctgag gcacaagaat ctgcttgaac ccaagaagca gaggttgcag tgagccaaga 141120
tcgtgccact gcactccacc cagggcaaca gggtgagact ctgtcttgaa agaaaagaa  141180 aaaagaaaga aagaaaaga aaagttgac aatgcctttt tttttttttt ttttttttga 141240
gacagagtct tgctccgtca cccaggctgg agtgcagtgg tgcaatcttg gctcactgca 141300
acctctgctc atagattggt ggggccagcc aggcacggtg gctcacgcct gtcatcccgg 141360
cactttggga ggctagggca ggcagacttg aggaccctgt ctttactaaa aattcaaaaa 141420
ttagctggac ctggtggcgg gcacctgtaa tcccagctac tggggagtct gaggcaggag 141480
aatcgcttga acccaacttc aagtggcacc ggataaccta gaggcaagat aaagcctttc 141540
caagagccac agaagcctga gaaggaagtc aagaaactga gatccctgtg aactcagccc 141600
gtaccaccca attttggttgg acctcagttt cctcatctgt tcagaggtag gagctactag 141660
```

```
ataaaataag gtgttaagct gagggccaag gggccatcat gggcaggctt agggagggcc    141720
atgagtgcct gagatcatat gcacatgtgt gtatgtatgc atgtatttct gggaaaaaga    141780
gtcctggctt tcactttctc acaggaagtt ctgaactcac aaaaggggaa gaactagtgt    141840
ccggaatctt ttttttttt tgagatgagt ttccctcct gttgcccagg ctggagtgcg    141900
atggtgtgat ctcagctcac tgcaacctcc gtctcccggg ttcaagcaat tctcctgcct    141960
cagcctctca agtacctggg attacaggca tgtgccacca tgcctggcta attttttgta    142020 ttttagtag aggctgggtt tcaccatgtt ggtcaggctg gtctcaaact cctgacctca    142080
ggtgacccac ccacctcggc ctcccaaagt gctgggatta caggcatgag ccaccgcacc    142140
cggctcagaa tcatctttaa tatgcagttc aaccctagct ggggttctga gatcctagga    142200
tttgaacaat ctgtgatact gttatccaag tcagcagctc tccacgtgag ctcccaggac    142260
cagcggcagc atcacctggg aactatggga aatgcagatt ctcaggtggc accccaggcc    142320
actgaaatca gaaattgtgt gcaggactgg gaacaacagt ccgtgttgaa caagccgtct    142380
aggtgatcct ctgactcatt ttttcagcac acattcgggg cctaccctgc accgggcctt    142440 gggatacccca cagcccttgc ccttgccaag cctcttccgt ccagtctctc aagacctagg    142500
ccaggtgcag tgactcacgc ctgtaatctc agcactttgg gaagccaaga ccggtgaatc    142560
gcttgagccc aaggagttta agaccagcct ggggagcata gtgagaccct gtcgctacaa    142620 aacttttat aaataaaga cccaacagag actgtttgtt gagtcaaaga tctacttagg    142680
gccccagggg agcccagagg cctcacatcc atcttggatg ttggagaaag gggttaggaa    142740
ggaggtagtg ttcgagctgc cttaagaaca aattttccta tgaaagtttt ttttttttt    142800 ttttgagatg gagtcttgct ctgttgcccc aggctggagt gcagtggtgc aatcttggct    142860
cactgcaacc tccatgtccc aagttcaagc aattctcctg gctcagcctc ccaagtagct    142920
gggattacag gcacacacca ccatacccag ctaattttc tgtatttta gtagagacag    142980 ggtttcacca tgttggacag gctggtctcg aactcctgac ctcatgtgat ccacccgcct    143040
cagccttcca aagtgctggg attacaggtg tgagccaccg cgtccagctg aaagtttca    143100 gatgtacaca aaagcagctt caacaatgac caactcatgg ccaatttcca ttgcatctct    143160 accctatcc actatctctt tttttttttt ttttgagaca ggatctcact ctgtcaccca    143220
ggctggagtg cagtggtgca atcacagctc actgtggcct ccagctcctg gggctcaagc    143280
caacctccca cctcagcctc ctgagtagct gggacaaaag gtacacacca ccaggcccag    143340
ctacttttca tatttttt tttgggagat ggggtttcac catattgccc aggctggtct    143400
ccaactctta ggctcaagca atcctcctgc cttggcctcc caaagtggtg ggattatagc    143460
tgtgagccac tgcagccagc cgacaatggt ttatctcaaa gcacatgcaa tccaccgtgt    143520
tgcttcatcc ataaatattt caaatgtatc tctaattaag actactttaa aacacagtca    143580
caataccatg taagaaaatt aacaattcct tgatatctag aggaatatct agacagagtt    143640
cacatttacc caactgtctc ataaatatct tttttttta agcctgtgta aataaggatt    143700
caagtaaggt ctacacattg caattggttg atatgtctct taggattttt tttttttt    143760 aatttttgag atggagtctc actctgtcac ccaggatgca gtgaagtggt gcaatctcgg    143820
gtcactgcaa cctgtgcctc ccaggttcaa gtgattctcc tgcctcagtc tcccaagtag    143880
ctaagactac aggcgcctgc caccataccc tgctaatttt tgtatttta attatttatt    143940 tattttttg agacgggagt ctcactcttg ttgcccaggc tggagtgcaa tggcgcgacc    144000
tcggctcact gcaacctcca cttcctgggt tcaagcagtt ctcctgcctc agcctcaaga    144060
```

```
gtagctggga ttacagggcc cgccaccacg cctggctcat ttttgaattt ttagtagaga   144120
ggaggtttca ccacgttggc cagactggtc tcgaactcct gacctcaggt ggtccaccca   144180
ccttggcctc ccaaagtgct gggattacag gtgtgagcca cgacagctgg cctgattttt   144240 gtattttag tacagacagg gtttcaccat gttggccagg ctggtctcca actcctgacc    144300
tcaagtgatc cacctgcctc agcctcccaa agtgctggga ttacgggcgt gagctaccat   144360
acctggcctc tcttaggact tttttcaaaa tctacaaaat catctctctc tctctctgta   144420
tatatattca gggtcaacta tatatagact gacccttgga catgggtttg aactacatgg   144480
gtcctcttac aaaattcacc acttacaggt gaattttct tccacctctg ccctgagaca    144540
gcaagaccaa caccttttct tcctcctcct cagcctactc aacatgaaga cctttatgat   144600
aagccacttc cactcaatga atggaaaata tacttcctct tccttatgat tttcttaagg   144660
acattttctt ttctctatct tatttttaaa atgcaggcat aggccgggag cagtggttca   144720
agcctgtaag gccagcactt tgggaggccg aggctgatgg atcacctgag gtcaggagtt   144780
caagaccagc ctggccaaca tggtgaaacc ccgtctctac taaaaataca aaattaccc    144840 gggtgcgatg gcggatgcct gaaatcacag ctatttggga gactgaggca ggagaattgc   144900
ttgaacctgg gaggcggagg ttgcagtgag ctgagatcac ttcactgcac tccagcctgg   144960
gtgacacagc tagactctgt ctcaaaaaaa aaacaaaga atacggccgg gtgcgtggct   145020 caccctgca atcccagcac tttgggaggc tgaggcgggt agatcacttg aggtcaggag   145080
ttcaagacca gcctggccaa catggtgaaa ccccacctct actaaaaata caaaagttag   145140
ccgggcatgg tggcaggtgc ctataatccc aactactcag gaggctgaag caggagaatt   145200
gcttgaaccc ccgggaggtg gaggttgccg tgagctgaga ttgtgccatt acactccagc   145260
ctgagtgaca acagcgaaac tccgtctcaa aaaaaaaaa aggggatata ggacataata   145320
cataaaacat gcaaaatatg tattattcgg ccgggagcag tggctcatgc ctgtaatcct   145380
agcactttgg gaggctgagg tgggcggatt gcctgacctc aggagttcaa gaccagcctg   145440
ggcaatacgg tgaaacccca tctctactaa aatacaaaaa attagctggg cgtggcggtg   145500
ggcacctgtg gtcccagcta ctcgggaggc tgaagcaaga gaatcacttg aacccgggag   145560
gcagaagctg cagtgagccg agaccgcacc actgcactcc agcctgaatg acagagactc   145620
tgtctccaaa aaaaaaaaaa agtattaatc aactgtttat gttgtggata aagcagaatt   145680
ccagtccaca gtaggctatt aatagttaag ttttgggga gtcaaaactt gtatgtgaat   145740
ttttggttgc atgggggta cgtgtgtgtg tgtgtgtgct ttccccttct ttgcattgta    145800
tttgatgaag aaactgggtg aggtttcttg cagtctgagt tttgctgacc atttcctctg   145860
ttcctgtctt tctagaaaac tgttaggatc tacagtcctg atcagattca ggtttgattt   145920
tttttttttt ttcctgagac aaggtcctgc tctgtcctga aatgcagtgg cgtgatcctg   145980
gctgactgca gccacaacct cctaggctca agcactcctg cctcagcctc ccaagtagct   146040
gggactacag gcacacacca cccagccagc tagttttttt gtatttcttg tacagaggca   146100
gggttttaac atgttgcaca agctggtctt gaactcctaa gctcaagcga tctgcctgcc   146160
ttggcctccc aaagtgctgg gattacaggc atgagccacc gcacctggcc ttcaggtttg   146220
attttttgcc aagacttcct aggcaacatt gggtccctcc ctacgaggc tgacatggct    146280 ggctatctcc ctttgtaatg tcaggagctg ttggcactca agacctcaat ttgtggccgg   146340
gcgcagtggt tcatgcctgt aatcccagca ctttgggagg ccgaggcggg tggatcacga   146400
ggtcaggagt tcgagaccag cctgaccaac atggtgaaac ccagtgtcta ctaaaaaac    146460
```

```
caaaaattag ccgggtgtgg tggcacacgc ctgtaatccc agctactcag gaggctgagg 146520
caggagaatc acttgaacct gggaggcgga ggttgcagtg agccgagatc acgccactgc 146580
actccagcct gggcaacaga gcgagactct gtctcaaaaa agacctcaat ttgttcattg 146640
acagcgttgc tgggctgatg gcgctaagat ctggtggtga aggagcctgg gagcagggct 146700
gattttctgg cagggaaaca gccggtaaca aagcccagag acaggaccaa aatattttaa 146760
gcaagggagg aataaggtca gatgatcact ctaaatttac aacattctaa ctctccattt 146820
caactttcta ggaatccaac atttcagctt tcttagattg cagtattagc attccagcat 146880
cttatgattc taacattctg acagcatctt caactctcta ggattccccc tttccaacct 146940
ttgaggatct tggcattcct gaattccagt atgccagtat tgcatcccaa cattccaaag 147000
ttctgagcca tcactcaaga ggttcaaact gacactttct ttcttttttt tttttttttt 147060
tttttttaga tggagtctcg catcattgcc caggccggag tgcagtggcg cgatctcggt 147120
tcactgcaac ctccaccccc gaggttccag tgattctcct gccccagcct gggtacctgg 147180
atagccgtaa tcccagccga gtagctggga ttacaggtgc cagccaccac acctggctaa 147240
tttttgtatt tttaatagag atggggtttc accatgttgg ccaggctggt cttgaactcc 147300
agacctcagg gatccgccca cctcagcctc ccaaagtgct ggaattatag gcgtgagcca 147360
ccgcgcccag cctgctgcca cttttctatta ataaaatccc agcattctaa tattctaaca 147420
ttccaacact gagttccaac atgctgagat accaatattc tgctttctcc aactccaaca 147480
tttgtggatg tgaatatttc aaaacagaat tctaccactg tgagcccaat attcaaggac 147540
tccaatctgc caacactggt atccacaatt ggccagtggt gcaggaattc cacatgggcc 147600
atcttcccat tttgaatccc caaattctag gattccaatg tttcagcttt ccttgagtcc 147660 gacatttttcc atttcagtaa ttaacaccaa attctagcat tctagaatcc cagcattcta 147720
gaacctcaac ctgccaacaa tttagggatt caagatggtg accttccaac tttgaattcc 147780
aacaatcaca gggttcaact ttctaacatt ctgtgattcc aacactccag caagaaagca 147840
aggctgggcg tggtggctca cacctgtaat cccagcactt cgggaggctg aggcaggcgg 147900
atcacgaggt caggagatca agaccatcct ggctaacatg gtgaaaccca gtctctacta 147960
aagatacaaa aaattaggcc gggcgcgttg gctcacgcct gtaatcccag cactttggga 148020
ggctgaggtg ggtgtatcac gaggtcagga gatggagacc atcctggcta acacagtgaa 148080
accccatctc tactaaaaat acaaaaaaat tagctgggcg tggtggcacg tgcctgtagt 148140
cctagctact cgggaggctg agacaggaga atcgtgtgaa cccgggaggt ggagcttgca 148200
gtgaatcaag atagcgccac tgcactccag cccaggtgac agagcgagac tctgtctcaa 148260
aaaaaaaaaa aaaaaaaaaa aaaggaacct gatcccaaca ttacaagact cccagttctt 148320
tttttgtttt ttgtggctgg gattataggc gcccaccacg cctggctaat ttttggattt 148380
ttagtagaga cgggtttcac catgttggcc agacaggtct caaactcctc acttcaggtg 148440
atccacctgc ctcagcctcc caaagtgttg ggattacagg cgtgagccac cgcacctggc 148500
acaagactcc tggttcttac acccagacct catcccctga gccctccaag ctaaaggaga 148560
cagatgctca gcccaagcac agcagcagcc aggtgtccaa cctggagcac ctggtcagca 148620
gatggcagtc atgcccccag cctggaaggc ctccatccag gctacaaggc tcacctgaag 148680
caatagttgg tgtccagggc tcggcggtgc cgggagcttt gcagatgctg ggccctctcc 148740
agcggggtgg ccatgagaag caggaaaggc cggttcatgc catgaatggt ggccaggtca 148800
cctcggcggc cggtagtgaa ccctgctttg gtgtgggagt caggggatag gggacataca 148860
```

```
cacacactct cagagggata gataagtggg gcgtggggca gatgggaaca cacacacgca    148920
cacacgtcac aactgggcat ggccgggaa gcaggcctca ccgttgatgt ccacttgcag     148980
tgtgttatcc ctgctgtcac aggagcagtg ggcgctaagg cgaaagccct caatttcccc   149040
tgtaggagtg gcgagaggga agccagtctg agagtgcagc tcacccagcc cctggaggaa   149100
gaggaaggaa ggagcaaacc ccaggggctt ccttcctgcc tcccccaccc accccactct   149160
gccctctcac tgcagctctc tcttttttt tttttttttt ttttttgagac aaggtctcgc   149220 agcctcaatc tccaaggccc aagcaatcct cccatctcag cctcccgagt agctgggacc   149280
acaggcgcgt gctaccacgc atggctaatt ttttttttt ttttgagatg gagtctggct    149340
ctgttgccca ggctggagtt cagtggcgtg atatcagctc actgcaacct ccacctccca   149400
ggttcaaacg attctcctgc ctcagcctcc caagtagctg ggataacagg catgcgccac   149460
cacacccggc taattttttg tattttagt agagatgggg tttcaccatg ctggccaggc    149520
tggtctcaaa ctcctgacct caggtgatcc gcctgcttg gcatcccaaa gtgctggat     149580 tacaggcttg agccactgca tccggcctac acggctactt tttaaattct ctgtagagac   149640
agaggtctca ctatgttgcc caggctgggc tcaagcaatc ctcctgccct ggcctcccga   149700
agtgctggga ttacaggcat gagccactgc acccagccag catcaatctc ttgaatgaat   149760
gagtgaatga tgttttctag gctcctacaa tgtgccgaag cctgtgctgt gtgcttggga   149820
ctcagcattg accaagacag atgagctcct tctaggcctt tgtcgaacag cccaggacac   149880
tcctcccagt gcccacctgc tccctaatcc ctatttttt ttttctttt ctttttttt     149940 tttgagacgg agtttcactg ttgttgccca ggctggagtg caatggcacg atcttggctc   150000
actgaaacct ccacctcctg ggttcaagca attctcctgc ctcagcctcc cgagtagctg   150060
ggattacagg catgcatcac cacgccgagc taattatgta ttttagtag agacggggtt    150120 tctccatgtt ggtcaggctg gtctcgaact cccgatctca ggtgatccac ccacctcggc   150180
ctctcaaagt gctgggatta caggcgtgag ccaccatgcc aggccccta atccctttt     150240 tttcatgtgg ccaaactact atttatcctg tgagtctcca cacaatcacc ctcacccagc   150300
aagccctcct agactcccca gatgggtcca ggtgccttct ctgggctccc aacagcactt   150360
agggcgttcc cccatcctgc atgcctccct gtcccagcct tgtcctccct gctggtgcct   150420
ccccatccca ttcttgatca ttctaggtca ttcctgcctg gtggggcctt gacaagatct   150480
cttaggtgtc cagaagtgac tgtgggcccc atgagggcag aactgagggc tgtcttggtt   150540
atcactatgt cccccacacc acccagcaca tggccaggca cacagcagga acctgtgggc   150600
aattattgaa taaaagcata aatgagaggg aggtgaggga gagagatagg ggcaccatgg   150660
gccctgccag aaaccagaca gagacaatca tctcctggac agatcaaatg agttagttag   150720
gctctccctg gcctccaggc ctttgcacag gctgttccct ttgcctggaa tctttttt     150780 tttttttt ttgagatggg atctcactct ttcatgtagg ctggattgca gtagtgtgat    150840
tatgactcac tgcagcctcg acctcccagg ctcaggtgat tctcccacct cagtctccca   150900
agcagctgga actacaggca cgtaacagca tgcatggcta attttttgtat ttttgtgtag  150960 agaccgggtt tcgccatgtt gcccaggctg ctctcaaaac tcctgagctc cagtgatcca   151020
tcctccttgg ccttcaaaag tgctgggatt ataggcataa gccaccatgc ccagcccag    151080 aatactctta cacctctcct tttcctgacc attctactca tcccttcaac atcagctatg   151140
gtgcccctcc tccaggaagc cctccctgat tctgggctgg gtcaggtacc tcctttgggc   151200
tccccatccc agtcccaccc actctgggtc atcactgcct tacaggtctg ttccccagct   151260
```

```
acctagccaa tggactatat gagctctgtg agggcaagga tgggctgtt ttggtcattg   151320 ctgtgtcctt ggcatcaccc atcacagggc agggcagaga ggtgctcagg aaacagatta   151380
gccaatcact caggtttcca tgccacagag gggagccagg tctcagcact ttcacaccag   151440
tatggggcgg agaggggtcc taggcaaagt gaccccagga caaacaatgg ggtggacccc   151500
agggagaaac aggggtggga cacacaagta atcctcacct ccacggctca accactgccg   151560
cacaactccg gtgacatcaa aagataacca ctctggcgag tcgctgggtg ccagcagccg   151620
gttgctgagg tatcgccagg aattgttgct gtatttctag aggatgatga aggcaggaga   151680
gagacagtgg gtagatggtg tcacgacccc acatacacta actgaatcct tcaccccatc   151740
tgcttcccca aacaggcttc cagaaagttc ccaggcacta ccctctcaga cagccacctg   151800
tgtggtcctg tggcacccat cctccccaac agtacccatg agaggagggg tggagaaaaa   151860
gctcaggctg cggtcaagtc accttcacac agctcagccg aaggtgtttt cttgccttct   151920
cgaggcctgt ttcctcattg gtgaaatgct aagccccact cagcgtggac agcccacaat   151980
gctaaaattc tgctgctaac attctgggcc gggcgcagtg gctcacgcct gtaatcccag   152040
cactttggga gccaaggtg ggtggatcac ttgaggtcag gagttcaaga ccagcctggc   152100
caacatagtg aaacccatc tctactaaaa atacaaaaat tagccaggca tggtggcaca   152160
cgcctgtagt cgccactatt tgggaggctg aggcaggaga attgcttgag cccgggagac   152220
acagactgca gtgagccaag atcacgccac tgcactccag cctgggcgac aggacgagac   152280
ttcgtctcaa aataataata ataaataaaa taaaattctg ctgcaaacat tctgggtttt   152340
actgagcata cggttctgca aatttgacac cctgaattct cagtaactta gaagtcattt   152400
ctaatgattc cggctgggca cggtggctca cgcctgttat cccagcactt tgggaggcca   152460
aggcgggtgg atctcctgag gtcaggagtt caagaccagc ctggcaaca aagtgaaacc   152520 tcgtctctac taaaaataca aaaattagcc aggcgtggtg gcacacgcct gtaatcccag   152580
ctactcagga ggctgaggca ggagaatcac ttgaacccaa gacacagagg ttgcagtgag   152640
ccgagattgc accactgcac tctagccagg gtgacagagt gagactctgt ctcaaaaaaa   152700
aaaaaagtca ttttgtgatt caaatgtttg ataatatccc aagatttcca cttctagagc   152760
ctgagaagct ttagaagact aatgttctat aaacccaaga gtctgccatg ccgcacctag   152820
atgctgcagg tacccaacat ctgtgtagaa taattttctg ggccaggcac agtcgctcac   152880
gcttgtaatc ccagcacttt gggaggccga ggagggtgga tcaccagagg tcagaagttc   152940
gagaccagcc tgaccaatat ggagaaacac cgtctctact aaaaatacaa aattagctag   153000
gtgtggtggt gcatgcctgt aatcccagct gctcgggtgg ctgaggcagg agaatcgctt   153060
gaacccagga agcaaaggtt gtggtgagcc aagatggtgc cattgcactc cagcctgggc   153120
aacaggagca aaactccatc acacacacac acaaaaaaaa gaagaatttt ctggggctgg   153180
atagtccact ccagggactg cagaataaag ctgaattccc cagactccaa gaagccaagc   153240
taacatagga caaagttctc tcactgtgaa agtctgaaat ctaccatcct atgagttaac   153300
attccctctg atatggattc tagctcatag aaactgctag agcctccagc ccttccagat   153360
gccccagtcc tcttggaagc tccctatctt ctagagcagt gctgtcctaa agaactttct   153420
ggaaatgtgc tttatctgca acatccaaaa tagtagctgc taaccacatg tgactataga   153480
gtactagaaa tatggccagt gagaatgagg atttcttttt catttttatt tttttgagac   153540
agagtctcgc tctgttgccc aggctggagt gcagtggtat gatctccgct cactgcagtc   153600
tccacctcct ggggtcaagc gattctccca cctcagcctc ccaagtagct gggattacag   153660
```

```
gtgcctgcca ccacacctgg ctaattttg tatttttagt agagatggag tttcgtcatg  153720
ttggccaggc tggtcttgaa ctcctgacct caagtgatcc acccacctg gcctcccaaa  153780
gtgctgggat tgcaggcatg agccaccacg cctggcctat atatatatat ttttgagacg  153840
gtctcgctcc atcacccagg ctggaatgca gtggtgcaat cacagttcac tacagcctcg  153900
acctcctggg ctcaatcaat cctcccacct cagactactg agtagctggg actagaggca  153960
cgcatcacca taacaggcta attttagtat tttttgtaga gacgaagttt caacatgttg  154020
cccagactgg tctcggactc ctgggctcaa gcaatctgcc tgcctcggct tcccaaagtt  154080
ctgggattag aggtgtgagc cactatgcct ggccctaaat ttttaattta atttttaaaca  154140
atttaaattt taatcaagct aaatgtgact agtggctgtc atattggaca gaatgattct  154200
agagccccca acctttttcag agattccaac tttcaagaat cctgtgtcct aaagagtcc  154260
aactcctaag attccagcct tctaagtgtt taacatccta ggatgcaaag agtctgaaca  154320
tttaaaagtg ctctaggttc cgggtgcagt ggctcacacc tgtaatccca gcactctggg  154380
aggctcaggt aggagaatca cttgagggca ggagtttgag acaagcctgg ccaacatgat  154440
aaaactctgt ctctactaaa aatacaaaaa ttagcccagc gtgttggcac atgcctgtaa  154500
tcccagctac tcgggtggct gaggcaggag aatcacttga acccaggagg cggaggttgc  154560
agtgagccga gatcacccca ttgtactcca gcctgggcga cagagcaaga ctccatctca  154620
aaaaaaaaaa aaaaaaaaa agaggccagg cgcagtggct cacgcctgta atctgagcac  154680
tttgggagac cgaggcaggt ggatcacgag gtcaggagat cgagaccatc ctggccaaca  154740
tggtaaaacc ccatctctac caaaaataca aaaattagct gggcgtggtg gcgcacacct  154800
gtaatcccag ctacttggga ggctgaggca ggagaatcac tggaacccag gaggcggaga  154860
ttgcagtgag ctgaggtcat accactgcac tccagcttgg caacagagtg agacactgtc  154920
tcaaaaaaaa aaaaaaagcg ttctaggatt gtatggtttg tgttcttcta tccttcaggg  154980
accatctagg tggaccttgt aaccagccga cccacagcca cccccttggt cacagctcac  155040
cctctccagc ccatgccctg accttccttc tggctcatgt cctcacctgg tacagctcca  155100
cgtgctgctc cactttaac ttgagcctca gcagacgcag ctctgcccgg gagagcaaca  155160
cgggttcagg taccgcttct cggagctctg atgtgttgaa gaacatatat atgctgtgtg  155220
tactctgctt gaacttgtca tagatttcta gcagggagaa atgaagggag gcgatcaggg  155280
gtttggcaga ggtgagggga gctggtgctc ccaactctag gagttttgga gctgacagct  155340
ctggggtgga gtcagtctct gatacctttt atttattat ttatttattt atttattat  155400
ttatttattt aaatgaattt tttttttttt ttgagacgga gactcgctct gtcacccagg  155460
cttggagtgc agtggcgcaa tctctgctca ctgcaacctc cgcctccagg gttcaagcaa  155520
ttctcctgcc tcagcctccc gagcagctgg gactaaaggc tcatgccacc atgcccagct  155580
aattttttgta tttttagtag agatgggggtt tcaccatgtt ggccaggatg gtctcgatct  155640
cctgacctcg tgatccaccc gcctcggcct cccaaagtgc tgggattaca ggtgtgagcc  155700
accacgccca gccctgactg tgatactttt tagctgtgtg accttgagga agtggttct  155760
ccccctaggt ttgtttcctc ctctgtaaaa taggtcctaa ccacattcct ctctcatgta  155820
gcatcatctc tcaagtcgac taaggctggc accaaggggga accactctgt ttgctctggc  155880
cttccttgcc ccaaatgcaa gagcccctaa aatgcagagt aaggatcaaa ggcacaggct  155940
ttggactcag atagtgcctc tgctgcctct tggctgtgtg accatgggca gttaacacc  156000
tctttctgaa tgtcagtttc ctgttattct ttgaaaaaca gcaataacat taagctccct  156060
```

```
gcattcccac acagactctc ctaatttaag cgctgtgtaa ccttgggcaa gtgaattcct 156120
ctctctgagc caggtgtaag acaagacaga gtgactctag aacccattcc agtattatag 156180
tgggaaatta gatgacccag gtcaagccat gtggcaccaa ttctgcatac actggtcact 156240
caatcatgta tacgtctaag agtgctggct gggcgcagtg gctcacgcct gtaatcccag 156300
cactttggga ggccgaggtg gattgattac ttgaggtcgg gagttcgaga ccagcctggc 156360
caacatggtg aaacccgtt tctactaaaa atacaaaaat tggccaggca tggtgccgga 156420
cggctctaat cccagctact tgggaggttg aggcatgaga atcgcttgaa cctgagaggc 156480
agaggttata gtgtgccgag attgcgccac tgcactccag cctgggtgac agagtaagac 156540
tctgtctcaa aaacaacaac aacaaaaaac cacaaacag cgctatttac cagatgctat 156600
ctaaagcact ttacaaagat gaagacattt aaacctcaca accttatact attattatac 156660
ccgtttaata gatgagaaac tgaggcaccg agattaagta atttgcccca aggtcacata 156720
gctgcagact gggattcaaa ctcaagctgt ctcattccag agactgtgct tttttttttt 156780
cttcccccaa gagacagggt ctcactctgt cccccagacg gaagtgcagt agcacaacca 156840
tggctcacgg caggctggaa ctcctgggct caagggatcc tcacgcctca gcctcccaat 156900
atgttgagat cacaggcatg agccaccaca cccacccagc tagagactgt gctcttaacc 156960
cctaagtgat tcttctactt attttatta ttagttttcc acccttaact cccttcccca 157020
gctggttagg gaaagtgaag ttcattctgg gtaggaatgg ctgtagtggg gagaaaagga 157080
attaaggtgt tttcttttct tttttttttt tttttttga gatggagttt ctgtcgccca 157140
ggctggagtg cagtggcgcg atcttggctc atagcaacct ctgcctccca ggttcaagcg 157200
attctcctgc ctcagcctcc caagtagctg ggattacagg cgccgcccgc caccccgccc 157260
agctaatttt tgtattttta gtagagaccg ggtttcacca tgttggccag gctggtctcc 157320
aactcctgac ctcaggtggt ccacccacct tggcctccca aagtgctggg attacaggcg 157380
tgagccaccg cgcccagcca aggtattttc tagtttagga aaagtttggg gatggggatg 157440
agggaacagg ccatgaactg ctggatcaac tggggcaact gcttccagcc tcccatagtg 157500
ggggtgtgaa aagagactgg tgagaaaggc agaggaaacc cctcccctac ggccccccttc 157560 gatcctcctc ctcctcccca gtctccctcc ccacccagcc ccagtaagcc ctattcttgg 157620
cccggaggtt actcagcaaa ccccaaagga aaggcagagc cttggctggg gaagacagat 157680
agggaggaag acagagagga gggagaggaa gggttggagg gtgatgcaga gagggagagg 157740
cggggagatg tcagagacgg agacgaggca acaggaccgt ggaggagaaa aatagaaagg 157800
gagagaaaat agtcggagag acaaaaacca ggagacccat gcgtggacag aaagactaac 157860
ggagacgaaa agaaagaggc agatgggag acacgtgcga gacgagacac atgtgcattt 157920
gttggggaga agaggattgg aggtgtcagt gttaaaggaa cctctacaac gaaggtgaag 157980
ccacggaaga taaggtaagg ctgagacttg ggtgcggagt gcgcgtcatt gggctggagc 158040
tgtaaactgg cgcagaaatg ggcagggaac ccgcaagccc acaccgccca agagtcagtg 158100
aaacctgagg gatcttcccc aaggctctga accacgcggg acgcctgggt cctcgcatgg 158160
atgccgacgg ggccggctga gtgggagccc cgcccgtagc tggggtgagg agggcgggag 158220
gcgccgcagc caggagggcg gggaccagac ctgcccgtc tcgcccgggg ctccgcgagc 158280
gatccccgcc tccgccgggg gcatgggaag gaaagggaag ggagggggat gaggccgccg 158340
gacgctgggt ttccccagc caccctgaga ggaactggga ctttggggtc cagactgcca 158400
gcgtttagcg cagcggggtc ctcctgcccc ttggtggaag cgcaggctcc tccccccgcg 158460
```

```
cgtggcaccc acgtggggct ttctcactcc tcccagcttg gttttctcac ctcggtcttg   158520
tagagtcacc ccccacccag cacttcccct gcggctggac tccgctcagc ccattcccct   158580
gcatcctgcg gggaatgcag cgtggatggc gctgggtatc tctcctcctc cccgctcaca   158640
ccacctttcc cacgcctgtc tccctctcg gtaaagccct tcccatgacc caggactcta    158700
ggtcttctgg aagctcgatt cctccgctgg gctccccact ctgtccctca cgtccctgtg   158760
tgaaacaccg aggacacctc tgcatcccgg gcgccctccc gagtctccgc tcctctcccg   158820
cttgcctcct ccttccaata acctcccgtc cctttctccc cacatttatc acacgcacct   158880
ctgtttctct ttctacgact ctcccccacc ccgcatccc gcgtgttcct ggcagcctct    158940
ggaagtgggt ccgctctcac tttcctggca ccctctgggg ttgccttcat ctagcttttc   159000
tgtccttctt gaatctttcc acctcaggac ccccaagctc tgggtcaact ttctccagcg   159060
cctctccttt cccaaatgct ggggtcttcg cttctcccac accaggctcc cttctctgca   159120
cctggcaccc cacgaccccc cccccattc aacgcgtcct ggaagaggga gccttctacc    159180 ctcccctat tgcttgtctc cctctagggg actgccccca cgaccccgca tgtttctgtc    159240
gcactctaga gcggtccac ttcgctatct cctcctctcc aagaccagac acctgggtgg    159300 taggggctc agtgccatcc tctttcggac accccctcc caccatcaca cgttcccttt     159360
gccccggggt gtcctcttcc tccagccagt ttcttctgcc agtcacttcc tacccgtggc   159420
cccggcactc cggcgccccc tgggggcccc cctcccggct ccctgcccc tccgagctca    159480 ccgttgtggg tttccaccat tagcacgcgg gtgacctcct tggcgtagta gtcggcctca   159540
ggctcgggct ccggttctgc actctccccg gccaccggt cgcgggtgct gttgtacagg    159600
gcgagcacgg cctcgggcag cgggccggc ggcacctccc cctggctcgg ggggctggcg    159660
agccgcagct tggacaggat ctggccgcgg atggcctcga tgcgcttccg cttcaccagc   159720
tccatgtcga tagtcttgca ggtggatagt cccgcggccg gccggccagg cgtcagcacc   159780
agtagccaca gcagcggtag cagcagcggc agcagccgca gcccggaggg cggcatgggg   159840
gaggcggcgc ccccggcac tgccgagagc gcgaacaggg ctggtgtggt ggggaggccc    159900
cgcccctgca ggggctgggg gtctcccggc aaaaggtagg agggcctcga gggaaagctg   159960
aggtcctcag ggagaagggc gcagtggtgg aggggaggct tggaccgggg gtgtctcagt   160020
atcccacgga aataacctag atgggcgcga tctggtacca gaaggtgggt ggtcttgaat   160080
aggggatctg tggcaggtcg gagagagatc cgtctcctgg aggagaaagg gtctaggatg   160140
cgcgggggct caggagacag gccggggatg aaggcggcgt gcaggggtg cgcccgaggt    160200 ctggggaaaa gtctttgcgg gaggccgggt cggcgactcc cgagggctgg tccggaatgg   160260
gggcgcctga gggacgccgt gtaggggca gggagggagc aagcgtcccc ggcggcaaag    160320
ggaggcggtc tggggtcccc aagtcctgcc tcctcgcggg gcagcgtcgc gccaagaggt   160380
ccccgcgcct ccggctccca gcggcaacgg aaaagtctca aaagttttt tcctcttctc    160440 ccgaccagct cgtccctcct cccgctcctc ctcccctcc tccccgcagt ggcggggcg     160500 gcggcggctc gtctcagact ctgggcctc aggctgctcc tcgcgactc cttcctccgc     160560 tccgggccga ggccggcccc gcgggcggct cagagccggg gggtgcccc ggacggggcg    160620 tcccccctgc cccggccgg ggcctcgct gtctggctgc tccgcggagg gaggtgggag     160680
ggagatggcc cagggcgcga agggcggcgg cggcggggac cggctgggtc ggcaggggt    160740 tttgaagccg ccccggccc cacccaggaa gcgcacgggg cggagcggg gcggccccc     160800 aggggaggg catgggggg ctgggccacc gtcctcatct cgcgtgggcg ggctccgagg     160860
```

-continued

| | |
|---|---|
| ggggtccctt cagccctggg ggaaagggg cgggcacccc ggctccgccc cgcaaacagg | 160920 |
| gtgctgcctc ctggcggcca agcgccacca aagcgggtga tccagatgcg ctgtggcttt | 160980 |
| gcgggcggtg tgggtcacca gagaaagagg accaggcgga gaaggcttaa tccgggggat | 161040 |
| gagacacagg ggagccgacc agaggagggg gacccagaac ggaaggagag tcaggctggg | 161100 |
| aaacaaggta ggagaagagg gtctgtcaac atgggggcct ccggagggtg tcagtgggag | 161160 |
| gagggggcaa caggacacct gaaggatgga agggtcagga ggcagacacc tgtaagaatt | 161220 |
| gctctccttt actgagcacc tcccatgtgg ctaagcagcc tcctgtcact caacaccctg | 161280 |
| cgaccccata catttactgt ccccaattta cagatagggg aactgggccc agagggaccc | 161340 |
| cgaggtccta gaaaggacag aagcggtgcc atgccttagc tggggtcagc tctgacagtc | 161400 |
| tctagagtct gtgctcttga ccactgtgcc atcctccccc atcactgggt gtccggggtg | 161460 |
| tggatggtgg tgacgttgga ggcagagtcc ctcagcactc cacgccgtag cggtcgaagt | 161520 |
| tgcggagcag caggccgatc tccaggtgca cggtgccacc agcagctgtg tgcaggcgat | 161580 |
| agcggtcggc cccactgtag atggtgtccc catgcagcag ctgcggccca ccacccacga | 161640 |
| aagcccgtgc caactgttct cgccaactgc ccaggggccg ccacgtgggg caggccagct | 161700 |
| ggtgggtgcc cgggctactg ggcacatggc aaaatccata gcctgcaagc tggcagcggc | 161760 |
| caaagctgtc ctgggaccac acctggaaat ggagccgggg ccagcctgca ggaaaggaga | 161820 |
| gagaggggaa aggagggatg ggtggggacc agactcctgc tgattcccca ctccctgata | 161880 |
| ctcactggag accccaggcc cagtcttttc ctctctgggt ttctgtccca gagtttccaa | 161940 |
| cccagcctcc tttctaggct cccaccgtct tatctatccc cacacagcag ccaaagtgat | 162000 |
| cttttccaaat ccatgttact cccctgctaa ggatccttcc atagctcccc agtgccctca | 162060 |
| gtataaagtc caacctcttc aacattcaag gcccttctaa tcagacctct gctgaatttc | 162120 |
| ctctctgtgt tatcctcctc catgacccca tgtcagggca gcccattgct cctccagtcc | 162180 |
| ccaggtaacc atcatgggcc ttg | 162203 |

<210> SEQ ID NO 2
<211> LENGTH: 2346
<212> TYPE: DNA
<213> ORGANISM: Homo sapiens
<220> FEATURE:
<221> NAME/KEY: CDS
<222> LOCATION: (868)..(2037)
<223> OTHER INFORMATION: TGF1B coding sequence

<400> SEQUENCE: 2

| | |
|---|---|
| ccttcgcgcc ctgggccatc tccctcccac ctccctccgc ggagcagcca gacagcgagg | 60 |
| gccccggccg ggggcagggg ggacgccccg tccggggcac ccccccggct ctgagccgcc | 120 |
| cgcggggccg gcctcggccc ggagcggagg aaggagtcgc cgaggagcag cctgaggccc | 180 |
| cagagtctga gacgagccgc cgccgccccc gccactgcgg ggaggagggg gaggaggagc | 240 |
| gggaggaggg acgagctggt cgggagaaga ggaaaaaaac ttttgagact tttccgttgc | 300 |
| cgctgggagc cggaggcgcg gggacctctt ggcgcgacgc tgccccgcga ggaggcagga | 360 |
| cttggggacc ccagaccgcc tccctttgcc gcgggacg cttgctccct ccctgccccc | 420 |
| tacacgcgt ccctcaggcg ccccccattc ggaccagccc tcgggagtcg ccgacccggc | 480 |
| ctcccgcaaa gacttttccc cagacctcgg gcgcacccc tgcacgccgc cttcatcccc | 540 |
| ggcctgtctc ctgagccccc gcgcatccta gacccttct cctccaggag acggatctct | 600 |
| ctccgacctg ccacagatcc cctattcaag accacccacc ttctggtacc agatcgcgcc | 660 |

```
catctaggtt atttccgtgg gatactgaga cacccccggt ccaagcctcc cctccaccac      720
tgcgcccttc tccctgagga cctcagcttt ccctcgaggc cctcctacct tttgccggga      780 gaccccagc ccctgcaggg gcggggcctc cccaccacac cagccctgtt cgcgctctcg       840
gcagtgccgg ggggcgccgc ctccccc atg ccg ccc tcc ggg ctg cgg ctg ctg      894
                               Met Pro Pro Ser Gly Leu Arg Leu Leu
                                1               5 ccg ctg ctg cta ccg ctg ctg tgg cta ctg gtg ctg acg cct ggc cgg        942
Pro Leu Leu Leu Pro Leu Leu Trp Leu Leu Val Leu Thr Pro Gly Arg
 10              15                  20                  25 ccg gcc gcg gga cta tcc acc tgc aag act atc gac atg gag ctg gtg        990
Pro Ala Ala Gly Leu Ser Thr Cys Lys Thr Ile Asp Met Glu Leu Val
             30                  35                  40 aag cgg aag cgc atc gag gcc atc cgc ggc cag atc ctg tcc aag ctg        1038
Lys Arg Lys Arg Ile Glu Ala Ile Arg Gly Gln Ile Leu Ser Lys Leu
         45                  50                  55 cgg ctc gcc agc ccc ccg agc cag ggg gag gtg ccg ccc ggc ccg ctg        1086
Arg Leu Ala Ser Pro Pro Ser Gln Gly Glu Val Pro Pro Gly Pro Leu
     60                  65                  70 ccc gag gcc gtg ctc gcc ctg tac aac agc acc cgc gac cgg gtg gcc        1134
Pro Glu Ala Val Leu Ala Leu Tyr Asn Ser Thr Arg Asp Arg Val Ala
 75                  80                  85 ggg gag agt gca gaa ccg gag ccc gag cct gag gcc gac tac tac gcc        1182
Gly Glu Ser Ala Glu Pro Glu Pro Glu Pro Glu Ala Asp Tyr Tyr Ala
 90                  95                 100                 105 aag gag gtc acc cgc gtg cta atg gtg gaa acc cac aac gaa atc tat        1230
Lys Glu Val Thr Arg Val Leu Met Val Glu Thr His Asn Glu Ile Tyr
             110                 115                 120 gac aag ttc aag cag agt aca cac agc ata tat atg ttc ttc aac aca        1278
Asp Lys Phe Lys Gln Ser Thr His Ser Ile Tyr Met Phe Phe Asn Thr
         125                 130                 135 tca gag ctc cga gaa gcg gta cct gaa ccc gtg ttg ctc tcc cgg gca        1326
Ser Glu Leu Arg Glu Ala Val Pro Glu Pro Val Leu Leu Ser Arg Ala
     140                 145                 150 gag ctg cgt ctg ctg agg ctc aag tta aaa gtg gag cag cac gtg gag        1374
Glu Leu Arg Leu Leu Arg Leu Lys Leu Lys Val Glu Gln His Val Glu
 155                 160                 165 ctg tac cag aaa tac agc aac aat tcc tgg cga tac ctc agc aac cgg        1422
Leu Tyr Gln Lys Tyr Ser Asn Asn Ser Trp Arg Tyr Leu Ser Asn Arg
170                 175                 180                 185 ctg ctg gca ccc agc gac tcg cca gag tgg tta tct ttt gat gtc acc        1470
Leu Leu Ala Pro Ser Asp Ser Pro Glu Trp Leu Ser Phe Asp Val Thr
             190                 195                 200 gga gtt gtg cgg cag tgg ttg agc cgt gga ggg gaa att gag ggc ttt        1518
Gly Val Val Arg Gln Trp Leu Ser Arg Gly Gly Glu Ile Glu Gly Phe
         205                 210                 215 cgc ctt agc gcc cac tgc tcc tgt gac agc agg gat aac aca ctg caa        1566
Arg Leu Ser Ala His Cys Ser Cys Asp Ser Arg Asp Asn Thr Leu Gln
     220                 225                 230 gtg gac atc aac ggg ttc act acc ggc cgc cga ggt gac ctg gcc acc        1614
Val Asp Ile Asn Gly Phe Thr Thr Gly Arg Arg Gly Asp Leu Ala Thr
 235                 240                 245 att cat ggc atg aac cgg cct ttc ctg ctt ctc atg gcc acc ccg ctg        1662
Ile His Gly Met Asn Arg Pro Phe Leu Leu Leu Met Ala Thr Pro Leu
250                 255                 260                 265 gag agg gcc cag cat ctg caa agc tcc cgg cac cgc cga gcc ctg gac        1710
Glu Arg Ala Gln His Leu Gln Ser Ser Arg His Arg Arg Ala Leu Asp
             270                 275                 280 acc aac tat tgc ttc agc tcc acg gag aag aac tgc tgc gtg cgg cag        1758
Thr Asn Tyr Cys Phe Ser Ser Thr Glu Lys Asn Cys Cys Val Arg Gln
```

```
                    285                 290                 295
ctg tac att gac ttc cgc aag gac ctc ggc tgg aag tgg atc cac gag    1806
Leu Tyr Ile Asp Phe Arg Lys Asp Leu Gly Trp Lys Trp Ile His Glu
        300                 305                 310 ccc aag ggc tac cat gcc aac ttc tgc ctc ggg ccc tgc ccc tac att    1854
Pro Lys Gly Tyr His Ala Asn Phe Cys Leu Gly Pro Cys Pro Tyr Ile
315                 320                 325 tgg agc ctg gac acg cag tac agc aag gtc ctg gcc ctg tac aac cag    1902
Trp Ser Leu Asp Thr Gln Tyr Ser Lys Val Leu Ala Leu Tyr Asn Gln
330                 335                 340                 345 cat aac ccg ggc gcc tcg gcg gcg ccg tgc tgc gtg ccg cag gcg ctg    1950
His Asn Pro Gly Ala Ser Ala Ala Pro Cys Cys Val Pro Gln Ala Leu
            350                 355                 360 gag ccg ctg ccc atc gtg tac tac gtg ggc cgc aag ccc aag gtg gag    1998
Glu Pro Leu Pro Ile Val Tyr Tyr Val Gly Arg Lys Pro Lys Val Glu
        365                 370                 375 cag ctg tcc aac atg atc gtg cgc tcc tgc aag tgc agc tgaggtccg      2047
Gln Leu Ser Asn Met Ile Val Arg Ser Cys Lys Cys Ser
    380                 385                 390 ccccgccccg cccgccccg gcaggccgg ccccacccg cccgccccc gctgccttgc       2107 ccatggggc tgtatttaag gacacccgtg ccccaagccc acctgggcc ccattaaaga    2167 tggagagagg actgcggatc tctgtgtcat tgggcgcctg cctggggtct ccatccctga  2227
cgttccccca ctcccactcc ctctctctcc ctctctgcct cctcctgcct gtctgcacta  2287
ttcctttgcc cggcatcaag gcacagggga ccagtgggga acactactgt agttagatc   2346

<210> SEQ ID NO 3
<211> LENGTH: 390
<212> TYPE: PRT
<213> ORGANISM: Homo sapiens

<400> SEQUENCE: 3

Met Pro Pro Ser Gly Leu Arg Leu Leu Pro Leu Leu Leu Pro Leu Leu
1               5                   10                  15

Trp Leu Leu Val Leu Thr Pro Gly Arg Pro Ala Ala Gly Leu Ser Thr
            20                  25                  30

Cys Lys Thr Ile Asp Met Glu Leu Val Lys Arg Lys Arg Ile Glu Ala
        35                  40                  45

Ile Arg Gly Gln Ile Leu Ser Lys Leu Arg Leu Ala Ser Pro Pro Ser
    50                  55                  60

Gln Gly Glu Val Pro Pro Gly Pro Leu Pro Glu Ala Val Leu Ala Leu
65                  70                  75                  80

Tyr Asn Ser Thr Arg Asp Arg Val Ala Gly Glu Ser Ala Glu Pro Glu
                85                  90                  95

Pro Glu Pro Glu Ala Asp Tyr Tyr Ala Lys Glu Val Thr Arg Val Leu
            100                 105                 110

Met Val Glu Thr His Asn Glu Ile Tyr Asp Lys Phe Lys Gln Ser Thr
        115                 120                 125

His Ser Ile Tyr Met Phe Phe Asn Thr Ser Glu Leu Arg Glu Ala Val
    130                 135                 140

Pro Glu Pro Val Leu Leu Ser Arg Ala Glu Leu Arg Leu Leu Arg Leu
145                 150                 155                 160

Lys Leu Lys Val Glu Gln His Val Glu Leu Tyr Gln Lys Tyr Ser Asn
                165                 170                 175

Asn Ser Trp Arg Tyr Leu Ser Asn Arg Leu Leu Ala Pro Ser Asp Ser
            180                 185                 190
```

```
Pro Glu Trp Leu Ser Phe Asp Val Thr Gly Val Val Arg Gln Trp Leu
        195                 200                 205

Ser Arg Gly Gly Glu Ile Glu Gly Phe Arg Leu Ser Ala His Cys Ser
    210                 215                 220

Cys Asp Ser Arg Asp Asn Thr Leu Gln Val Asp Ile Asn Gly Phe Thr
225                 230                 235                 240

Thr Gly Arg Arg Gly Asp Leu Ala Thr Ile His Gly Met Asn Arg Pro
                245                 250                 255

Phe Leu Leu Leu Met Ala Thr Pro Leu Glu Arg Ala Gln His Leu Gln
            260                 265                 270

Ser Ser Arg His Arg Arg Ala Leu Asp Thr Asn Tyr Cys Phe Ser Ser
        275                 280                 285

Thr Glu Lys Asn Cys Cys Val Arg Gln Leu Tyr Ile Asp Phe Arg Lys
    290                 295                 300

Asp Leu Gly Trp Lys Trp Ile His Glu Pro Lys Gly Tyr His Ala Asn
305                 310                 315                 320

Phe Cys Leu Gly Pro Cys Pro Tyr Ile Trp Ser Leu Asp Thr Gln Tyr
                325                 330                 335

Ser Lys Val Leu Ala Leu Tyr Asn Gln His Asn Pro Gly Ala Ser Ala
            340                 345                 350

Ala Pro Cys Cys Val Pro Gln Ala Leu Glu Pro Leu Pro Ile Val Tyr
        355                 360                 365

Tyr Val Gly Arg Lys Pro Lys Val Glu Gln Leu Ser Asn Met Ile Val
    370                 375                 380

Arg Ser Cys Lys Cys Ser
385                 390

<210> SEQ ID NO 4
<211> LENGTH: 3344
<212> TYPE: DNA
<213> ORGANISM: Homo sapiens
<220> FEATURE:
<221> NAME/KEY: CDS
<222> LOCATION: (123)..(1151)
<223> OTHER INFORMATION: MGC20255 coding sequence

<400> SEQUENCE: 4
gcctgggcgc agcggtgcac ccggacccgg aacattctca ggcgaaagtg tctcttgcgt    60
gcgtgggccg gaggttagtg tgcggggccc gccgggcggt tgaaaagtcc gagagaatca   120 gg atg gag gcc gtg gcg acg gcg acg gcg gcg aag gaa ccc gat aag      167
   Met Glu Ala Val Ala Thr Ala Thr Ala Ala Lys Glu Pro Asp Lys
   1               5                   10                  15 ggc tgc ata gag cct gga cct ggg cac tgg ggt gag ctg agc cgg aca      215
Gly Cys Ile Glu Pro Gly Pro Gly His Trp Gly Glu Leu Ser Arg Thr
                20                  25                  30 cca gtc cca tct aaa ccc cag gac aaa gtg gaa gca gct gag gca aca      263
Pro Val Pro Ser Lys Pro Gln Asp Lys Val Glu Ala Ala Glu Ala Thr
            35                  40                  45 cca gtg gcc ctg gac agt gac acc tcc ggg gct gaa aat gca gca gtg      311
Pro Val Ala Leu Asp Ser Asp Thr Ser Gly Ala Glu Asn Ala Ala Val
        50                  55                  60 agt gct atg ctg cac gct gta gcc gcc agc cgc ctg cct gtt tgc agc      359
Ser Ala Met Leu His Ala Val Ala Ala Ser Arg Leu Pro Val Cys Ser
    65                  70                  75 cag cag cag ggt gaa ccc gac ttg aca gag cat gag aaa gtg gcc atc      407
Gln Gln Gln Gly Glu Pro Asp Leu Thr Glu His Glu Lys Val Ala Ile
80                  85                  90                  95 ctg gcc cag ctg tac cac gag aag cca ctg gtg ttc ctg gag cgc ttc      455
```

-continued

```
                Leu Ala Gln Leu Tyr His Glu Lys Pro Leu Val Phe Leu Glu Arg Phe
                                100                 105                 110 cgc aca ggc ctc cgt gag gag cat ctg gcc tgc ttt ggc cac gtg cgt             503
Arg Thr Gly Leu Arg Glu Glu His Leu Ala Cys Phe Gly His Val Arg
                115                 120                 125 ggc gac cac cgt gca gac ttc tac tgt gct gag gtg gcc cgg cag ggc             551
Gly Asp His Arg Ala Asp Phe Tyr Cys Ala Glu Val Ala Arg Gln Gly
                130                 135                 140 act gcc cgg ccc cgc acc ctg cgt acc cgc ctg cgt aac cgg cgc tat             599
Thr Ala Arg Pro Arg Thr Leu Arg Thr Arg Leu Arg Asn Arg Arg Tyr
        145                 150                 155 gct gcc ctg cga gag ctg atc caa ggg ggc gag tac ttc agt gat gag             647
Ala Ala Leu Arg Glu Leu Ile Gln Gly Gly Glu Tyr Phe Ser Asp Glu
160                 165                 170                 175 cag atg cgg ttc cgg gcc ccc ctg cta tat gag cag tac atc ggg cag             695
Gln Met Arg Phe Arg Ala Pro Leu Leu Tyr Glu Gln Tyr Ile Gly Gln
                180                 185                 190 tat ctc acc cag gag gag ctc agt gcc cgc acc cca acc cac cag ccc             743
Tyr Leu Thr Gln Glu Glu Leu Ser Ala Arg Thr Pro Thr His Gln Pro
                195                 200                 205 ccc aag ccc ggg tcc ccc ggg aga cct gct tgc ccg ctc tcc aac ttg             791
Pro Lys Pro Gly Ser Pro Gly Arg Pro Ala Cys Pro Leu Ser Asn Leu
        210                 215                 220 ctg ctc cag tcc tac gag gag cgg gag cta cag cag cgt ctg ctc caa             839
Leu Leu Gln Ser Tyr Glu Glu Arg Glu Leu Gln Gln Arg Leu Leu Gln
225                 230                 235 cag cag gag gag gag gag gcc tgc ttg gag gaa gag gaa gag gag gag             887
Gln Gln Glu Glu Glu Glu Ala Cys Leu Glu Glu Glu Glu Glu Glu Glu
240                 245                 250                 255 gac agt gac gag gaa gac cag agg tca ggc aag gac tcg gag gcc tgg             935
Asp Ser Asp Glu Glu Asp Gln Arg Ser Gly Lys Asp Ser Glu Ala Trp
                260                 265                 270 gtt ccc gac tcg gag gag agg ctg atc ctg cga gag gag ttc acc agc             983
Val Pro Asp Ser Glu Glu Arg Leu Ile Leu Arg Glu Glu Phe Thr Ser
                275                 280                 285 cgc atg cac cag cgc ttc cta gat ggc aag gac ggg gac ttt gac tac             1031
Arg Met His Gln Arg Phe Leu Asp Gly Lys Asp Gly Asp Phe Asp Tyr
        290                 295                 300 agc aca gta gac gac aac ccc gac ttc gac aac ctc gac atc gtg gca             1079
Ser Thr Val Asp Asp Asn Pro Asp Phe Asp Asn Leu Asp Ile Val Ala
305                 310                 315 cgg gat gag gag gag agg tac ttt gat gag gaa gaa cct gag gat gcg             1127
Arg Asp Glu Glu Glu Arg Tyr Phe Asp Glu Glu Glu Pro Glu Asp Ala
320                 325                 330                 335 ccc agc cca gag ctg gat ggg gac tgatggccgc cacccttccc accgcctgcc            1181
Pro Ser Pro Glu Leu Asp Gly Asp
                340 ccatccccat ccccaacaag gcagctgatt ccaggcctgc tcagtgaccc tttctctagg           1241 gggacatcag ggcagtgccc cacaacccac acacaccacc atctcactgg gtctagtctc           1301 atctcagaca accccacccc ccactgtttc tggggttccc tttctcatct ctcccaccct           1361 gtctcctgcc tctgtctttc ttggtgtctg tctgggcttc tttctgtctc tttctgtctt           1421 tctgtctctc tccctacccc cgctccctct ttccagtgct ctggctggct gtctctccct           1481 ttctcccctt ctctctctgc cttaggtctct gtctccaccg cagggcccaa ggtgaaagtc          1541 ctcccccttgc cggaggccag ctggcagggc ctttcgtggc tggaagtggc cagtttggtt         1601 ccggtgctga cccctaggcc ccagcgcagc tgcctcccgt gctgtctgtc tcccctctc           1661 tgtttatgtc tgcgctgtgt ctcacactca gagcctcctt gcttctgtta ggttcccatc          1721
```

```
tctccttctg cctcactctg ggcctcttct ttctacttgt acatttccac ctctctaggc      1781
ctctgctctc actgtccctc tctgtctgtc tctcagcctt tatctctggg ttttgatccc      1841
ccactccagg ctctgggccc cttcttcccc cttccctcaa acctggctgc tataggcagc      1901
agaaccctga ccactgagta atacagcccc aggggaggga ggagacccca ggcagggagg      1961
atgggggcag ctctcttctc tccccaggac ccaggctgtg gatcacgggg cctgccagct      2021
tgagtgtaga gggaggggg  actctaccct tctcagcccc accagccccc ctctgcccaa      2081
ccacaatttt cccttcctcc gccttcctct ccctctcctg tttacactcc ccaaatgcgc      2141
acaggctgtt atcatgggtc ctgagtcatc ccacacacag cctgccccag cgtccctgcc      2201
cccagctggc cgcagggccc gccccatgga gccccctgcc gccctgggct aatgggagcc      2261
agatggccgc ctggtgactc agccaccggg cctgtgggaa cccaggcgtc ccgccttccc      2321
atgcccccac acccggctcc tgctccccca gcagacacac acaggagggc ctggccactg      2381 ttgaggggc  acacagggca aggtcacca  agtcggggcc tagggactcc tcatgcctct      2441
gagatggaat ggtggtatcc tgccgtggcc aagcctgaag gaccctcaaa actgcctcct      2501
ggagtccacg gttcctgacc tccgagcctc agctatgccc tctgggtcaa ccagaattag      2561
agccagacag ggaaagtgag agctggatgg aggcagacaa gatgctcaga gcgactatta      2621
aagaacgaaa gcctctgcta cggagcgctt ctgtcctctg tcaggcccga gcgaagtgcc      2681
tgacaccggg ttggatcctc agatggcccc atgaactagt gaagtgggtc aaaggaggcc      2741
tggaaagatg ttgcttcctc aaggccactc ggccatcaga ggcagaaatg aaacaggaac      2801
ccaggcctag aatcacaaag gtcctagaaa ccacttggct gtctggcctc tcaggtgtca      2861
gggccatcca gagtgagaca gcattggagg acaagtgtg  catgcagatg tcctcagacg      2921
ggaaggtttg agaagggtca gatggtaggc gggcctaaca agggctccgt gctagccact      2981
gtcccgcaca cagacaggat caggtcatct tgatatggag atcagtcccc aaatcactga      3041
attgtcccag cagtgctatg ccctaggtac taccaatatc actcctctat ttcccagagg      3101
aggaagcagc agctagactc caggaccttg gggtcatatc tctcagaaag ccaagagtgc      3161
aggatgagag ctgtctgtct cttacctgcc tgtatttgtg ccccattttt aaagagcaga      3221
gggcctgggc cacaggaaag gtatcagccc ttggtgatag cacattttt  taccagtcta      3281 tcatttggtc attaaatttg tttacaatat actttgctat aaaaaaaaaa aaaaaaaaa      3341 aaa                                                                   3344
```

<210> SEQ ID NO 5
<211> LENGTH: 343
<212> TYPE: PRT
<213> ORGANISM: Homo sapiens

<400> SEQUENCE: 5

```
Met Glu Ala Val Ala Thr Ala Thr Ala Ala Lys Glu Pro Asp Lys Gly
1               5                   10                  15

Cys Ile Glu Pro Gly Pro Gly His Trp Gly Glu Leu Ser Arg Thr Pro
            20                  25                  30

Val Pro Ser Lys Pro Gln Asp Lys Val Glu Ala Ala Glu Ala Thr Pro
        35                  40                  45

Val Ala Leu Asp Ser Asp Thr Ser Gly Ala Glu Asn Ala Ala Val Ser
    50                  55                  60

Ala Met Leu His Ala Val Ala Ser Arg Leu Pro Val Cys Ser Gln
65                  70                  75                  80
```

Gln Gln Gly Glu Pro Asp Leu Thr Glu His Glu Lys Val Ala Ile Leu
             85                  90                  95

Ala Gln Leu Tyr His Glu Lys Pro Leu Val Phe Leu Glu Arg Phe Arg
            100                 105                 110

Thr Gly Leu Arg Glu Glu His Leu Ala Cys Phe Gly His Val Arg Gly
            115                 120                 125

Asp His Arg Ala Asp Phe Tyr Cys Ala Glu Val Ala Arg Gln Gly Thr
        130                 135                 140

Ala Arg Pro Arg Thr Leu Arg Thr Arg Leu Arg Asn Arg Arg Tyr Ala
145                 150                 155                 160

Ala Leu Arg Glu Leu Ile Gln Gly Gly Tyr Phe Ser Asp Glu Gln
            165                 170                 175

Met Arg Phe Arg Ala Pro Leu Leu Tyr Glu Gln Tyr Ile Gly Gln Tyr
            180                 185                 190

Leu Thr Gln Glu Glu Leu Ser Ala Arg Thr Pro Thr His Gln Pro Pro
            195                 200                 205

Lys Pro Gly Ser Pro Gly Arg Pro Ala Cys Pro Leu Ser Asn Leu Leu
        210                 215                 220

Leu Gln Ser Tyr Glu Glu Arg Glu Leu Gln Gln Arg Leu Leu Gln Gln
225                 230                 235                 240

Gln Glu Glu Glu Glu Ala Cys Leu Glu Glu Glu Glu Glu Asp
                245                 250                 255

Ser Asp Glu Glu Asp Gln Arg Ser Gly Lys Asp Ser Glu Ala Trp Val
            260                 265                 270

Pro Asp Ser Glu Glu Arg Leu Ile Leu Arg Glu Phe Thr Ser Arg
        275                 280                 285

Met His Gln Arg Phe Leu Asp Gly Lys Asp Gly Asp Phe Asp Tyr Ser
            290                 295                 300

Thr Val Asp Asp Asn Pro Asp Phe Asp Asn Leu Asp Ile Val Ala Arg
305                 310                 315                 320

Asp Glu Glu Glu Arg Tyr Phe Asp Glu Glu Pro Glu Asp Ala Pro
                325                 330                 335

Ser Pro Glu Leu Asp Gly Asp
            340

<210> SEQ ID NO 6
<211> LENGTH: 3039
<212> TYPE: DNA
<213> ORGANISM: Homo sapiens
<220> FEATURE:
<221> NAME/KEY: CDS
<222> LOCATION: (277)..(2544)
<223> OTHER INFORMATION: HNRPUL1 coding sequence

<400> SEQUENCE: 6
gcctcctgac aggaaaggtt taaggggac agagccctgg gaggccgggc cgggctcggg    60 ggccacccccg ggggcccggg ccatggatgt gcgccgtctg aaggtgaacg aacttcgcga   120
ggagctgcag cgccgcggcc tggacactcg aggcctcaag gccgagcttg ctgagcggct   180
gcaggcggcg ttggaggccg aggagcctga cgacgagcgg gagctcgacg ccgacgacga   240 accgggggcga cccgggcaca tcaacgagga gatgcc atg gac aat att acc agg   294
                                      Met Asp Asn Ile Thr Arg
                                       1               5 cag aac caa ttc tac gat acc caa gtc atc aaa caa gaa aac gag tca   342
Gln Asn Gln Phe Tyr Asp Thr Gln Val Ile Lys Gln Glu Asn Glu Ser
        10                  15                  20 ggc tac gag agg aga cca ctg gaa atg gag cag cag cag gcc tat cgt   390

```
                Gly Tyr Glu Arg Arg Pro Leu Glu Met Glu Gln Gln Ala Tyr Arg
                             25                  30                  35 cca gaa atg aag aca gag atg aag caa gga gca ccc acc agc ttc ctc          438
Pro Glu Met Lys Thr Glu Met Lys Gln Gly Ala Pro Thr Ser Phe Leu
 40                  45                  50 ccg cct gaa gct tct caa ctc aag cca gac agg cag caa ttc cag agt          486
Pro Pro Glu Ala Ser Gln Leu Lys Pro Asp Arg Gln Gln Phe Gln Ser
 55                  60                  65                      70 cga aag agg cct tat gaa gaa aac cgg gga cgg ggg tac ttt gag cac          534
Arg Lys Arg Pro Tyr Glu Glu Asn Arg Gly Arg Gly Tyr Phe Glu His
                 75                  80                  85 cga gag gat agg agg ggc cgc tct cct cag cct cct gct gaa gag gat          582
Arg Glu Asp Arg Arg Gly Arg Ser Pro Gln Pro Pro Ala Glu Glu Asp
                     90                  95                 100 gaa gat gac ttt gat gat acc ctt gtt gct att gac acc tat aac tgc          630
Glu Asp Asp Phe Asp Asp Thr Leu Val Ala Ile Asp Thr Tyr Asn Cys
             105                 110                 115 gac ctc cac ttc aag gtg gcc cga gat cgg agt agt ggc tat ccg ctc          678
Asp Leu His Phe Lys Val Ala Arg Asp Arg Ser Ser Gly Tyr Pro Leu
         120                 125                 130 aca att gag ggc ttt gca tac ctg tgg tca gga gcc cgt gcc agc tat          726
Thr Ile Glu Gly Phe Ala Tyr Leu Trp Ser Gly Ala Arg Ala Ser Tyr
135                 140                 145                 150 ggg gtc aga agg ggc cgt gta tgc ttc gag atg aag atc aat gag gaa          774
Gly Val Arg Arg Gly Arg Val Cys Phe Glu Met Lys Ile Asn Glu Glu
                155                 160                 165 atc tcc gtg aag cac ctt ccg tct aca gag cct gac ccc cac gtg gtc          822
Ile Ser Val Lys His Leu Pro Ser Thr Glu Pro Asp Pro His Val Val
            170                 175                 180 cgt atc ggc tgg tcc ctg gac tcc tgc agc acc cag cta ggc gaa gag          870
Arg Ile Gly Trp Ser Leu Asp Ser Cys Ser Thr Gln Leu Gly Glu Glu
        185                 190                 195 cct ttc tcc tat ggc tat gga ggc act ggg aag aag tcc acc aat agc          918
Pro Phe Ser Tyr Gly Tyr Gly Gly Thr Gly Lys Lys Ser Thr Asn Ser
200                 205                 210 cgg ttt gaa aac tac gga gac aag ttt gca gag aac gat gtg att ggc          966
Arg Phe Glu Asn Tyr Gly Asp Lys Phe Ala Glu Asn Asp Val Ile Gly
215                 220                 225                 230 tgc ttt gcg gat ttt gaa tgt gga aat gac gtg gaa ctg tct ttt acc         1014
Cys Phe Ala Asp Phe Glu Cys Gly Asn Asp Val Glu Leu Ser Phe Thr
                235                 240                 245 aag aat gga aag tgg atg ggc att gct ttc cga atc cag aag gaa gcc         1062
Lys Asn Gly Lys Trp Met Gly Ile Ala Phe Arg Ile Gln Lys Glu Ala
            250                 255                 260 ttg ggg ggt cag gcc ctc tat cct cat gtc ctg gtg aag aat tgc gca         1110
Leu Gly Gly Gln Ala Leu Tyr Pro His Val Leu Val Lys Asn Cys Ala
        265                 270                 275 gtg gag ttc aac ttc gga cag aga gca gag ccc tac tgt tct gtc ctc         1158
Val Glu Phe Asn Phe Gly Gln Arg Ala Glu Pro Tyr Cys Ser Val Leu
280                 285                 290 ccg ggg ttt acc ttc atc cag cac ctt ccc ctt agt gag cgt atc cgg         1206
Pro Gly Phe Thr Phe Ile Gln His Leu Pro Leu Ser Glu Arg Ile Arg
295                 300                 305                 310 ggc acc gtt gga cca aag agc aag gca gaa tgt gag att ctg atg atg         1254
Gly Thr Val Gly Pro Lys Ser Lys Ala Glu Cys Glu Ile Leu Met Met
                315                 320                 325 gtg ggc ctg cct gct gct ggc aag acc aca tgg gcc atc aaa cat gca         1302
Val Gly Leu Pro Ala Ala Gly Lys Thr Thr Trp Ala Ile Lys His Ala
            330                 335                 340 gcc tcc aac cct tcc aag aag tac aac atc ctg ggt acc aat gcc atc         1350
```

```
                                                   -continued
Ala Ser Asn Pro Ser Lys Lys Tyr Asn Ile Leu Gly Thr Asn Ala Ile
        345                 350                 355 atg gat aag atg cgg gtg atg ggc cta cgg cag cgg aac tat gct       1398
Met Asp Lys Met Arg Val Met Gly Leu Arg Arg Gln Arg Asn Tyr Ala
360                 365                 370 ggc cgc tgg gat gtc ctg atc cag cag gcc acc cag tgc ctc aac cgc   1446
Gly Arg Trp Asp Val Leu Ile Gln Gln Ala Thr Gln Cys Leu Asn Arg
375                 380                 385                 390 ctc atc cag att gct gcc cgc aag aaa cgc aac tat atc cta gat cag   1494
Leu Ile Gln Ile Ala Ala Arg Lys Lys Arg Asn Tyr Ile Leu Asp Gln
                395                 400                 405 aca aat gtt tat ggg tca gcc cag aga cga aaa atg aga cca ttt gaa   1542
Thr Asn Val Tyr Gly Ser Ala Gln Arg Arg Lys Met Arg Pro Phe Glu
            410                 415                 420 ggc ttc cag cgc aaa gct att gta att tgt ccc act gac gag gac cta   1590
Gly Phe Gln Arg Lys Ala Ile Val Ile Cys Pro Thr Asp Glu Asp Leu
        425                 430                 435 aaa gac cga aca ata aag cga acc gac gag gaa ggg aag gat gtc cca   1638
Lys Asp Arg Thr Ile Lys Arg Thr Asp Glu Glu Gly Lys Asp Val Pro
    440                 445                 450 gat cat gcg gtc tta gaa atg aaa gcc aac ttc acg ttg cca gat gtt   1686
Asp His Ala Val Leu Glu Met Lys Ala Asn Phe Thr Leu Pro Asp Val
455                 460                 465                 470 ggg gac ttc ctg gat gag gtt ctg ttc att gag ctg cag cgg gag gaa   1734
Gly Asp Phe Leu Asp Glu Val Leu Phe Ile Glu Leu Gln Arg Glu Glu
                475                 480                 485 gcg gac aag cta gtg agg cag tac aac gag gaa ggc cgc aag gct ggg   1782
Ala Asp Lys Leu Val Arg Gln Tyr Asn Glu Glu Gly Arg Lys Ala Gly
            490                 495                 500 cca ccc cct gaa aag cgc ttt gac aac cga ggt ggt ggt ttc cgg       1830
Pro Pro Pro Glu Lys Arg Phe Asp Asn Arg Gly Gly Gly Phe Arg
        505                 510                 515 ggc cgc ggg ggt ggt ggt ggc ttc cag cgc tat gaa aac cga gga ccc   1878
Gly Arg Gly Gly Gly Gly Phe Gln Arg Tyr Glu Asn Arg Gly Pro
    520                 525                 530 cct gga ggc aac cgt ggc ggc ttc cag aac cga ggg gga ggc agc ggt   1926
Pro Gly Gly Asn Arg Gly Gly Phe Gln Asn Arg Gly Gly Gly Ser Gly
535                 540                 545                 550 gga gga ggc aac tac cga gga ggt ttc aac cgc agc gga ggt ggt ggc   1974
Gly Gly Gly Asn Tyr Arg Gly Gly Phe Asn Arg Ser Gly Gly Gly Gly
                555                 560                 565 tat agc cag aac cgc tgg ggt aac aac aac cgg gat aac aac aac tcc   2022
Tyr Ser Gln Asn Arg Trp Gly Asn Asn Asn Arg Asp Asn Asn Asn Ser
            570                 575                 580 aac aac aga ggc agc tac aac cgg gct ccc cag caa cag ccg cca cca   2070
Asn Asn Arg Gly Ser Tyr Asn Arg Ala Pro Gln Gln Gln Pro Pro Pro
        585                 590                 595 cag cag cct ccg cca cca cag cca cca ccc cag cag cca ccg cca cca   2118
Gln Gln Pro Pro Pro Pro Gln Pro Pro Gln Gln Pro Pro Pro Pro
    600                 605                 610 ccc agc tac agc cct gct cgg aac ccc cca ggg gcc agc acc tac aat   2166
Pro Ser Tyr Ser Pro Ala Arg Asn Pro Pro Gly Ala Ser Thr Tyr Asn
615                 620                 625                 630 aag aac agc aac atc cct ggc tca agc gcc aat acc agc acc ccc acc   2214
Lys Asn Ser Asn Ile Pro Gly Ser Ser Ala Asn Thr Ser Thr Pro Thr
                635                 640                 645 gtc agc agc tac agc cct cca cag ccg agt tac agc cag cca ccc tac   2262
Val Ser Ser Tyr Ser Pro Pro Gln Pro Ser Tyr Ser Gln Pro Pro Tyr
            650                 655                 660 aac cag gga ggt tac agc cag ggc tac aca gcc cca ccg cct cca cct   2310
```

```
            Asn Gln Gly Gly Tyr Ser Gln Gly Tyr Thr Ala Pro Pro Pro Pro
                        665                 670                 675 cca cca cca cct gcc tac aac tat ggg agc tac ggc ggt tac aac ccg       2358
Pro Pro Pro Ala Tyr Asn Tyr Gly Ser Tyr Gly Gly Tyr Asn Pro
        680                 685                 690 gcc ccc tat acc cca ccg cca ccc ccc acc gca cag acc tac cct cag       2406
Ala Pro Tyr Thr Pro Pro Pro Pro Pro Thr Ala Gln Thr Tyr Pro Gln
695                 700                 705                 710 ccc agc tat aac cag tat cag cag tat gcc cag cag tgg aac cag tac       2454
Pro Ser Tyr Asn Gln Tyr Gln Gln Tyr Ala Gln Gln Trp Asn Gln Tyr
                715                 720                 725 tat cag aac cag ggc cag tgg ccg cca tac tac ggg aac tac gac tac       2502
Tyr Gln Asn Gln Gly Gln Trp Pro Pro Tyr Tyr Gly Asn Tyr Asp Tyr
            730                 735                 740 ggg agc tac tcc ggg aac aca cag ggt ggc aca agt aca cag              2544
Gly Ser Tyr Ser Gly Asn Thr Gln Gly Gly Thr Ser Thr Gln
        745                 750                 755 tagccagtgt gacccagagg ctcccggagg cccctgccgg cttcctccac cagcgcctgc     2604
ctcggcccct cctctgcccc cgccagatcc cgtggtgctg gggatggggt catcccaggg     2664
ctgcctccct ccagcccact gcctcccctc tgaggggctt ccttccctc catagggcca     2724 ggcatttttt tctggattca aacaggcaac aatgaccttt tattttctgt tgtccccac      2784 ctccccagcc ttccacctcc tgttcttcct accttcttcc tttttgacta aataatcccc     2844
acctcccttg atcatacagt gaggctacag tgactgaggg gagaatcccc tcctgttcac     2904
tctcccaacc ctgctccagc ccctcagctt cccagaccct catgcagttg gttgtaaatt    2964
ctcccaggag ctgttttact gtctactttt caggattaaa aaaaaaatca aaacttaaaa    3024
aaaaaaaaaa aaaaa                                                     3039

<210> SEQ ID NO 7
<211> LENGTH: 756
<212> TYPE: PRT
<213> ORGANISM: Homo sapiens

<400> SEQUENCE: 7

Met Asp Asn Ile Thr Arg Gln Asn Gln Phe Tyr Asp Thr Gln Val Ile
1               5                   10                  15

Lys Gln Glu Asn Glu Ser Gly Tyr Glu Arg Arg Pro Leu Glu Met Glu
            20                  25                  30

Gln Gln Gln Ala Tyr Arg Pro Glu Met Lys Thr Glu Met Lys Gln Gly
        35                  40                  45

Ala Pro Thr Ser Phe Leu Pro Pro Glu Ala Ser Gln Leu Lys Pro Asp
    50                  55                  60

Arg Gln Gln Phe Gln Ser Arg Lys Arg Pro Tyr Glu Glu Asn Arg Gly
65                  70                  75                  80

Arg Gly Tyr Phe Glu His Arg Glu Asp Arg Gly Arg Ser Pro Gln
                85                  90                  95

Pro Pro Ala Glu Glu Asp Glu Asp Phe Asp Thr Leu Val Ala
            100                 105                 110

Ile Asp Thr Tyr Asn Cys Asp Leu His Phe Lys Val Ala Arg Asp Arg
        115                 120                 125

Ser Ser Gly Tyr Pro Leu Thr Ile Glu Gly Phe Ala Tyr Leu Trp Ser
    130                 135                 140

Gly Ala Arg Ala Ser Tyr Gly Val Arg Gly Arg Val Cys Phe Glu
145                 150                 155                 160

Met Lys Ile Asn Glu Glu Ile Ser Val Lys His Leu Pro Ser Thr Glu
```

```
                    165                 170                 175
Pro Asp Pro His Val Val Arg Ile Gly Trp Ser Leu Asp Ser Cys Ser
            180                 185                 190

Thr Gln Leu Gly Glu Glu Pro Phe Ser Tyr Gly Tyr Gly Gly Thr Gly
            195                 200                 205

Lys Lys Ser Thr Asn Ser Arg Phe Glu Asn Tyr Gly Asp Lys Phe Ala
            210                 215                 220

Glu Asn Asp Val Ile Gly Cys Phe Ala Asp Phe Glu Cys Gly Asn Asp
225                 230                 235                 240

Val Glu Leu Ser Phe Thr Lys Asn Gly Lys Trp Met Gly Ile Ala Phe
            245                 250                 255

Arg Ile Gln Lys Glu Ala Leu Gly Gly Gln Ala Leu Tyr Pro His Val
            260                 265                 270

Leu Val Lys Asn Cys Ala Val Glu Phe Asn Phe Gly Gln Arg Ala Glu
            275                 280                 285

Pro Tyr Cys Ser Val Leu Pro Gly Phe Thr Phe Ile Gln His Leu Pro
            290                 295                 300

Leu Ser Glu Arg Ile Arg Gly Thr Val Gly Pro Lys Ser Lys Ala Glu
305                 310                 315                 320

Cys Glu Ile Leu Met Met Val Gly Leu Pro Ala Ala Gly Lys Thr Thr
                    325                 330                 335

Trp Ala Ile Lys His Ala Ala Ser Asn Pro Ser Lys Lys Tyr Asn Ile
                    340                 345                 350

Leu Gly Thr Asn Ala Ile Met Asp Lys Met Arg Val Met Gly Leu Arg
                    355                 360                 365

Arg Gln Arg Asn Tyr Ala Gly Arg Trp Asp Val Leu Ile Gln Gln Ala
            370                 375                 380

Thr Gln Cys Leu Asn Arg Leu Ile Gln Ile Ala Ala Arg Lys Lys Arg
385                 390                 395                 400

Asn Tyr Ile Leu Asp Gln Thr Asn Val Tyr Gly Ser Ala Gln Arg Arg
                    405                 410                 415

Lys Met Arg Pro Phe Glu Gly Phe Gln Arg Lys Ala Ile Val Ile Cys
            420                 425                 430

Pro Thr Asp Glu Asp Leu Lys Asp Arg Thr Ile Lys Arg Thr Asp Glu
            435                 440                 445

Glu Gly Lys Asp Val Pro Asp His Ala Val Leu Glu Met Lys Ala Asn
            450                 455                 460

Phe Thr Leu Pro Asp Val Gly Asp Phe Leu Asp Glu Val Leu Phe Ile
465                 470                 475                 480

Glu Leu Gln Arg Glu Glu Ala Asp Lys Leu Val Arg Gln Tyr Asn Glu
                    485                 490                 495

Glu Gly Arg Lys Ala Gly Pro Pro Glu Lys Arg Phe Asp Asn Arg
                    500                 505                 510

Gly Gly Gly Gly Phe Arg Gly Arg Gly Gly Gly Phe Gln Arg
                    515                 520                 525

Tyr Glu Asn Arg Gly Pro Pro Gly Gly Asn Arg Gly Phe Gln Asn
            530                 535                 540

Arg Gly Gly Ser Gly Gly Gly Asn Tyr Arg Gly Phe Asn
545                 550                 555                 560

Arg Ser Gly Gly Gly Tyr Ser Gln Asn Arg Trp Gly Asn Asn
                    565                 570                 575

Arg Asp Asn Asn Asn Ser Asn Asn Arg Gly Ser Tyr Asn Arg Ala Pro
                    580                 585                 590
```

```
Gln Gln Gln Pro Pro Gln Gln Pro Pro Pro Gln Pro Pro
        595             600             605

Gln Gln Pro Pro Pro Pro Ser Tyr Ser Pro Ala Arg Asn Pro Pro
    610             615             620

Gly Ala Ser Thr Tyr Asn Lys Asn Ser Asn Ile Pro Gly Ser Ser Ala
625             630             635             640

Asn Thr Ser Thr Pro Thr Val Ser Ser Tyr Ser Pro Gln Pro Ser
            645             650             655

Tyr Ser Gln Pro Pro Tyr Asn Gln Gly Gly Tyr Ser Gln Gly Tyr Thr
            660             665             670

Ala Pro Pro Pro Pro Pro Pro Pro Ala Tyr Asn Tyr Gly Ser
            675             680             685

Tyr Gly Gly Tyr Asn Pro Ala Pro Tyr Thr Pro Pro Pro Pro Thr
690             695             700

Ala Gln Thr Tyr Pro Gln Pro Ser Tyr Asn Gln Tyr Gln Tyr Ala
705             710             715             720

Gln Gln Trp Asn Gln Tyr Tyr Gln Asn Gln Gly Gln Trp Pro Pro Tyr
            725             730             735

Tyr Gly Asn Tyr Asp Tyr Gly Ser Tyr Ser Gly Asn Thr Gln Gly Gly
            740             745             750

Thr Ser Thr Gln
        755

<210> SEQ ID NO 8
<211> LENGTH: 2657
<212> TYPE: DNA
<213> ORGANISM: Homo sapiens
<220> FEATURE:
<221> NAME/KEY: CDS
<222> LOCATION: (56)..(1567)
<223> OTHER INFORMATION: CYP2S1 coding sequence

<400> SEQUENCE: 8
aactagccca gccgcgcgga gcgcctggga gaggagaagg agccgacctg ccgag atg      58
                                                           Met
                                                             1 gag gcg acc ggc acc tgg gcg ctg ctg ctg gcg ctg gcg ctg ctc ctg     106
Glu Ala Thr Gly Thr Trp Ala Leu Leu Leu Ala Leu Ala Leu Leu Leu
         5                  10                  15 ctg ctg acg ctg gcg ctg tcc ggg acc agg gcc cga ggc cac ctg ccc     154
Leu Leu Thr Leu Ala Leu Ser Gly Thr Arg Ala Arg Gly His Leu Pro
     20                  25                  30 ccc ggg ccc acg ccg cta cca ctg ctg gga aac ctc ctg cag cta cgg     202
Pro Gly Pro Thr Pro Leu Pro Leu Leu Gly Asn Leu Leu Gln Leu Arg
 35                  40                  45 ccc ggg gcg ctg tat tca ggg ctc atg cgg ctg agt aag aag tac gga     250
Pro Gly Ala Leu Tyr Ser Gly Leu Met Arg Leu Ser Lys Lys Tyr Gly
 50                  55                  60                  65 ccg gtg ttc acc atc tac ctg gga ccg tgg cgg cct gtg gtg gtc ctg     298
Pro Val Phe Thr Ile Tyr Leu Gly Pro Trp Arg Pro Val Val Val Leu
                 70                  75                  80 gtt ggg cag gag gct gtg cgg gag gcc ctg gga ggt cag gct gag gag     346
Val Gly Gln Glu Ala Val Arg Glu Ala Leu Gly Gly Gln Ala Glu Glu
             85                  90                  95 ttc agc ggc cgg gga acc gta gcg atg ctg gaa ggg act ttt gat ggc     394
Phe Ser Gly Arg Gly Thr Val Ala Met Leu Glu Gly Thr Phe Asp Gly
        100                 105                 110 cat ggg gtt ttc ttc tcc aac ggg gag cgg tgg agg cag ctg agg aag     442
His Gly Val Phe Phe Ser Asn Gly Glu Arg Trp Arg Gln Leu Arg Lys
    115                 120                 125
```

| | | |
|---|---|---|
| ttt acc atg ctt gct ctg cgg gac ctg ggc atg ggg aag cga gaa ggc<br>Phe Thr Met Leu Ala Leu Arg Asp Leu Gly Met Gly Lys Arg Glu Gly<br>130                       135                    140                   145 | 490 |
| gag gag ctg atc cag gcg gag gcc cgg tgt ctg gtg gag aca ttc cag<br>Glu Glu Leu Ile Gln Ala Glu Ala Arg Cys Leu Val Glu Thr Phe Gln<br>                  150                    155                   160 | 538 |
| ggg aca gaa gga cgc cca ttc gat ccc tcc ctg ctg gcc cag gcc<br>Gly Thr Glu Gly Arg Pro Phe Asp Pro Ser Leu Leu Ala Gln Ala<br>               165                  170                  175 | 586 |
| acc tcc aac gta gtc tgc tcc ctc ctc ttt ggc ctc cgc ttc tcc tat<br>Thr Ser Asn Val Val Cys Ser Leu Leu Phe Gly Leu Arg Phe Ser Tyr<br>         180                  185                    190 | 634 |
| gag gat aag gag ttc cag gcc gtg gtc cgg gca gct ggt ggt acc ctg<br>Glu Asp Lys Glu Phe Gln Ala Val Val Arg Ala Ala Gly Gly Thr Leu<br>195                       200                    205 | 682 |
| ctg gga gtc agc tcc cag ggg ggt cag acc tac gag atg ttc tcc tgg<br>Leu Gly Val Ser Ser Gln Gly Gly Gln Thr Tyr Glu Met Phe Ser Trp<br>210                       215                    220                  225 | 730 |
| ttc ctg cgg ccc ctg cca ggc ccc cac aag cag ctc ctc cac cac gtc<br>Phe Leu Arg Pro Leu Pro Gly Pro His Lys Gln Leu Leu His His Val<br>                      230                    235                   240 | 778 |
| agc acc ttg gct gcc ttc aca gtc cgg cag gtg cag cag cac cag ggg<br>Ser Thr Leu Ala Ala Phe Thr Val Arg Gln Val Gln Gln His Gln Gly<br>               245                  250                  255 | 826 |
| aac ctg gat gct tcg ggc ccc gca cgt gac ctt gtc gat gcc ttc ctg<br>Asn Leu Asp Ala Ser Gly Pro Ala Arg Asp Leu Val Asp Ala Phe Leu<br>         260                  265                    270 | 874 |
| ctg aag atg gca cag gag gaa caa aac cca ggc aca gaa ttc acc aac<br>Leu Lys Met Ala Gln Glu Glu Gln Asn Pro Gly Thr Glu Phe Thr Asn<br>275                       280                    285 | 922 |
| aag aac atg ctg atg aca gtc att tat ttg ctg ttt gct ggg acg atg<br>Lys Asn Met Leu Met Thr Val Ile Tyr Leu Leu Phe Ala Gly Thr Met<br>290                       295                    300                  305 | 970 |
| acg gtc agc acc acg gtc ggc tat acc ctc ctg ctc atg aaa tac<br>Thr Val Ser Thr Thr Val Gly Tyr Thr Leu Leu Leu Met Lys Tyr<br>                    310                    315                  320 | 1018 |
| cct cat gtc caa aag tgg gta cgt gag gag ctg aat cgg gag ctg ggg<br>Pro His Val Gln Lys Trp Val Arg Glu Glu Leu Asn Arg Glu Leu Gly<br>               325                  330                  335 | 1066 |
| gct ggc cag gca cca agc cta ggg gac cgt acc cgc ctc cct tac acc<br>Ala Gly Gln Ala Pro Ser Leu Gly Asp Arg Thr Arg Leu Pro Tyr Thr<br>         340                  345                    350 | 1114 |
| gac gcg gtt ctg cat gag gcg cag cgg ctg ctg gcg ctg gtg ccc atg<br>Asp Ala Val Leu His Glu Ala Gln Arg Leu Leu Ala Leu Val Pro Met<br>355                       360                    365 | 1162 |
| gga ata ccc cgc acc ctc atg cgg acc acc cgc ttc cga ggg tac acc<br>Gly Ile Pro Arg Thr Leu Met Arg Thr Thr Arg Phe Arg Gly Tyr Thr<br>370                       375                    380                  385 | 1210 |
| ctg ccc cag ggc acg gag gtc ttc ccc ctc ctt ggc tcc atc ctg cat<br>Leu Pro Gln Gly Thr Glu Val Phe Pro Leu Leu Gly Ser Ile Leu His<br>                    390                    395                  400 | 1258 |
| gac ccc aac atc ttc aag cac cca gaa gag ttc aac cca gac cgt ttc<br>Asp Pro Asn Ile Phe Lys His Pro Glu Glu Phe Asn Pro Asp Arg Phe<br>               405                  410                  415 | 1306 |
| ctg gat gca gat gga cgg ttc agg aag cat gag gcg ttc ctg ccc ttc<br>Leu Asp Ala Asp Gly Arg Phe Arg Lys His Glu Ala Phe Leu Pro Phe<br>         420                  425                    430 | 1354 |
| tcc tta ggg aag cgt gtc tgc ctt gga gag ggc ctg gca aaa gcg gag<br>Ser Leu Gly Lys Arg Val Cys Leu Gly Glu Gly Leu Ala Lys Ala Glu<br>435                       440                    445 | 1402 |

```
ctc ttc ctc ttc ttc acc acc atc cta caa gcc ttc tcc ctg gag agc    1450
Leu Phe Leu Phe Phe Thr Thr Ile Leu Gln Ala Phe Ser Leu Glu Ser
450                 455                 460                 465 ccg tgc ccg ccg gac acc ctg agc ctc aag ccc acc gtc agt ggc ctt    1498
Pro Cys Pro Pro Asp Thr Leu Ser Leu Lys Pro Thr Val Ser Gly Leu
                470                 475                 480 ttc aac att ccc cca gcc ttc cag ctg caa gtc cgt ccc act gac ctt    1546
Phe Asn Ile Pro Pro Ala Phe Gln Leu Gln Val Arg Pro Thr Asp Leu
            485                 490                 495 cac tcc acc acg cag acc aga tgaaggaagg caacttggaa gtggtgggtg       1597
His Ser Thr Thr Gln Thr Arg
                500 cccaggacgg tgcctccagc ctcaacagtg ggcatggaca gggttaatgt ctccagagtg    1657 tacactgcag gcagccacat ttacacgcct gcagttgttt tccggagtct gtcccacggc    1717 ccacacgctc acttgactca tgctgctaag atgcacaacc gcacacccat acacaactac    1777 aagggccaca aagcaactgc tgggttagct ttccacagac ataaatatag tccatctgca    1837 atcacaagca catagccagg taacccacca actcccctgg atctgcagcc cacacgtggg    1897 agtctggctg tcaccttcac aagccacaga acggccaca catgttcaca gctcacacgc    1957 cctctccatt catcgaactt ctcagtgtcc ctgtccctgg tgcctggcac agggaacagc    2017 atgccccctc cggggtcatg ccacccgag actgtcgctg tctatggccc caactcatgc    2077 tccctctctt ggctacacca ctctcccagc ctgtgaccac cgatgtccac acaccccaa    2137 ccacttgtcc acacagctac ccacgtacga catcgtcctg ctccccaga gtatcttccc    2197 actgagacac gccgcccca cagaggcaca gtccccagcc acctctgcaa ctgcagccct    2257 cagtcaccc tttttaagca ccctgattct accaaatgca aacacatctg ggtctgcgat    2317 tatgcacaga gactttggac atacgaggac cctcagaccg gaggaacacc tgcccaaccc    2377 caacacgtgc ttatgtaacc acgtggaaag cggcccctgc tgcccctcca cacacacata    2437 cacactcact gatctacagc ccctgttcgg cgtcagagtc cccactagac ccagtggaag    2497 gggttagaga ccaagtaggg gccagttttcc aattcaccct gtcagggagt gagccggatc    2557 tgacgttcct tgtgacttaa gggtccggct tgggaattaa agtttgtttc tggcctttag    2617 cctaaaaaaa aaaaaaaaa aaaaaaaaaa aaaaaaaaa                           2657
```

<210> SEQ ID NO 9
<211> LENGTH: 504
<212> TYPE: PRT
<213> ORGANISM: Homo sapiens
<400> SEQUENCE: 9

```
Met Glu Ala Thr Gly Thr Trp Ala Leu Leu Ala Leu Ala Leu Leu
1               5                   10                  15

Leu Leu Leu Thr Leu Ala Leu Ser Gly Thr Arg Ala Arg Gly His Leu
            20                  25                  30

Pro Pro Gly Pro Thr Pro Leu Pro Leu Leu Gly Asn Leu Leu Gln Leu
        35                  40                  45

Arg Pro Gly Ala Leu Tyr Ser Gly Leu Met Arg Leu Ser Lys Lys Tyr
    50                  55                  60

Gly Pro Val Phe Thr Ile Tyr Leu Gly Pro Trp Arg Pro Val Val Val
65                  70                  75                  80

Leu Val Gly Gln Glu Ala Val Arg Glu Ala Leu Gly Gly Gln Ala Glu
                85                  90                  95

Glu Phe Ser Gly Arg Gly Thr Val Ala Met Leu Glu Gly Thr Phe Asp
```

```
                100             105              110
Gly His Gly Val Phe Ser Asn Gly Glu Arg Trp Arg Gln Leu Arg
            115             120             125
Lys Phe Thr Met Leu Ala Leu Arg Asp Leu Gly Met Gly Lys Arg Glu
130             135             140
Gly Glu Glu Leu Ile Gln Ala Glu Ala Arg Cys Leu Val Glu Thr Phe
145             150             155             160
Gln Gly Thr Glu Gly Arg Pro Phe Asp Pro Ser Leu Leu Leu Ala Gln
            165             170             175
Ala Thr Ser Asn Val Val Cys Ser Leu Leu Phe Gly Leu Arg Phe Ser
            180             185             190
Tyr Glu Asp Lys Glu Phe Gln Ala Val Val Arg Ala Ala Gly Gly Thr
            195             200             205
Leu Leu Gly Val Ser Ser Gln Gly Gly Gln Thr Tyr Glu Met Phe Ser
            210             215             220
Trp Phe Leu Arg Pro Leu Pro Gly Pro His Lys Gln Leu Leu His His
225             230             235             240
Val Ser Thr Leu Ala Ala Phe Thr Val Arg Gln Val Gln Gln His Gln
            245             250             255
Gly Asn Leu Asp Ala Ser Gly Pro Ala Arg Asp Leu Val Asp Ala Phe
            260             265             270
Leu Leu Lys Met Ala Gln Glu Gln Asn Pro Gly Thr Glu Phe Thr
            275             280             285
Asn Lys Asn Met Leu Met Thr Val Ile Tyr Leu Leu Phe Ala Gly Thr
            290             295             300
Met Thr Val Ser Thr Thr Val Gly Tyr Thr Leu Leu Leu Met Lys
305             310             315             320
Tyr Pro His Val Gln Lys Trp Val Arg Glu Glu Leu Asn Arg Glu Leu
            325             330             335
Gly Ala Gly Gln Ala Pro Ser Leu Gly Asp Arg Thr Arg Leu Pro Tyr
            340             345             350
Thr Asp Ala Val Leu His Glu Ala Gln Arg Leu Leu Ala Leu Val Pro
            355             360             365
Met Gly Ile Pro Arg Thr Leu Met Arg Thr Thr Arg Phe Arg Gly Tyr
            370             375             380
Thr Leu Pro Gln Gly Thr Glu Val Phe Pro Leu Leu Gly Ser Ile Leu
385             390             395             400
His Asp Pro Asn Ile Phe Lys His Pro Glu Glu Phe Asn Pro Asp Arg
            405             410             415
Phe Leu Asp Ala Asp Gly Arg Phe Arg Lys His Glu Ala Phe Leu Pro
            420             425             430
Phe Ser Leu Gly Lys Arg Val Cys Leu Gly Glu Gly Leu Ala Lys Ala
            435             440             445
Glu Leu Phe Leu Phe Thr Thr Ile Leu Gln Ala Phe Ser Leu Glu
            450             455             460
Ser Pro Cys Pro Pro Asp Thr Leu Ser Leu Lys Pro Thr Val Ser Gly
465             470             475             480
Leu Phe Asn Ile Pro Pro Ala Phe Gln Leu Gln Val Arg Pro Thr Asp
            485             490             495
Leu His Ser Thr Thr Gln Thr Arg
            500

<210> SEQ ID NO 10
<211> LENGTH: 3227
```

```
<212> TYPE: DNA
<213> ORGANISM: Homo sapiens
<220> FEATURE:
<221> NAME/KEY: CDS
<222> LOCATION: (159)..(2813)
<223> OTHER INFORMATION: AXL coding sequence

<400> SEQUENCE: 10
gctgggcaaa gccggtggca agggcctccc ctgccgctgt gccaggcagg cagtgccaaa      60
tccggggagc tggagctggg gggagggcc ggggacagcc cggccctgcc ccctcccccg      120
ctgggagccc agcaacttct gaggaaagtt tggcaccc atg gcg tgg cgg tgc ccc     176
                                         Met Ala Trp Arg Cys Pro
                                           1               5 agg atg ggc agg gtc ccg ctg gcc tgg tgc ttg gcg ctg tgc ggc tgg       224
Arg Met Gly Arg Val Pro Leu Ala Trp Cys Leu Ala Leu Cys Gly Trp
         10                  15                  20 gcg tgc atg gcc ccc agg ggc acg cag gct gaa gaa agt ccc ttc gtg       272
Ala Cys Met Ala Pro Arg Gly Thr Gln Ala Glu Glu Ser Pro Phe Val
     25                  30                  35 ggc aac cca ggg aat atc aca ggt gcc cgg gga ctc acg ggc acc ctt       320
Gly Asn Pro Gly Asn Ile Thr Gly Ala Arg Gly Leu Thr Gly Thr Leu
 40                  45                  50 cgg tgt cag ctc cag gtt cag gga gag ccc ccg gag gta cat tgg ctt       368
Arg Cys Gln Leu Gln Val Gln Gly Glu Pro Pro Glu Val His Trp Leu
55                  60                  65                  70 cgg gat gga cag atc ctg gag ctc gcg gac agc acc cag acc cag gtg       416
Arg Asp Gly Gln Ile Leu Glu Leu Ala Asp Ser Thr Gln Thr Gln Val
                 75                  80                  85 ccc ctg ggt gag gat gaa cag gat gac tgg ata gtg gtc agc cag ctc       464
Pro Leu Gly Glu Asp Glu Gln Asp Asp Trp Ile Val Val Ser Gln Leu
         90                  95                 100 aga atc acc tcc ctg cag ctt tcc gac acg gga cag tac cag tgt ttg       512
Arg Ile Thr Ser Leu Gln Leu Ser Asp Thr Gly Gln Tyr Gln Cys Leu
     105                 110                 115 gtg ttt ctg gga cat cag acc ttc gtg tcc cag cct ggc tat gtt ggg       560
Val Phe Leu Gly His Gln Thr Phe Val Ser Gln Pro Gly Tyr Val Gly
 120                 125                 130 ctg gag ggc ttg cct tac ttc ctg gag gag ccc gaa gac agg act gtg       608
Leu Glu Gly Leu Pro Tyr Phe Leu Glu Glu Pro Glu Asp Arg Thr Val
135                 140                 145                 150 gcc gcc aac acc ccc ttc aac ctg agc tgc caa gct cag gga ccc cca       656
Ala Ala Asn Thr Pro Phe Asn Leu Ser Cys Gln Ala Gln Gly Pro Pro
                 155                 160                 165 gag ccc gtg gac cta ctc tgg ctc cag gat gct gtc ccc ctg gcc acg       704
Glu Pro Val Asp Leu Leu Trp Leu Gln Asp Ala Val Pro Leu Ala Thr
         170                 175                 180 gct cca ggt cac ggc ccc cag cgc agc ctg cat gtt cca ggg ctg aac       752
Ala Pro Gly His Gly Pro Gln Arg Ser Leu His Val Pro Gly Leu Asn
     185                 190                 195 aag aca tcc tct ttc tcc tgc gaa gcc cat aac gcc aag ggg gtc acc       800
Lys Thr Ser Ser Phe Ser Cys Glu Ala His Asn Ala Lys Gly Val Thr
 200                 205                 210 aca tcc cgc aca gcc acc atc aca gtg ctc ccc cag cag ccc cgt aac       848
Thr Ser Arg Thr Ala Thr Ile Thr Val Leu Pro Gln Gln Pro Arg Asn
215                 220                 225                 230 ctc cac ctg gtc tcc cgc caa ccc acg gag ctg gag gtg gct tgg act       896
Leu His Leu Val Ser Arg Gln Pro Thr Glu Leu Glu Val Ala Trp Thr
                 235                 240                 245 cca ggc ctg agc ggc atc tac ccc ctg acc cac tgc acc ctg cag gct       944
Pro Gly Leu Ser Gly Ile Tyr Pro Leu Thr His Cys Thr Leu Gln Ala
         250                 255                 260
```

| | |
|---|---|
| gtg ctg tca gac gat ggg atg ggc atc cag gcg gga gaa cca gac ccc<br>Val Leu Ser Asp Asp Gly Met Gly Ile Gln Ala Gly Glu Pro Asp Pro<br>265                          270                    275 | 992 |
| cca gag gag ccc ctc acc tcg caa gca tcc gtg ccc ccc cat cag ctt<br>Pro Glu Glu Pro Leu Thr Ser Gln Ala Ser Val Pro Pro His Gln Leu<br>    280                      285                    290 | 1040 |
| cgg cta ggc agc ctc cat cct cac acc cct tat cac atc cgc gtg gca<br>Arg Leu Gly Ser Leu His Pro His Thr Pro Tyr His Ile Arg Val Ala<br>295                          300                    305                  310 | 1088 |
| tgc acc agc agc cag ggc ccc tca tcc tgg acc cac tgg ctt cct gtg<br>Cys Thr Ser Ser Gln Gly Pro Ser Ser Trp Thr His Trp Leu Pro Val<br>                  315                    320                    325 | 1136 |
| gag acg ccg gag gga gtg ccc ctg ggc ccc cct aag aac att agt gct<br>Glu Thr Pro Glu Gly Val Pro Leu Gly Pro Pro Lys Asn Ile Ser Ala<br>            330                    335                    340 | 1184 |
| acg cgg aat ggg agc cag gcc ttc gtg cat tgg caa gag ccc cgg gcg<br>Thr Arg Asn Gly Ser Gln Ala Phe Val His Trp Gln Glu Pro Arg Ala<br>345                          350                    355 | 1232 |
| ccc ctg cag ggt acc ctg tta ggg tac cgg ctg gcg tat caa ggc cag<br>Pro Leu Gln Gly Thr Leu Leu Gly Tyr Arg Leu Ala Tyr Gln Gly Gln<br>    360                      365                    370 | 1280 |
| gac acc cca gag gtg cta atg gac ata ggg cta agg caa gag gtg acc<br>Asp Thr Pro Glu Val Leu Met Asp Ile Gly Leu Arg Gln Glu Val Thr<br>375                          380                    385                  390 | 1328 |
| ctg gag ctg cag ggg gac ggg tct gtg tcc aat ctc aca gtg tgt gtg<br>Leu Glu Leu Gln Gly Asp Gly Ser Val Ser Asn Leu Thr Val Cys Val<br>                  395                    400                    405 | 1376 |
| gca gcc tac act gct gct ggg gat gga ccc tgg agc ctc cca gta ccc<br>Ala Ala Tyr Thr Ala Ala Gly Asp Gly Pro Trp Ser Leu Pro Val Pro<br>            410                    415                    420 | 1424 |
| ctg gag gcc tgg cgc cca gtg aag gaa cct tca act cct gcc ttc tcg<br>Leu Glu Ala Trp Arg Pro Val Lys Glu Pro Ser Thr Pro Ala Phe Ser<br>425                          430                    435 | 1472 |
| tgg ccc tgg tgg tat gta ctg cta gga gca gtc gtg gcc gct gcc tgt<br>Trp Pro Trp Trp Tyr Val Leu Leu Gly Ala Val Val Ala Ala Ala Cys<br>    440                      445                    450 | 1520 |
| gtc ctc atc ttg gct ctc ttc ctt gtc cac cgg cga aag aag gag acc<br>Val Leu Ile Leu Ala Leu Phe Leu Val His Arg Arg Lys Lys Glu Thr<br>455                          460                    465                  470 | 1568 |
| cgt tat gga gaa gtg ttt gaa cca aca gtg gaa aga ggt gaa ctg gta<br>Arg Tyr Gly Glu Val Phe Glu Pro Thr Val Glu Arg Gly Glu Leu Val<br>                  475                    480                    485 | 1616 |
| gtc agg tac cgc gtg cgc aag tcc tac agt cgt cgg acc act gaa gct<br>Val Arg Tyr Arg Val Arg Lys Ser Tyr Ser Arg Arg Thr Thr Glu Ala<br>            490                    495                    500 | 1664 |
| acc ttg aac agc ctg ggc atc agt gaa gag ctg aag gag aag ctg cgg<br>Thr Leu Asn Ser Leu Gly Ile Ser Glu Glu Leu Lys Glu Lys Leu Arg<br>505                          510                    515 | 1712 |
| gat gtg atg gtg gac cgg cac aag gtg gcc ctg ggg aag act ctg gga<br>Asp Val Met Val Asp Arg His Lys Val Ala Leu Gly Lys Thr Leu Gly<br>    520                      525                    530 | 1760 |
| gag gga gag ttt gga gct gtg atg gaa ggc cag ctc aac cag gac gac<br>Glu Gly Glu Phe Gly Ala Val Met Glu Gly Gln Leu Asn Gln Asp Asp<br>535                          540                    545                  550 | 1808 |
| tcc atc ctc aag gtg gct gtg aag acg atg aag att gcc atc tgc acg<br>Ser Ile Leu Lys Val Ala Val Lys Thr Met Lys Ile Ala Ile Cys Thr<br>                  555                    560                    565 | 1856 |
| agg tca gag ctg gag gat ttc ctg agt gaa gcg gtc tgc atg aag gaa<br>Arg Ser Glu Leu Glu Asp Phe Leu Ser Glu Ala Val Cys Met Lys Glu<br>            570                    575                    580 | 1904 |

| | |
|---|---|
| ttt gac cat ccc aac gtc atg agg ctc atc ggt gtc tgt ttc cag ggt<br>Phe Asp His Pro Asn Val Met Arg Leu Ile Gly Val Cys Phe Gln Gly<br>585                  590                595 | 1952 |
| tct gaa cga gag agc ttc cca gca cct gtg gtc atc tta cct ttc atg<br>Ser Glu Arg Glu Ser Phe Pro Ala Pro Val Val Ile Leu Pro Phe Met<br>600                  605                610 | 2000 |
| aaa cat gga gac cta cac agc ttc ctc ctc tat tcc cgg ctc ggg gac<br>Lys His Gly Asp Leu His Ser Phe Leu Leu Tyr Ser Arg Leu Gly Asp<br>615                  620                625                630 | 2048 |
| cag cca gtg tac ctg ccc act cag atg cta gtg aag ttc atg gca gac<br>Gln Pro Val Tyr Leu Pro Thr Gln Met Leu Val Lys Phe Met Ala Asp<br>                635                640                645 | 2096 |
| atc gcc agt ggc atg gag tat ctg agt acc aag aga ttc ata cac cgg<br>Ile Ala Ser Gly Met Glu Tyr Leu Ser Thr Lys Arg Phe Ile His Arg<br>650                  655                660 | 2144 |
| gac ctg gcg gcc agg aac tgc atg ctg aat gag aac atg tcc gtg tgt<br>Asp Leu Ala Ala Arg Asn Cys Met Leu Asn Glu Asn Met Ser Val Cys<br>665                  670                675 | 2192 |
| gtg gcg gac ttc ggg ctc tcc aag aag atc tac aat ggg gac tac tac<br>Val Ala Asp Phe Gly Leu Ser Lys Lys Ile Tyr Asn Gly Asp Tyr Tyr<br>680                  685                690 | 2240 |
| cgc cag gga cgt atc gcc aag atg cca gtc aag tgg att gcc att gag<br>Arg Gln Gly Arg Ile Ala Lys Met Pro Val Lys Trp Ile Ala Ile Glu<br>695                  700                705                710 | 2288 |
| agt cta gct gac cgt gtc tac acc agc aag agc gat gtg tgg tcc ttc<br>Ser Leu Ala Asp Arg Val Tyr Thr Ser Lys Ser Asp Val Trp Ser Phe<br>                715                720                725 | 2336 |
| ggg gtg aca atg tgg gag att gcc aca aga ggc caa acc cca tat ccg<br>Gly Val Thr Met Trp Glu Ile Ala Thr Arg Gly Gln Thr Pro Tyr Pro<br>730                  735                740 | 2384 |
| ggc gtg gag aac agc gag att tat gac tat ctg cgc cag gga aat cgc<br>Gly Val Glu Asn Ser Glu Ile Tyr Asp Tyr Leu Arg Gln Gly Asn Arg<br>745                  750                755 | 2432 |
| ctg aag cag cct gcg gac tgt ctg gat gga ctg tat gcc ttg atg tcg<br>Leu Lys Gln Pro Ala Asp Cys Leu Asp Gly Leu Tyr Ala Leu Met Ser<br>760                  765                770 | 2480 |
| cgg tgc tgg gag cta aat ccc cag gac cgg cca agt ttt aca gag ctg<br>Arg Cys Trp Glu Leu Asn Pro Gln Asp Arg Pro Ser Phe Thr Glu Leu<br>775                  780                785                790 | 2528 |
| cgg gaa gat ttg gag aac aca ctg aag gcc ttg cct cct gcc cag gag<br>Arg Glu Asp Leu Glu Asn Thr Leu Lys Ala Leu Pro Pro Ala Gln Glu<br>                795                800                805 | 2576 |
| cct gac gaa atc ctc tat gtc aac atg gat gag ggt gga ggt tat cct<br>Pro Asp Glu Ile Leu Tyr Val Asn Met Asp Glu Gly Gly Gly Tyr Pro<br>810                  815                820 | 2624 |
| gaa ccc cct gga gct gca gga gga gct gac ccc cca acc cag cca gac<br>Glu Pro Pro Gly Ala Ala Gly Gly Ala Asp Pro Pro Thr Gln Pro Asp<br>825                  830                835 | 2672 |
| cct aag gat tcc tgt agc tgc ctc act gcg gct gag gtc cat cct gct<br>Pro Lys Asp Ser Cys Ser Cys Leu Thr Ala Ala Glu Val His Pro Ala<br>840                  845                850 | 2720 |
| gga cgc tat gtc ctc tgc cct tcc aca acc cct agc ccc gct cag cct<br>Gly Arg Tyr Val Leu Cys Pro Ser Thr Thr Pro Ser Pro Ala Gln Pro<br>855                  860                865                870 | 2768 |
| gct gat agg ggc tcc cca gca gcc cca ggg cag gag gat ggt gcc<br>Ala Asp Arg Gly Ser Pro Ala Ala Pro Gly Gln Glu Asp Gly Ala<br>                875                880                885 | 2813 |
| tgagacaacc ctccacctgg tactccctct caggatccaa gctaagcact gccactgggg | 2873 |
| aaaactccac cttcccactt ttccacccca cgccttatcc ccacttgcag ccctgtcttc | 2933 |

-continued

```
ctacctatcc cacctccatc ccagacaggt ccctcccctt ctctgtgcag tagcatcacc    2993
ttgaaagcag tagcatcacc atctgtaaaa ggaagggggtt ggattgcaat atctgaagcc   3053
ctcccaggtg ttaacattcc aagactctag agtccaaggt ttaaagagtc tagattcaaa   3113
ggttctaggt ttcaaagatg ctgtgagtct ttggttctaa ggacctgaaa ttccaaagtc   3173
tctaattcta ttaaagtgct aaggttctaa ggcaaaaaaa aaaaaaaaaa aaaa          3227
```

<210> SEQ ID NO 11
<211> LENGTH: 885
<212> TYPE: PRT
<213> ORGANISM: Homo sapiens

<400> SEQUENCE: 11

```
Met Ala Trp Arg Cys Pro Arg Met Gly Arg Val Pro Leu Ala Trp Cys
1               5                   10                  15

Leu Ala Leu Cys Gly Trp Ala Cys Met Ala Pro Arg Gly Thr Gln Ala
            20                  25                  30

Glu Glu Ser Pro Phe Val Gly Asn Pro Gly Asn Ile Thr Gly Ala Arg
        35                  40                  45

Gly Leu Thr Gly Thr Leu Arg Cys Gln Leu Gln Val Gln Gly Glu Pro
    50                  55                  60

Pro Glu Val His Trp Leu Arg Asp Gly Gln Ile Leu Glu Leu Ala Asp
65                  70                  75                  80

Ser Thr Gln Thr Gln Val Pro Leu Gly Glu Asp Glu Gln Asp Asp Trp
                85                  90                  95

Ile Val Val Ser Gln Leu Arg Ile Thr Ser Leu Gln Leu Ser Asp Thr
            100                 105                 110

Gly Gln Tyr Gln Cys Leu Val Phe Leu Gly His Gln Thr Phe Val Ser
        115                 120                 125

Gln Pro Gly Tyr Val Gly Leu Glu Gly Leu Pro Tyr Phe Leu Glu Glu
    130                 135                 140

Pro Glu Asp Arg Thr Val Ala Ala Asn Thr Pro Phe Asn Leu Ser Cys
145                 150                 155                 160

Gln Ala Gln Gly Pro Pro Glu Pro Val Asp Leu Leu Trp Leu Gln Asp
                165                 170                 175

Ala Val Pro Leu Ala Thr Ala Pro Gly His Gly Pro Gln Arg Ser Leu
            180                 185                 190

His Val Pro Gly Leu Asn Lys Thr Ser Ser Phe Ser Cys Glu Ala His
        195                 200                 205

Asn Ala Lys Gly Val Thr Thr Ser Arg Thr Ala Thr Ile Thr Val Leu
    210                 215                 220

Pro Gln Gln Pro Arg Asn Leu His Leu Val Ser Arg Gln Pro Thr Glu
225                 230                 235                 240

Leu Glu Val Ala Trp Thr Pro Gly Leu Ser Gly Ile Tyr Pro Leu Thr
                245                 250                 255

His Cys Thr Leu Gln Ala Val Leu Ser Asp Asp Gly Met Gly Ile Gln
            260                 265                 270

Ala Gly Glu Pro Asp Pro Pro Glu Glu Pro Leu Thr Ser Gln Ala Ser
        275                 280                 285

Val Pro Pro His Gln Leu Arg Leu Gly Ser Leu His Pro His Thr Pro
    290                 295                 300

Tyr His Ile Arg Val Ala Cys Thr Ser Ser Gln Gly Pro Ser Ser Trp
305                 310                 315                 320

Thr His Trp Leu Pro Val Glu Thr Pro Glu Gly Val Pro Leu Gly Pro
```

```
                    325                 330                 335
Pro Lys Asn Ile Ser Ala Thr Arg Asn Gly Ser Gln Ala Phe Val His
                340                 345                 350

Trp Gln Glu Pro Arg Ala Pro Leu Gln Gly Thr Leu Leu Gly Tyr Arg
            355                 360                 365

Leu Ala Tyr Gln Gly Gln Asp Thr Pro Glu Val Leu Met Asp Ile Gly
        370                 375                 380

Leu Arg Gln Glu Val Thr Leu Glu Leu Gln Gly Asp Gly Ser Val Ser
385                 390                 395                 400

Asn Leu Thr Val Cys Val Ala Ala Tyr Thr Ala Ala Gly Asp Gly Pro
                405                 410                 415

Trp Ser Leu Pro Val Pro Leu Glu Ala Trp Arg Pro Val Lys Glu Pro
            420                 425                 430

Ser Thr Pro Ala Phe Ser Trp Pro Trp Trp Tyr Val Leu Leu Gly Ala
        435                 440                 445

Val Val Ala Ala Ala Cys Val Leu Ile Leu Ala Leu Phe Leu Val His
    450                 455                 460

Arg Arg Lys Lys Glu Thr Arg Tyr Gly Glu Val Phe Glu Pro Thr Val
465                 470                 475                 480

Glu Arg Gly Glu Leu Val Val Arg Tyr Arg Val Arg Lys Ser Tyr Ser
                485                 490                 495

Arg Arg Thr Thr Glu Ala Thr Leu Asn Ser Leu Gly Ile Ser Glu Glu
            500                 505                 510

Leu Lys Glu Lys Leu Arg Asp Val Met Val Asp Arg His Lys Val Ala
        515                 520                 525

Leu Gly Lys Thr Leu Gly Glu Gly Glu Phe Gly Ala Val Met Glu Gly
    530                 535                 540

Gln Leu Asn Gln Asp Asp Ser Ile Leu Lys Val Ala Val Lys Thr Met
545                 550                 555                 560

Lys Ile Ala Ile Cys Thr Arg Ser Glu Leu Glu Asp Phe Leu Ser Glu
                565                 570                 575

Ala Val Cys Met Lys Glu Phe Asp His Pro Asn Val Met Arg Leu Ile
            580                 585                 590

Gly Val Cys Phe Gln Gly Ser Glu Arg Glu Ser Phe Pro Ala Pro Val
        595                 600                 605

Val Ile Leu Pro Phe Met Lys His Gly Asp Leu His Ser Phe Leu Leu
    610                 615                 620

Tyr Ser Arg Leu Gly Asp Gln Pro Val Tyr Leu Pro Thr Gln Met Leu
625                 630                 635                 640

Val Lys Phe Met Ala Asp Ile Ala Ser Gly Met Glu Tyr Leu Ser Thr
                645                 650                 655

Lys Arg Phe Ile His Arg Asp Leu Ala Ala Arg Asn Cys Met Leu Asn
            660                 665                 670

Glu Asn Met Ser Val Cys Val Ala Asp Phe Gly Leu Ser Lys Lys Ile
        675                 680                 685

Tyr Asn Gly Asp Tyr Tyr Arg Gln Gly Arg Ile Ala Lys Met Pro Val
    690                 695                 700

Lys Trp Ile Ala Ile Glu Ser Leu Ala Asp Arg Val Tyr Thr Ser Lys
705                 710                 715                 720

Ser Asp Val Trp Ser Phe Gly Val Thr Met Trp Glu Ile Ala Thr Arg
                725                 730                 735

Gly Gln Thr Pro Tyr Pro Gly Val Glu Asn Ser Glu Ile Tyr Asp Tyr
            740                 745                 750
```

-continued

```
Leu Arg Gln Gly Asn Arg Leu Lys Gln Pro Ala Asp Cys Leu Asp Gly
        755                 760                 765
Leu Tyr Ala Leu Met Ser Arg Cys Trp Glu Leu Asn Pro Gln Asp Arg
    770                 775                 780
Pro Ser Phe Thr Glu Leu Arg Glu Asp Leu Glu Asn Thr Leu Lys Ala
785                 790                 795                 800
Leu Pro Pro Ala Gln Glu Pro Asp Glu Ile Leu Tyr Val Asn Met Asp
                805                 810                 815
Glu Gly Gly Gly Tyr Pro Glu Pro Pro Gly Ala Ala Gly Gly Ala Asp
                820                 825                 830
Pro Pro Thr Gln Pro Asp Pro Lys Asp Ser Cys Ser Cys Leu Thr Ala
                835                 840                 845
Ala Glu Val His Pro Ala Gly Arg Tyr Val Leu Cys Pro Ser Thr Thr
        850                 855                 860
Pro Ser Pro Ala Gln Pro Ala Asp Arg Gly Ser Pro Ala Ala Pro Gly
865                 870                 875                 880
Gln Glu Asp Gly Ala
                885

<210> SEQ ID NO 12
<211> LENGTH: 30
<212> TYPE: DNA
<213> ORGANISM: Homo sapiens

<400> SEQUENCE: 12
acgttggatg gctatttctg ctgggatggg                                         30

<210> SEQ ID NO 13
<211> LENGTH: 30
<212> TYPE: DNA
<213> ORGANISM: Homo sapiens

<400> SEQUENCE: 13
acgttggatg tccaaggtgt ctccatcatg                                         30

<210> SEQ ID NO 14
<211> LENGTH: 30
<212> TYPE: DNA
<213> ORGANISM: Homo sapiens

<400> SEQUENCE: 14
acgttggatg ttctgcaccc tgggcttact                                         30

<210> SEQ ID NO 15
<211> LENGTH: 30
<212> TYPE: DNA
<213> ORGANISM: Homo sapiens

<400> SEQUENCE: 15
acgttggatg gctgagtcag tattcctcac                                         30

<210> SEQ ID NO 16
<211> LENGTH: 22
<212> TYPE: DNA
<213> ORGANISM: Homo sapiens

<400> SEQUENCE: 16
acaccaacac caccacgtta gg                                                 22

<210> SEQ ID NO 17
<211> LENGTH: 42
```

```
<212> TYPE: DNA
<213> ORGANISM: Homo sapiens

<400> SEQUENCE: 17
gggacaccgc tgatcgtata gcattcctgg gcataggtgt ag              42

<210> SEQ ID NO 18
<211> LENGTH: 30
<212> TYPE: DNA
<213> ORGANISM: Homo sapiens

<400> SEQUENCE: 18
acgttggatg ccctatggaa ttacacatgc                            30

<210> SEQ ID NO 19
<211> LENGTH: 29
<212> TYPE: DNA
<213> ORGANISM: Homo sapiens

<400> SEQUENCE: 19
acgttggatg tgagtgagtg aaattgtgt                             29

<210> SEQ ID NO 20
<211> LENGTH: 18
<212> TYPE: DNA
<213> ORGANISM: Homo sapiens

<400> SEQUENCE: 20
gacacagcag gggacgaa                                         18

<210> SEQ ID NO 21
<211> LENGTH: 41
<212> TYPE: DNA
<213> ORGANISM: Homo sapiens

<400> SEQUENCE: 21
gggacaccgc tgatcgtata ctccaaatct atcccttcc c                41

<210> SEQ ID NO 22
<211> LENGTH: 30
<212> TYPE: DNA
<213> ORGANISM: Homo sapiens

<400> SEQUENCE: 22
acgttggatg ccactctgag tgtgccattc                            30

<210> SEQ ID NO 23
<211> LENGTH: 30
<212> TYPE: DNA
<213> ORGANISM: Homo sapiens

<400> SEQUENCE: 23
acgttggatg tggcaacaag tgtcaagctc                            30

<210> SEQ ID NO 24
<211> LENGTH: 30
<212> TYPE: DNA
<213> ORGANISM: Homo sapiens

<400> SEQUENCE: 24
acgttggatg atcacccctt tgggtcccag                            30

<210> SEQ ID NO 25
<211> LENGTH: 30
```

```
<212> TYPE: DNA
<213> ORGANISM: Homo sapiens

<400> SEQUENCE: 25
acgttggatg aggttccttc actatcaggg                                           30

<210> SEQ ID NO 26
<211> LENGTH: 30
<212> TYPE: DNA
<213> ORGANISM: Homo sapiens

<400> SEQUENCE: 26
ggatttcaga tgtgcaccaa cacacctggc                                           30

<210> SEQ ID NO 27
<211> LENGTH: 30
<212> TYPE: DNA
<213> ORGANISM: Homo sapiens

<400> SEQUENCE: 27
gttcaagcaa ttctcctgcc tcagtctccc                                           30

<210> SEQ ID NO 28
<211> LENGTH: 30
<212> TYPE: DNA
<213> ORGANISM: Homo sapiens

<400> SEQUENCE: 28
gatgtggccc cattccctgg caattcagtt                                           30

<210> SEQ ID NO 29
<211> LENGTH: 29
<212> TYPE: DNA
<213> ORGANISM: Homo sapiens

<400> SEQUENCE: 29
cgtgggcgag gggcggggtg tctggactg                                            29

<210> SEQ ID NO 30
<211> LENGTH: 30
<212> TYPE: DNA
<213> ORGANISM: Homo sapiens

<400> SEQUENCE: 30
acgttggatg aactggatgc gtctgatctg                                           30

<210> SEQ ID NO 31
<211> LENGTH: 30
<212> TYPE: DNA
<213> ORGANISM: Homo sapiens

<400> SEQUENCE: 31
acgttggatg gccacacact atctctactc                                           30

<210> SEQ ID NO 32
<211> LENGTH: 30
<212> TYPE: DNA
<213> ORGANISM: Homo sapiens

<400> SEQUENCE: 32
acgttggatg accactctta gttgagctcc                                           30

<210> SEQ ID NO 33
<211> LENGTH: 30
```

```
<212> TYPE: DNA
<213> ORGANISM: Homo sapiens

<400> SEQUENCE: 33
acgttggatg gcggttcatg aagaaccctg                                      30

<210> SEQ ID NO 34
<211> LENGTH: 30
<212> TYPE: DNA
<213> ORGANISM: Homo sapiens

<400> SEQUENCE: 34
acgttggatg tacacatccc caccaaagac                                      30

<210> SEQ ID NO 35
<211> LENGTH: 30
<212> TYPE: DNA
<213> ORGANISM: Homo sapiens

<400> SEQUENCE: 35
acgttggatg ttatctggtg ggatccaagg                                      30

<210> SEQ ID NO 36
<211> LENGTH: 30
<212> TYPE: DNA
<213> ORGANISM: Homo sapiens

<400> SEQUENCE: 36
acgttggatg ctgagaggac tatggtcatg                                      30

<210> SEQ ID NO 37
<211> LENGTH: 30
<212> TYPE: DNA
<213> ORGANISM: Homo sapiens

<400> SEQUENCE: 37
acgttggatg ggaccctctc ctaaaagatg                                      30

<210> SEQ ID NO 38
<211> LENGTH: 30
<212> TYPE: DNA
<213> ORGANISM: Homo sapiens

<400> SEQUENCE: 38
acgttggatg acacataggc tagtgtctac                                      30

<210> SEQ ID NO 39
<211> LENGTH: 30
<212> TYPE: DNA
<213> ORGANISM: Homo sapiens

<400> SEQUENCE: 39
acgttggatg aactctcaga tccctatgac                                      30

<210> SEQ ID NO 40
<211> LENGTH: 30
<212> TYPE: DNA
<213> ORGANISM: Homo sapiens

<400> SEQUENCE: 40
acgttggatg tacacagtga gcacacaagg                                      30

<210> SEQ ID NO 41
<211> LENGTH: 30
```

```
<212> TYPE: DNA
<213> ORGANISM: Homo sapiens

<400> SEQUENCE: 41
acgttggatg cagccccttta tttctagcac                                        30

<210> SEQ ID NO 42
<211> LENGTH: 30
<212> TYPE: DNA
<213> ORGANISM: Homo sapiens

<400> SEQUENCE: 42
acgttggatg cagttccacg tcatttccac                                         30

<210> SEQ ID NO 43
<211> LENGTH: 30
<212> TYPE: DNA
<213> ORGANISM: Homo sapiens

<400> SEQUENCE: 43
acgttggatg tcacatttga ctcccagtgc                                         30

<210> SEQ ID NO 44
<211> LENGTH: 30
<212> TYPE: DNA
<213> ORGANISM: Homo sapiens

<400> SEQUENCE: 44
acgttggatg ataggaacag agctgcacac                                         30

<210> SEQ ID NO 45
<211> LENGTH: 30
<212> TYPE: DNA
<213> ORGANISM: Homo sapiens

<400> SEQUENCE: 45
acgttggatg gggcatttaa gatgcatctg                                         30

<210> SEQ ID NO 46
<211> LENGTH: 30
<212> TYPE: DNA
<213> ORGANISM: Homo sapiens

<400> SEQUENCE: 46
acgttggatg aaagttaagt ccctctccc                                          30

<210> SEQ ID NO 47
<211> LENGTH: 30
<212> TYPE: DNA
<213> ORGANISM: Homo sapiens

<400> SEQUENCE: 47
acgttggatg ttcctatgac cagatgccac                                         30

<210> SEQ ID NO 48
<211> LENGTH: 30
<212> TYPE: DNA
<213> ORGANISM: Homo sapiens

<400> SEQUENCE: 48
acgttggatg aggaagggac aaagcagaag                                         30

<210> SEQ ID NO 49
<211> LENGTH: 30
```

```
<212> TYPE: DNA
<213> ORGANISM: Homo sapiens

<400> SEQUENCE: 49
acgttggatg actcagtttg tccttccctg                                          30

<210> SEQ ID NO 50
<211> LENGTH: 30
<212> TYPE: DNA
<213> ORGANISM: Homo sapiens

<400> SEQUENCE: 50
acgttggatg ctcctgagtt cacccagttc                                          30

<210> SEQ ID NO 51
<211> LENGTH: 30
<212> TYPE: DNA
<213> ORGANISM: Homo sapiens

<400> SEQUENCE: 51
acgttggatg attagccagg catggtggtg                                          30

<210> SEQ ID NO 52
<211> LENGTH: 30
<212> TYPE: DNA
<213> ORGANISM: Homo sapiens

<400> SEQUENCE: 52
acgttggatg ttacaggagc ctgtgcatac                                          30

<210> SEQ ID NO 53
<211> LENGTH: 30
<212> TYPE: DNA
<213> ORGANISM: Homo sapiens

<400> SEQUENCE: 53
acgttggatg cagagagctt caatcctgag                                          30

<210> SEQ ID NO 54
<211> LENGTH: 30
<212> TYPE: DNA
<213> ORGANISM: Homo sapiens

<400> SEQUENCE: 54
acgttggatg tagtcagttt ccctcccttg                                          30

<210> SEQ ID NO 55
<211> LENGTH: 30
<212> TYPE: DNA
<213> ORGANISM: Homo sapiens

<400> SEQUENCE: 55
acgttggatg aattcagccc caatcttccc                                          30

<210> SEQ ID NO 56
<211> LENGTH: 30
<212> TYPE: DNA
<213> ORGANISM: Homo sapiens

<400> SEQUENCE: 56
acgttggatg gcctaccaat ctgaaatgcc                                          30

<210> SEQ ID NO 57
<211> LENGTH: 30
```

```
<212> TYPE: DNA
<213> ORGANISM: Homo sapiens

<400> SEQUENCE: 57
acgttggatg cagggaagag aatgggacag                                    30

<210> SEQ ID NO 58
<211> LENGTH: 30
<212> TYPE: DNA
<213> ORGANISM: Homo sapiens

<400> SEQUENCE: 58
acgttggatg gacacagaag ccttctgaac                                    30

<210> SEQ ID NO 59
<211> LENGTH: 30
<212> TYPE: DNA
<213> ORGANISM: Homo sapiens

<400> SEQUENCE: 59
acgttggatg tgttgtggtc acaaggatgc                                    30

<210> SEQ ID NO 60
<211> LENGTH: 30
<212> TYPE: DNA
<213> ORGANISM: Homo sapiens

<400> SEQUENCE: 60
acgttggatg gggtaagatt gctggcagga                                    30

<210> SEQ ID NO 61
<211> LENGTH: 30
<212> TYPE: DNA
<213> ORGANISM: Homo sapiens

<400> SEQUENCE: 61
acgttggatg caaagaaact gctcggactc                                    30

<210> SEQ ID NO 62
<211> LENGTH: 30
<212> TYPE: DNA
<213> ORGANISM: Homo sapiens

<400> SEQUENCE: 62
acgttggatg tgtcagcatg caggacaatg                                    30

<210> SEQ ID NO 63
<211> LENGTH: 30
<212> TYPE: DNA
<213> ORGANISM: Homo sapiens

<400> SEQUENCE: 63
acgttggatg agactagggc cccacaaaca                                    30

<210> SEQ ID NO 64
<211> LENGTH: 30
<212> TYPE: DNA
<213> ORGANISM: Homo sapiens

<400> SEQUENCE: 64
acgttggatg agctcgtgta caactgtgtc                                    30

<210> SEQ ID NO 65
<211> LENGTH: 30
```

<212> TYPE: DNA
<213> ORGANISM: Homo sapiens

<400> SEQUENCE: 65
acgttggatg cacaggacat gtgtgtgtac        30

<210> SEQ ID NO 66
<211> LENGTH: 30
<212> TYPE: DNA
<213> ORGANISM: Homo sapiens

<400> SEQUENCE: 66
acgttggatg catgcacaca catgcttgga        30

<210> SEQ ID NO 67
<211> LENGTH: 30
<212> TYPE: DNA
<213> ORGANISM: Homo sapiens

<400> SEQUENCE: 67
acgttggatg ggcacctgag tgtgtgtatg        30

<210> SEQ ID NO 68
<211> LENGTH: 30
<212> TYPE: DNA
<213> ORGANISM: Homo sapiens

<400> SEQUENCE: 68
acgttggatg ctgtgtgcgc aagcactcat        30

<210> SEQ ID NO 69
<211> LENGTH: 30
<212> TYPE: DNA
<213> ORGANISM: Homo sapiens

<400> SEQUENCE: 69
acgttggatg atacacagga agatagaggc        30

<210> SEQ ID NO 70
<211> LENGTH: 30
<212> TYPE: DNA
<213> ORGANISM: Homo sapiens

<400> SEQUENCE: 70
acgttggatg acagtgacga ggaaggtgag        30

<210> SEQ ID NO 71
<211> LENGTH: 30
<212> TYPE: DNA
<213> ORGANISM: Homo sapiens

<400> SEQUENCE: 71
acgttggatg atgaagtgga gacagacagg        30

<210> SEQ ID NO 72
<211> LENGTH: 30
<212> TYPE: DNA
<213> ORGANISM: Homo sapiens

<400> SEQUENCE: 72
acgttggatg ttgtgattgc ccctgccgtg        30

<210> SEQ ID NO 73
<211> LENGTH: 30

```
<212> TYPE: DNA
<213> ORGANISM: Homo sapiens

<400> SEQUENCE: 73
acgttggatg ccagattcca ttcaagagcc                                      30

<210> SEQ ID NO 74
<211> LENGTH: 30
<212> TYPE: DNA
<213> ORGANISM: Homo sapiens

<400> SEQUENCE: 74
acgttggatg ctctcagcct ttatctctgg                                      30

<210> SEQ ID NO 75
<211> LENGTH: 30
<212> TYPE: DNA
<213> ORGANISM: Homo sapiens

<400> SEQUENCE: 75
acgttggatg tatagcagcc aggtttgagg                                      30

<210> SEQ ID NO 76
<211> LENGTH: 30
<212> TYPE: DNA
<213> ORGANISM: Homo sapiens

<400> SEQUENCE: 76
acgttggatg acaatttcc cttcctccgc                                       30

<210> SEQ ID NO 77
<211> LENGTH: 30
<212> TYPE: DNA
<213> ORGANISM: Homo sapiens

<400> SEQUENCE: 77
acgttggatg tcaggaccca tgataacagc                                      30

<210> SEQ ID NO 78
<211> LENGTH: 30
<212> TYPE: DNA
<213> ORGANISM: Homo sapiens

<400> SEQUENCE: 78
acgttggatg acaatttcc cttcctccgc                                       30

<210> SEQ ID NO 79
<211> LENGTH: 30
<212> TYPE: DNA
<213> ORGANISM: Homo sapiens

<400> SEQUENCE: 79
acgttggatg ctcaggaccc atgataacag                                      30

<210> SEQ ID NO 80
<211> LENGTH: 30
<212> TYPE: DNA
<213> ORGANISM: Homo sapiens

<400> SEQUENCE: 80
acgttggatg agctagactc caggaccttg                                      30

<210> SEQ ID NO 81
<211> LENGTH: 30
```

<212> TYPE: DNA
<213> ORGANISM: Homo sapiens

<400> SEQUENCE: 81
acgttggatg tacaggcagg taagagacag                              30

<210> SEQ ID NO 82
<211> LENGTH: 29
<212> TYPE: DNA
<213> ORGANISM: Homo sapiens

<400> SEQUENCE: 82
acgttggatg gtgtctcctg tccgtcctg                               29

<210> SEQ ID NO 83
<211> LENGTH: 30
<212> TYPE: DNA
<213> ORGANISM: Homo sapiens

<400> SEQUENCE: 83
acgttggatg ttgctttggc aggacgcatg                              30

<210> SEQ ID NO 84
<211> LENGTH: 30
<212> TYPE: DNA
<213> ORGANISM: Homo sapiens

<400> SEQUENCE: 84
acgttggatg ccttgttttt cccatgcctc                              30

<210> SEQ ID NO 85
<211> LENGTH: 30
<212> TYPE: DNA
<213> ORGANISM: Homo sapiens

<400> SEQUENCE: 85
acgttggatg gaacagagat ggagaatggc                              30

<210> SEQ ID NO 86
<211> LENGTH: 30
<212> TYPE: DNA
<213> ORGANISM: Homo sapiens

<400> SEQUENCE: 86
acgttggatg actcctgacc tcaagtgatc                              30

<210> SEQ ID NO 87
<211> LENGTH: 30
<212> TYPE: DNA
<213> ORGANISM: Homo sapiens

<400> SEQUENCE: 87
acgttggatg aaagtcctaa gagaggccag                              30

<210> SEQ ID NO 88
<211> LENGTH: 30
<212> TYPE: DNA
<213> ORGANISM: Homo sapiens

<400> SEQUENCE: 88
acgttggatg agcaatagtt ggtgtccagg                              30

<210> SEQ ID NO 89
<211> LENGTH: 30

```
<212> TYPE: DNA
<213> ORGANISM: Homo sapiens

<400> SEQUENCE: 89
acgttggatg accattcatg gcatgaaccg                                    30

<210> SEQ ID NO 90
<211> LENGTH: 30
<212> TYPE: DNA
<213> ORGANISM: Homo sapiens

<400> SEQUENCE: 90
acgttggatg aacaaggtag gagaagaggg                                    30

<210> SEQ ID NO 91
<211> LENGTH: 30
<212> TYPE: DNA
<213> ORGANISM: Homo sapiens

<400> SEQUENCE: 91
acgttggatg ttcttacagg tgtctgcctc                                    30

<210> SEQ ID NO 92
<211> LENGTH: 21
<212> TYPE: DNA
<213> ORGANISM: Homo sapiens

<400> SEQUENCE: 92
gggcaggttc ctggtagagg g                                             21

<210> SEQ ID NO 93
<211> LENGTH: 20
<212> TYPE: DNA
<213> ORGANISM: Homo sapiens

<400> SEQUENCE: 93
cttactgttg gctcctccac                                               20

<210> SEQ ID NO 94
<211> LENGTH: 20
<212> TYPE: DNA
<213> ORGANISM: Homo sapiens

<400> SEQUENCE: 94
aaaaacagtc aagacacaat                                               20

<210> SEQ ID NO 95
<211> LENGTH: 24
<212> TYPE: DNA
<213> ORGANISM: Homo sapiens

<400> SEQUENCE: 95
tgcccaggaa tgctcataag taca                                          24

<210> SEQ ID NO 96
<211> LENGTH: 15
<212> TYPE: DNA
<213> ORGANISM: Homo sapiens

<400> SEQUENCE: 96
agacacaacc cctgc                                                    15

<210> SEQ ID NO 97
<211> LENGTH: 17
```

-continued

<212> TYPE: DNA
<213> ORGANISM: Homo sapiens

<400> SEQUENCE: 97
gtgtgccatt cctcggg                                                    17

<210> SEQ ID NO 98
<211> LENGTH: 20
<212> TYPE: DNA
<213> ORGANISM: Homo sapiens

<400> SEQUENCE: 98
cagagagctg gatccaaggc                                                 20

<210> SEQ ID NO 99
<211> LENGTH: 24
<212> TYPE: DNA
<213> ORGANISM: Homo sapiens

<400> SEQUENCE: 99
cagcaagagc gatgtggtag gtgc                                            24

<210> SEQ ID NO 100
<211> LENGTH: 21
<212> TYPE: DNA
<213> ORGANISM: Homo sapiens

<400> SEQUENCE: 100
gaggacctgg tcacaaatac a                                               21

<210> SEQ ID NO 101
<211> LENGTH: 17
<212> TYPE: DNA
<213> ORGANISM: Homo sapiens

<400> SEQUENCE: 101
acgcctgttt gtttacg                                                    17

<210> SEQ ID NO 102
<211> LENGTH: 20
<212> TYPE: DNA
<213> ORGANISM: Homo sapiens

<400> SEQUENCE: 102
acctgcagat gccttctgga                                                 20

<210> SEQ ID NO 103
<211> LENGTH: 22
<212> TYPE: DNA
<213> ORGANISM: Homo sapiens

<400> SEQUENCE: 103
gttgacaatt tctgaggata cc                                              22

<210> SEQ ID NO 104
<211> LENGTH: 23
<212> TYPE: DNA
<213> ORGANISM: Homo sapiens

<400> SEQUENCE: 104
aggactatgg tcatgaaaca act                                             23

<210> SEQ ID NO 105
<211> LENGTH: 20

```
<212> TYPE: DNA
<213> ORGANISM: Homo sapiens

<400> SEQUENCE: 105
gacataccta actttccctt                                              20

<210> SEQ ID NO 106
<211> LENGTH: 17
<212> TYPE: DNA
<213> ORGANISM: Homo sapiens

<400> SEQUENCE: 106
gtgagctatc actgcaa                                                 17

<210> SEQ ID NO 107
<211> LENGTH: 20
<212> TYPE: DNA
<213> ORGANISM: Homo sapiens

<400> SEQUENCE: 107
ggaatatgat tgccaactct                                              20

<210> SEQ ID NO 108
<211> LENGTH: 17
<212> TYPE: DNA
<213> ORGANISM: Homo sapiens

<400> SEQUENCE: 108
gctgcacaca caaggac                                                 17

<210> SEQ ID NO 109
<211> LENGTH: 23
<212> TYPE: DNA
<213> ORGANISM: Homo sapiens

<400> SEQUENCE: 109
cttctttgac tccattccta aaa                                          23

<210> SEQ ID NO 110
<211> LENGTH: 24
<212> TYPE: DNA
<213> ORGANISM: Homo sapiens

<400> SEQUENCE: 110
agagtaagat caaaaagaa atca                                          24

<210> SEQ ID NO 111
<211> LENGTH: 19
<212> TYPE: DNA
<213> ORGANISM: Homo sapiens

<400> SEQUENCE: 111
tctcctgcct cagcctccc                                               19

<210> SEQ ID NO 112
<211> LENGTH: 20
<212> TYPE: DNA
<213> ORGANISM: Homo sapiens

<400> SEQUENCE: 112
gggcactggc tttccaagaa                                              20

<210> SEQ ID NO 113
<211> LENGTH: 17
```

```
<212> TYPE: DNA
<213> ORGANISM: Homo sapiens

<400> SEQUENCE: 113
ccttgttttt gttgccc                                                17

<210> SEQ ID NO 114
<211> LENGTH: 20
<212> TYPE: DNA
<213> ORGANISM: Homo sapiens

<400> SEQUENCE: 114
caatctgaaa tgccacttct                                             20

<210> SEQ ID NO 115
<211> LENGTH: 21
<212> TYPE: DNA
<213> ORGANISM: Homo sapiens

<400> SEQUENCE: 115
agccttctga acaagacaca c                                           21

<210> SEQ ID NO 116
<211> LENGTH: 20
<212> TYPE: DNA
<213> ORGANISM: Homo sapiens

<400> SEQUENCE: 116
cagtcacagc ctatggtgct                                             20

<210> SEQ ID NO 117
<211> LENGTH: 20
<212> TYPE: DNA
<213> ORGANISM: Homo sapiens

<400> SEQUENCE: 117
atgcaggaca atgcagcaga                                             20

<210> SEQ ID NO 118
<211> LENGTH: 17
<212> TYPE: DNA
<213> ORGANISM: Homo sapiens

<400> SEQUENCE: 118
cctgcccatg gacgtgt                                                17

<210> SEQ ID NO 119
<211> LENGTH: 20
<212> TYPE: DNA
<213> ORGANISM: Homo sapiens

<400> SEQUENCE: 119
atacacagga agatagaggc                                             20

<210> SEQ ID NO 120
<211> LENGTH: 20
<212> TYPE: DNA
<213> ORGANISM: Homo sapiens

<400> SEQUENCE: 120
catgcaggca cctgaggtca                                             20

<210> SEQ ID NO 121
<211> LENGTH: 17
```

```
<212> TYPE: DNA
<213> ORGANISM: Homo sapiens

<400> SEQUENCE: 121
tgagggccag tagcagg                                                    17

<210> SEQ ID NO 122
<211> LENGTH: 21
<212> TYPE: DNA
<213> ORGANISM: Homo sapiens

<400> SEQUENCE: 122
agccatggtc accagagcct c                                               21

<210> SEQ ID NO 123
<211> LENGTH: 17
<212> TYPE: DNA
<213> ORGANISM: Homo sapiens

<400> SEQUENCE: 123
tctgggtttt gatcccc                                                    17

<210> SEQ ID NO 124
<211> LENGTH: 17
<212> TYPE: DNA
<213> ORGANISM: Homo sapiens

<400> SEQUENCE: 124
ctccgccttc ctctccc                                                    17

<210> SEQ ID NO 125
<211> LENGTH: 17
<212> TYPE: DNA
<213> ORGANISM: Homo sapiens

<400> SEQUENCE: 125
ttacactccc caaatgc                                                    17

<210> SEQ ID NO 126
<211> LENGTH: 17
<212> TYPE: DNA
<213> ORGANISM: Homo sapiens

<400> SEQUENCE: 126
aggaccttgg ggtcata                                                    17

<210> SEQ ID NO 127
<211> LENGTH: 17
<212> TYPE: DNA
<213> ORGANISM: Homo sapiens

<400> SEQUENCE: 127
gctcgctggc ctggccg                                                    17

<210> SEQ ID NO 128
<211> LENGTH: 17
<212> TYPE: DNA
<213> ORGANISM: Homo sapiens

<400> SEQUENCE: 128 cccaccttttt ccactcc                                                   17

<210> SEQ ID NO 129
<211> LENGTH: 17
```

```
<212> TYPE: DNA
<213> ORGANISM: Homo sapiens

<400> SEQUENCE: 129
agtgctggga ttacggg                                              17

<210> SEQ ID NO 130
<211> LENGTH: 17
<212> TYPE: DNA
<213> ORGANISM: Homo sapiens

<400> SEQUENCE: 130
gggccctctc cagcggg                                              17

<210> SEQ ID NO 131
<211> LENGTH: 21
<212> TYPE: DNA
<213> ORGANISM: Homo sapiens

<400> SEQUENCE: 131 aggggggcaac aggacacctg a                                        21

<210> SEQ ID NO 132
<211> LENGTH: 38
<212> TYPE: DNA
<213> ORGANISM: Homo sapiens

<400> SEQUENCE: 132
gccaccgggt ctagcttcta caccctctac caggaacc                       38

<210> SEQ ID NO 133
<211> LENGTH: 38
<212> TYPE: DNA
<213> ORGANISM: Homo sapiens

<400> SEQUENCE: 133
gccaccgggt ctagcttcta cgccctctac caggaacc                       38

<210> SEQ ID NO 134
<211> LENGTH: 35
<212> TYPE: DNA
<213> ORGANISM: Homo sapiens

<400> SEQUENCE: 134
ggcccacggg gggaacagca cgtggaggag ccaac                          35

<210> SEQ ID NO 135
<211> LENGTH: 35
<212> TYPE: DNA
<213> ORGANISM: Homo sapiens

<400> SEQUENCE: 135
ggcccacggg gggaacagca ggtggaggag ccaac                          35

<210> SEQ ID NO 136
<211> LENGTH: 40
<212> TYPE: DNA
<213> ORGANISM: Homo sapiens

<400> SEQUENCE: 136
cagtcaagac acaatacgtg aactcccta tggaattaca                      40

<210> SEQ ID NO 137
<211> LENGTH: 40
```

```
<212> TYPE: DNA
<213> ORGANISM: Homo sapiens

<400> SEQUENCE: 137
cagtcaagac acaataggtg aactccccta tggaattaca                    40

<210> SEQ ID NO 138
<211> LENGTH: 35
<212> TYPE: DNA
<213> ORGANISM: Homo sapiens

<400> SEQUENCE: 138
ggaatgctca taagtacaca gctgaacaca atttc                         35

<210> SEQ ID NO 139
<211> LENGTH: 35
<212> TYPE: DNA
<213> ORGANISM: Homo sapiens

<400> SEQUENCE: 139
ggaatgctca taagtacata gctgaacaca atttc                         35

<210> SEQ ID NO 140
<211> LENGTH: 40
<212> TYPE: DNA
<213> ORGANISM: Homo sapiens

<400> SEQUENCE: 140
acgaaacaga cacaaccccct gccctcctag agctgacatt                   40

<210> SEQ ID NO 141
<211> LENGTH: 40
<212> TYPE: DNA
<213> ORGANISM: Homo sapiens

<400> SEQUENCE: 141
acgaaacaga cacaaccccct gctctcctag agctgacatt                   40

<210> SEQ ID NO 142
<211> LENGTH: 52
<212> TYPE: DNA
<213> ORGANISM: Homo sapiens

<400> SEQUENCE: 142
ccactctgag tgtgccattc ctcgggcgga ataggtatgg gaacctgtgc cg      52

<210> SEQ ID NO 143
<211> LENGTH: 52
<212> TYPE: DNA
<213> ORGANISM: Homo sapiens

<400> SEQUENCE: 143
ccactctgag tgtgccattc ctcgggtgga ataggtatgg gaacctgtgc cg      52

<210> SEQ ID NO 144
<211> LENGTH: 37
<212> TYPE: DNA
<213> ORGANISM: Homo sapiens

<400> SEQUENCE: 144
gaggaacagg tcatggatga agccttggat ccagctc                       37

<210> SEQ ID NO 145
<211> LENGTH: 37
```

```
<212> TYPE: DNA
<213> ORGANISM: Homo sapiens

<400> SEQUENCE: 145
gaggaacagg tcatggatga ggccttggat ccagctc                        37

<210> SEQ ID NO 146
<211> LENGTH: 40
<212> TYPE: DNA
<213> ORGANISM: Homo sapiens

<400> SEQUENCE: 146
caagagcgat gtggtaggtg cactcccgcc aagagtgggg                     40

<210> SEQ ID NO 147
<211> LENGTH: 40
<212> TYPE: DNA
<213> ORGANISM: Homo sapiens

<400> SEQUENCE: 147
caagagcgat gtggtaggtg cgctcccgcc aagagtgggg                     40

<210> SEQ ID NO 148
<211> LENGTH: 40
<212> TYPE: DNA
<213> ORGANISM: Homo sapiens

<400> SEQUENCE: 148
aggaggacct ggtcacaaat acagagactg aaactcagac                     40

<210> SEQ ID NO 149
<211> LENGTH: 40
<212> TYPE: DNA
<213> ORGANISM: Homo sapiens

<400> SEQUENCE: 149
aggaggacct ggtcacaaat acaaagactg aaactcagac                     40

<210> SEQ ID NO 150
<211> LENGTH: 54
<212> TYPE: DNA
<213> ORGANISM: Homo sapiens

<400> SEQUENCE: 150
ctctactcag acaaaggcac accccgcaga cgtaaacaaa caggcgtgcg tcag     54

<210> SEQ ID NO 151
<211> LENGTH: 54
<212> TYPE: DNA
<213> ORGANISM: Homo sapiens

<400> SEQUENCE: 151
ctctactcag acaaaggcac accccgcagt cgtaaacaaa caggcgtgcg tcag     54

<210> SEQ ID NO 152
<211> LENGTH: 59
<212> TYPE: DNA
<213> ORGANISM: Homo sapiens

<400> SEQUENCE: 152
cggttcatga agaaccctgg accaaagcat ccagaaggca tctgcaggtc caggagctc    59

<210> SEQ ID NO 153
<211> LENGTH: 59
```

```
<212> TYPE: DNA
<213> ORGANISM: Homo sapiens

<400> SEQUENCE: 153
cggttcatga agaaccctgg accaaagcgt ccagaaggca tctgcaggtc caggagctc      59

<210> SEQ ID NO 154
<211> LENGTH: 63
<212> TYPE: DNA
<213> ORGANISM: Homo sapiens

<400> SEQUENCE: 154
ccaaagacat gtgttgacaa tttctgagga taccctgaa gccccatcct tggatcccac      60
cag                                                                   63

<210> SEQ ID NO 155
<211> LENGTH: 63
<212> TYPE: DNA
<213> ORGANISM: Homo sapiens

<400> SEQUENCE: 155
ccaaagacat gtgttgacaa tttctgagga taccgctgaa gccccatcct tggatcccac      60
cag                                                                   63

<210> SEQ ID NO 156
<211> LENGTH: 48
<212> TYPE: DNA
<213> ORGANISM: Homo sapiens

<400> SEQUENCE: 156
ggataagaat tgattcttca cagaaaagtt gtttcatgac catagtcc                   48

<210> SEQ ID NO 157
<211> LENGTH: 48
<212> TYPE: DNA
<213> ORGANISM: Homo sapiens

<400> SEQUENCE: 157
ggataagaat tgattcttca cagaacagtt gtttcatgac catagtcc                   48

<210> SEQ ID NO 158
<211> LENGTH: 70
<212> TYPE: DNA
<213> ORGANISM: Homo sapiens

<400> SEQUENCE: 158
gcactcatat gacataccta acttttcctt attttttttt tcagtatttc tagtcatagg      60
gatctgagag                                                            70

<210> SEQ ID NO 159
<211> LENGTH: 70
<212> TYPE: DNA
<213> ORGANISM: Homo sapiens

<400> SEQUENCE: 159
gcactcatat gacataccta acttttcctt tttttttttt tcagtatttc tagtcatagg      60
gatctgagag                                                            70

<210> SEQ ID NO 160
<211> LENGTH: 81
<212> TYPE: DNA
<213> ORGANISM: Homo sapiens
```

```
<400> SEQUENCE: 160
ccacttcagt cccagcccct tatttctagc acagtgcctg acatcttgca gtgatagctc    60
acattccttg tgtgctcact g                                             81

<210> SEQ ID NO 161
<211> LENGTH: 81
<212> TYPE: DNA
<213> ORGANISM: Homo sapiens

<400> SEQUENCE: 161
ccacttcagt cccagcccct tatttctagc acagtgcctg acattttgca gtgatagctc    60
acattccttg tgtgctcact g                                             81

<210> SEQ ID NO 162
<211> LENGTH: 45
<212> TYPE: DNA
<213> ORGANISM: Homo sapiens
<220> FEATURE:
<221> NAME/KEY: misc_feature
<222> LOCATION: (26)..(26)
<223> OTHER INFORMATION: n is a, c, g, or t

<400> SEQUENCE: 162
ggaatatgat tgccaactct cgccanaggc actgggagtc aaatg                   45

<210> SEQ ID NO 163
<211> LENGTH: 45
<212> TYPE: DNA
<213> ORGANISM: Homo sapiens
<220> FEATURE:
<221> NAME/KEY: misc_feature
<222> LOCATION: (26)..(26)
<223> OTHER INFORMATION: n is a, c, g, or t

<400> SEQUENCE: 163
ggaatatgat tgccaactct tgccanaggc actgggagtc aaatg                   45

<210> SEQ ID NO 164
<211> LENGTH: 43
<212> TYPE: DNA
<213> ORGANISM: Homo sapiens

<400> SEQUENCE: 164
cagagctgca cacacaagga catgaattgt atctaatcag tac                     43

<210> SEQ ID NO 165
<211> LENGTH: 43
<212> TYPE: DNA
<213> ORGANISM: Homo sapiens

<400> SEQUENCE: 165
cagagctgca cacacaagga cgtgaattgt atctaatcag tac                     43

<210> SEQ ID NO 166
<211> LENGTH: 50
<212> TYPE: DNA
<213> ORGANISM: Homo sapiens

<400> SEQUENCE: 166
gaccagatgc cacgttctgc tttgctttta ggaatggagt caaagaagag              50

<210> SEQ ID NO 167
<211> LENGTH: 50
```

```
<212> TYPE: DNA
<213> ORGANISM: Homo sapiens

<400> SEQUENCE: 167
gaccagatgc cacgttctgc tttggtttta ggaatggagt caaagaagag         50

<210> SEQ ID NO 168
<211> LENGTH: 54
<212> TYPE: DNA
<213> ORGANISM: Homo sapiens

<400> SEQUENCE: 168
ctttactcag tttgtccttc cctggctccc caatgatttc tttttgatc ttac     54

<210> SEQ ID NO 169
<211> LENGTH: 54
<212> TYPE: DNA
<213> ORGANISM: Homo sapiens

<400> SEQUENCE: 169
ctttactcag tttgtccttc cctggctccc cagtgatttc tttttgatc ttac     54

<210> SEQ ID NO 170
<211> LENGTH: 54
<212> TYPE: DNA
<213> ORGANISM: Homo sapiens

<400> SEQUENCE: 170
ccagttctcc tgcctcagcc tcccaagtag ctgggactac aggtgtccac cacc    54

<210> SEQ ID NO 171
<211> LENGTH: 54
<212> TYPE: DNA
<213> ORGANISM: Homo sapiens

<400> SEQUENCE: 171
ccagttctcc tgcctcagcc tcccgagtag ctgggactac aggtgtccac cacc    54

<210> SEQ ID NO 172
<211> LENGTH: 59
<212> TYPE: DNA
<213> ORGANISM: Homo sapiens

<400> SEQUENCE: 172
gcttcaatcc tgagcagctc caggctcagt tcccattctt ggaaagccag tgccctggc   59

<210> SEQ ID NO 173
<211> LENGTH: 59
<212> TYPE: DNA
<213> ORGANISM: Homo sapiens

<400> SEQUENCE: 173
gcttcaatcc tgagcagctc caggctcagt tcccgttctt ggaaagccag tgccctggc   59

<210> SEQ ID NO 174
<211> LENGTH: 42
<212> TYPE: DNA
<213> ORGANISM: Homo sapiens

<400> SEQUENCE: 174
ctcccttgtt tttgttgccc atctcccctt cacaaggctc tg                 42

<210> SEQ ID NO 175
<211> LENGTH: 42
```

```
<212> TYPE: DNA
<213> ORGANISM: Homo sapiens

<400> SEQUENCE: 175
ctcccttgtt tttgttgccc gtctcccctt cacaaggctc tg                    42

<210> SEQ ID NO 176
<211> LENGTH: 49
<212> TYPE: DNA
<213> ORGANISM: Homo sapiens

<400> SEQUENCE: 176
gatcagaatt tagtagatgt cagaagtggc atttcagatt ggtaggctg             49

<210> SEQ ID NO 177
<211> LENGTH: 49
<212> TYPE: DNA
<213> ORGANISM: Homo sapiens

<400> SEQUENCE: 177
gatcagaatt tagtagatgt tagaagtggc atttcagatt ggtaggctg             49

<210> SEQ ID NO 178
<211> LENGTH: 46
<212> TYPE: DNA
<213> ORGANISM: Homo sapiens

<400> SEQUENCE: 178
cacagaagcc ttctgaacaa gacacacggt gaaaaccatg aaggaa                46

<210> SEQ ID NO 179
<211> LENGTH: 46
<212> TYPE: DNA
<213> ORGANISM: Homo sapiens

<400> SEQUENCE: 179
cacagaagcc ttctgaacaa gacacactgt gaaaaccatg aaggaa                46

<210> SEQ ID NO 180
<211> LENGTH: 45
<212> TYPE: DNA
<213> ORGANISM: Homo sapiens

<400> SEQUENCE: 180
gaaactgctc ggactcctgg cctctgcagc accataggct gtgac                 45

<210> SEQ ID NO 181
<211> LENGTH: 45
<212> TYPE: DNA
<213> ORGANISM: Homo sapiens

<400> SEQUENCE: 181
gaaactgctc ggactcctgg cctctgtagc accataggct gtgac                 45

<210> SEQ ID NO 182
<211> LENGTH: 50
<212> TYPE: DNA
<213> ORGANISM: Homo sapiens

<400> SEQUENCE: 182
gtcagcatgc aggacaatgc agcagaagtt gtgtgtctct aggttgtgtg            50

<210> SEQ ID NO 183
<211> LENGTH: 50
```

```
<212> TYPE: DNA
<213> ORGANISM: Homo sapiens

<400> SEQUENCE: 183
gtcagcatgc aggacaatgc agcagaggtt gtgtgtctct aggttgtgtg                50

<210> SEQ ID NO 184
<211> LENGTH: 33
<212> TYPE: DNA
<213> ORGANISM: Homo sapiens

<400> SEQUENCE: 184
gtgtacatag gccatgcaca cgtccatggg cag                                   33

<210> SEQ ID NO 185
<211> LENGTH: 33
<212> TYPE: DNA
<213> ORGANISM: Homo sapiens

<400> SEQUENCE: 185
gtgtacatag gccatgtaca cgtccatggg cag                                   33

<210> SEQ ID NO 186
<211> LENGTH: 49
<212> TYPE: DNA
<213> ORGANISM: Homo sapiens

<400> SEQUENCE: 186
gaatacacag gaagatagag gccgggccac atacacacac tcaggtgcc                  49

<210> SEQ ID NO 187
<211> LENGTH: 49
<212> TYPE: DNA
<213> ORGANISM: Homo sapiens

<400> SEQUENCE: 187
gaatacacag gaagatagag gctgggccac atacacacac tcaggtgcc                  49

<210> SEQ ID NO 188
<211> LENGTH: 40
<212> TYPE: DNA
<213> ORGANISM: Homo sapiens

<400> SEQUENCE: 188
cgagtaatca catgcacatg acctcaggtg cctgcatgag                            40

<210> SEQ ID NO 189
<211> LENGTH: 40
<212> TYPE: DNA
<213> ORGANISM: Homo sapiens

<400> SEQUENCE: 189
cgagtaatca catgcacgtg acctcaggtg cctgcatgag                            40

<210> SEQ ID NO 190
<211> LENGTH: 56
<212> TYPE: DNA
<213> ORGANISM: Homo sapiens

<400> SEQUENCE: 190
ctggggtgtc tggaatctgg ggtctccctg ctactggccc tcaccttcct cgtcac          56

<210> SEQ ID NO 191
<211> LENGTH: 56
```

```
<212> TYPE: DNA
<213> ORGANISM: Homo sapiens

<400> SEQUENCE: 191
ctggggtgtc tggaatctgg ggtcttcctg ctactggccc tcaccttcct cgtcac        56

<210> SEQ ID NO 192
<211> LENGTH: 43
<212> TYPE: DNA
<213> ORGANISM: Homo sapiens

<400> SEQUENCE: 192
ccatggtcac cagagcctcc tcccattctg ggatccctgg ctc                      43

<210> SEQ ID NO 193
<211> LENGTH: 43
<212> TYPE: DNA
<213> ORGANISM: Homo sapiens

<400> SEQUENCE: 193
ccatggtcac cagagcctct tcccattctg ggatccctgg ctc                      43

<210> SEQ ID NO 194
<211> LENGTH: 45
<212> TYPE: DNA
<213> ORGANISM: Homo sapiens

<400> SEQUENCE: 194
ggaagaaggg gcccagagcc tggagtcggg gatcaaaacc cagag                    45

<210> SEQ ID NO 195
<211> LENGTH: 45
<212> TYPE: DNA
<213> ORGANISM: Homo sapiens

<400> SEQUENCE: 195
ggaagaaggg gcccagagcc tggagtgggg gatcaaaacc cagag                    45

<210> SEQ ID NO 196
<211> LENGTH: 36
<212> TYPE: DNA
<213> ORGANISM: Homo sapiens

<400> SEQUENCE: 196
gggagtgtaa acaggagagg gagaggaagg cggagg                              36

<210> SEQ ID NO 197
<211> LENGTH: 36
<212> TYPE: DNA
<213> ORGANISM: Homo sapiens

<400> SEQUENCE: 197
gggagtgtaa acaggagtgg gagaggaagg cggagg                              36

<210> SEQ ID NO 198
<211> LENGTH: 38
<212> TYPE: DNA
<213> ORGANISM: Homo sapiens

<400> SEQUENCE: 198
ccatgataac agcctgtgcg catttgggga gtgtaaac                            38

<210> SEQ ID NO 199
<211> LENGTH: 38
```

```
<212> TYPE: DNA
<213> ORGANISM: Homo sapiens

<400> SEQUENCE: 199
ccatgataac agcctgtgtg catttgggga gtgtaaac                    38

<210> SEQ ID NO 200
<211> LENGTH: 45
<212> TYPE: DNA
<213> ORGANISM: Homo sapiens

<400> SEQUENCE: 200
gcactcttgg ctttctgaga gatatgaccc caaggtcctg gagtc             45

<210> SEQ ID NO 201
<211> LENGTH: 45
<212> TYPE: DNA
<213> ORGANISM: Homo sapiens

<400> SEQUENCE: 201
gcactcttgg ctttctgaga ggtatgaccc caaggtcctg gagtc             45

<210> SEQ ID NO 202
<211> LENGTH: 50
<212> TYPE: DNA
<213> ORGANISM: Homo sapiens

<400> SEQUENCE: 202
ctggccctgg cctggctcgc tggcctggcc gacacccgc ccccacgtc          50

<210> SEQ ID NO 203
<211> LENGTH: 50
<212> TYPE: DNA
<213> ORGANISM: Homo sapiens

<400> SEQUENCE: 203
ctggccctgg cctggctcgc tggcctggcc gccacccgc ccccacgtc          50

<210> SEQ ID NO 204
<211> LENGTH: 35
<212> TYPE: DNA
<213> ORGANISM: Homo sapiens

<400> SEQUENCE: 204 ccacctttc cactccatgt ccccagccat tctcc                        35

<210> SEQ ID NO 205
<211> LENGTH: 35
<212> TYPE: DNA
<213> ORGANISM: Homo sapiens

<400> SEQUENCE: 205 ccacctttc cactccgtgt ccccagccat tctcc                        35

<210> SEQ ID NO 206
<211> LENGTH: 49
<212> TYPE: DNA
<213> ORGANISM: Homo sapiens

<400> SEQUENCE: 206
gaggccaggt atggtagctc acacccgtaa tcccagcact ttgggaggc         49

<210> SEQ ID NO 207
<211> LENGTH: 49
```

```
<212> TYPE: DNA
<213> ORGANISM: Homo sapiens

<400> SEQUENCE: 207
gaggccaggt atggtagctc acgcccgtaa tcccagcact ttgggaggc         49

<210> SEQ ID NO 208
<211> LENGTH: 33
<212> TYPE: DNA
<213> ORGANISM: Homo sapiens

<400> SEQUENCE: 208
cctgcttctc atggccaccc cgctggagag ggc                          33

<210> SEQ ID NO 209
<211> LENGTH: 33
<212> TYPE: DNA
<213> ORGANISM: Homo sapiens

<400> SEQUENCE: 209
cctgcttctc atggccatcc cgctggagag ggc                          33

<210> SEQ ID NO 210
<211> LENGTH: 46
<212> TYPE: DNA
<213> ORGANISM: Homo sapiens

<400> SEQUENCE: 210
ctgcctcctg acccttccat ccctcaggtg tcctgttgcc ccctcc            46

<210> SEQ ID NO 211
<211> LENGTH: 46
<212> TYPE: DNA
<213> ORGANISM: Homo sapiens

<400> SEQUENCE: 211
ctgcctcctg acccttccat ccttcaggtg tcctgttgcc ccctcc            46
```

METHODS FOR PREDICTING THE RESPONSE OF MULTIPLE SCLEROSIS PATIENTS TO INTERFERON THERAPY AND DIAGNOSING MULTIPLE SCLEROSIS

This application is the National Phase of International Application PCT/EP2007/001689, filed Feb. 27, 2007 which designated the U.S. and that International Application was published under PCT Article 21(2) in English, and claims priority to European Application Serial No. 06 00 3978.1, filed Feb. 27, 2006.

The present invention provides a method of diagnosing a predisposition of a multiple sclerosis (MS) patient for responsiveness to a treatment of MS by administration of interferon-α (IFN-α) and/or interferon-β (IFN-β) and means to perform the method. Furthermore, the invention provides a method of diagnosing a predisposition of a patient for developing multiple sclerosis (MS) and corresponding means.

A variety of documents is cited throughout this specification. The disclosure content of said documents including manufacturer's manuals is herewith incorporated by reference in its entirety.

Multiple sclerosis (MS) is a chronic inflammatory disease of the central nervous system involving the destruction of myelin on neuronal axons (i.e. demyelination) which leads to the formation of multifocal plaques. MS can be divided into two categories: relapsing-remitting, and chronic-progressive. Chronic-progressive MS is further subdivided into primary-progressive, secondary-progressive, and progressive-relapsing.

Multiple sclerosis (MS) is the most common chronic inflammatory disease of the central nervous system in young adults. Over 1 million individuals worldwide are afflicted with MS. It's prevalence is estimated at 60-100/100.000 in the northern United States and northern Europe (see Kesselring Ed. "Epidemiologie." 3 ed. Psychiatrie, Neurologie, Klinische Psychologie. Stuttgart: Kohlhammer, 70-76, 1997). Although the mortality due to MS is low, neurological sequelae often occur early in life and prohibit private and professional development. Symptoms of MS include optic neuritis, fatigue, poor coordination, spasticity, dizziness, tremors, speech difficulties, swallowing difficulties, pain, and emotional mood swings.

In about 80 to 90% of patients, the disease starts with a clinically isolated syndrome which proceeds to a relapsing-remitting course. After several years there is an increasing tendency for the patient to enter a phase of slow, steady or fluctuating deterioration of neurologic function, which is then called a secondary progressive course. Only 10-15% of patients demonstrate a primary progressive deterioration without any relapses just from the beginning.

The pathological hallmark of MS is the demyelinated plaque with relative axonal sparing and glial scar formation (Pnneas "The Neuropathology of Multiple Sclerosis." Ed. J. C. Koetsier. Amsterdam: Elsevier Science Publishers, 213-257, 1985; Lassmann (1998) Mult Scler 4: 93-98). MS has been considered an autoimmune disorder consisting of autoreactive T cells and autoantibodies that drive an inflammatory process, leading to macrophage recruitment, and subsequent destruction of myelin/oligodendrocytes and axons. Recent detailed studies on large collections of MS lesions, however, have indicated that structural features of the plaques are extremely variable and the events involved in the immunopathogenesis of MS may be more complicated (Lucchinetti et al. (2000) Ann Neurol 47:707-717; Lassmann et al. (2001) Trends Mol Med 7: 115-121). A structural analysis of oligodendrocyte pathology demonstrated two principal patterns of oligodendrocyte pathology in MS lesions with oligodendrocyte survival or progenitor recruitment in the first and extensive destruction of myelinating cells in the second pattern. In addition quite diverse patterns of myelin destruction were observed and grouped into four subtypes: (1) Macrophage-mediated demyelination; (2) Antibody-mediated demyelination; (3) distal oligodendrogliopathy and apoptosis; and (4) primary oligodendroglia degeneration (Lassmann et al. (2001) Trends Mol Med 7: 115-121). The finding of such heterogeneity is also supported by experimental data in animal models of MS.

The majority of MS cases is sporadic. However, about 15% of the MS patients have an affected relative with the highest risk of recurrence being observed in siblings (Ebers et al. (1986) N Engl J Med 315: 1638-1642). In a large population-based study, it was found that almost 20% of the index cases had an affected relative, again with the highest risk in siblings (Sadovnick et al. (1988) Am J Med Genet. 29: 533-541). The case for heritability is supported also by studies in twins in whom one of each pair is known to have MS. Ebers et al. verified the diagnosis in 7 of 27 pairs of monozygotic twins (26%) and in only one of 43 pairs of dizygotic twins (2.3%). In two clinically normal monozygotic twins, lesions were detected by MRI, bringing the concordance rate to 33% (Ebers et al. (1986) N Engl J Med 315: 1638-1642). The concordance rate in dizygotic pairs is similar to that in non-twin siblings. Within families with more than one affected member, no consistent genetic pattern has emerged. Studies dealing with the epidemiology and genetics of MS indicate multifactorial origin with environmental and genetic factors affecting disease susceptibility. (Sadovnick et al. (1988) Am J Med Genet. 29: 533-541). Several genome screens have verified the association with HLA-DR2 and identified a number of markers with increased sharing in MS families with somewhat discouraging results (Dyment et al. (2001) Neurogenetics. 3: 145-151; Sawcer et al. (2002) Brain 125: 1337-1347). This finding is not surprising with respect to the described heterogeneity of the disease. However, a study, which correlates genetic markers with responders versus non-responders to a given therapy has not been done so far.

There are presently three major categories of therapies for the treatment of MS: (1) type I interferons (type I IFN) such as interferon-beta (IFN-β), which includes interferon-beta1a (IFN-β1a), or interferon beta1b (IFN-β1b), and interferon-alpha (IFN-α); (2) glatiramer acetate; and (3) mitoxantrone. Several clinical trials have evaluated the various therapeutic options, for example, interferon-β, glatiramer acetate, immunoglobulins and mitoxantrone for patients suffering from different clinical subtypes of MS such as relapsing-remitting, primary or secondary-chronic progressive disease. Randomized, placebo-controlled, double-blind clinical trials with different preparations of IFN-β1a (Avonex®, Rebif®) and IFN-β1b (Betaferon®) were completed between 1993 and 1998 and resulted in the approval of these drugs for relapsing-remitting MS (RRMS). These studies found that IFN-β reduced relapse rates by approximately 30% and inhibited new magnetic resonance imaging (MRI) lesions by approximately 70% (Rudick et al. (2004) Ann Neurol 56: 548-55). Similar results were also obtained with IFN-α (Durelli et al. (1995) Mult Scler 1 Suppl 1:S32-S37; Myhr et al. (1999) Neurology 52:1049-1056). Despite of extensive research, the exact mechanism of IFN-β and IFN-α in treatment of MS remains unclear. Several hypotheses have been proposed which are based on the suppression of lymphocyte proliferation, suppression of antigen presentation, suppression of migration of proinflammatory cells across the blood brain barrier, or a cytokine shift from TH1 to TH2 (Hartung et al. (2004) J Neurol 251: v12-v29).

It is widely assumed that individual patients differ in their therapeutic response to interferon treatment. Patients who continue to experience disease activity during therapy are termed non-responders, suboptimal responders, or breakthrough patients. The Expanded Disability Status Scale (EDSS) scale is often used as measurement of clinical deterioration (Kurtzke (1983) Neurology 33:1444-1452). Criteria, however, vary among the different studies and lack validation. Response has been defined as having a lower relapse rate during IFN-β treatment compared with 1 to 2 years before therapy. A study of 262 patients from the European Database for Multiple Sclerosis found that 33% of individuals were non-responders while the remaining individuals were classified as responders (Waubant et al. (2003) Neurology 61: 184-189). Another study found that half of the patients treated with IFN-β demonstrates no benefit based on the EDSS as a measure of deterioration during treatment (R10 et al. (2002) Ann Neurol 52: 400-406). A recent study found that new MRI lesion activity during IFN-β1a treatment correlated with poor response to IFN-β1a (Rudick et al. (2004) Ann Neurol 56: 548-555). Some smaller studies correlated the response to treatment with IFN-β to biological markers such as reduced IFN-γ production (Petereit et al. (2002) Mult Scler 8: 492-494), decreased mitogen driven T cell proliferation (Killestein et al. (2002) J Neuroimmunol 133: 217-224), or the early and sustained induction of the tumour necrosis factor-related apoptosis-inducing ligand (TRAIL) (Wandinger et al. (2003) Lancet 361: 2036-2043). In a set of 70 selected genes, nine sets of gene triplets were identified which predicted response to therapy in 52 patients with 86% accuracy (Baranzini et al. (2005) PLoS Biol 3: 166-176). Using microarray technology, non-responder and responder phenotypes to IFN-β were assessed by longitudinal gadolinium-enhanced MRI scans and clinical disease activity was shown to differ in their ex vivo gene expression profile (Sturzebecher et al. (2003) Brain 126: 1419-1429).

However, there presently exist no reliable methods to predict the response of an individual patient to the chosen therapy prior to treatment. An observation period of 1 to 2 years during therapy is necessary to classify the individual patient as responder or non-responder by means of relapse rate and measurement of clinical deterioration. Furthermore IFN-β therapy is associated with a number of adverse reactions, including flu-like symptoms, transient laboratory abnormalities, increased spasticity and injection site reactions. Therefore, there is an unmet need in the field of MS for methods and kits for assessing and predicting the response to therapy.

At present, the clinical subtypes do not correlate with the histopathologically defined subtypes, which indicates that different immunopathological mechanisms operate within the clinically defined subtypes (Lucchinetti et al. (2000) Ann Neurol 47: 707-717). Although brain biopsy can help to determine the response of a MS patient to therapy (Keegan et al. (2005) Lancet 366: 579-82), it is an invasive method that is not ethically justified in MS patients with typical clinical and radiological findings. An identification of genotypes that respond to a given therapy without major side effects would enable an individualized therapy with therapeutic drugs.

Finally, a more efficient, individualized immunomodulatory therapy will not only be a major breakthrough for the large number of MS patients, but also lead to a dramatic cost reduction in the health system by decreasing hospitalization time and disease related disability.

A long list of potential susceptibility gene candidates have been associated with MS. For example, polymorphisms in the interferon receptor 1 gene (IFNAR1) and interferon receptor 2 gene (IFNAR2) have been shown to confer susceptibility to MS, but not to predict response to IFN-β treatment (Leyva et al. (2005) J Neuroimmunol 163:165-171). Other potential gene candidates for MS susceptibility include the PRKCA, PTPRC, NOS2a, Ncf1, LAG3 and CD24 genes (Barton et al., (2004) Brain 127:1717-1722; Barcellos et al. (2004) Ann Neurol 55:793-800; Vyshkina et al (2004) Mult Scler 10:614-617; Hultqvist et al. (2004) Proc Natl Acad Sci USA 101: 12646-12651; WO05/054810; WO03/031655). The growth factor TGFB1 has also been proposed as a potential susceptibility gene for MS (Green et al (2001) J Neuroimmunol 116:116-124). However, several studies have shown that polymorphisms in TGFB1 do not contribute in a major way to susceptibility to MS (He et al. (1998) J Neuroimmunol 86:13-19; McDonnell et al. (1999) Mult Scler 5:105-109; Weinshenker et al. (2001) J Neuroimmunol 120:138-145). Furthermore, WO05/054810 discloses methods for predicting the likelihood that an individual will develop MS and the rate of MS progression by testing for polymorphisms in CD24. WO03/014319 relates to a collection of polymorphic sites in genes known or suspected to have a role in MS. EP 1 114 998 relates to methods for determining the success rate of treatment of MS by determining the amount of at least one of the cytokines from the group consisting of IL-18, IL-12p40, IFN-γ, IL-4, IL-10, TGF-β, IL-12Rβ1, IL-12Rβ2 and/or IL-12p35.

Presently, the major histocompatibility complex (MHC) on the chromosome 6p region is the only confirmed susceptibility locus for MS (Ibrahim and Gold (2005) Curr Opin Neurol 18:231-235). However, no effect between HLA-DR2 polymorphisms of the MHC and the age of onset was observed. In addition, no differences between HLA-DR2 polymorphisms and the course of initial clinical symptoms or the distribution of responders and non-responders to an IFN type I therapy was observed (Villoslada et al. (2002) J Neuroimmunol 130:194-201).

Thus, the technical problem underlying the present invention was to provide means and methods for a physician for the verification of a diagnosis of multiple sclerosis (MS) of an individual patient and for a prediction of the likelihood of a responsiveness of an individual MS-patient to a treatment with interferon-α (IFN-α) and/or interferon-β (IFN-β).

The solution to this technical problem is achieved by the embodiments characterized in the claims.

Accordingly, the present invention relates in a first embodiment to a method of diagnosing a predisposition of a multiple sclerosis (MS) patient for responsiveness to a treatment of MS by administration of interferon-α (IFN-α) and/or interferon-β (IFN-β) comprising determining in a sample from the patient the presence of at least one nucleic acid sequence motive selected from the group consisting of:

(a) a nucleic acid sequence motive in the 5'UTR region of the gene encoding HNRPUL1 selected from the nucleic acid sequence motives of Table A:

TABLE A

| Gene | start position relative to SEQ ID NO: 1 | nucleic acid sequence motive |
|---|---|---|
| HNRPUL1 | 69912 | TT |
| HNRPUL1 | 74951 | TT |

(b) a nucleic acid sequence motive in the intergenic region located between the genes encoding AXL, HNRPUL1, MGC20255, TGFB1 or MGC4093 selected from the nucleic acid sequence motives of Table B:

TABLE B

| Intergenic region between genes | start position relative to SEQ ID NO 1 | nucleic acid sequence motive |
|---|---|---|
| AXL + HNRPUL1 | 68874 | AA |
| HNRPUL1 + MGC20255 | 115299 | TT |
| MGC20255 + TGFB1 | 132083 | CC |
| MGC20255 + TGFB1 | 132394 | GG |
| TGFB1 + MGC4093 | 161183 | GG |

(c) a nucleic acid sequence motive in the intron sequence of a gene encoding CYP2S1, AXL, HNRPUL1, MGC20255 or TGFB1 selected from the nucleic acid sequence motives of Table C:

TABLE C

| Gene | start position relative to SEQ ID NO 1 | nucleic acid sequence motive |
|---|---|---|
| CYP2S1 | 1230 | TC or CC |
| CYP2S1 | 13000 | CC or GG |
| AXL | 35377 | CC or CG |
| AXL | 35447 | CT or TT |
| AXL | 35553 | CC or CT |
| AXL | 41782 | CT or TT |
| AXL | 49640 | CT or TT |
| AXL | 63412 | GG |
| HNRPUL1 | 82380 | CC |
| HNRPUL1 | 86169 | TT |
| HNRPUL1 | 92979 | TT |
| HNRPUL1 | 97359 | TT |
| HNRPUL1 | 98998 | AA |
| HNRPUL1 | 100362 | TT |
| HNRPUL1 | 105863 | GG |
| HNRPUL1 | 108567 | CC |
| HNRPUL1 | 109136 | GG |
| HNRPUL1 | 111531 | AA |
| MGC20255 | 123873 | TT |
| MGC20255 | 124054 | GG |
| MGC20255 | 125354 | GG |
| MGC20255 | 125772 | TT |
| MGC20255 | 125868 | TT |

TABLE C-continued

| Gene | start position relative to SEQ ID NO 1 | nucleic acid sequence sequence motive |
|---|---|---|
| MGC20255 | 126025 | CC |
| MGC20255 | 126073 | AA |
| MGC20255 | 126663 | AA |
| MGC20255 | 128007 | CC |
| TGFB1 | 144348 | TT |
| TGFB1 | 148747 | GG |

(d) a nucleic acid sequence motive in the 3'UTR region of a gene encoding MGC20255 selected from the nucleic acid sequence motives of Table D:

TABLE D

| Gene | start position relative to SEQ ID NO 1 | nucleic acid sequence motive |
|---|---|---|
| MGC20255 | 130196 | GG |
| MGC20255 | 130468 | AA |
| MGC20255 | 130493 | GG |
| MGC20255 | 131493 | TT | and
(e) a nucleic acid sequence motive which is complementary to a nucleotide sequence motive as defined in any one of (a) to (d);
wherein the presence of one or more of the above nucleic acid sequence motives is indicative for an inferior response of the patient to a treatment of MS with IFN-α and/or IFN-β.

Interferon-α (IFN-α) and interferon-β (IFN-β) are well known type I interferons. The cytokines bind to a receptor designated as IFN-α/β receptor or CD118.

The term "nucleic acid sequence motive" defines a part of a polynucleotide having a characteristic sequence of nucleotides. In accordance with the present invention the term "polynucleotide" defines a nucleic acid molecule consisting of more than 30 nucleotides. The group of molecules subsumed under polynucleotides also comprises complete genes. Also included by said definition are vectors such as cloning and expression vectors. The term "oligonucleotides" describes in the context of the invention nucleic acid molecules consisting of at least ten and up to 30 nucleotides.

Nucleic acid molecules (comprising polynucleotides and oligonucleotides), in accordance with the present invention, include DNA, such as cDNA or genomic DNA, RNA (e.g. mRNA), also in synthetic or semisynthetic form, further synthetic or semisynthetic derivatives of DNA or RNA (e.g. PNA or phosphorothioates) and mixed polymers, both sense and antisense strands. They may contain additional non-natural or derivatized nucleotide bases, as will be readily appreciated by those skilled in the art. Synthetic or semisynthetic derivatives of DNA or RNA are, of course, not comprised in a sample derived from a patient, but may be used as detective means in the method of the invention.

For the purposes of the present invention, a peptide nucleic acid (PNA) is a polyamide type of DNA analog and the monomeric units for the derivatives of adenine, guanine, thymine and cytosine are available commercially (Perceptive Biosystems). Certain components of DNA, such as phosphorus, phosphorus oxides, or deoxyribose derivatives, are not present in PNAs. As disclosed by Nielsen et al., Science 254:1497 (1991); and Egholm et al., Nature 365:666 (1993), PNAs bind specifically and tightly to complementary DNA strands and are not degraded by nucleases. In fact, PNA binds more strongly to DNA than DNA itself does. This is probably because there is no electrostatic repulsion between the two strands, and also the polyamide backbone is more flexible. Because of this, PNA/DNA duplexes bind under a wider range of stringency conditions than DNA/DNA duplexes, making it easier to perform multiplex hybridization. Smaller probes can be used than with DNA due to the strong binding. In addition, it is more likely that single base mismatches can be determined with PNA/DNA hybridization because a single mismatch in a PNA/DNA 15-mer lowers the melting point ($T_m$) by 8°-20° C., vs. 4°-16° C. for the DNA/DNA 15-mer duplex. Also, the absence of charge groups in PNA means that hybridization can be done at low ionic strengths and reduce possible interference by salt during the analysis.

The term "(poly)peptide" as used herein describes a group of molecules which comprises the group of peptides, consisting of up to 30 amino acids, as well as the group of polypeptides, consisting of more than 30 amino acids. In accordance with the invention, the group of polypeptides comprises "proteins" as long as the proteins consist of a single polypeptide. Also in line with the definition the term "(poly)peptide" describes fragments of proteins. (Poly)peptides may further form dimers, trimers and higher oligomers, i.e. consisting of more than one (poly)peptide molecule. (Poly)peptide molecules forming such dimers, trimers etc. may be identical or non-identical. The corresponding higher order structures are, consequently, termed homo- or heterodimers, homo- or heterotrimers etc. Homo- or heterodimers etc. also fall under the definition of the term "protein". The terms "polypeptide" and "protein" also refer to naturally modified polypeptides/proteins wherein the modification is effected e.g. by glycosylation, acetylation, phosphorylation and the like. Such modifications are well known in the art.

The term "position" used in accordance with the present invention means the position of either a nucleotide within a nucleic acid sequence depicted herein or the position of an amino acid within an amino acid sequence depicted herein. The start position for a sequence motive in a given nucleic acid sequence identifies the position at which a sequence motive starts. The nucleotide following the start position in a nucleic acid sequence is the nucleotide at the 3' position of the starting nucleotide. Thus, the motives are in a 5'→3' orientation in the genomic strand which corresponds in the sequence of exon regions of a gene with the sequence of the mRNA which is translated (+strand). The genomic strand which is complementary thereto is the –strand. Nucleotide sequence motives defined as being complementary to the nucleotide sequence motives in the +strand are at the position which is complementary to the referred relative position in the +strand depicted in SEQ ID NO: 1. The term "start position relative to SEQ ID NO 1" defines the position at which the "nucleic acid sequence motive" starts relative to SEQ ID NO: 1. More specifically, the term defines the situation that the specified nucleic acid sequence motive replaces nucleotides in SEQ ID NO: 1, starting with the position in SEQ ID NO: 1 indicated in the table. In other terms, whereas the sequence of SEQ ID NO: 1 stands for the wild-type allele (at least for the positions of interest indicated in the tables), the nucleic acid sequence motive (representing a SNP) replaces the nucleotides in the wild-type allele, starting with the position indicated in the respective table. This nucleic acid sequence motive is associated with a specific phenotype such as the inferior response to a treatment of MS with a type I IFN. The presence of at least one of the referred nucleic acid sequence motives at the indicated positions instead of nucleotides present in the wild-type sequence of SEQ ID NO:1 is indicative of the respective phenotype.

According to the invention the presence of at least one (one or more) of the referred sequence motives in a sample from a patient is indicative for an inferior response of the patient to a treatment of MS with a type I IFN. Accordingly, a patient which comprises at least one allele for a motive associated with an inferior response in the +strand, respectively the complementary motive in the –strand, shows an inferior response to a treatment of MS with a type I IFN.

A positive response of a patient to a treatment of MS with a type I IFN is clinically characterized by a stable course during therapy for at least 2 years. This means no relapse or a reduction of relapse rate $\geq \frac{2}{3}$ compared to the relapse rate before interferon therapy and no progression in MS associated symptoms, i.e. deterioration in EDSS <1 point during the 2 years of therapy.

The term "inferior response of the patient to a treatment of MS with IFN-α and/or IFN-β" describes a response of a patient to such treatment, which is significantly reduced compared to the one of a patient with a positive response to a treatment of MS with a type I IFN. Accordingly, the lack of a response to such treatment is comprised by the definition of an inferior response.

As described herein above, the gene encoding the growth factor TGF-β has been proposed as a potential susceptibility gene for MS (Green et al. (2001) loc cit.). However, a connection between the individual sequence of the gene in a sample isolated from an MS-patient and the potential success of a treatment of MS comprising the administration of a type I IFN was never described or suggested. The nucleic acid sequence and the amino acid sequence of the human TGFB1 gene are disclosed in SEQ ID NOs: 2 and 3. The nucleic acid sequence of the complete TGFB1 gene corresponds to the sequence from position 137537 to position 160703 in SEQ ID NO: 1. Further human nucleic acids for TGFB1 are disclosed in Genbank Accession numbers NM_000660, AY871240, AY871239, AY871245, AY871244, AY871243, AY871242, AY871241, AY871238, AY871237, AY871236, AY871235, AY871234, AY871233, AY871232, BC000125, BC022242, BC001180, AY330202, AY330201, AH013154.

The MGC20255 gene is located on chromosome 19q13.2 and was first identified during the generation of more than 15,000 full-length human and mouse cDNA sequence (Strausberg et al. (2002) Proc Natl Acad Sci USA 99:16899-16903), and in the characterization of 21,243 full-length human cDNAs (Ota et al. (2004) Nat Genet. 36:40-45). The nucleic acid sequence and the amino acid sequence of the human MGC20255 are disclosed in SEQ ID NOs: 4 and 5. The nucleic acid sequence of the complete MGC20255 gene corresponds to the sequence from position 116980 to position 131674 in SEQ ID NO: 1. Further human nucleic acids for MGC20255 are disclosed in Genbank Accession numbers DQ052389, NM_052848, BC011577, NT_011109, and BC019597.

HNRPUL1 (also known has heterogeneous nuclear ribonucleoprotein U-like 1, E1B-AP5) is a nuclear RNA-binding protein of the hnRNP family. HNRPUL1 was first identified as an interacting partner of the adenovirus type 5 early 1B 55-kDa protein (Gabler et al. (1998) J Virol 72:7960-7971) and has also been found to interact with p53, BRD7, and HRMT1L1 (Barral et al. (2005) FEBS Letters 579:2752-

2758; Kzhyshkowska et al. (2003) Biochem. J. 371:385-393; Kzhyshkowska et al. (2001) Biochem. J. 358:305-314). The nucleic acid sequence and the amino acid sequence of the human HNRPUL1 are disclosed in SEQ ID NOs: 6 and 7. The nucleic acid sequence of the complete HNRPUL1 gene corresponds to the sequence from position 69310 to position 114485 in SEQ ID NO: 1. Further human nucleic acids for HNRPUL1 are disclosed in Genbank Accession numbers NM_007040, NM_144734, NM_144733, NM_144732, DR005039, DN999074, DN997940, DN993239, BC002564, BC027713, NT_086903, NT_011109; BC004242, BC009988, and BC014232. HNRPUL1 can bind to mRNA, and has been shown to be involved in the transport and processing of RNA, and is involved in transcriptional regulation.

CYP2S1 is a dioxin-inducible member of the cytochrome P450 superfamily (Rylander et al (2001) Biochem Bioph Res Co 281:529-535). The nucleic acid sequence and the amino acid sequence of the human CYP2S1 are disclosed in SEQ ID NOs: 8 and 9. The nucleic acid sequence of the complete CYP2S1 gene corresponds to the sequence from position 1 to position 14330 in SEQ ID NO: 1. Human nucleic acids for CYP2S1 are also disclosed in Genbank Accession numbers NM_030622, DQ052387, BC033691, DR004638, NT_086903, NT_011109, and in WO04/091150. CYP2S1 has been shown to be involved in the metabolism of some aromatic hydrocarbons as well as retinoic acid, suggesting a role in biotransformaUon of both exogenous and endogenous compounds. Moreover, CYP2S1 has been suggested to play a functional role in the metabolism of topical drugs and in mediating the response to photochemotherapy in psoriasis (Smith et al (2003) Lancet. 361:1336-1343). mRNA in situ hybridization analysis has shown that CYP2S1 is highly expressed in epithelial cell types, especially in the epithelia frequently exposed to xenobiotics. In the respiratory tract, the expression was strong in nasal cavity, bronchi, and bronchioli, whereas it was low in the alveolar lining cells. Similarly, CYP2S1 is highly expressed in the epithelial cells throughout the gastrointestinal tract. Strong epithelial expression is also observed in uterine cervix, urinary bladder, and skin. In many exocrine glands (e.g., adrenal gland and pancreas), secretory epithelial cells showed moderate to strong expression levels. In the liver, CYP2S1 expression was low (Saarikoski et al. (2005) J Histochem Cytochem 53:549-556). Genetic polymorphisms in CYP2S1 have been described in a Finnish Caucasian population (Saarikoski et al (2004) Mut Res 554:267-277).

AXL (also called UFO, ARK, and Tyro7) is a receptor tyrosine kinase which was first identified as a transforming gene in human leukemias (O'Bryan et al. (1991) Mol Cell Biol 11:5016-5031; Janssen et al. (1991) Oncogene 6:2113-2120). The nucleic acid sequence and the amino acid sequence of the human AXL are disclosed in SEQ ID NOs: 10 and 11. The nucleic acid sequence of the complete AXL gene corresponds to the sequence from position 25709 to position 68557 in SEQ ID NO: 1. Human nucleic acids for AXL are further disclosed in Genbank Accession numbers NM_001699, NM_021913, NT_086903, NT_011109, and BC032229. The structure of the AXL extracellular domain makes it unique among receptor tyrosine kinases in that there is a juxtaposition of two immunoglobulin-like repeats and two fibronectin type III repeats (O'Bryan et al. (1991) Mol Cell Biol 11:5016-5031). This pattern of structural elements is reminiscent of many cell adhesion molecules, and has been implicated in cell-cell interactions. The natural ligand of AXL is Gas6 (Stitt et al. (1995) Cell 80:661-670; Varnum et al. (1995) Nature 373:623-626). AXL has been proposed to be a novel regulator of vascular cell function (Melaragno et al. (1999) Trends Cardiovasc Med. 9:250-253), may be involved in the progression of kidney diseases (Yanagita (2004) Clin Exp Nephrol 8:304-309) and may control cell growth (Crosier and Crosier (1997) Pathology 29:131-135).

As described herein above, it has been observed in the state of the art that the therapeutic response of an individual MS-patient to a therapy comprising the administration of interferon-α (IFN-α) and/or interferon-β (IFN-β) differs. The verified identification of a patient as a responder, i.e. a patient which shows a positive anamnesis on such therapy, requires according to the state of the art an observation period of at least one or two years. The treatment of patients which are identified 1 or 2 years after the start of a therapy with a type I IFN as an inferior responder (including no-responder) may result in side effects of the treatment such as a flu like syndrome (fever, headache, myalgia), injection site reactions (inflammation, necrosis), anaemia, leukopenia, lymphocytopenia, neutropenia, thrombocytopenia, elevation of liver enzymes, hepatitis, nausea, diarrhoea, exanthema, thyroiditis, depression, anaphylaxis, alopecia, or seizures. Accordingly, the prediction of the potential success of such therapy is of benefit for patients identified as responder type, as well as for patients identified as non- or inferior responder type.

It has been surprisingly found that single nucleotide polymorphisms (SNPs) in the identified nucleic acid sequence motives of a gene selected from MGC20255, HNRPUL1, CYP2S1, AXL, and TGFB1 are predictive of an inferior response of an MS patient to a treatment with IFN-α and/or IFN-β.

Accordingly, the present invention is based on the finding that presence of specific nucleic acid sequence motives in the recited genes are linked to an inferior responsiveness of an individual MS-patient to a therapy comprising the administration of interferon-α (IFN-α) and/or interferon-β (IFN-β).

The first type of SNPs (herein encompassed in the recited sequence motives) which contribute to a motive indicative for an inferior responder type are SNPs in the 5'UTR of the genes identified in item (a). Examples of such SNPs resulting in an inferior nucleic acid sequence motive are described herein above in table A. In the following table A2 the nucleic acid sequence motive found in the sample of a patient which shows an inferior response to a treatment of MS with a type I IFN is compared vis-à-vis the motive of the responder type. This type of SNPs can only be detected at the nucleic acid level.

TABLE A2

| Gene | start position relative to SEQ ID NO 1 | inferior response sequence motive | responder sequence motive |
|---|---|---|---|
| HNRPUL1 | 69912 | TT | AA or AT |
| HNRPUL1 | 74951 | TT | CC or CT |

A second type of SNPs in sequence motives which may contribute to a motive indicative for an inferior responder type are SNPs in exons of the genes identified herein, which lead to amino acid substitutions in the corresponding amino acid sequence. Such SNPs resulting in an inferior nucleic acid sequence motive can be detected at the nucleic acid level as well as on protein level.

A third type of SNPs in sequence motives which may contribute to a motive indicative for an inferior responder type are SNPs in exons which do not lead to amino acid substitutions in the corresponding amino acid sequence. Such SNPs resulting in an inferior nucleic acid sequence motive can be detected only at the nucleic acid level. A forth type of SNPs in sequence motives which contribute to a motive indicative for an inferior responder type are SNPs in the intergenic region of the genes identified in item (b). The intergenic region is the nucleic acid sequence located between two adjacent genes. Examples of such SNPs resulting in an inferior nucleic acid sequence motive are described herein above in table B. In the following table B2 the nucleic acid sequence motive found in the sample of a patient which shows an inferior response to a treatment of MS with a type I IFN is compared vis-à-vis the motive of the responder type. This type of SNPs can only be detected at the nucleic acid level.

TABLE B2

| Intergenic region between genes | start position relative to SEQ ID NO 1 | inferior response sequence motive | responder sequence motive |
|---|---|---|---|
| AXL + HNRPUL1 | 68874 | AA | GG |
| HNRPUL1 + MGC20255 | 115299 | TT | CC or CT |
| MGC20255 + TGFB1 | 132083 | CC | AA or AC |
| MGC20255 + TGFB1 | 132394 | GG | AA or AG |
| TGFB1 + MGC4093 | 161183 | GG | AA or AG |

A fifth type of SNPs in sequence motives which contribute to a motive indicative for the prediction of an inferior responder type are SNPs in the intron sequence of the genes identified in item (c). Examples of such SNPs resulting in an inferior nucleic acid sequence motive are described herein above in table C. In the following table C2 the nucleic acid sequence motive found in the sample of a patient which shows an inferior response to a treatment of MS with a type I IFN is compared vis-à-vis the motive of the responder type. This type of SNPs can only be detected at the nucleic acid level.

TABLE C2

| Gene | start position relative to SEQ ID NO 1 | inferior response sequence motive | responder sequence motive |
|---|---|---|---|
| CYP2S1 | 1230 | TC or CC | TT |
| CYP2S1 | 13000 | CC or GG | CG |
| AXL | 35377 | CC or CG | GG |
| AXL | 35447 | CT or TT | CC |
| AXL | 35553 | CC or CT | TT |
| AXL | 41782 | CT or TT | CC |
| AXL | 49640 | CT or TT | CC |
| AXL | 63412 | GG | GA or AA |
| HNRPUL1 | 82380 | CC | GG or CG |
| HNRPUL1 | 86169 | TT | GG or GT |
| HNRPUL1 | 92979 | TT | AA or AT |
| HNRPUL1 | 97359 | TT | CC or CT |
| HNRPUL1 | 98998 | AA | GG or GA |
| HNRPUL1 | 100362 | TT | CC or CT |
| HNRPUL1 | 105863 | GG | CC or CG |
| HNRPUL1 | 108567 | CC | TT or TC |

TABLE C2-continued

| Gene | start position relative to SEQ ID NO 1 | inferior response sequence motive | responder sequence motive |
|---|---|---|---|
| HNRPUL1 | 109136 | GG | AA or AG |
| HNRPUL1 | 111531 | AA | GG or GA |
| MGC20255 | 123873 | TT | CC or CT |
| MGC20255 | 124054 | GG | TT or TG |
| MGC20255 | 125354 | GG | AA or AG |
| MGC20255 | 125772 | TT | CC or CT |
| MGC20255 | 125868 | TT | CC or CT |
| MGC20255 | 126025 | CC | TT or TC |
| MGC20255 | 126073 | AA | GG or GA |
| MGC20255 | 126663 | AA | GG or GA |
| MGC20255 | 128007 | CC | TT or TC |
| TGFB1 | 144348 | TT | CC or CT |
| TGFB1 | 148747 | GG | GA |

A last type of SNPs in sequence motives contributing to a motive indicative for an inferior responder type are SNPs in the 3'UTR region of the genes identified in item (d). Examples of such SNPs resulting in an inferior nucleic acid sequence motive are described herein above in table D. In the following table D2 the nucleic acid sequence motive found in the sample of a patient which shows an inferior response to a treatment of MS with a type I IFN is compared vis-à-vis the motive of the responder type. This type of SNPs can only be detected at the nucleic acid level.

TABLE D2

| Gene | start position relative to SEQ ID NO 1 | inferior response sequence motive | responder sequence motive |
|---|---|---|---|
| MGC20255 | 130196 | GG | CC or CG |
| MGC20255 | 130468 | AA | TT or TA |
| MGC20255 | 130493 | GG | AA or AG |
| MGC20255 | 131493 | TT | CC or CT |

In line with the above, the SNPs which contribute to the sequence motives which are indicative of a specific phenotype can be located in different regions of a gene. It is known that polymorphisms in promoter and enhancer regions can affect gene function by modulating transcription, particularly if they are situated at recognition sites for DNA binding proteins (Fishman et al., J. Clin. Invest. 102 (1998), 1369-1376). The term "polymorphism" which is used in the present invention means single nucleotide substitution, nucleotide insertion and nucleotide deletion which in the case of insertion and deletion includes insertion or deletion of one or more nucleotides at a position of a gene and corresponding alterations in expressed proteins. Polymorphisms in the 5' untranslated region (5'UTR) of genes can affect the efficiency with which proteins are translated. A representative example of this is in the c-myc gene where a C-G SNP that creates an internal ribosome entry site is associated with increased efficiency of c-myc translation and myeloma (Chappell et al., Oncogene 19 (2000), 4437-4440). Polymorphisms in the 3'UTR can affect gene function by altering the secondary structure of RNA and efficiency of translation or by affecting motifs in the RNA that bind proteins which regulate RNA degradation. Polymorphisms within introns can affect gene function by affecting RNA splicing resulting in aberrant polypeptides. Another way in which intronic polymorphisms can affect gene function is when they affect regulatory motifs within introns. Examples are the Sp1 binding site polymorphism within intron 1 of the COLIA1 gene (Mann et al., J. Clin. Invest 107 (2001), 899-907) and a repeat polymorphisms within the IL-1Ra gene (Keen et al., Bone 23 (1998), 367-371). Further examples between intronic SNPs and gene function are described in Caceres and Komblihft, Trends Genet. 4 (2002), 186-93.

It is preferred for the method of the invention that the presence of the at least one nucleic acid sequence motive is determined by assays based on physical separation of nucleic acid molecules, ligase chain reaction assay, cleavage and digestion assay, sequencing assay, nucleic acid amplification assay, hybridization assay or assays based on protein detection.

Examples for assays based on physical separation of nucleic acid molecules include without limitation MALDI-TOF, denaturing gradient gel electrophoresis and other such methods known in the art, see for example Petersen et al., Hum. Mutat. 20 (2002) 253-259; Hsia et al., Theor. Appl. Genet. 111 (2005) 218-225; Tost and Gut, Clin. Biochem. 35 (2005) 335-350; Palais et al., Anal. Biochem. 346 (2005) 167-175.

Examples for cleavage and digestion assays include without limitation restriction digestion assays such as restriction fragments length polymorphism assays (RFLP assays), RNase protection assays, assays based on chemical cleavage methods and enzyme mismatch cleavage assays, see e.g. Youil et al., Proc. Natl. Acad. Sci. U.S.A. 92 (1995) 87-91; Todd et al., J. Oral Maxil. Surg. 59 (2001) 660-667; Amar et al., J. Clin. Microbiol. 40 (2002) 446-452.

Examples for nucleic acid amplification assays and means to perform such include without limitation PCR, (including nested PCR, RT-PCR, PCR extension assays, Nucleic Acid Sequence Base Amplification (NASBA), single-strand confirmation polymorphism (SSCP) PCR), amplification refractory mutation systems (ARMSTM) and amplification refractory mutation system linear extension (ALEXTM) assays. Details of such methods can be found in art, see, for example, Newton et al., Nucleic Acids Res. 17 (1989) 2503-2516; Agrawal (Ed.), "Protocols for Oligonucleotides and Analogs: Synthesis and Properties (Methods in Molecular Biology, 20)", Humana Press, 1993; Haque et al., Diagn. Mol. Pathol. 7 (1998) 248-252; Innis et al. (Ed.), "PCR Applications: Protocols for Functional Genomics", Academic Press, 1999; Chen and Janes (Ed.), "PCR Cloning Protocols: From Molecular Cloning to Genetic", 2nd edition, Humana Press, 2002; Pissardet al., Clin. Chem. 48 (2002) 769-772; Steemers et al., Nature Meth. 3 (2006) 31-33; Kakavas et al., J. Clin. Lab. Anal. 20 (2006) 1-7.

Examples for sequencing assays comprise without limitation approaches of sequence analysis by direct sequencing, fluorescent SSCP in an automated DNA sequencer and Pyrosequencing. These procedures are common in the art, see e.g. Adams et al. (Ed.), "Automated DNA Sequencing and Analysis", Academic Press, 1994; Alphey, "DNA Sequencing: From Experimental Methods to Bioinformatics", Springer Verlag Publishing, 1997; Ramon et al., J. Transl. Med. 1 (2003) 9; Meng et al., J. Clin. Endocrinol. Metab. 90 (2005) 3419-3422.

Examples for hybridization assays comprise without limitation Northern and Southern blot assays, heteroduplex analysis, detection of mutations by sequence specific oligonucleotide hybridization, allele-specific oligonucleotide hybridization on DNA chips, assays based on the Illumina's® technology, assays based on the BeadArray® technology, see, for example, Barnes et al., Nucleic Acids Res. 33 (2005) 5914-5923; Fan et al., Biotechniques 39 (2005) 583-588; Shen et al., Mutat. Res.-Fund. Mol. M. 573 (2005) 70-82; Steemers and Gunderson, Pharmacogenomics, 6 (2005) 777-782.

Examples for assays based on protein detection include without limitation method steps such as ion exchange chromatography, gel filtration chromatography, affinity chromatography, high pressure liquid chromatography (HPLC), reversed phase HPLC, disc gel electrophoresis, Western blot analysis, immunoprecipitation, see, for example, Soejima and Koda, Transfusion 45 (2005) 1934-1939; Yeh et al., Anesth. Analg. 101 (2005) 1401-1406; Chou et al., Am. J. Clin. Pathol. 124 (2005) 330-338.

The above described assays are known in the art, e.g. from standard text books such as Sambrook, Russell "Molecular Cloning, A Laboratory Manual", Cold Spring Harbor Laboratory, N.Y. (2001); Ausubel, "Current Protocols in Molecular Biology", Green Publishing Associates and Wiley Interscience, N.Y. (1989); Higgins and Hames (Eds.) "Nucleic acid hybridization, a practical approach" IRL Press Oxford, Washington D.C., (1985); Nollau et al, Clin. Chem. 43 (1997), 1114-1128; Burczak and Mardis (Ed.), "Polymorphism Detection & Analysis Techniques", Eaton Pub Co, 2000; Cotton et al. (Ed.), "Mutation Detection: A Practical Approach", Irl Press, 1998; Taylor (Ed.), "Laboratory Methods for the Detection of Mutations and Polymorphisms in DNA", CRC Press, 1997; Taylor and Day (Ed.) "Guide to Mutation Detection", Wiley, 2005. The use of some of the recited assays is described in the appended examples.

In a preferred embodiment of the method of diagnosing a predisposition of a multiple sclerosis (MS) patient for a responsiveness to a treatment of MS by administration of interferon-α (IFN-α) and/or interferon-β (IFN-β) of the invention, the nucleic acid amplification assay is a PCR performed by the use of one or more nucleic acid molecules as primers comprising a sequence as depicted in SEQ ID NOs: 12 to 91. In an alternatively preferred embodiment of this method the nucleic acid amplification assay is a PCR extension assay performed by the use of one or more nucleic acid molecules as primers comprising a sequence as depicted in SEQ ID NOs: 92 to 131.

It is also preferred for the method of diagnosing a predisposition of a multiple sclerosis (MS) patient for a responsiveness to a treatment of MS by administration of interferon-α (IFN-α) and/or interferon-β (IFN-β) of the invention that the hybridization assay is performed by the use of one or more nucleic acid molecules as probes comprising a sequence as depicted in SEQ ID NOs: 132 to 211.

The term "hybridizes/hybridizing" as used herein refers to a pairing of a polynucleotide to a (partially) complementary strand of this polynucleotide which thereby form a hybrid. Said complementary strand polynucleotides are, e.g. parts of polynucleotides (such as oligonucleotides) comprising at least 10, preferably at least 15 such as at least 25 consecutive nucleotides thereof. More preferably, these polynucleotides comprise at least 30, at least 35, at least 100, even more preferably at least 200, and most preferably at least 500 nucleotides in length. Said complementary polynucleotides may be useful as probes in Northern or Southern blot analysis of RNA or DNA preparations, respectively.

It is well known in the art how to perform hybridization experiments with nucleic acid molecules. Correspondingly, the person skilled in the art knows what hybridization conditions s/he has to use to allow for a successful hybridization in accordance with item (e), above. The establishment of suitable hybridization conditions is referred to in standard text books such as Sambrook, Russell (2001), loc cit.; Ausubel (1989), loc cit.; or Higgins and Hames (1985), loc cit. In one preferred embodiment, the hybridization assay is effected under stringent conditions.

"Stringent hybridization conditions" refers to conditions which comprise, e.g. an overnight incubation at 65° C. in 4×SSC (600 mM NaCl, 60 mM sodium citrate) followed by washing at 65° C. in 0.1×SSC for one hour. Alternatively, hybridization conditions can comprise: an overnight incubation at 42° C. in a solution comprising 50% formamide, 5×SSC (750 mM NaCl, 75 mM sodium citrate), 50 mM sodium phosphate (pH 7.6), 5×Denhardt's solution, 10% dextran sulfate, and 20 µg/ml denatured, sheared salmon sperm DNA, followed by washing the filters in 0.1×SSC at about 65° C. Said conditions for hybridization are also known by a person skilled in the art as "highly stringent conditions for hybridization". Also contemplated are nucleic acid molecules that hybridize to the polynucleotides of the invention at lower stringency hybridization conditions ("low stringency conditions for hybridization"). Changes in the stringency of hybridization and signal detection are primarily accomplished through the manipulation of formamide concentration (lower percentages of formamide result in lowered stringency), salt conditions, or temperature. For example, lower stringency conditions include an overnight incubation at 50° C. in 4×SSC or an overnight incubation at 37° C. in a solution comprising 6×SSPE (20×SSPE=3M NaCl; 0.2M NaH$_2$PO4; 0.02M EDTA, pH 7.4), 0.5% SDS, 30% formamide, 100 µg/ml salmon sperm blocking DNA; followed by washes at 50° C. with 1×SSPE, 0.1% SDS. In addition, to achieve an even lower stringency, washes performed following stringent hybridization can be done at higher salt concentrations (e.g. 5×SSC). It is of note that variations in the above conditions may be accomplished through the inclusion and/or substitution of alternate blocking reagents used to suppress background in hybridization experiments. Typical blocking reagents include Denhardt's reagent, BLOTTO, heparin, denatured salmon sperm DNA, and commercially available proprietary formulations. The inclusion of specific blocking reagents may require modification of the hybridization conditions described above, due to problems with compatibility. Such modifications can generally be effected by the skilled person without further ado. A hybridization complex may be formed in solution (e.g., Cot or Rot analysis) or between one nucleic acid sequence present in solution and another nucleic acid sequence immobilized on a solid support (e.g., membranes, filters, chips, pins or glass slides to which, e.g., cells have been fixed).

It is preferred for the method of the invention that the hybridization assay is performed by the use of one or more nucleic acid molecules which are synthetic or semisynthetic nucleic acid molecules such as PNA.

In an alternative embodiment the invention provides a solid support comprising one or more of the nucleic acid molecules as depicted in SEQ ID NOs: 12 to 211 or the complementary strand thereof.

A solid support according to the invention provides a surface for the attachment of the one or more of the nucleic acid molecules. Said surface according to the invention may be any surface. The surface may be a coating applied to the support or carrier, or the surface of the support or carrier itself may be used. Support or carrier materials commonly used in the art and comprising, for example, glass, plastic, gold and silicon are envisaged for the purpose of the present invention. Coatings according to the invention, if present, include poly-L-lysine- and amino-silane-coatings as well as epoxy- and aldehyde-activated surfaces.

In a preferred embodiment said solid support is a DNA chip. Methods for the production of DNA chips as well as the use of DNA chip technology are well known in the art and described e.g. in Kohara et al. (2002) Nucleic Acids Res. 30 (16) e87; Flavell et al. (2003) Nucleic Acids Res. 31 (19): e115; Gunderson et al. (2005) Nature Genetics 37:549-554.

Furthermore, the invention provides a diagnostic composition or kit for diagnosing a predisposition of a patient for a responsiveness to a treatment of MS by administration of IFN-α and/or IFN-β comprising one or more of the above described nucleic acid molecules as depicted in SEQ ID NOs: 12 to 211 or the complementary strand thereof or the solid support according to the invention. The diagnostic composition or kit may comprise appropriate packaging and instructions for the use in the method of the invention. Said composition or kit may further comprise appropriate buffer(s), and enzymes such as reverse transcriptase, thermostable polymerases etc.

In an alternative embodiment the invention also provides a method of diagnosing a predisposition of a patient for developing multiple sclerosis (MS) comprising determining in a sample from the patient the presence of at least one nucleic acid sequence motive selected from the group consisting of:

(a) a nucleic acid sequence motive in the intergenic region located between the genes encoding MGC20255 and TGFB1 selected from the nucleic acid sequence motive of Table E:

TABLE E

| Intergenic region between genes | start position relative to SEQ ID NO 1 | nucleic acid sequence motive |
|---|---|---|
| MGC20255 + TGFB1 | 132083 | CC |

(b) a nucleic acid sequence motive in the intron sequence of a gene encoding MGC20255 or HNRPUL1 selected from the nucleic acid sequence motives of Table F:

TABLE F

| Gene | start position relative to SEQ ID NO 1 | nucleic acid sequence motive |
|---|---|---|
| HNRPUL1 | 109136 | AA and AG |
| HNRPUL1 | 111531 | AG and GG |
| MGC20255 | 124054 | GT and TT |
| MGC20255 | 125354 | GA and AA |
| MGC20255 | 125868 | TC and CC |
| MGC20255 | 126073 | AG and GG |
| MGC20255 | 126663 | AG and GG |
| MGC20255 | 128007 | CT and TT |

(c) a nucleic acid sequence motive in the 3'UTR region of a gene encoding MGC20255 selected from the nucleic acid sequence motives of Table G:

TABLE G

| Gene | start position relative to SEQ ID NO 1 | nucleic acid sequence motive |
|---|---|---|
| MGC20255 | 130196 | GC and CC |
| MGC20255 | 130468 | AT and TT |
| MGC20255 | 130493 | GA and AA |
| MGC20255 | 131493 | TC and CC |

(d) a nucleic acid sequence motive which is complementary to a nucleotide sequence motive as defined in any one of (a) to (c);

wherein the presence of one or more of the above nucleic acid sequence motives is indicative for a predisposition of the patient for developing MS.

The term "sequence motive associated with MS" describes sequence motives, the presence of at least one of these in a sample from an individual subject (patient) is indicative for MS. Accordingly, the identification of the presence of at least one of these sequence motives indicates that the patient suffers from MS or will develop MS. In contrast, the term "wt sequence motive" defines the sequence motives which are found in individuals which do not suffer from MS or will not develop MS.

The meaning of further recited terms has been described herein above in the context of the method of diagnosing a predisposition of a multiple sclerosis (MS) patient for a responsiveness to a treatment of MS by administration of interferon-α (IFN-α) and/or interferon-β (IFN-β).

As described herein above, MS is a disease which starts in about 80 to 90% of the patients with a clinically isolated syndrome which proceeds to a relapsing-remitting course. Accordingly, generally MS is diagnosed after associating the isolated syndrome with MS. It has been surprisingly found that nucleotide polymorphisms in a haplotype block comprising the genes encoding MGC2055 and HNRPUL1 are susceptible genes for MS. By use of the method of the invention it becomes possible to detect a predisposition of a patient for the development of MS prior to the first clinical indications for the disease. Several clinical studies have shown that an early diagnosis of MS permits the beginning of pre-emptive therapy which reduces the risk and slows disease progression (Trapp et al. (1999) Curr. Opin. Neurol. 12: 295-302; Johnson et al. (2000) Multiple Sclerosis 6: 255-266; Jacobs et al. (2000) New Engl. J. Med. 343: 898-904; Comi et al. (2001) The Lancet 357: 1576-1582).

The first type of SNPs which may contribute to a sequence motive associated with MS are SNPs in exons of the genes identified herein, which lead to amino acid substitutions in the corresponding amino acid sequence. Such SNPs can be detected at the nucleic acid level as well as on protein level.

A second type of SNPs which may contribute to a sequence motive associated with MS are SNPs in exons of the genes identified herein, which do not lead to amino acid substitutions in the corresponding amino acid sequence. Such SNPs can be only detected at the nucleic acid level.

A third type of SNPs which may contribute to a sequence motive associated with MS are SNPs in the 5'UTR region of the genes identified herein. This type of SNPs can only be detected at the nucleic acid level.

A forth type of SNPs contributing to a sequence motive associated with MS are SNPs in the intergenic region of the genes identified in item (a) of the alternative embodiment. Examples of such SNPs are described herein above in table E. In the following table E2 the nucleic acid sequence associated with MS is compared vis-à-vis with the wt sequence motive found in individuals without a predisposition for MS. This type of SNPs can only be detected at the nucleic acid level.

TABLE E2

| Intergenic region between genes | start position relative to SEQ ID NO 1 | sequence motive associated with MS | wt sequence motive |
|---|---|---|---|
| MGC20255 + TGFB1 | 132083 | CC | CA and AA |

A fifth type of SNPs contributing to a sequence motive associated with MS are SNPs in the intron sequence of the genes identified in item (b) of the alternative embodiment. Examples of such SNPs are described herein above in table F. In the following table F2 the nucleic acid sequence associated with MS is compared vis-à-vis with the wt sequence motive found in individuals without a predisposition for MS. This type of SNPs can only be detected at the nucleic acid level.

TABLE F2

| Gene | start position relative to SEQ ID NO 1 | sequence motive associated with MS | wt sequence motive |
|---|---|---|---|
| HNRPUL1 | 109136 | AA and AG | GG |
| HNRPUL1 | 111531 | AG and GG | AA |
| MGC20255 | 124054 | GT and TT | GG |
| MGC20255 | 125354 | GA and AA | GG |
| MGC20255 | 125868 | TC and CC | TT |
| MGC20255 | 126073 | AG and GG | AA |
| MGC20255 | 126663 | AG and GG | AA |
| MGC20255 | 128007 | CT and TT | CC |

A last type of SNPs contributing to a sequence motive associated with MS are SNPs in the 3'UTR region of the genes identified in item (c) of the alternative embodiment. Examples of such SNPs are described herein above in table G. In the following table G2 the nucleic acid sequence associated with MS is compared vis-à-vis with the wt sequence motive found in individuals without a predisposition for MS. This type of SNPs can only be detected at the nucleic acid level.

TABLE G2

| Gene | start position relative to SEQ ID NO 1 | sequence motive associated with MS | wt sequence motive |
|---|---|---|---|
| MGC20255 | 130196 | GC and CC | GG |
| MGC20255 | 130468 | AT and TT | AA |
| MGC20255 | 130493 | GA and AA | GG |
| MGC20255 | 131493 | TC and CC | TT |

It is preferred for the method of diagnosing a predisposition of a patient for developing MS, that the presence of the at least one nucleic acid sequence motive is determined by assays based on physical separation of nucleic acid molecules, ligase chain reaction assay, cleavage and digestion assay, sequencing assay, nucleic acid amplification assay, hybridization assay or assays based on protein detection. Corresponding methods have been described herein above.

It is further preferred for the method of diagnosing a predisposition of a patient for developing MS, that the nucleic acid amplification assay is a PCR performed by the use of one or more nucleic acid molecules as primers comprising a sequence as depicted in SEQ ID NOs: 50 to 53, 58 to 61, 64 to 65 and 68 to 83. Alternatively it is preferred for this method, that the nucleic acid amplification assay is a PCR extension assay performed by the use of one or more nucleic acid molecules as primers comprising a sequence as depicted in SEQ ID NOs: 111 to 112, 115 to 116, 118, 120 to 127.

Moreover, it is preferred for the method of diagnosing a predisposition of a patient for developing MS, that the hybridization assay is performed by the use of one or more nucleic acid molecules as probes comprising a sequence as depicted in SEQ ID NOs: 170 to 173, 178 to 181, 184 to 185, 188 to 203.

It is preferred for the method of the invention that the hybridization assay is performed by the use of one or more nucleic acid molecules which are synthetic or semisynthetic nucleic acid molecules such as PNA.

The invention also provides a solid support comprising one or more of the nucleic acid molecules as depicted in SEQ ID NOs: 50 to 53, 58 to 61, 64 to 65 and 68 to 83, SEQ ID NOs: 111 to 112, 115 to 116, 118, 120 to 127 SEQ ID NOs: 170 to 173, 178 to 181, 184 to 185, 188 to 203 or the complementary strand thereof. In a preferred embodiment said solid support is a DNA chip.

Finally, the invention provides a diagnostic composition for diagnosing a predisposition of a patient for MS comprising one or more of the nucleic acid molecules as depicted in SEQ ID NOs: 50 to 53, 58 to 61, 64 to 65 and 68 to 83, SEQ ID NOs: 111 to 112, 115 to 116, 118, 120 to 127 or SEQ ID NOs: 170 to 173, 178 to 181, 184 to 185, 188 to 203 or the complementary strand thereof or the solid support comprising one or more of the recited nucleic acid molecules.

THE FIGURES SHOW

FIG. 1:
Pairwise LD in control group in the explored region. On the upper left diagonal are the r2 measures and in the lower right diagonal D' measures are presented.

Figure 2:
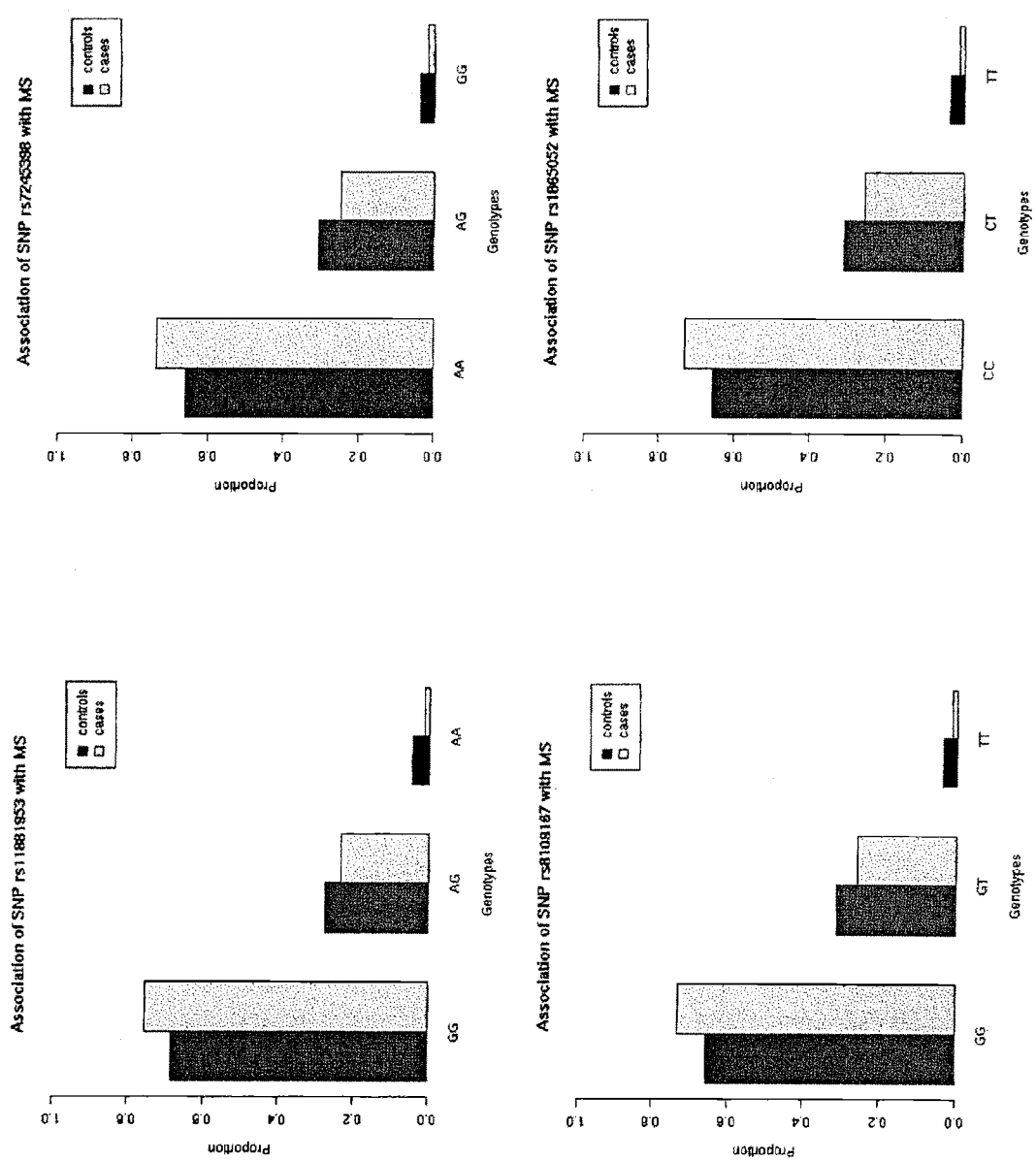

FIG. 2:
Association of the rs11881953, rs7245398 polymorphisms in the HNRPUL1 locus and the rs8109167, rs1865052 polymorphisms in the MGC20255 locus with increased susceptibility to MS. Each graphic depicts the proportion of genotypes in individuals with MS compared to control individuals without MS.

Figure 3:
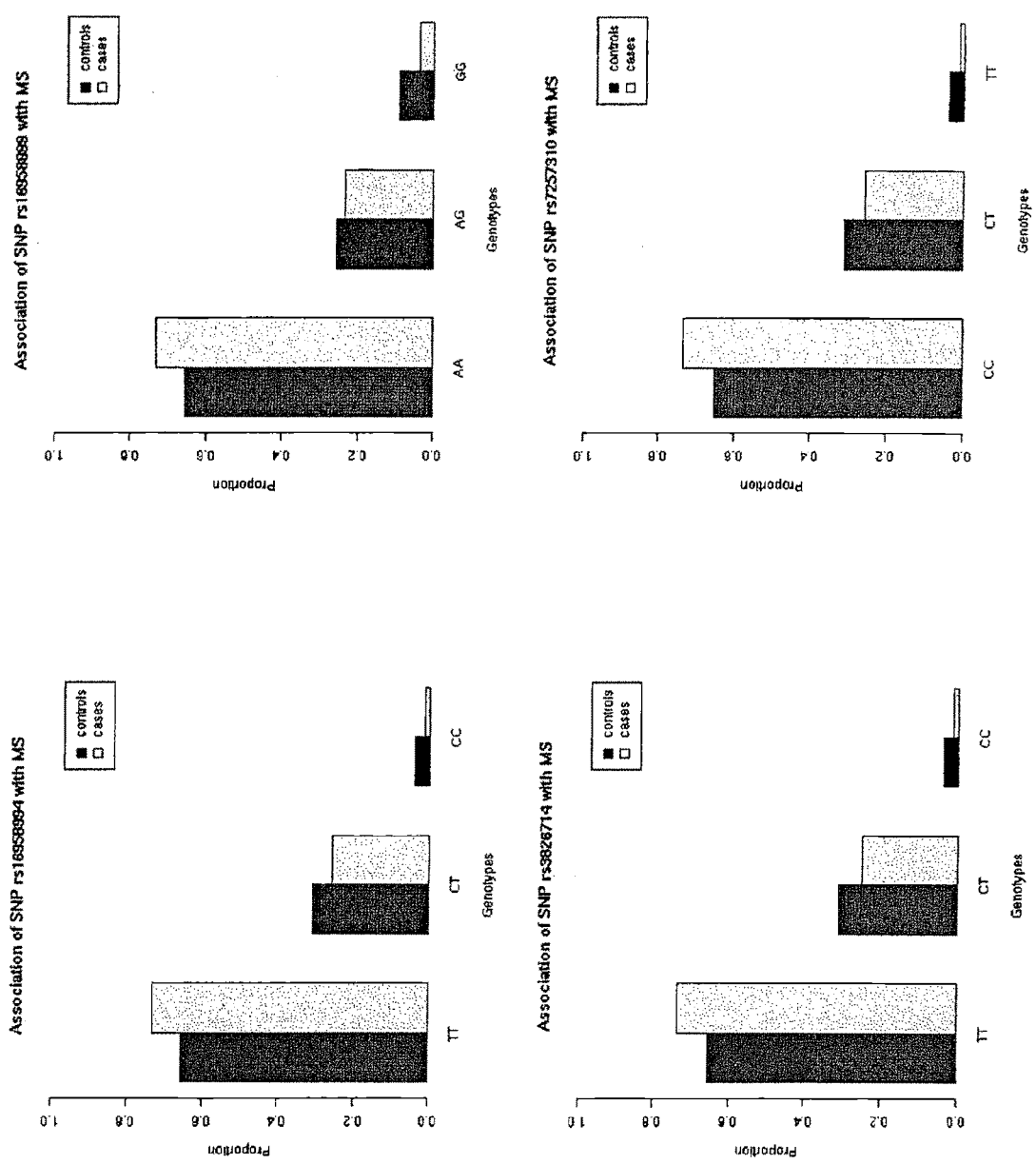

FIG. 3:
Association of the rs16958994, rs16958999, rs3826714, and rs7257310 polymorphisms in the MGC20255 locus with increased susceptibility to MS. Each graphic depicts the proportion of genotypes in individuals with MS compared to control individuals without MS.

Figure 4:
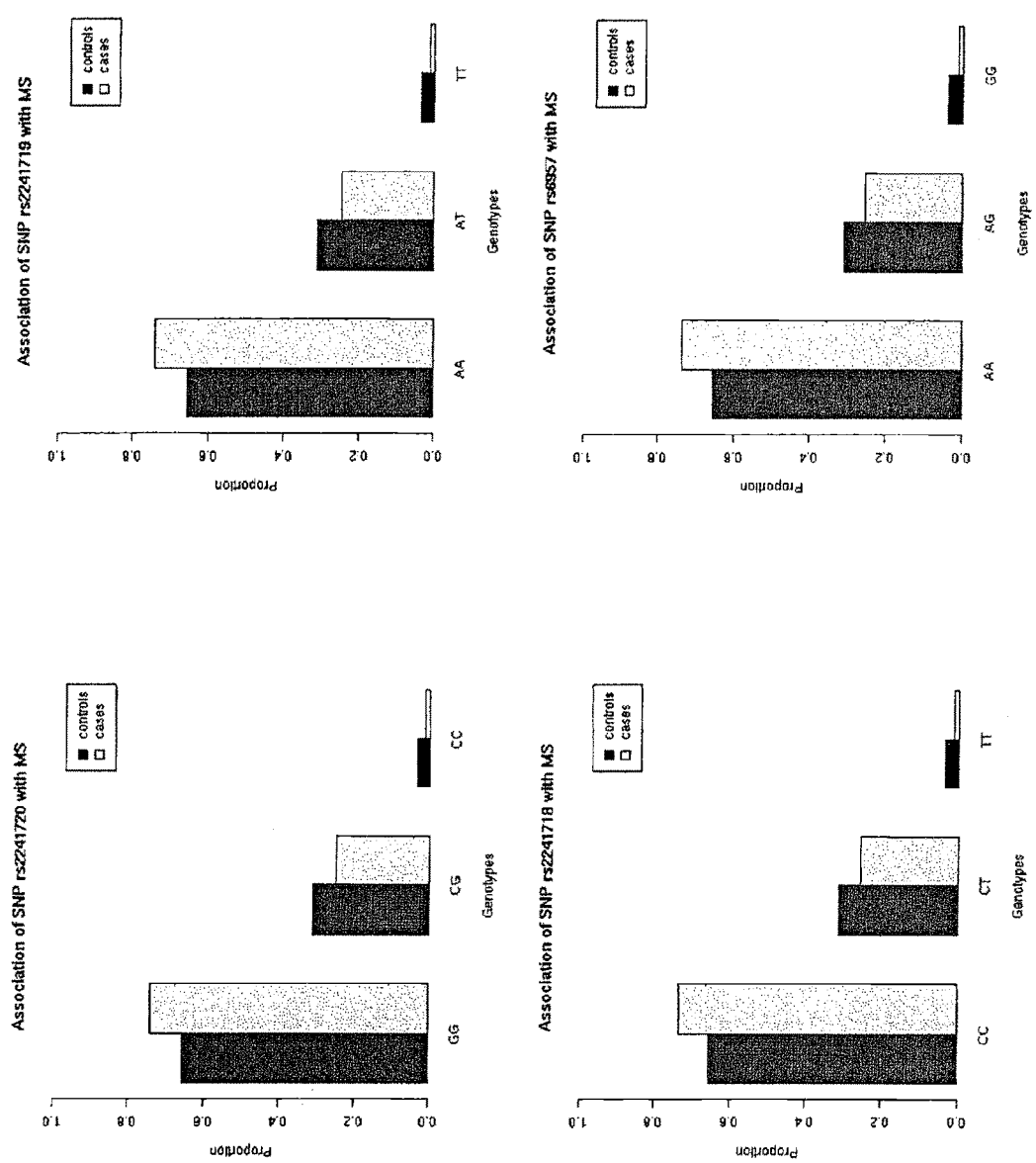

FIG. 4:
Association of the rs2241720, rs2241719, rs2241718, and rs6957 polymorphisms in the MGC20255 locus with increased susceptibility to MS. Each graphic depicts the proportion of genotypes in individuals with MS compared to control individuals without MS.

Figure 5:
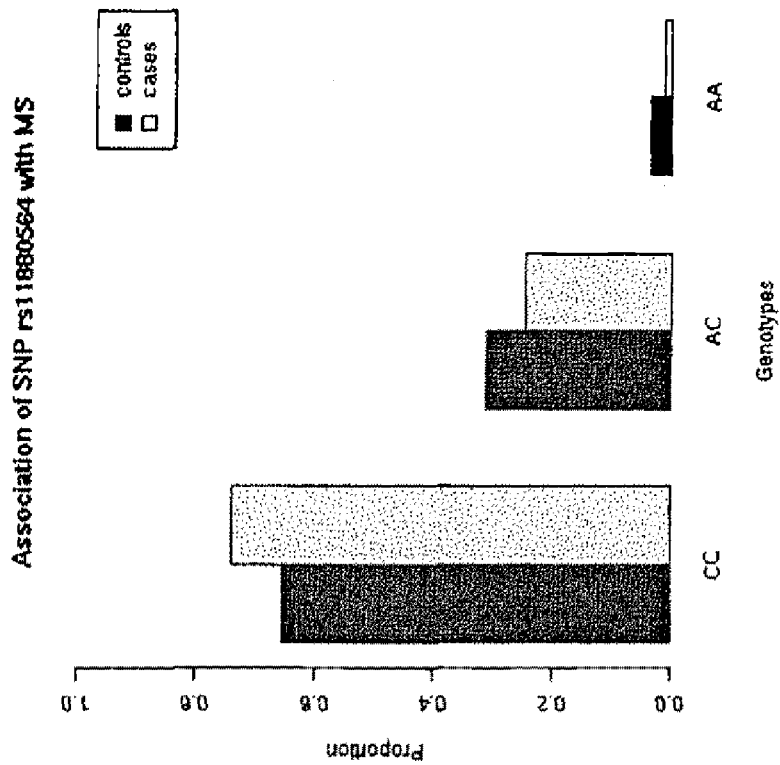

FIG. 5:
Association of the rs11880564 polymorphism in the MGC20255 locus with increased susceptibility to MS. The graphic depicts the proportion of genotypes in individuals with MS compared to control individuals without MS.

Figure 6:
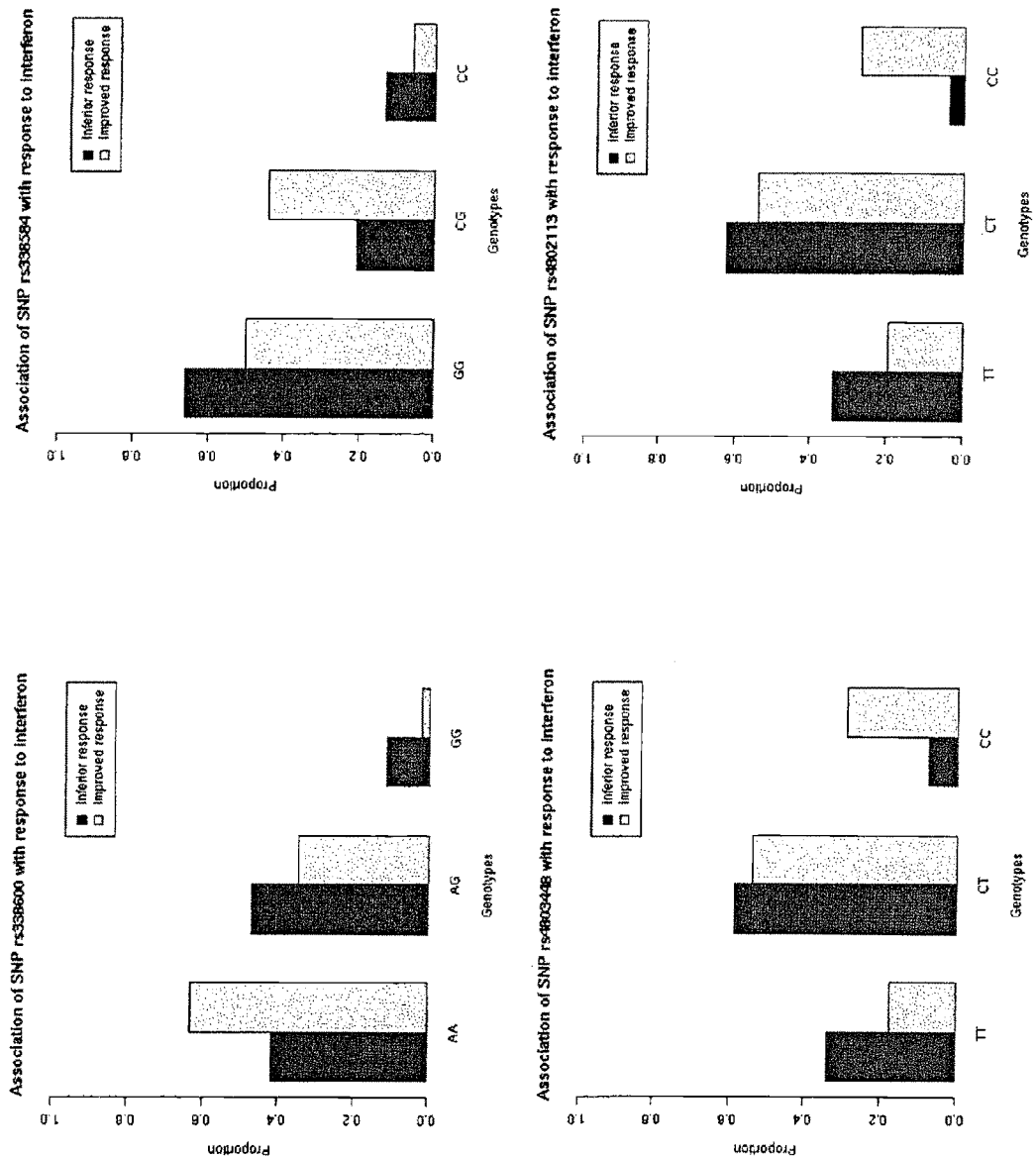

FIG. 6:
Association of the rs338600, rs338584 polymorphisms in the CYP2S1 locus and the rs4803448, rs4802113 polymorphisms in the AXL locus with improved response to interferon treatment in MS individuals. Each graphic depicts the proportion of genotypes in inferior interferon response and improved interferon response groups respectively.

Figure 7:
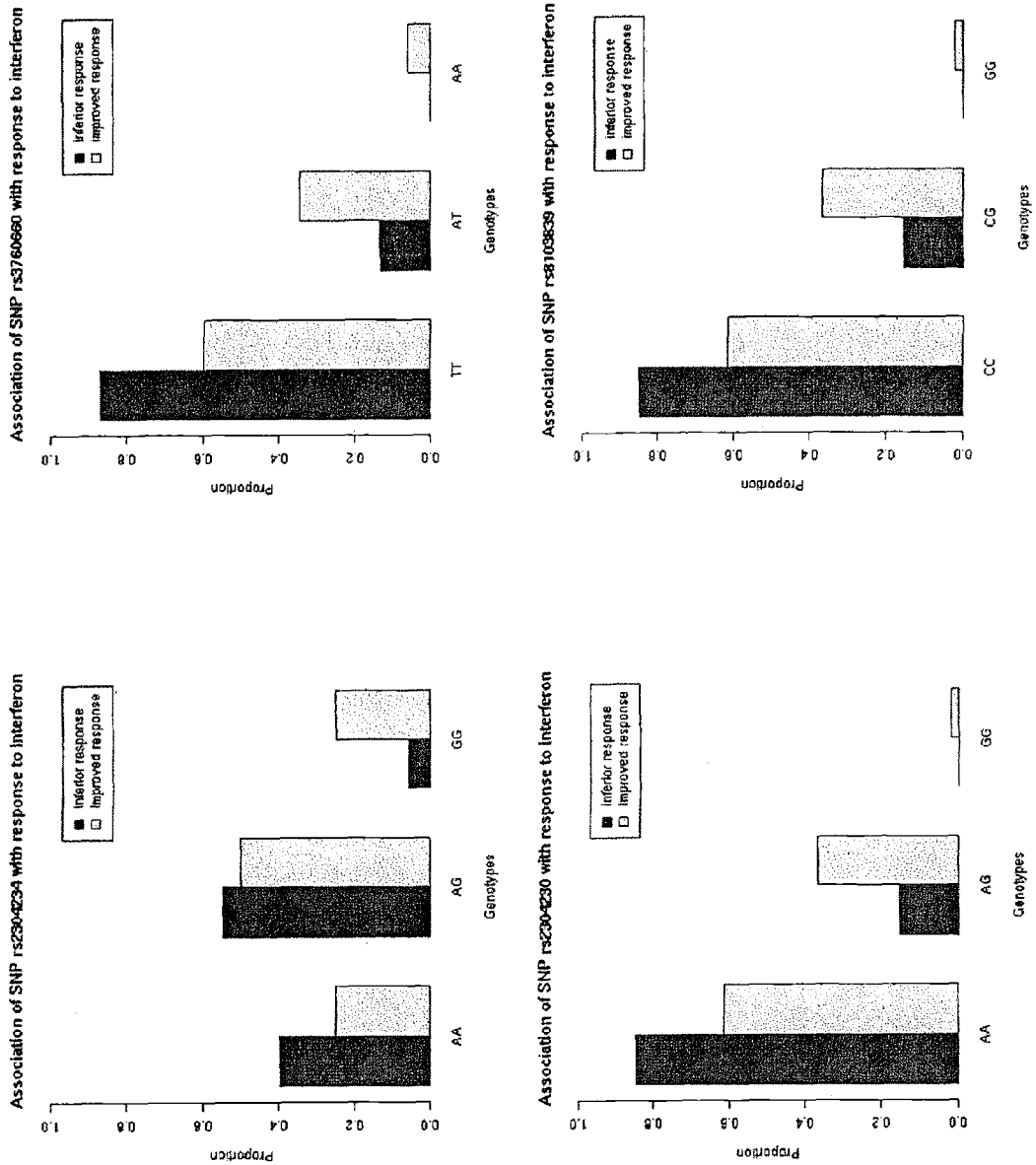

FIG. 7:
Association of the rs2304234 polymorphism in the AXL locus and the rs3760660, rs2304230, rs8103839 polymorphisms in the HNRPUL1 locus with improved response to interferon treatment in MS individuals. Each graphic depicts the proportion of genotypes in inferior interferon response and improved interferon response groups respectively.

Figure 8:
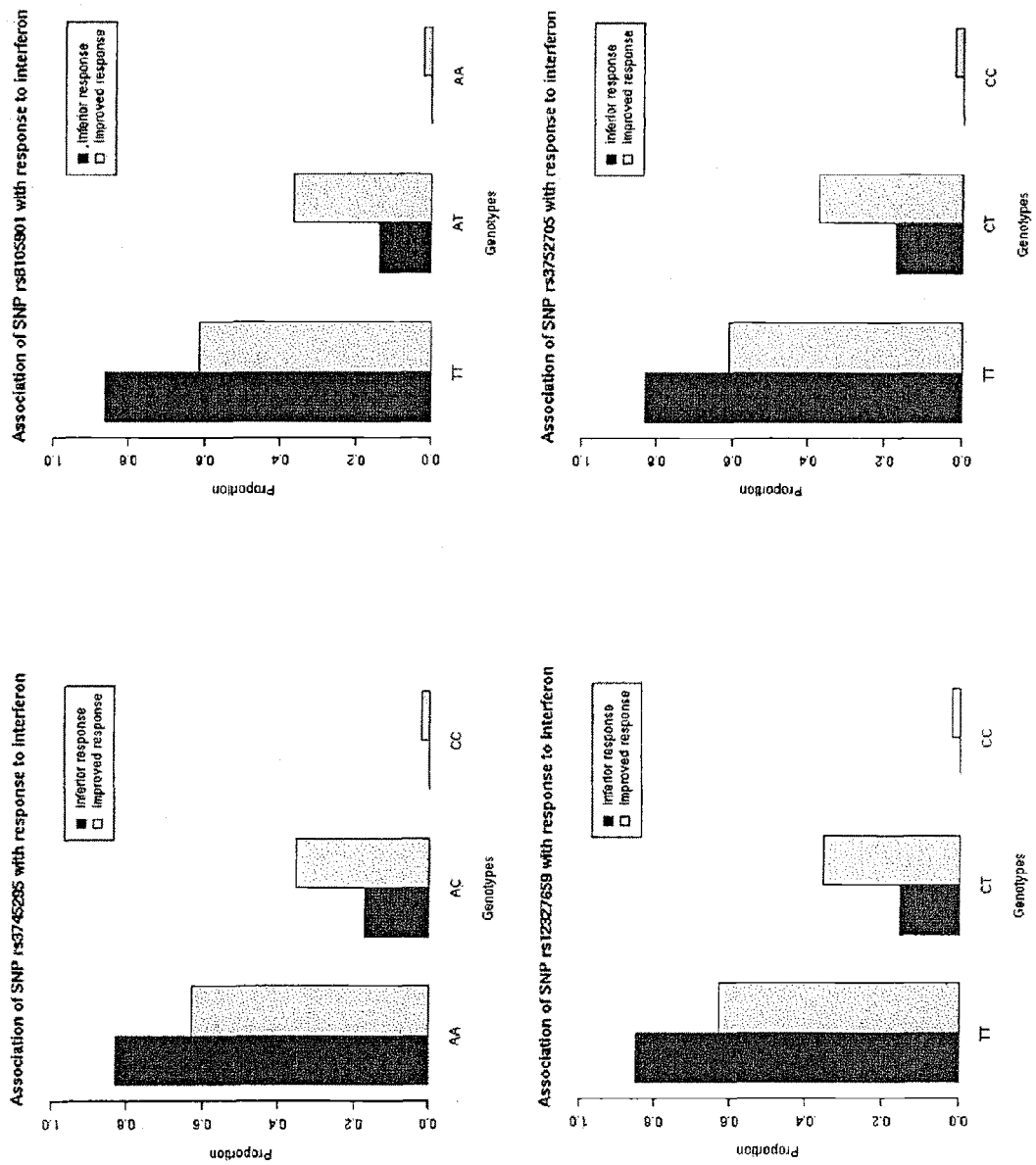

FIG. 8:
Association of the rs3745295, rs8105901, rs12327659, and rs3752705 polymorphisms in the HNRPUL1 locus with improved response to interferon treatment in MS individuals. Each graphic depicts the proportion of genotypes in inferior interferon response and improved interferon response groups respectively.

Figure 9:
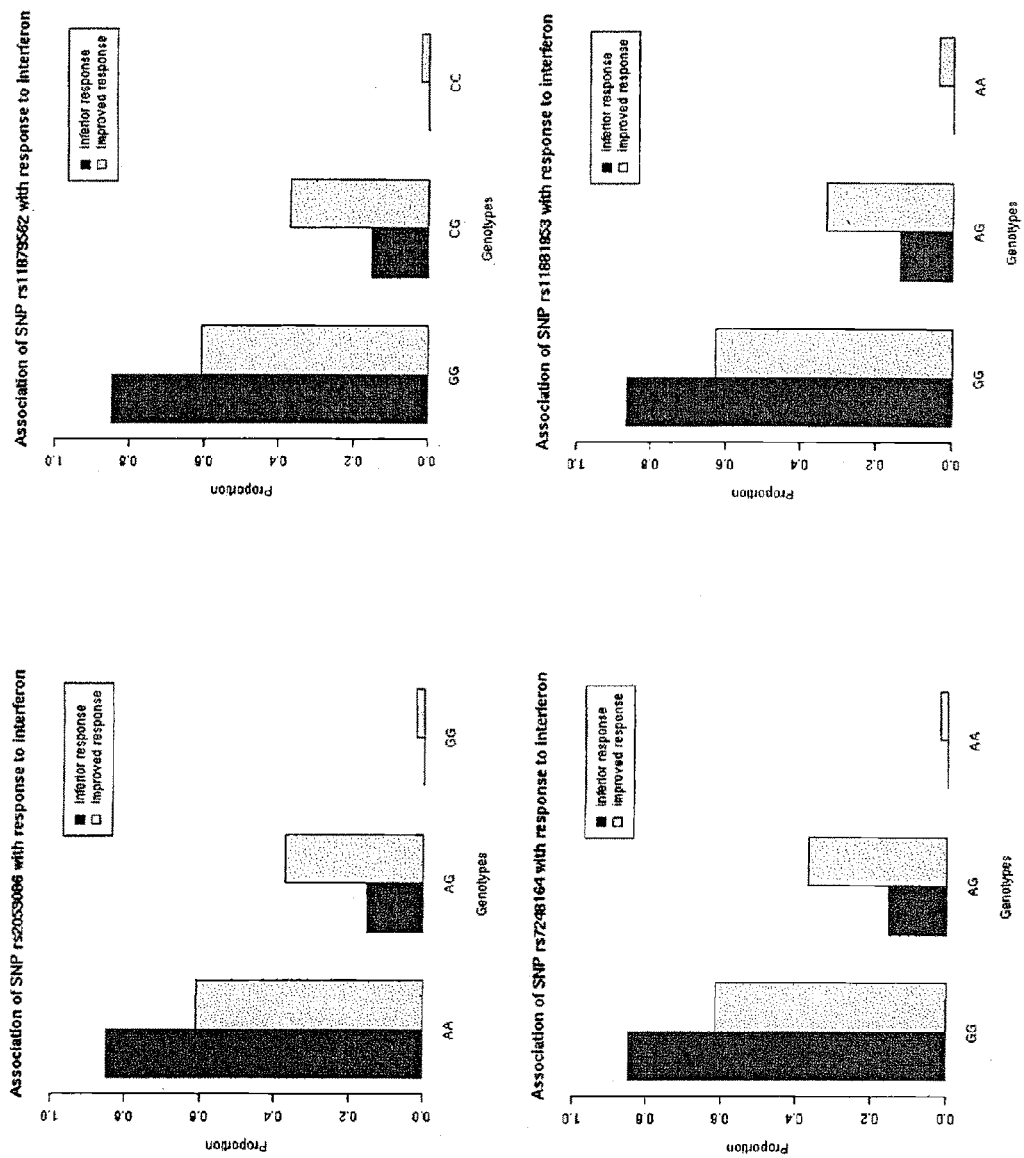

FIG. 9:
Association of the rs2053086, rs11879562, rs7248164, and rs11881953 polymorphisms in the HNRPUL1 locus with improved response to interferon treatment in MS individuals. Each graphic depicts the proportion of genotypes in inferior interferon response and improved interferon response groups respectively.

Figure 10:
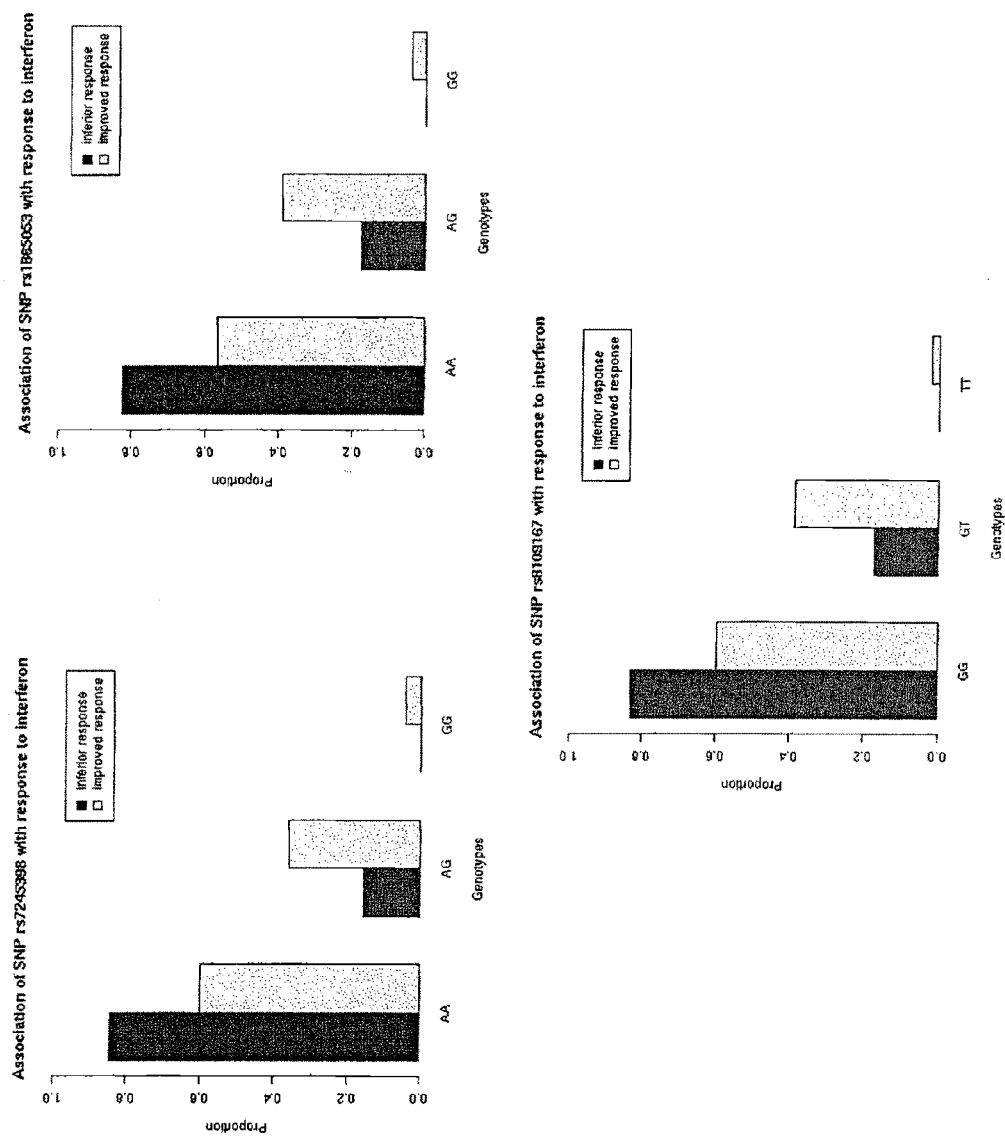

FIG. 10:
Association of the rs7245398, rs1865053 polymorphisms in the HNRPUL1 locus and the rs8109167 polymorphism in the MGC20255 locus with improved response to interferon treatment in MS individuals. Each graphic depicts the proportion of genotypes in inferior interferon response and improved interferon response groups respectively.

Figure 11:
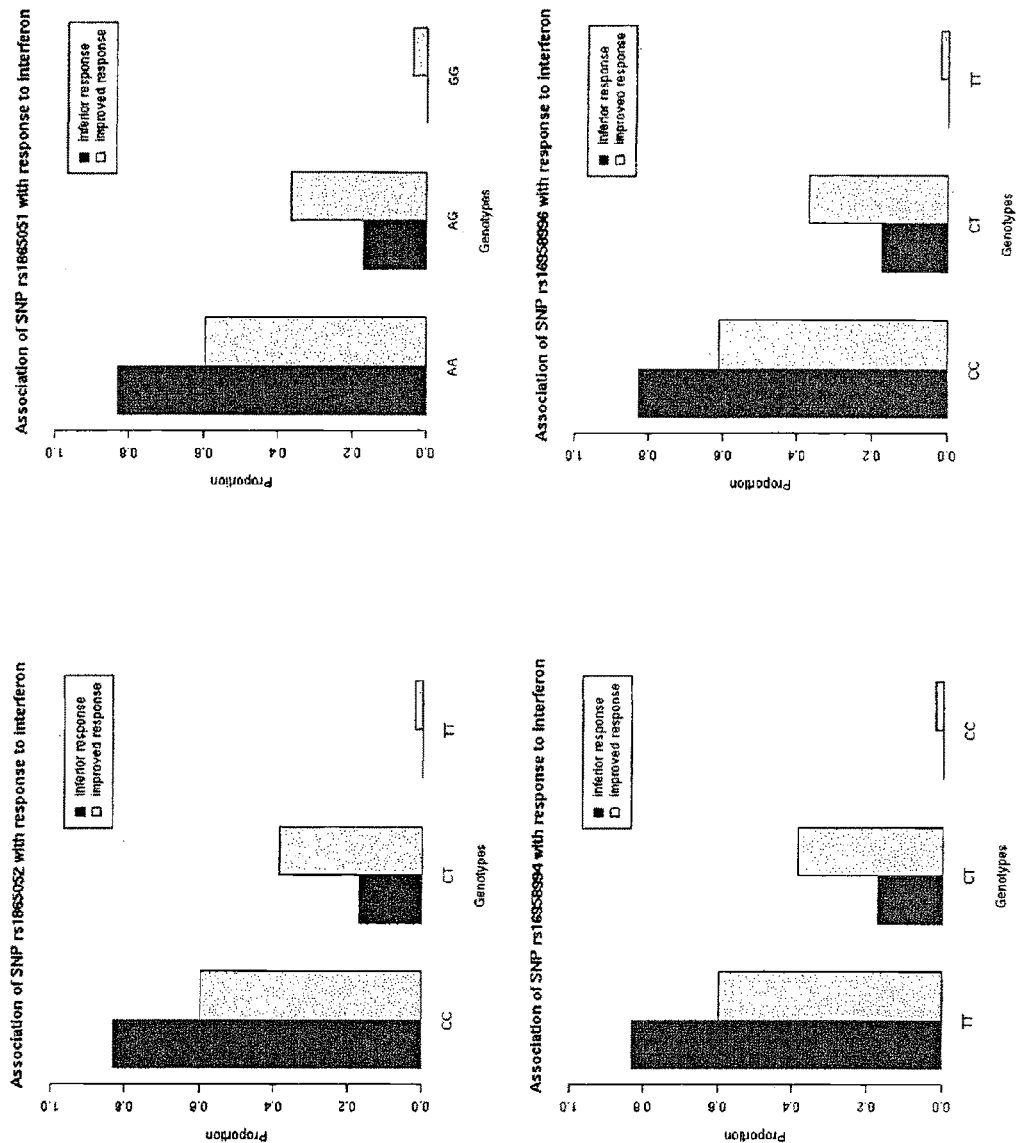

FIG. 11:
Association of the rs1865052, rs1865051, rs16958994, and rs16958996 polymorphisms in the MGC20255 locus with improved response to interferon treatment in MS individuals. Each graphic depicts the proportion of genotypes in inferior interferon response and improved interferon response groups respectively.

Figure 12:
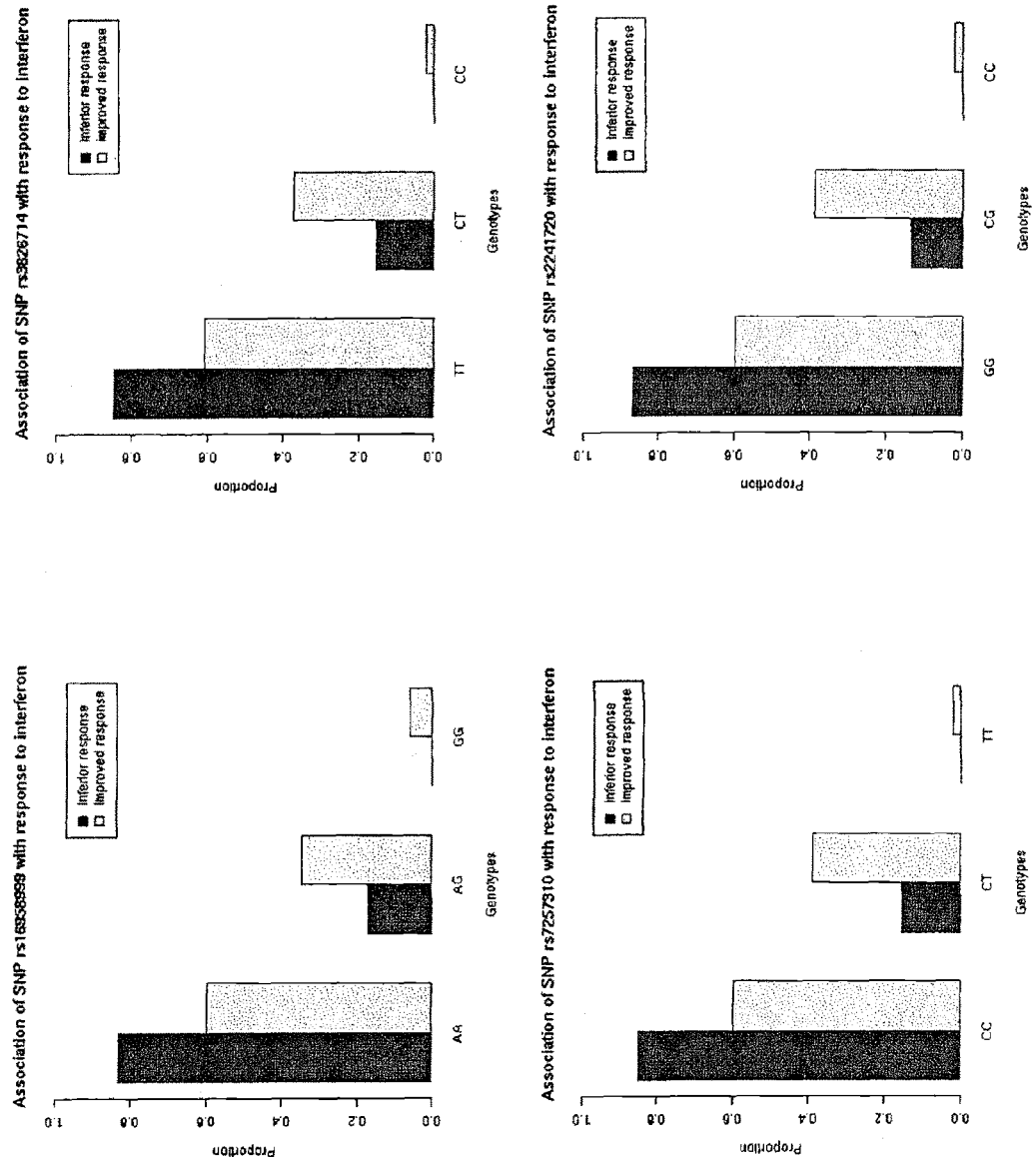

FIG. 12:
Association of the rs16958999, rs3826714, rs7257310, and rs2241720 polymorphisms in the MGC20255 locus with improved response to interferon treatment in MS individuals. Each graphic depicts the proportion of genotypes in inferior interferon response and improved interferon response groups respectively.

Figure 13:
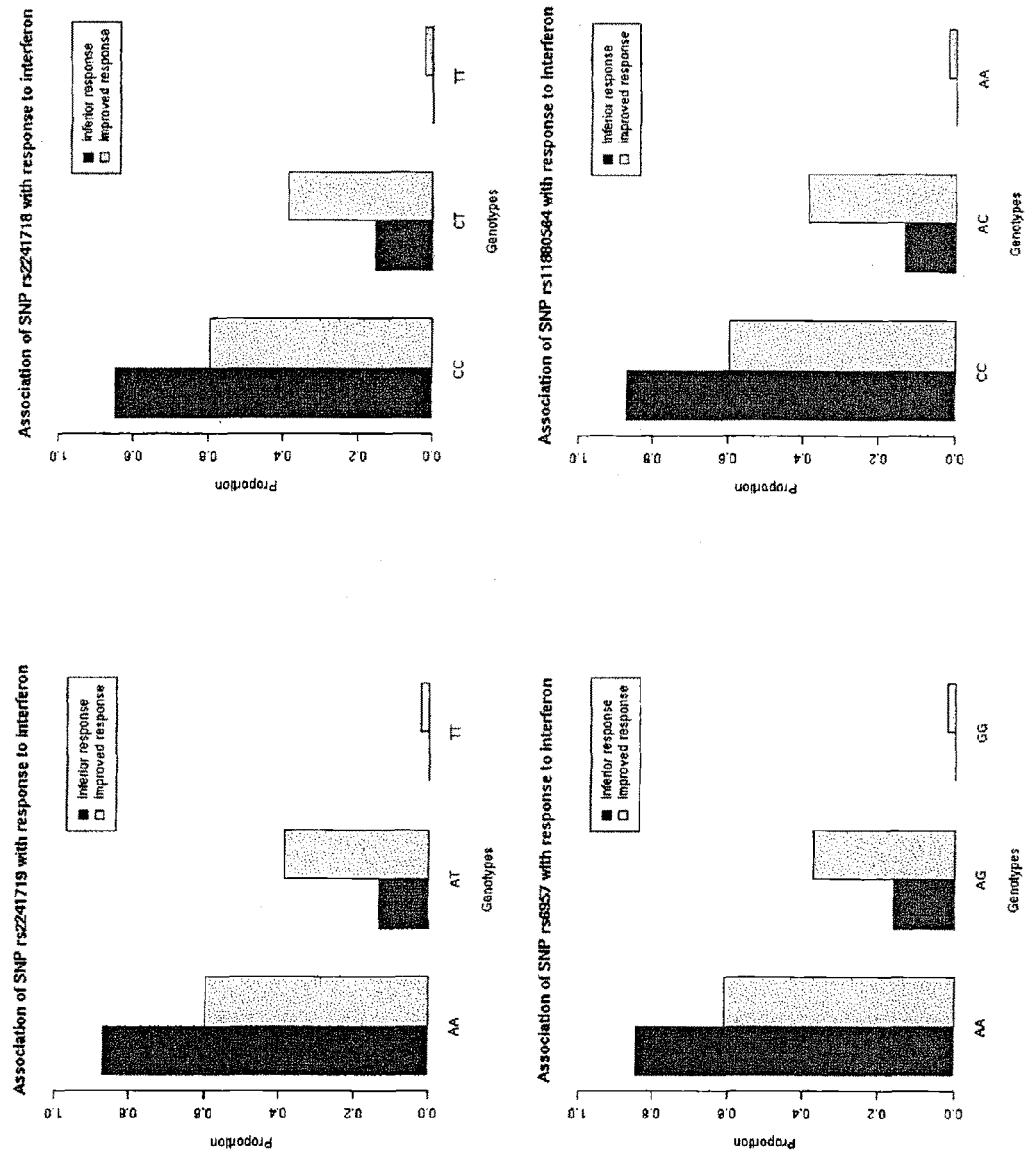

FIG. 13:
Association of the rs2241719, rs2241718, rs6957, and rs11880564 polymorphisms in the MGC20255 locus with improved response to interferon treatment in MS individuals. Each graphic depicts the proportion of genotypes in inferior interferon response and improved interferon response groups respectively.

Figure 14:
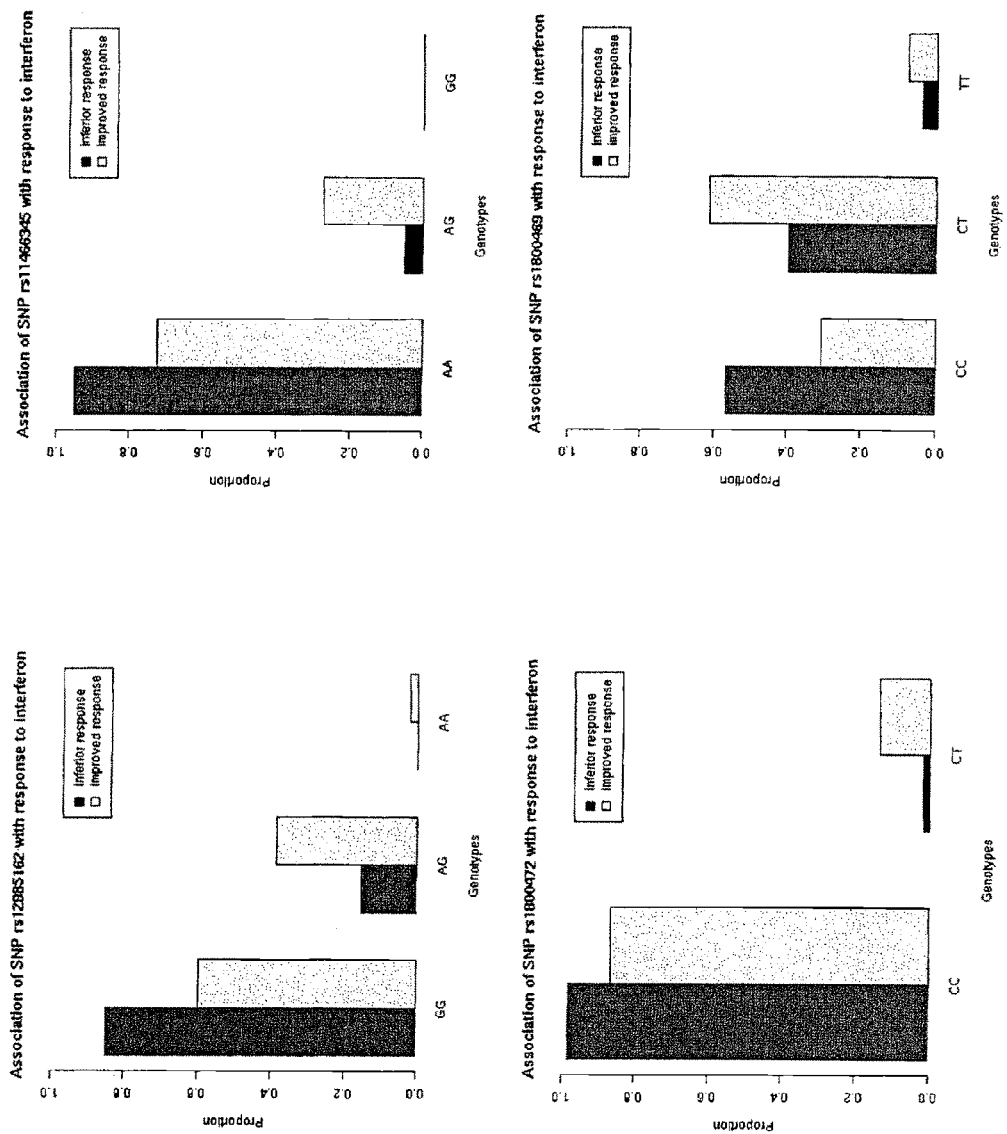

FIG. 14:
Association of the rs12985162 polymorphism in the MGC20255 locus and the rs11466345, rs1800472, and rs1800469 polymorphisms in the TGFB1 locus with improved response to interferon treatment in MS individuals. Each graphic depicts the proportion of genotypes in inferior interferon response and improved interferon response groups respectively.

The invention will now be described by reference to the following examples which are merely illustrative and are not to be construed as a limitation of scope of the present invention.

EXAMPLE 1

Polymorphisms in the TGFB1, MGC20255, HNRPUL1, CYP2S1, and/or AXL Genes can be Used to Predict Response to Interferon Treatment 105 patients diagnosed with MS were selected according to their response to interferon treatment. 53 patients responded to interferon therapy while 52 patients did not respond to interferon treatment. All patient were 18 years and older and MS was diagnosed according to criterias disclosed by Poser (Poser, et al. (1983) Ann. Neurol. 13: 227-231) or McDonaids (McDonald et al. (2001) Ann. Neurol. 50: 121-127). All individuals showed no severe internal or psychiatric disease, which can interfere with the course of MS, and received no additional immunomodulatory or immunosuppressive therapy with the exception of corticosteroids.

Patients who responded to interferon treatment were clinically stable during therapy for at least 2 years, suffered from no relapse or had a reduction of relapse rate $\geq 2/3$ compared to the relapse rate before interferon therapy, and had no progression in MS associated symptoms (deterioration in EDSS <1 during the two years of therapy).

Patients who did not respond to interferon treatment were clinically unstable during therapy during a period of 9 months or longer, no reduction of relapse rate with at least one relapse occurring after 6 months of therapy, and a progression of MS associated symptoms (deterioration in EDSS ≧1 point within one year, such deterioration not related to side effects of therapy).

EDTA blood was collected after informed consent. The study was approved by the local ethic committee of all participating centers. DNA was extracted using the Puregene Kit (Gentra, Minneapolis, USA) with little modifications. Amount of DNA was quantified by UV-absorption and using the picogreen method. Quality of the DNA was assessed by PCR and determination of the melting point in selected samples.

SNPs were selected from the public SNP database dbSNP (http://www.ncbi.nlm.nih.gov:80/). The SNP search tool at _http://ihg.gsf.de/ihg/snps.html_was used to download SNP sequences from public databases. Prior to genotyping, the relevant regions were amplified by PCR. Primers used for PCR amplification are depicted in table 2, see herein below. These primers are also depicted in SEQ ID NOs: 12 to 91.

Genotyping was performed on a MALDI-TOF mass-spectrometer (MassArray® system) employing the Spectrodesigner software (Sequenom™, CA) for primer selection and multiplexing and the homogeneous mass-extension (hMe) process for producing primer extension products. Primers used in the primer extension assays are depicted in table 3, see herein below. These primers are also depicted in SEQ ID NOs: 92 to 131.

Genotyping was also performed by genomewide single nucleotide polymorphism (SNP) genotyping using the Infiniumil assay with the product "Sentrix Bead Chip Array HumanHap300 Genotyping Beach Chip 317k" (Illumina Inc., San Diego, USA) according to the manufacturer's protocols. Starting material was 750 ng native human genomic DNA per chip. Genotype calling was done by cluster analysis of measured fluorescence intensities, using the BeadStudio Software Ver. 2.3.43 (Illumina Inc.)."

All analyses for binary outcomes were performed using logistic regression correcting for the effects of age and sex using both R and SPSS (version 11), as well as by exact contingency table analyses using both R and SPSS. Quantitative variables were analyzed using regression analysis. Linkage disequilibrium was calculated using the "Haploview" software and visualised using "GOLD".

Results are illustrated in table 1. Positions on chromosome 19 are according to Genbank Accession number NT_011109.15.

TABLE 1

| Polymorphism | gene | Position on Chr. 19 | −log10 (p-value) | maf |
|---|---|---|---|---|
| rs338600 | CYP2S1 | 46392183 | 1.487 | 0.270 |
| rs338593 | CYP2S1 | 46396144 | 0.447 | 0.477 |
| rs338585 | CYP2S1 | 46403655 | 0.873 | 0.421 |
| rs338584 | CYP2S1 | 46403953 | 1.854 | 0.235 |
| rs168109 | CYP2S1 | 46408111 | 0.151 | 0.495 |
| rs2271546 | AXL | 46419037 | 0.656 | 0.125 |
| rs4802112 | AXL | 46426330 | 2.000 | 0.282 |
| rs4803448 | AXL | 46426400 | 2.292 | 0.459 |
| rs4803449 | AXL | 46426506 | 2.523 | 0.331 |
| rs4802113 | AXL | 46432735 | 3.073 | 0.449 |
| rs2304234 | AXL | 46440593 | 1.955 | 0.412 |
| rs2304232 | AXL | 46454365 | 2.301 | 0.140 |

TABLE 1-continued

| Polymorphism | gene | Position on Chr. 19 | −log10 (p-value) | maf |
|---|---|---|---|---|
| rs1946612 | AXL | 46459827 | 1.824 | 0.238 |
| rs3760660 | HNRPUL1 | 46460865 | 2.959 | 0.148 |
| rs2304230 | HNRPUL1 | 46465904 | 2.103 | 0.155 |
| rs8103839 | HNRPUL1 | 46473333 | 1.969 | 0.153 |
| rs3745295 | HNRPUL1 | 46477122 | 1.605 | 0.156 |
| rs8105901 | HNRPUL1 | 46483932 | 2.287 | 0.154 |
| rs12327659 | HNRPUL1 | 46488312 | 1.940 | 0.155 |
| rs3752705 | HNRPUL1 | 46489951 | 1.839 | 0.156 |
| rs2053086 | HNRPUL1 | 46491315 | 2.063 | 0.154 |
| rs11879562 | HNRPUL1 | 46496816 | 2.134 | 0.156 |
| rs7248164 | HNRPUL1 | 46499540 | 2.103 | 0.156 |
| rs11881953 | HNRPUL1 | 46500089 | 2.362 | 0.163 |
| rs7245398 | HNRPUL1 | 46502484 | 2.246 | 0.174 |
| rs15052 | HNRPUL1 | 46505215 | 0.933 | 0.150 |
| rs1865053 | HNRPUL1 | 46506252 | 2.242 | 0.190 |
| rs8109627 | MGC20255 | 46514826 | 1.585 | 0.238 |
| rs8109167 | MGC20255 | 46515007 | 1.882 | 0.173 |
| rs1865052 | MGC20255 | 46516307 | 1.882 | 0.174 |
| rs1865051 | MGC20255 | 46516725 | 2.056 | 0.175 |
| rs16958994 | MGC20255 | 46516821 | 1.882 | 0.174 |
| rs16958996 | MGC20255 | 46516978 | 1.610 | 0.173 |
| rs16958999 | MGC20255 | 46517026 | 2.152 | 0.196 |
| rs3826714 | MGC20255 | 46517616 | 2.105 | 0.174 |
| rs7257310 | MGC20255 | 46518960 | 2.273 | 0.175 |
| rs2241720 | MGC20255 | 46521149 | 2.576 | 0.171 |
| rs2241719 | MGC20255 | 46521421 | 2.576 | 0.172 |
| rs2241718 | MGC20255 | 46521446 | 2.140 | 0.173 |
| rs16959007 | MGC20255 | 46521976 | 0.513 | 0.002 |
| rs11668308 | MGC20255 | 46522276 | NA | 0.003 |
| rs6957 | MGC20255 | 46522446 | 2.019 | 0.174 |
| rs11880564 | MGC20255 | 46523036 | 2.576 | 0.172 |
| rs12985162 | MGC20255 | 46523347 | 2.140 | 0.170 |
| rs10426316 | MGC20255 | 46523489 | 0.658 | 0.001 |
| rs8179181 | TGFB11 | 46530046 | 1.144 | 0.249 |
| rs11466345 | TGFB1 | 46535301 | 2.248 | 0.093 |
| rs1800472 | TGFB1 | 46539700 | 1.776 | 0.032 |
| rs2241715 | TGFB1 | 46548726 | 0.790 | 0.323 |
| rs12462166 | TGFB1 | 46549244 | 1.265 | 0.327 |
| rs1800469 | TGFB1 | 46552136 | 1.463 | 0.324 |
| rs1800468 | MGC4093 | 46552427 | 0.649 | 0.075 |
| rs11668109 | MGC4093 | 46555617 | 0.825 | 0.318 |
| rs1982072 | MGC4093 | 46556349 | 0.825 | 0.317 |
| rs2241714 | MGC4093 | 46561232 | 1.186 | 0.324 |
| rs2241713 | MGC4093 | 46561308 | 0.413 | 0.389 |
| rs2241712 | MGC4093 | 46561596 | 1.117 | 0.321 |
| rs9797885 | MGC4093 | 46564841 | 0.823 | 0.449 |
| rs8106934 | MGC4093 | 46567159 | 0.739 | 0.061 |
| rs1046909 | MGC4093 | 46574552 | 0.103 | 0.332 |

P-values are given as their negative decadic logarithm. Thus, a −log10 p-value equal or above 1.30103 correspond to a p-value equal or below 0.05. Consequently, a −log10 p-value equal or above 1.30103 is considered significant.

The SNPs rs338600, rs338584, rs4802112, rs4803448, rs4803449, rs4802113, rs2304234, rs2304232, rs1946612, rs3760660, rs2304230, rs8103839, rs3745295, rs8105901, rs12327659, rs3752705, rs2053086, rs11879562, rs7248164, rs11881953, rs7245398, rs1865053, rs8109627, rs8109167, rs1865052, rs1865051, rs16958994, rs16958996, rs16958999, rs3826714, rs7257310, rs2241720, rs2241719, rs2241718, rs6957, rs11880564, rs12985162, rs11466345, rs1800472, and rs1800469 showed association with response and non-response to interferon therapy.

The association between response and non-response to interferon therapy for each allele of rs338600, rs338584, rs4803448, rs4802113, rs2304234, rs3760660, rs2304230, rs8103839, rs3745295, rs8105901, rs12327659, rs3752705, rs2053086, rs11879562, rs7248164, rs11881953, rs7245398, rs1865053, rs8109167, rs1865052, rs1865051, rs16958994, rs16958996, rs16958999, rs3826714, rs7257310, rs2241720, rs2241719, rs2241718, rs6957, rsi1880564, rs12985162, rs11466345, rs1800472, and rs1800469 is further illustrated in FIGS. 6 to 14.

Thus, assessment of the three haplotype blocks comprise at least one polymorphism selected from the group of rs338600, rs338584, rs4802112, rs4803448, rs4803449, rs4802113, rs2304234, rs2304232, rs1946612, rs3760660, rs2304230, rs8103839, rs3745295, rs8105901, rs12327659, rs3752705, rs2053086, rs11879562, rs7248164, rs11881953, rs7245398, rs1865053, rs8109627, rs8109167, rs1865052, rs1865051, rs16958994, rs16958996, rs16958999, rs3826714, rs7257310, rs2241720, rs2241719, rs2241718, rs6957, rs11880564, rs12985162, rs11466345, rs1800472, or rs1800469 can be used to predict and determine response to interferon therapy in MS patients.

EXAMPLE 2

MGC20255 and HNRPUL1 are Susceptibility Genes for MS 245 patients diagnosed with MS and 486 control individuals were enrolled in a study to identify susceptibility genes in MS. The age of individuals were 18 years and older. MS was diagnosed according to criterias disclosed by Poser (Poser, et al. (1983) Ann. Neurol. 13: 227-231) or McDonalds (McDonald et al. (2001) Ann. Neurol. 50: 121-127). All individuals showed no severe internal or psychiatric disease, which can interfere with the course of MS.

EDTA blood was collected after informed consent. The study was approved by the local ethic committee of all participating centers. DNA was extracted using the Puregene Kit (Gentra, Minneapolis, USA) with little modifications. Amount of DNA was quantified by UV-absorption and using the picogreen method. Quality of the DNA was assessed by PCR and determination of the melting point in selected samples.

SNPs were selected from the public SNP database dbSNP (http://www.ncbi.nim.nih.gov:80/). The SNP search tool at _http://ihg.gsf.de/ihg/snps.html_was used to download SNP sequences from public databases. Prior to genotyping, the relevant regions were amplified by PCR. Table 2 shows the PCR primers used. These primers are also depicted in SEQ ID NOs: 12 to 91.

TABLE 2

| SNP_ID | forward primer | reverse primer |
|---|---|---|
| rs338600 | ACGTTGGATGGCTATTTCTGCTGGGATGGG | ACGTTGGATGTCCAAGGTGTCTCCATCATG |
| rs338593 | ACGTTGGATGTGTCCATCCATCTTTCCCTG | ACGTTGGATGTGTGATGGAGCCAGGCAGAG |
| rs338585 | ACGTTGGATGACTATAAACCCCTTCCCACC | ACGTTGGATGTTGTGAACTAGTGTCCCTGG |
| rs338584 | ACGTTGGATGTTCTGCACCCTGGGCTTACT | ACGTTGGATGGCTGAGTCAGTATTCCTCAC |
| rs4802112 | ACACCAACACCACCACGTTAGG | GGGACACCGCTGATCGTATAGCATTCCTGGGC ATAGGTGTAG |
| rs168109 | ACGTTGGATGGAAAGATGAGATTGGAATCAG | ACGTTGGATGCTTATCAATTTATTAAGGCT |
| rs2271546 | ACGTTGGATGTATGTTGGGCTGGAGGGTGA | ACGTTGGATGATTCCTGACTTCCCACAACC |
| rs4803448 | ACGTTGGATGCCCTATGGAATTACACATGC | ACGTTGGATGTGAGTGAGTGAAATTGTGT |
| rs4803449 | GACACAGCAGGGGACGAA | GGGACACCGCTGATCGTATACTCCAAATCTAT CCCCTTCCC |
| rs4802113 | ACGTTCGATGCCACTCTGAGTGTGCCATTC | ACGTTGGATGTGGCAACAAGTGTCAAGCTC |
| rs2304234 | ACGTTGGATGATCACCCCTTTGGGTCCCAG | ACGTTGGATGAGGTTCCTTCACTATCAGGG |
| rs2304232 | GGATTTCAGATGTGCACCAACACACCTGGC | GTTCAAGCAATTCTCCTGCCTCAGTCTCCC |
| rs1946612 | GATGTGGCCCCATTCCCTGGCAATTCAGTT | CGTGGGCGAGGGCGGGGTGTCTGGACTG |
| rs3760660 | ACGTTGGATGAACTGGATGCGTCTGATCTG | ACGTTGGATGGCCACACACTATCTCTACTC |
| rs2304230 | ACGTTGGATGACCACTCTTAGTTGAGCTCC | ACGTTGCATGGCGGTTCATGAAGAACCCTG |
| rs8103839 | ACGTTGGATGTACACATCCCCACCAAAGAC | ACGTTGGATGTTATCTGGTGGGATCCAAGG |
| rs3745295 | ACGTTGGATGCTGAGAGGACTATGGTCATG | ACGTTGGATGGGACCCTCTCCTAAAAGATG |
| rs8105901 | ACGTTGGATGACACATAGGCTAGTGTCTAC | ACGTTGGATGAACTCTCAGATCCCTATGAC |
| rs12327659 | ACGTTGGATGTACACAGTGAGCACACAAGG | ACGTTGGATGCAGCCCCTTATTTCTAGCAC |
| rs3752705 | ACGTTGGATGCAGTTCCACGTCATTTCCAC | ACGTTGGATGTCACATTTGACTCCCAGTGC |
| rs2053086 | ACGTTGGATGATAGGAACAGAGCTGCACAC | ACGTTGGATGGGGCATTTAAGATGCATCTG |
| rs11879562 | ACGTTGGATGAAAGTTAAGTCCCCTCTCCC | ACGTTGGATGTTCCTATGACCAGATGCCAC |
| rs7248164 | ACGTTGGATGAGGAAGGGACAAAGCAGAAG | ACGTTGGATGACTCAGTTTGTCCTTCCCTG |
| rs11881953 | ACGTTGGATGCTCCTGAGTTCACCCAGTTC | ACGTTGGATGATTAGCCAGGCATGGTGGTG |
| rs7245398 | ACGTTGGATGTTACAGGAGCCTGTGCATAC | ACGTTGGATGCAGAGAGCTTCAATCCTGAG |

TABLE 2-continued

| SNP_ID | forward primer | reverse primer |
|---|---|---|
| rs15052 | ACGTTGGATGAAAGCTTTTGGGTCTGGCAC | ACGTTGGATGGCTCCTTCCCTTCAGAACTT |
| rs1865053 | ACGTTGGATGTAGTCAGTTTCCCTCCCTTC | ACGTTGGATGAATTCAGCCCCAATCTTCCC |
| rs8109627 | ACGTTGGATGGCCTACCAATCTGAAATGCC | ACGTTGGATGCAGGGAAGAGAATGGGACAG |
| rs8109167 | ACGTTGGATGGACACAGAAGCCTTCTGAAC | ACGTTGGATGTGTTGTGGTCACAAGGATGC |
| rs1865052 | ACGTTGGATGGGGTAAGATTGCTGGCAGGA | ACGTTGGATGCAAAGAAACTGCTCGGACTC |
| rs1865051 | ACGTTGGATGTGTCAGCATGCAGGACAATG | ACGTTGGATGAGACTAGGGCCCCACAAACA |
| rs16958994 | ACGTTGGATGAGCTCGTGTACAACTGTGTC | ACGTTGGATGCACAGGACATGTGTGTGTAC |
| rs16958996 | ACGTTGGATGCATGCACACACATGCTTGGA | ACGTTGGATGGGCACCTGAGTGTGTGTATG |
| rs16958999 | ACGTTGGATGCTGTGTGCGCAAGCACTCAT | ACGTTGGATGATACACAGGAAGATAGAGGC |
| rs3826714 | ACGTTGGATGACAGTGACGAGGAAGGTGAG | ACGTTGGATGATGAAGTGGAGACAGACAGG |
| rs7257310 | ACGTTGCATGTTGTGATTGCCCCTGCCGTG | ACGTTGGATGCCAGATTCCATTCAAGAGCC |
| rs2241720 | ACGTTGGATGCTCTCAGCCTTTATCTCTGG | ACGTTGGATGTATAGCAGCCAGGTTTGAGG |
| rs2241719 | ACGTTGGATGACAATTTTCCCTTCCTCCGC | ACGTTGGATGTCAGGACCCATGATAACAGC |
| rs2241718 | ACGTTGGATGACAATTTTCCCTTCCTAAGC | ACGTTGGATGCTCAGGACCCATGATAACAG |
| rs16959007 | ACGTTGGATGAGAACGAAAGCCTCTGCTAC | ACGTTGGATGCCCACTTCACTAGTTCATGG |
| rs11668308 | ACGTTGGATGTGAGAAGGGTCAGATGGTAG | ACGTTGGATGATGACCTGATCCTGTCTGTG |
| rs6957 | ACGTTGGATGAGCTAGACTCCAGGACCTTG | ACGTTGGATGTACAGGCAGGTAAGAGACAG |
| rs11880564 | ACGTTGGATGGTGTCTCCTGTCCGTCCTG | ACGTTGGATGTTGCTTTGGCAGGACGCATG |
| rs12985162 | ACGTTGGATGCCTTGTTTTTCCCATGCCTC | ACGTTGGATGGAACAGAGATGGAGAATGGC |
| rs10426316 | ACGTTGGATGTCTCCTCACTTTGCCCTTTC | ACGTTGGATGTGTGGGAGACAGAGGAGATG |
| rs8179181 | ACGTTGGATGAGTTCTTCTCCGTGGAGCTG | ACGTTGGATGGGCATCTGGCTTCTATGGTG |
| rs11466345 | ACGTTGGATGACTCCTGACCTCAAGTGATC | ACGTTGGATGAAAGTCCTAAGAGAGGCCAG |
| rs1800472 | ACGTTGGATGAGCAATAGTTGGTGTCCAGG | ACGTTGGATGACCATTCATGGCATGAACCG |
| rs2241715 | ACGTTGGATGTTGGAGGGTGATGCAGAGAG | ACGTTGGATGCTCCGACTATTTTCTCTCCC |
| rs12462166 | ACGTTGGATGACCAGACCTGCCCCGTCTC | ACGTTGGATGCTTCCCTTTCCTTCCCATGC |
| rs1800469 | ACGTTGGATGAACAAGGTAGGAGAAGAGGG | ACGTTGGATGTTCTTACAGGTGTCTGCCTC |
| rs1800468 | ACGTTGGATGATCACTGGGTGTCCGGGGT | ACGTTGGATGTCCGCAACTTCGACCGCTAC |
| rs11668109 | ACGTTGGATGACAGGTCTTGGTGTTCCCAG | ACGTTGGATGAGGTCTTCAAGGTGGGTATC |
| rs1982072 | ACGTTGGATGCATAGTGAGCACGGGATAAG | ACGTTGGATGCCCCATCTTAATCCTTGGAC |
| rs2241714 | ACGTTGGATGGAGGCTACTTTCCGAGAAAC | ACGTTGGATGTATTTTCCCCTCCCAGGGC |
| rs2241713 | ACGTTGGATGAGTTTCCCCCCCGTCAAATG | ACGTTGGATGATCACGTGCACCTCAGCCAT |
| rs2241712 | ACGTTGGATGTCGGACCTGAACTCATAACG | ACGTTGGATGAGCGCAAAAGACCCGCCTTC |
| rs9797885 | ACGTTGGATGAGGAGCATCACTTGAACCTG | ACGTTGGATGAGTAGAAGTCTGGCTCTGTC |
| rs8106934 | ACGTTGGATGTGGACTTCCTGCACTCAAGG | ACGTTGGATGGGTTTTGCCATGTATGGCCG |
| rs1046909 | ACGTTGGATGGCTTCCTGAACCCTCGCAAT | ACGTTGGATGTAGAGCAAAGCGCAAGGTCC |

Genotyping was performed on a MALDI-TOF mass-spectrometer (MassArray® system) employing the Spectrodesigner software (Sequenom™, CA) for primer selection and multiplexing and the homogeneous mass-extension (hMe) process for producing primer extension products. Table 3 shows the primers used for the primer extension assays. These primers are also depicted in SEQ ID NOs: 92 to 131.

TABLE 3

| SNP_ID | extension primer |
|---|---|
| rs338600 | GGGCAGGTTCCTGGTAGAGGG |
| rs338593 | CTCTGGTTGGGTTCAGC |
| rs338585 | CCCTTCCCACCCCAGTC |
| rs338584 | CTTACTGTTGGCTCCTCCAC |
| rs4802112 | AAAAACAGTCAAGACACAAT |
| rs168109 | TTGCCACCTCCTAGCTG |
| rs2271546 | GGGTCAGAGGACATGTGG |
| rs4803448 | TGCCCAGGAATGCTCATAAGTACA |
| rs4803449 | AGACACAACCCCTGC |
| rs4802113 | GTGTGCCATTCCTCGGG |
| rs2304234 | CAGAGAGCTGGATCCAAGGC |
| rs2304232 | CAGCAAGAGCGATGTGGTAGGTGC |
| rs1946612 | GAGGACCTGGTCACAAATACA |
| rs3760660 | ACGCCTGTTTGTTTACG |
| rs2304230 | ACCTGCAGATGCCTTCTGGA |
| rs8103839 | GTTGACAATTTCTGAGGATACC |
| rs3745295 | AGGACTATGGTCATGAAACAACT |
| rs8105901 | GACATACCTAACTTTTCCTT |
| rs12327659 | GTGAGCTATCACTGCAA |
| rs3752705 | GGAATATGATTGCCAACTCT |
| rs2053086 | GCTGCACACACAAGGAC |
| rs11879562 | CTTCTTTGACTCCATTCCTAAAA |
| rs7248164 | AGAGTAAGATCAAAAAAGAAATCA |
| rs11881953 | TCTCCTGCCTCAGCCTCCC |
| rs7245398 | GGGCACTGGCTTTCCAAGAA |
| rs15052 | AGAGGAGGCAGTGGGAG |
| rs1865053 | CCTTGTTTTTGTTGCCC |
| rs8109627 | CAATCTGAAATGCCACTTCT |
| rs8109167 | AGCCTTCTGAACAAGACACAC |
| rs1865052 | CAGTCACAGCCTATGGTGCT |
| rs1865051 | ATGCAGGACAATGCAGCAGA |
| rs16958994 | CCTGCCCATGGACCTGT |
| rs16958996 | ATACACAGGAAGATAGAGGC |
| rs16958999 | CATGCAGGCACCTGAGGTCA |
| rs3826714 | TGAGGGCCAGTAGCAGG |
| rs7257310 | AGCCATGGTCACCAGAGCCTC |
| rs2241720 | TCTGGGTTTTGATCCCC |
| rs2241719 | CTCCGCCTTCCTCTCCC |
| rs2241718 | TTACACTCCCCAAATGC |

TABLE 3-continued

| SNP_ID | extension primer |
|---|---|
| rs16959007 | TTCTGTCCTCTGTCAGGCCC |
| rs11668308 | GCGGGCCTAACAAGGGCTCC |
| rs6957 | AGGACCTTGGGGTCATA |
| rs11880564 | GCTCGCTGGCCTGGCCG |
| rs12985162 | CCCACCTTTTCCACTCC |
| rs10426316 | GCTGCTGTGTGTCTTGGCCC |
| rs8179181 | GCTGCAGGCAGGAGAGACGC |
| rs11466345 | AGTGCTGGGATTACGGG |
| rs1800472 | GGGCCCTCTCCAGCGGG |
| rs2241715 | CAGAGACGGAGACGAGGCAAC |
| rs12462166 | CTCCGCGAGCGATCCCCGCC |
| rs1800469 | AGGGGGCAACAGGACACCTGA |
| rs1800468 | CGGGGTGTGGATGGTGGTGA |
| rs11668109 | CCCCTCCCCTCAGCCTGG |
| rs1982072 | ACGATTCTCACCCCATATTT |
| rs2241714 | TCCGAGAAACCGCTGGCCCC |
| rs2241713 | CCCCGTCAAATGGAGATAATACA |
| rs2241712 | GGGAAGCGGGGTGGCTG |
| rs9797885 | TTGCAGTGAGCCGAGATC |
| rs8106934 | GCACTCAAGGCATCCTC |
| rs1046909 | ACCCTCGCAATGACACT |

All analyses for binary outcomes were performed using logistic regression correcting for the effects of age and sex using both R and SPSS (version 11), as well as by exact contingency table analyses using both R and SPSS. Quantitative variables were analyzed using regression analysis. Linkage disequilibrium (LD) was calculated using the "Haploview" software and visualised using "GOLD". LD structure of the explored region is shown on the FIG. 1. All SNPs (in accordance with a preferred embodiment of the invention) are distributed in three LD blocks when the block is defined as a region with D' between all SNPs equal to 1. The biggest block includes MGC20255, HNRPUL1 genes and part of AXL. this region was analysed (in accordance with a preferred embodiment of the invention) using r squared, several small blocks are present, so that the genes discussed above form three separate LD blocks. All associated with MS SNPs are in tightly LD (r squared between 0.93 and 1). However, the r squared measures between SNPs associated with response to interferon therapy are more variable.

Association results are illustrated in table 4. Positions on chromosome 19 are according to Genbank Accession number NT_011109.15.

TABLE 4

| Polymorphism | gene | position on Chr. 19 | −log 10 (p-value) | maf |
|---|---|---|---|---|
| rs338600 | CYP2S1 | 46392183 | 0.153 | 0.270 |
| rs338593 | CYP2S1 | 46396144 | 0.319 | 0.477 |

TABLE 4-continued

| Polymorphism | gene | position on Chr. 19 | −log 10 (p-value) | maf |
|---|---|---|---|---|
| rs338585 | CYP2S1 | 46403655 | 0.720 | 0.421 |
| rs338584 | CYP2S1 | 46403953 | 0.436 | 0.227 |
| rs168109 | CYP2S1 | 46408111 | 0.048 | 0.495 |
| rs2271546 | AXL | 46419037 | 1.109 | 0.125 |
| rs4803448 | AXL | 46426400 | 0.401 | 0.459 |
| rs4802113 | AXL | 46432735 | 0.558 | 0.449 |
| rs2304234 | AXL | 46440593 | 0.262 | 0.412 |
| rs3760660 | HNRPUL1 | 46460865 | 0.501 | 0.148 |
| rs2304230 | HNRPUL1 | 46465904 | 1.166 | 0.155 |
| rs8103839 | HNRPUL1 | 46473333 | 0.897 | 0.153 |
| rs3745295 | HNRPUL1 | 46477122 | 0.983 | 0.156 |
| rs8105901 | HNRPUL1 | 46483932 | 1.098 | 0.154 |
| rs12327659 | HNRPUL1 | 46488312 | 1.261 | 0.155 |
| rs3752705 | HNRPUL1 | 46489951 | 1.142 | 0.156 |
| rs2053086 | HNRPUL1 | 46491315 | 0.809 | 0.154 |
| rs11879562 | HNRPUL1 | 46496816 | 1.182 | 0.156 |
| rs7248164 | HNRPUL1 | 46499540 | 1.221 | 0.156 |
| rs11881953 | HNRPUL1 | 46500089 | 1.394 | 0.163 |
| rs7245398 | HNRPUL1 | 46502484 | 1.381 | 0.174 |
| rs15052 | HNRPUL1 | 46505215 | 0.007 | 0.150 |
| rs1865053 | HNRPUL1 | 46506252 | 1.194 | 0.190 |
| rs8109627 | MGC20255 | 46514826 | 0.930 | 0.264 |
| rs8109167 | MGC20255 | 46515007 | 1.448 | 0.173 |
| rs1865052 | MGC20255 | 46516307 | 1.488 | 0.174 |
| rs1865051 | MGC20255 | 46516725 | 1.296 | 0.175 |
| rs16958994 | MGC20255 | 46516821 | 1.480 | 0.174 |
| rs16958996 | MGC20255 | 46516978 | 1.050 | 0.173 |
| rs16958999 | MGC20255 | 46517026 | 1.591 | 0.196 |
| rs3826714 | MGC20255 | 46517616 | 1.686 | 0.174 |
| rs7257310 | MGC20255 | 46518960 | 1.640 | 0.175 |
| rs2241720 | MGC20255 | 46521149 | 1.584 | 0.171 |
| rs2241719 | MGC20255 | 46521421 | 1.727 | 0.172 |
| rs2241718 | MGC20255 | 46521446 | 1.498 | 0.173 |
| rs16959007 | MGC20255 | 46521976 | 0.003 | 0.002 |
| rs11668308 | MGC20255 | 46522276 | 0.396 | 0.003 |
| rs6957 | MGC20255 | 46522446 | 1.559 | 0.174 |
| rs11880564 | MGC20255 | 46523036 | 1.727 | 0.172 |
| rs12985162 | MGC20255 | 46523347 | 1.276 | 0.170 |
| rs10426316 | MGC20255 | 46523489 | 0.289 | 0.001 |
| rs8179181 | TGFB1 | 46530046 | 0.260 | 0.249 |
| rs11466345 | TGFB1 | 46535301 | 0.482 | 0.093 |
| rs1800472 | TGFB1 | 46539700 | 0.535 | 0.032 |
| rs2241715 | TGFB1 | 46548726 | 0.545 | 0.323 |
| rs12462166 | TGFB1 | 46549244 | 0.642 | 0.327 |
| rs1800469 | TGFB1 | 46552136 | 0.787 | 0.324 |
| rs1800468 | MGC4093 | 46552427 | 0.838 | 0.075 |
| rs11668109 | MGC4093 | 46555617 | 0.491 | 0.318 |
| rs1982072 | MGC4093 | 46556349 | 0.534 | 0.317 |
| rs2241714 | MGC4093 | 46561232 | 0.395 | 0.324 |
| rs2241713 | MGC4093 | 46561308 | 0.162 | 0.389 |
| rs2241712 | MGC4093 | 46561596 | 0.304 | 0.321 |
| rs9797885 | MGC4093 | 46564841 | 0.667 | 0.449 |
| rs8106934 | MGC4093 | 46567159 | 0.410 | 0.061 |
| rs1046909 | MGC4093 | 46574552 | 0.220 | 0.332 |

P-values are given as their negative decadic logarithm. Thus, a −log10p-value equal or above 1.30103 correspond to a p-value equal or below 0.05. Consequently, a −log10 p-value equal or above 1.30103 is considered significant.

The SNPs rs11881953, rs7245398, rs8109167, rs1865052, rs16958994, rs16958999, rs3826714, rs7257310, rs2241720, rs2241719, rs2241718, rs6957, and rs11880564 showed association with MS.

The association with MS for each allele of rs11881953, rs7245398, rs8109167, rs1865052, rs16958994, rs16958999, rs3826714, rs7257310, rs2241720, rs2241719, rs2241718, rs6957, and rs11880564 is further illustrated in FIGS. 2 to 5.

Consequently, assessment of the haplotype block comprises at least one polymorphism selected from the group of rs11881953, rs7245398, rs8109167, rs1865052, rs16958994, rs16958999, rs3826714, rs7257310, rs2241720, rs2241719, rs2241718, rs6957, or rs11880564 can be used to diagnose and determine an individuals susceptibility to develop MS.

The invention claimed is:

1. A method for identifying a multiple sclerosis (MS) human patient having an inferior response to a treatment of MS by administration of interferon-alpha (IFN-α) and/or interferon-beta (IFN-β) comprising:
   (a) determining in a sample from the human patient the presence of polymorphisms in AXL and MGC20255, wherein the polymorphism in AXL is at position 41782 of SEQ ID NO:1, and the polymorphism in MGC20255 is at position 130468 of SEQ ID NO:1; and
   (b) identifying the human patient as having an inferior response to a treatment of MS with administration of interferon-alpha (IFN-α) and/or interferon-beta (IFN-β) when the patient has either CT or TT in AXL at position 41782 of SEQ ID NO:1, and AA in MGC20255 at position 130468 of SEQ ID NO:1.

2. The method according to claim 1, wherein the presence of the at least one nucleic acid sequence motive is determined by assays based on physical separation of nucleic acid molecules, ligase chain reaction assay, cleavage and digestion assay, sequencing assay, nucleic acid amplification assay, hybridization assay or assays based on protein detection.

3. The method according to claim 2, wherein the nucleic acid amplification assay is a PCR performed by the use of one or more nucleic acid molecules as primers comprising a sequence as depicted in SEQ. ID NOs:22, 23, 76 to 77.

4. The method according to claim 2 or 3, wherein the nucleic acid amplification assay is a PCR extension assay performed by the use of one or more nucleic acid molecules as primers comprising a sequence as depicted in SEQ. ID NOs: 97 to 124.

5. The method according to claim 2, wherein the hybridization assay is performed by the use of one or more nucleic acid molecules as probes comprising a sequence as depicted in SEQ. ID NOs:142 to 196.

6. The method according to claim 1, wherein the sample comprises blood.

* * * * *